United States Patent
Martinez et al.

(10) Patent No.: US 11,690,387 B2
(45) Date of Patent: Jul. 4, 2023

(54) METHODS AND RELATED COMPOSITIONS FOR MANUFACTURING FOOD AND FEED

(71) Applicant: Flagship Pioneering Innovations V, Inc., Cambridge, MA (US)

(72) Inventors: Ignacio Martinez, Lexington, MA (US); Zachary Garo Armen, Boston, MA (US); Christine Cezar, Sammamish, WA (US); Barry Andrew Martin, Boston, MA (US); Maier Steve Avendano Amado, Cambridge, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 802 days.

(21) Appl. No.: 16/480,037

(22) PCT Filed: Jan. 24, 2018

(86) PCT No.: PCT/US2018/015051
§ 371 (c)(1),
(2) Date: Jul. 23, 2019

(87) PCT Pub. No.: WO2018/140496
PCT Pub. Date: Aug. 2, 2018

(65) Prior Publication Data
US 2020/0128856 A1    Apr. 30, 2020

Related U.S. Application Data

(60) Provisional application No. 62/584,011, filed on Nov. 9, 2017, provisional application No. 62/450,038, filed on Jan. 24, 2017.

(51) Int. Cl.
*A23K 10/18*    (2016.01)
*A23K 10/20*    (2016.01)
(Continued)

(52) U.S. Cl.
CPC ............ *A23K 10/18* (2016.05); *A23K 10/20* (2016.05); *A23K 20/142* (2016.05); *A23K 50/90* (2016.05); *A23L 13/00* (2016.08)

(58) Field of Classification Search
CPC ...... A23K 10/18; A23K 10/20; A23K 20/142; A23K 50/90; A23L 13/00; C12N 1/20
See application file for complete search history.

(56) References Cited

U.S. PATENT DOCUMENTS 5,631,024 A    5/1997    Kevan et al.
8,025,552 B2    9/2011    Cohen et al.
(Continued)

FOREIGN PATENT DOCUMENTS

CN    1246893 A    3/2000
CN    1499932 A    5/2004
(Continued)

OTHER PUBLICATIONS

Al-Ghamdi et al., "Effect of gut bacterial isolates from *Apis mellifera jementica* on *Paenibacillus larvae* infected bee larvae," Saudi J Biol Sci. 25(2):383-87 (2018).
(Continued)

*Primary Examiner* — Trevor Love
(74) *Attorney, Agent, or Firm* — Clark & Elbing LLP

(57) ABSTRACT

Provided herein are methods and compositions for food and feed applications, e.g., for targeting one or more microorganisms resident in a host insect, the modulation resulting in an increase in the fitness of the host. The invention features a composition that includes a modulating agent (e.g., phage, peptide, small molecule, antibiotic, or combinations thereof) that can alter the host's microbiota in a manner that is beneficial to the host. By promoting favorable microbial levels, microbial activity, microbial metabolism, and/or microbial diversity, the modulating agent described herein
(Continued)

may be used to increase the fitness of a variety of insects utilized in human food or animal feed industries.

11 Claims, 5 Drawing Sheets

Specification includes a Sequence Listing.

(51) Int. Cl.
   *A23K 20/142*     (2016.01)
   *A23K 50/90*      (2016.01)
   *A23L 13/00*      (2016.01)
   *C12N 1/20*       (2006.01)

(56) References Cited

U.S. PATENT DOCUMENTS

| | | |
|---|---|---|
| 8,334,366 B1 | 12/2012 | Hughes et al. |
| 10,086,024 B2 | 10/2018 | Kovarik |
| 11,350,648 B2 | 6/2022 | Martinez et al. |
| 2008/0295207 A1 | 11/2008 | Baum et al. |
| 2009/0285937 A1* | 11/2009 | Vadis ............... A23K 40/25 426/573 |
| 2011/0145939 A1 | 6/2011 | O'Neill |
| 2011/0150780 A1 | 6/2011 | Krieger et al. |
| 2011/0209228 A1 | 8/2011 | Cocks et al. |
| 2011/0229937 A1* | 9/2011 | Pompejus ............ C07K 14/34 435/106 |
| 2011/0263487 A1 | 10/2011 | Meagher |
| 2012/0148712 A1 | 6/2012 | Guilfoyle et al. |
| 2014/0065186 A1 | 3/2014 | Tokura et al. |
| 2014/0302194 A1 | 10/2014 | Marsala et al. |
| 2014/0349917 A1 | 11/2014 | Eckert et al. |
| 2017/0015716 A1 | 1/2017 | Walensky et al. |
| 2017/0151293 A1 | 6/2017 | Kovarik |
| 2019/0015528 A1 | 1/2019 | Moran et al. |
| 2019/0191741 A1 | 6/2019 | Martinez et al. |
| 2020/0129565 A1 | 4/2020 | Martinez et al. |
| 2021/0195917 A1 | 7/2021 | Martinez et al. |

FOREIGN PATENT DOCUMENTS

| | | |
|---|---|---|
| CN | 101636073 A | 1/2010 |
| CN | 105814190 A | 7/2016 |
| CN | 106472882 A | 3/2017 |
| CN | 106962696 A | 7/2017 |
| CN | 107028037 A | 8/2017 |
| CN | 108782465 A | 11/2018 |
| CN | 108783118 A | 11/2018 |
| CN | 108812552 A | 11/2018 |
| CN | 108813226 A | 11/2018 |
| CN | 109055268 A | 12/2018 |
| EP | 2949220 A1 | 12/2015 |
| EP | 3165092 A1 | 5/2017 |
| FR | 2985664 A1 | 7/2013 |
| JP | H2-222654 A | 9/1990 |
| JP | 2010-136668 A | 6/2010 |
| JP | 2010-525809 A | 7/2010 |
| JP | 2013-158315 A | 8/2013 |
| KR | 2010-0125747 A | 12/2010 |
| KR | 2012-0123975 A | 11/2012 |
| KR | 2013-0101370 A | 9/2013 |
| MD | 1193 Y | 9/2017 |
| RU | 2305935 C1 | 9/2007 |
| RU | 2511304 C2 | 4/2014 |
| RU | 2552672 C1 | 6/2015 |
| RU | 2579266 C1 | 4/2016 |
| WO | WO-88/00976 A1 | 2/1988 |
| WO | WO-95/16776 A1 | 6/1995 |
| WO | WO-2005/034863 A2 | 4/2005 |
| WO | WO-2008/084074 A2 | 7/2008 |
| WO | WO-2013/052536 A2 | 4/2013 |
| WO | WO-2014/097338 A1 | 6/2014 |
| WO | WO-2015/020516 A1 | 2/2015 |
| WO | WO-2015/100432 A2 | 7/2015 |
| WO | WO-2015/191744 A1 | 12/2015 |
| WO | WO-2016/004312 A1 | 1/2016 |
| WO | WO-2018/051344 A1 | 3/2018 |

OTHER PUBLICATIONS

Alberoni et al., "Beneficial microorganisms for honey bees: problems and progresses," Appl Microbiol Biotechnol. 100(22):9469-82 (2016).

Alberoni et al., "Impact of beneficial bacteria supplementation on the gut microbiota, colony development and productivity of *Apis mellifera* L.," Beneficial Microbes. 9(2):269-78 (2018).

Amos, "UBC students give bees a chance," University of British Columbia News, <http://news.ubc.ca/2015/09/18/ubc-students-give-bees-a-chance/>, dated Sep. 18, 2015 (3 pages).

Anderson et al., "An emerging paradigm of colony health: microbial balance of the honey bee and hive (*Apis mellifera*)" Insect Soc. 58:431-44 (2011).

Audisio et al., "Effect of *Lactobacillus johnsonii* CRL1647 on different parameters of honeybee colonies and bacterial populations of the bee gut," Benef Microbes. 6(5):687-95 (2015).

Audisio, "Gram-positive bacteria with probiotic potential for the *Apis mellifera* L. honey bee: the experience in the northwest of Argentina," Probiotics & Antimicro Prot. 9(1):22-31 (2017).

Baffoni et al., "Effect of dietary supplementation of *Bifidobacterium* and *Lactobacillus* strains in *Apis mellifera* L. against *Nosema ceranae*," Beneficial Microbes. 7(1):45-51 (2016).

Broderick et al., "Gut-associated microbes of *Drosophila melanogaster*," Gut Microbes. 3(4): 307-321 (2012).

Camiletti et al. "*Drosophila* As a Genetically Tractable Model for Social Insect Behavior," Front Ecol Evol. 4:1-9 (2016).

Chan et al., "Changes in protein expression during honey bee larval development," Genome Biol. 9(10):R156 (2008) (14 pages).

Chmiel et al. "Deleterious Effects of Neonicotinoid Pesticides on *Drosophila melanogaster* Immune Pathways," mBio. 10(5): (2019) (14 pages).

Corby-Harris et al., "The bacterial communities associated with honey bee (*Apis mellifera*) foragers," PLoS One. 9(4):e95056 (2014) (13 pages).

Crotti et al., "Microbial symbionts of honeybees: a promising tool to improve honeybee health," N Biotechnol. 30(6):716-22 (2013).

Crotti et al., "Microbial symbionts: a resource for the management of insect-related problems," Microb Biotechnol. 5(3):307-17 (2012).

Daisley et al. "Neonicotinoid-induced pathogen susceptibility is mitigated by *Lactobacillus plantarum* immune stimulation in a *Drosophila melanogaster* model," Sci Rep. 7(1): 2703 (2017) (13 pages).

Dearden et al. "Patterns of conservation and change in honey bee developmental genes," Genome Res. 16(11):1376-1384 (2006).

Dike et al., "Production of L-methionine by Bacillus cereus isolated from different soil eocvars in Owerri, South East Nigeria," Euro J Exp Biol 2(2):311-314 (2012).

Dong et al. "Overproduction of Aromatic Amino Acids from Cyanobacteria," The Summer Undergraduate Research Fellowship (SURF) Symposium, Aug. 2, West Lafayette, IN. (Abstract only) (2018).

Donkersley et al., "Bacterial communities associated with honeybee food stores are correlated with land use," Ecology and Evolution. 8(10):4743-56 (2018).

Douglas, "The *Drosophila* model for microbiome research," available in PMC Jun. 20, 2019, published in final edited form as: Lab Anim (NY). 47(6):157-164 (2018) (19 pages).

El Khoury et al., "Deleterious interaction between honeybees (*Apis mellifera*) and its microsporidian intracellular parasite *Nosema ceranae* was mitigated by administrating either endogenous or allochthonous gut microbiota strains," Front Ecol Evol. 6:58 (2018) (15 pages).

Evans et al., "Bacterial probiotics induce an immune response in the honey bee (Hymenoptera: Apidae)," J Econ Entomol. 97(3):752-6 (2004) (6 pages).

Extended European Search Report for European Patent Application No. 18744047.4 dated Jun. 9, 2020 (7 pages).

(56) References Cited

OTHER PUBLICATIONS

Forsgren et al., "Novel lactic acid bacteria inhibiting *Paenibacillus larvae* in honey bee larvae," Apidologie. 41(1):99-108 (2010).
Galang et al. "Analysis of the *Drosophila melanogaster* anti-ovarian response to honey bee queen mandibular pheromone," Insect Mol Biol. 28(1): 99-111 (2019).
Hamdi et al., "Gut microbiome dysbiosis and honeybee health," Journal of Applied Entomology. 135(7):524-533 (2011) (11 pages).
Hassan et al., "Isolation and Screening of Amino Acids Producing Bacteria from Milk," Biotechnology 2(2):18-29 (2003).
Hütter et al. "Amino Acid Overproduction," Industrial Aspects of Biochemistry and Genetics. 87:49-59 (1985).
International Preliminary Report on Patentability for International Patent Application No. PCT/US2018/015051 dated Jul. 30, 2019 (8 pages).
International Preliminary Report on Patentability for PCT Application No. PCT/US2018/015025, dated Jul. 30, 2019 (7 pages).
International Search Report and Written Opinion for International Application No. PCT/US18/15051, dated May 30, 2018 (23 pages).
International Search Report and Written Opinion for International Application No. PCT/US2018/015025, dated Apr. 13, 2018 (13 pages).
International Search Report and Written Opinion for International Application No. PCT/US2018/015077, dated Apr. 23, 2018 (16 pages).
Kaznowski et al., "The effects of probiotic supplementation on the content of intestinal microflora and chemical composition of worker honey bees (*Apis mellifera*)," J Apic Res. 44(1):10-4 (2005) (6 pages).
Kikuchi et al., "Symbiont-mediated insecticide resistance," Proc Natl Acad Sci U.S.A. 109(22):8618-22 (2012).
Kim et al. "Physiological responses of insects to microbial fermentation products: insights from the interactions between *Drosophila* and acetic acid," available in PMC Apr. 1, 2019, published in final edited form as: J Insect Physiol. 106(Pt 1 ):13-19 (2018) (20 pages).
Liu et al., "Disruption of methionine metabolism in *Drosophila melanogaster* impacts histone methylation and results in loss of viability," G3 (Bethesda). 6(1):121-32 (2015).
McCaughey et al., "Amino Acids and Protein Adequacy for Honey Bees of Pollens from Desert Plants and Other Floral Sources," Apidologie 11(1): 75-86 (1980).
Mondal et al., "Methionine Production by Microorganisms," Folia Microbiol (Praha). 41(6):465-472 (1996).
Notice of Reasons for Rejection for Japanese Patent Application No. 2019-560061, dated Nov. 24, 2021 (7 pages).
O'Callaghan, Maureen, "Microbial inoculation of seed for improved crop performance: issues and opportunities," Appl Microbiol Biotechnol. 100(13):5729-46 (2016).
Odunfa et al., "Evaluation of lysine and methionine production in some Lactobacilli and yeasts from ogi," Int J Food Microbiol 631(1-2):159-63 (2001).
Office Action for Chinese Patent Application No. 201880007655.8, dated Mar. 24, 2021 (15 pages).
Office Action for Russian Patent Application No. 2019126299, dated Apr. 26, 2021 (14 pages).
Pătruică et al., "The effect of using prebiotic and probiotic products on intestinal micro-flora of the honeybee (*Apis mellifera carpatica*)," Bull Entomol Res. 102(6):619-23 (2012).
Ptaszynska et al., "Are commericial probiotics and prebiotics effective in the treatment and prevention of honeybee nosemosis C?," Parasitol Res. 115:397-406 (2016) (11 pages).
Rodriguez et al. "Engineering *Escherichia coli* to overproduce aromatic amino acids and derived compounds," Microb Cell Fact. 13(1):126 (2014) (15 pages).
Sahm et al. "Metabolic design in amino acid producing bacterium *Corynebacterium glutamicum*," FEMS Microbiology Reviews. 16(2-3): 243-52 (1995).
Sanchez et al. "Our microbes not only produce antibiotics, they also overproduce amino acids," J Antibiot. 71: 26-36 (2018).
Sannasi, "Inhibition of ovary development of the fruit-fly, *Drosophila melanogaster* by synthetic queen substance," Life Sci. 8(14): 785-789 (1969).
Santo Domingo et al., "Characterization of the Cricket Hindgut Microbiota with Fluorescently Labeled rRNA-Targeted Oligonucleotide Probes," Appl Environ Microbiol. 64(2):752-5 (1998).
Schneider, "Using *Drosophila* as a model insect," Nat Rev Genet. 1(3):218-26 (2000).
Schwarz et al., "Early gut colonizers shape parasite susceptibility and microbiota composition in honey bee workers," Proc Natl Acad Sci U S A. 113(33):9345-50 (2016).
Sgobba et al., "Production of Food and Feed Additives From Non-food-competing Feedstocks: Valorizing N-acetylmuramic Acid for Amino Acid and Carotenoid Fermentation With Corynebacterium glutamicum," Front Microbiol. 9:2046.doi:10.3389/fmicb.2018.02046 (2018) (11 pages).
Shapira, "Gut Microbiotas and Host Evolution: Scaling Up Symbiosis," Trends Ecol Evol. 31(7):539-549 (2016).
Sharma et al., "Metabolism of 1-naphthyl-N-methyl carbamate (carbaryl) by bacterial isolates from honey bees and the effect of bacterial inoculations on carbaryl tolerance in bees," J Appl Bacteriol. 81:235-41 (1996).
Shin et al. "*Drosophila* Microbiome Modulates Host Developmental and Metabolic Homeostasis via Insulin Signaling," Science. 334(6056): 670-674 (2011) (6 pages).
Singh et al., "Microbial Degradation of Organophosphorus Compounds," FEMS Microbiol Rev. 30(3):428-71 (2006).
Sokolowski, "Social Interactions in "Simple" Model Systems," Neuron. 65(6): 780-94 (2010).
Storelli et al., "Lactobacillus plantarum Promotes *Drosophila* Systemic Growth by Modulating Hormonal Signals Through TOR-Dependent Nutrient Sensing," Cell Metab. 14(3): 403-414 (2011).
Tower, "Lactobacillus plantarum Gives *Drosophila* the Grow Signal," Cell Metab. 14(3): 283-284 (2011).
Trinder et al., "*Drosophila melanogaster* as a High-Throughput Model for Host-Microbiota Interactions," Front Microbiol. 8:751 (2017) (8 pages).
Trinder et al., "Probiotic Lactobacillus rhamnosus Reduces Organophosphate Pesticide Absorption and Toxicity to *Drosophila melanogaster*," Appl Environ Microbiol. 82(20):6204-13 (2016).
Trö tschel et al., "Characterization of methionine export in Corynebacterium glutamicum," J Bacteriol. 187(11):3786-94 (2005).
Volkova et al., "Effect of the folic acid and methionine on *Drosophila melanogaster*," Bulletin of Kharkiv National University for the Name of VN Karazin. Series: Biology. 17:69-83 (2013) (21 pages).
Written Opinion for Singaporean Patent Application No. 11201904929P, dated Oct. 11, 2021 (7 pages).
Zheng et al., "Honeybee Gut Microbiota Promotes Host Weight Gain via Bacterial Metabolism and Hormonal Signaling," Proc Natl Acad Sci USA. 114(18):4775-4780 (2017).
Broadway R. M. et al., Plant proteinase inhibitors: mechanism of action and effect on the growth and digestive physiology of larval Heliothis *Zea* and Spodoptera exiqua, Journal of Insect Physiology, 1986, vol. 32, N10, pp. 827-833.

\* cited by examiner

SEQUENCE LISTING

```
<160> NUMBER OF SEQ ID NOS: 228

<210> SEQ ID NO 1
<211> LENGTH: 1526
<212> TYPE: DNA
<213> ORGANISM: Carsonella ruddii

<400> SEQUENCE: 1
tatccagcca caggttcccc tacagctacc ttgttacgac ttcacccag ttacaaatca       60 taccgttgta atagtaaaat tacttatgat acaatttact tccatggtgt gacgggcggt      120
gtgtacaagg ctcgagaacg tattcaccgt aacattctga tttacgatta ctagcgattc      180
caacttcatg aaatcgagtt acagatttca atccgaacta agaatatttt ttaagattag      240
cattatgttg ccatatagca tataacttt tgtaatactc attgtagcac gtgtgtagcc      300
ctacttataa gggccatgat gacttgacgt cgtcctcacc ttcctccaat ttatcattgg      360
cagtttctta ttagttctaa tatattttta gtaaaataag ataagggttg cgctcgttat      420
aggacttaac ccaacatttc acaacacgag ctgacgacag ccatgcagca cctgtctcaa      480
agctaaaaaa gctttattat ttctaataaa ttctttggat gtcaaaagta ggtaagattt      540
ttcgtgttgt atcgaattaa accacatgct ccaccgcttg tgcgagcccc cgtcaattca      600
tttgagtttt aaccttgcgg tcgtaatccc caggcggtca acttaacgcg ttagcttttt      660
cactaaaaat atataacttt tttcataaa acaaaattac aattataata tttaataaat      720
agttgacatc gtttactgca tggactacca gggtatctaa tcctgtttgc tccccatgct      780
ttcgtgtatt agtgtcagta ttaaaataga aatacgcctt cgccactagt attctttcag      840
atatctaagc atttcactgc tactcctgaa attctaattt cttctttat actcaagttt      900 ataagtatta atttcaatat taaattactt taataaattt aaaaattaat tttaaaaac      960 aacctgcaca ccctttacgc ccaataattc cgattaacgc ttgcacccct cgtattaccg      1020
cggctgctgg cacgaagtta gccggtgctt cttttacaaa taacgtcaaa gataatattt      1080
ttttattata aaatctcttc ttactttgtt gaaagtgttt tacaaccta aggccttctt      1140 cacacacgcg atatagctgg atcaagcttt cgctcattgt ccaatatccc ccactgctgc      1200
cttccgtaaa agtttgggcc gtgtctcagt cccaatgtgg ttgttcatcc tctaagatca      1260
actacgaatc atagtcttgt taagctttta ctttaacaac taactaattc gatataagct      1320
cttctattag cgaacgacat tctcgttctt tatccattag gatacatatt gaattactat      1380
acatttctat atacttttct aatactaata ggtagattct tatatattac tcacccgttc      1440
gctgctaatt atttttttaa taattcgcac aacttgcatg tgttaagctt atcgctagcg      1500
ttcaatctga gctatgatca aactca                                          1526
```

<210> SEQ ID NO 2
<211> LENGTH: 1536
<212> TYPE: DNA
<213> ORGANISM: aleyrodidarum BT-B

<400> SEQUENCE: 2

```
aagagtttga tcatggctca gattgaacgc tagcggcaga cataacacat gcaagtcgag      60
cggcatcata caggttggca agcggcgcac gggtgagtaa tacatgtaaa tatacctaaa     120
agtggggaat aacgtacgga aacgtacgct aataccgcat aattattacg agataaagca     180
ggggcttgat aaaaaaaatc aaccttgcgc ttttagaaaa ttacatgccg gattagctag     240
ttggtagagt aaaagcctac caaggtaacg atccgtagct ggtctgagag gatgatcagc     300
cacactggga ctgagaaaag gcccagactc ctacgggagg cagcagtggg gaatattgga     360
caatgggggg aaccctgatc cagtcatgcc gcgtgtgtga agaaggcctt tgggttgtaa     420
agcactttca gcgaagaaga aaagttagaa aataaaaagt tataactatg acggtactcg     480
cagaagaagc accggctaac tccgtgccag cagccgcggt aagacggagg gtgcaagcgt     540
taatcagaat tactgggcgt aaagggcatg taggtggttt gttaagcttt atgtgaaagc     600
cctatgctta acataggaac ggaataaaga actgacaaac tagagtgcag aagaggaagg     660
tagaattccc ggtgtagcgg tgaaatgcgt agatatctgg aggaatacca gttgcgaagg     720
cgaccttctg ggctgacact gacactgaga tgcgaaagcg tggggagcaa acaggattag     780
ataccctggt agtccacgct gtaaacgata tcaactagcc gttggattct aaagaatttt     840
tgtggcgtag ctaacgcgat aagttgatcg cctgggagt acggtcgcaa ggctaaaact     900
caaatgaatt gacgggggcc cgcacaagcg gtggagcatg tggtttaatt cgatgcaacg     960
cgcaaaacct tacctactct tgacatccaa agtactttcc agagatggaa gggtgcctta    1020
gggaactttg agacaggtgc tgcatggctg tcgtcagctc gtgttgtgaa atgttgggtt    1080
aagtcccgta acgagcgcaa cccttgtcct tagttgccaa cgcataaggc gggaacttta    1140
aggagactgc tggtgataaa ccggaggaag gtggggacga cgtcaagtca tcatggccct    1200
taagagtagg gcaacacacg tgctacaatg gcaaaaacaa agggtcgcaa aatggtaaca    1260
tgaagctaat cccaaaaaaa ttgtcttagt tcggattgga gtctgaaact cgactccata    1320
aagtcggaat cgctagtaat cgtgaatcag aatgtcacgg tgaatacgtt ctcgggcctt    1380
gtacacaccg cccgtcacac catggaagtg aaatgcacca gaagtggcaa gtttaaccaa    1440
aaaacaggag aacagtcact acggtgtggt tcatgactgg ggtgaagtcg taacaaggta    1500
gctgtagggg aacctgtggc tggatcacct ccttaa                              1536
```

<210> SEQ ID NO 3
<211> LENGTH: 1540
<212> TYPE: DNA
<213> ORGANISM: Buchnera aphidicola str. APS (Acyrthosiphon pisum)

<400> SEQUENCE: 3

```
agagtttgat catggctcag attgaacgct ggcggcaagc ctaacacatg caagtcgagc      60
ggcagcgaga agagagcttg ctctctttgt cggcaagcgg caaacgggtg agtaatatct     120
ggggatctac ccaaaagagg gggataacta ctagaaatgg tagctaatac cgcataatgt     180
tgaaaaacca agtggggga ccttttggcc tcatgctttt ggatgaaccc agacgagatt     240
agcttgttgg tagagtaata gcctaccaag gcaacgatct ctagctggtc tgagaggata     300
accagccaca ctggaactga gacacggtcc agactcctac gggaggcagc agtggggaat     360
```

```
attgcacaat gggcgaaagc ctgatgcagc tatgccgcgt gtatgaagaa ggccttaggg      420
ttgtaaagta ctttcagcgg ggaggaaaaa aataaaacta ataattttat ttcgtgacgt      480
tacccgcaga agaagcaccg gctaactccg tgccagcagc cgcggtaata cggagggtgc      540
aagcgttaat cagaattact gggcgtaaag agcgcgtagg tggttttta agtcaggtgt       600
gaaatcccta ggctcaacct aggaactgca tttgaaactg gaaaactaga gtttcgtaga     660
gggaggtaga attctaggtg tagcggtgaa atgcgtagat atctggagga atacccgtgg      720
cgaaagcggc ctcctaaacg aaaactgaca ctgaggcgcg aaagcgtggg gagcaaacag      780
gattagatac cctggtagtc catgccgtaa acgatgtcga cttggaggtt gtttccaaga      840
gaagtgactt ccgaagctaa cgcattaagt cgaccgcctg gggagtacgg ccgcaaggct      900
aaaactcaaa tgaattgacg ggggcccgca caagcggtgg agcatgtggt ttaattcgat      960
gcaacgcgaa aaaccttacc tggtcttgac atccacagaa ttctttagaa ataaagaagt     1020
gccttcggga gctgtgagac aggtgctgca tggctgtcgt cagctcgtgt tgtgaaatgt     1080
tgggttaagt cccgcaacga gcgcaaccct tatcccctgt tgccagcggt tcggccggga     1140
actcagagga gactgccggt tataaaccgg aggaaggtgg ggacgacgtc aagtcatcat     1200
ggcccttacg accagggcta cacacgtgct acaatggttt atacaaagag aagcaaatct     1260
gcaaagacaa gcaaacctca taaagtaaat cgtagtccgg actggagtct gcaactcgac     1320
tccacgaagt cggaatcgct agtaatcgtg atcagaatg ccacggtgaa tacgttcccg      1380
ggccttgtac acaccgcccg tcacaccatg ggagtgggtt gcaaaagaag caggtatcct     1440
aacccttta aaggaaggcg cttaccactt tgtgattcat gactgggtg aagtcgtaac       1500
aaggtaaccg tagggaacc tgcggttgga tcacctcctt                             1540
```

<210> SEQ ID NO 4
<211> LENGTH: 1552
<212> TYPE: DNA
<213> ORGANISM: Buchnera aphidicola str. Sg (Schizaphis graminum)

<400> SEQUENCE: 4

```
aaactgaaga gtttgatcat ggctcagatt gaacgctggc ggcaagccta acacatgcaa      60
gtcgagcggc agcgaaaaga aagcttgctt tcttgtcggc gagcggcaaa cgggtgagta     120
atatctgggg atctgcccaa aagaggggga taactactag aaatggtagc taataccgca     180
taaagttgaa aaaccaaagt gggggacctt ttttaaaggc ctcatgcttt tggatgaacc     240
cagacgagat tagcttgttg gtaaggtaaa agcttaccaa gcaacgatc tctagctggt      300
ctgagaggat aaccagccac actggaactg agacacggtc cagactccta cgggaggcag    360
cagtgggga tattgcacaa tgggcgaaag cctgatgcag ctatgccgcg tgtatgaaga     420
aggccttagg gttgtaaagt actttcagcg gggaggaaaa aattaaaact aataatttta     480
ttttgtgacg ttacccgcag aagaagcacc ggctaactcc gtgccagcag ccgcggtaat    540
acggagggtg cgagcgttaa tcagaattac tgggcgtaaa gagcacgtag gtggtttttt     600
aagtcagatg tgaaatccct aggcttaacc taggaactgc atttgaaact gaaatgctag   660
agtatcgtag agggaggtag aattctaggt gtagcggtga atgcgtaga tatctggagg     720
aatacccgtg gcgaaagcgg cctcctaaac gaatactgac actgaggtgc gaaagcgtgg     780
ggagcaaaca ggattagata ccctggtagt ccatgccgta acgatgtcg acttggaggt      840
tgtttccaag agaagtgact tccgaagcta acgcgttaag tcgaccgcct ggggagtacg      900
gccgcaaggc taaaactcaa atgaattgac ggggccccgc acaagcggtg gagcatgtgg      960
```

```
tttaattcga tgcaacgcga aaaaccttac ctggtcttga catccacaga attttttaga     1020
aataaaaaag tgccttcggg aactgtgaga caggtgctgc atggctgtcg tcagctcgtg     1080
ttgtgaaatg ttgggttaag tcccgcaacg agcgcaaccc ttatcccctg ttgccagcgg     1140
ttcggccggg aactcagagg agactgccgg ttataaaccg gaggaaggtg gggacgacgt     1200
caagtcatca tggcccttac gaccagggct acacacgtgc tacaatggtt tatacaaaga     1260
gaagcaaatc tgtaaagaca agcaaacctc ataaagtaaa tcgtagtccg gactggagtc     1320
tgcaactcga ctccacgaag tcggaatcgc tagtaatcgt ggatcagaat gccacggtga     1380
atacgttccc gggccttgta cacaccgccc gtcacaccat gggagtgggt tgcaaaagaa     1440
gcagatttcc taaccacgaa agtggaaggc gtctaccact tgtgattca tgactggggt     1500 gaagtcgtaa caaggtaacc gtaggggaac ctgcggttgg atcacctcct ta             1552

<210> SEQ ID NO 5
<211> LENGTH: 1566
<212> TYPE: DNA
<213> ORGANISM: Buchnera aphidicola str. Bp (Baizongia pistaciae)

<400> SEQUENCE: 5
acttaaaatt gaagagtttg atcatggctc agattgaacg ctggcggcaa gcttaacaca     60
tgcaagtcga gcggcatcga agaaaagttt acttttctgg cggcgagcgg caaacgggtg     120
agtaacatct ggggatctac ctaaaagagg gggacaacca ttggaaacga tggctaatac     180
cgcataatgt tttaaataa accaaagtag gggactaaaa tttttagcct tatgcttta     240 gatgaaccca gacgagatta gcttgatggt aaggtaatgg cttaccaagg cgacgatctc     300
tagctggtct gagaggataa ccagccacac tggaactgag atacggtcca gactcctacg     360
ggaggcagca gtgggaata ttgcacaatg gctaaagcc tgatgcagct atgccgcgtg     420
tatgaagaag gccttagggt tgtaaagtac tttcagcggg gaggaaagaa ttatgtctaa     480
tatacatatt ttgtgacgtt acccgaagaa gaagcaccgg ctaactccgt gccagcagcc     540
gcggtaatac ggagggtgcg agcgttaatc agaattactg ggcgtaaaga gcacgtaggc     600
ggtttattaa gtcagatgtg aaatccctag gcttaactta ggaactgcat ttgaaactaa     660
tagactagag tctcatagag ggaggtagaa ttctaggtgt agcggtgaaa tgcgtagata     720
tctagaggaa tacccgtggc gaaagcgacc tcctaaatga aaactgacgc tgaggtgcga     780
aagcgtgggg agcaaacagg attagatacc ctggtagtcc atgctgtaaa cgatgtcgac     840
ttggaggttg tttcctagag aagtggcttc cgaagctaac gcattaagtc gaccgcctgg     900
ggagtacggt cgcaaggcta aaactcaaat gaattgacgg gggcccgcac aagcggtgga     960
gcatgtggtt taattcgatg caacgcgaag aaccttacct ggtcttgaca tccatagaat     1020
tttttagaga taaaagagtg ccttagggaa ctatgagaca ggtgctgcat ggctgtcgtc     1080
agctcgtgtt gtgaaatgtt gggttaagtc ccgcaacgag cgcaacccct atcctttgtt     1140
gccatcaggt tatgctggga actcagagga gactgccggt tataaaccgg aggaaggtgg     1200
ggatgacgtc aagtcatcat ggcccttacg accagggcta cacacgtgct acaatggcat     1260
atacaaagag atgcaactct gcgaagataa gcaaacctca taagtatgt cgtagtccgg     1320 actggagtct gcaactcgac tccacgaagt aggaatcgct agtaatcgtg gatcagaatg     1380
ccacggtgaa tacgttcccg ggccttgtac acaccgcccg tcacaccatg ggagtgggtt     1440
gcaaaagaag caggtagctt aaccagatta ttttattgga gggcgcttac cactttgtga     1500
```

```
ttcatgactg gggtgaagtc gtaacaaggt aaccgtaggg gaacctgcgg ttggatcacc    1560
tcctta                                                              1566
```

<210> SEQ ID NO 6
<211> LENGTH: 828
<212> TYPE: DNA
<213> ORGANISM: Buchnera aphidicola BCc

<400> SEQUENCE: 6

```
atgagatcat taatatataa aaatcatgtt ccaattaaaa aattaggaca aattttttta     60
cagaataaag aaattattaa tcagataatt aatttaataa atattaataa aaatgataat    120
attattgaaa taggatcagg attaggagcg ttaacttttc ctatttgtag aatcattaaa    180
aaaatgatag tattagaaat tgatgaagat cttgtgtttt ttttaactca aagtttattt    240
attaaaaaat tacaaattat aattgctgat attataaaat ttgattttg ttgttttttt    300 tctttacaga aatataaaaa ataggtttt attggtaatt taccatataa tattgctact    360
atattttttt taaaaacaat taaatttctt tataatataa ttgatatgca ttttatgttt    420 caaaagaag tagcaaagag attattagct actcctggta ctaaagaata tggtagatta    480
agtattattg cacaatattt ttataagata gaaactgtta ttaatgttaa taaatttaat    540 tttttttccta ctcctaaagt agattctact tttttacgat ttactcctaa atatttttaat    600 agtaaatata aaatagataa acatttttct gtttttagaat taattactag attttcttt     660 caacatagaa gaaattttt aaataataat ttaatatctt tattttctac aaaagaatta    720
atttctttag atattgatcc atattcaaga gcagaaatg tttctttaat tcaatattgt    780
aaattaatga atattatttt gaaagaaaa atttttatgtt tagattaa                828
```

<210> SEQ ID NO 7
<211> LENGTH: 921
<212> TYPE: DNA
<213> ORGANISM: Buchnera aphidicola (Cinara tujafilina)

<400> SEQUENCE: 7

```
ttatcttatt tcacatatac gtaatattgc gctgcgtgca cgaggatttt tttgaatttc     60
agatatattt ggtttaatac gttaataaaa acgtattttt ttttttattt ttcttatttg    120
caattcagta ataggaagtt ttttaggtat atttggataa ttactgtaat tcttaataaa    180 gtttttttaca atcctatctt caatagaatg aaaactaata atagcaattt ttgatccgga    240
atgtaatatg ttaataataa tttttaatat tttatgtaat tcatttatttt cttggttaat    300 atatattcga aaagcttgaa atgttctcgt agctggatgt ttaaatttgt catatttttgg    360 gattgatttt tttatgattt gaactaactc taacgtgctt gttatggttt tttttttat    420 ttgtaatatg atggctcggg atatttttttt tgcgtattt tcttcgccaa aatttttttat    480 tacctgttct attgttttttt ggtttgttt ttttaaccat tgactaactg atattccaga    540
tttagggttc atacgcatat ctaaaggtcc atcattcata aatgaaaatc ctcggatact    600
agaatttaac tgtattgaag aaatacctaa atctaataat attccatcta ttttatctct    660
atttttttct tttttttaata ttttttcaat attagaaaat ttacctaaaa atattttaaa    720
tcgcgaatct tttattttttt ttccgatttt tatagattgt gggtcttgat caatactata    780
taactttcca ttaacccta attcttgaag aattgctttt gaatgaccac cacctccaaa    840
tgtacaatca acatatgtac cgtcttttttt tattttttaag tattgtatga tttcttttgt    900
taaaacaggt ttatgaatca t                                             921
```

<210> SEQ ID NO 8
<211> LENGTH: 822
<212> TYPE: DNA
<213> ORGANISM: Buchnera aphidicola str. G002 (Myzus persicae)

<400> SEQUENCE: 8

| | | | | | | |
|---|---|---|---|---|---|---|
| atgaaaagta | taaaaacttt | taaaaaacac | tttcctgtga | aaaaatatgg | acaaaatttt | 60 |
| cttattaata | aagagatcat | aaaaaatatt | gttaaaaaaa | ttaatccaaa | tatagaacaa | 120 |
| acattagtag | aaatcggacc | aggattagct | gcattaactg | agcccatatc | tcagttatta | 180 |
| aaagagttaa | tagttattga | aatagactgt | aatctattat | attttttaaa | aaacaacca | 240 |
| ttttattcaa | aattaatagt | tttttgtcaa | gatgctttaa | actttaatta | tacaaattta | 300 |
| ttttataaaa | aaaataaatt | aattcgtatt | tttggtaatt | taccatataa | tatctctaca | 360 |
| tctttaatta | ttttttttatt | tcaacacatt | agagtaattc | aagatatgaa | ttttatgctt | 420 |
| caaaaagaag | ttgctgcaag | attaattgca | ttacctggaa | ataaatatta | cggtcgtttg | 480 |
| agcattatat | ctcaatatta | ttgtgatatc | aaaattttat | taaatgttgc | tcctgaagat | 540 |
| ttttggccta | ttccgagagt | tcattctata | tttgtaaatt | taacacctca | tcataattct | 600 |
| ccttattttg | tttatgatat | taatatttta | agccttatta | caaataaggc | tttccaaaat | 660 |
| agaagaaaaa | tattacgtca | tagtttaaaa | aattatttt | ctgaaacaac | tttattaaat | 720 |
| ttagatatta | atcccagatt | aagagctgaa | atatttctg | tttttcagta | ttgtcaatta | 780 |
| gctaattatt | tgtataaaaa | aaattatact | aaaaaaaatt | aa | | 822 |

<210> SEQ ID NO 9
<211> LENGTH: 822
<212> TYPE: DNA
<213> ORGANISM: Buchnera aphidicola str. Ak (Acyrthosiphon kondoi)

<400> SEQUENCE: 9

| | | | | | | |
|---|---|---|---|---|---|---|
| attataaaaa | attttaaaaa | acattttcct | ttaaaaaggt | atggacaaaa | ttttcttgtc | 60 |
| aatacaaaaa | ctattcaaaa | gataattaat | ataattaatc | caaacaccaa | acaaacatta | 120 |
| gtggaaattg | gacctggatt | agctgcatta | acaaaaccaa | tttgtcaatt | attagaagaa | 180 |
| ttaattgtta | ttgaaataga | tcctaattta | ttgttttttat | taaaaaaacg | ttcattttat | 240 |
| tcaaaattaa | cagttttta | tcaagacgct | ttaaatttca | attatacaga | tttgttttat | 300 |
| aagaaaaatc | aattaattcg | tgttttggga | aacttgccat | ataatatttc | tacatcttta | 360 |
| attatttctt | tattcaatca | tattaaagtt | attcaagata | tgaattttat | gttacagaaa | 420 |
| gaggttgctg | aaagattaat | ttctattcct | ggaaataaat | cttatggccg | tttaagcatt | 480 |
| atttctcagt | attattgtaa | aattaaaata | ttattaaatg | ttgtacctga | agattttcga | 540 |
| cctataccga | aagtgcattc | tgttttatc | aatttaactc | ctcataccaa | ttctccatat | 600 |
| tttgttatg | atacaaatat | cctcagttct | atcacaagaa | atgcttttca | aaatagaagg | 660 |
| aaaattttgc | gtcatagttt | aaaaaaattta | ttttctgaaa | aagaactaat | tcaattagaa | 720 |
| attaatccaa | atttacgagc | tgaaatatatt | tctatctttc | agtattgtca | attagctgat | 780 |
| tatttatata | aaaaattaaa | taatcttgta | aaaatcaatt | aa | | 822 |

<210> SEQ ID NO 10
<211> LENGTH: 822
<212> TYPE: DNA
<213> ORGANISM: Buchnera aphidicola str. Ua (Uroleucon ambrosiae)

```
<400> SEQUENCE: 10
atgatactaa ataaatataa aaaatttatt cctttaaaaa gatacggaca aaattttctt      60
gtaaatagag aaataatcaa aaatattatc aaaataatta atcctaaaaa aacgcaaaca     120
ttattagaaa ttggaccggg tttaggtgcg ttaacaaaac ctatttgtga atttttaaat     180
gaacttatcg tcattgaaat agatcctaat atattatctt tttaaagaa atgtatattt     240 tttgataaat taaaaatata ttgtcataat gctttagatt ttaattataa aaatatattc     300
tataaaaaaa gtcaattaat tcgtattttt ggaaatttac catataatat ttctacatct     360
ttaataatat atttatttcg gaatattgat attattcaag atgaatttt tatgttacaa      420 caagaagtgg ctaaaagatt agttgctatt cctggtgaaa aactttatgg tcgtttaagt     480
attatatctc aatattattg taatattaaa atattattac atattcgacc tgaaaatttt     540
caacctattc ctaaagttaa ttcaatgttt gtaaatttaa ctccgcatat tcattctcct     600
tattttgttt atgatattaa tttattaact agtattacaa aacatgcttt tcaacataga     660
agaaaaatat tgcgtcatag tttaagaaat ttttttctg agcaagattt aattcattta     720
gaaattaatc caaatttaag agctgaaaat gtttctatta ttcaatattg tcaattggct     780
aataatttat ataaaaaaca taaacagttt attaataatt aa                       822

<210> SEQ ID NO 11
<211> LENGTH: 816
<212> TYPE: DNA
<213> ORGANISM: Buchnera aphidicola (Aphis glycines)

<400> SEQUENCE: 11
atgaaaaagc atattcctat aaaaaaattt agtcaaaatt ttcttgtaga tttgagtgtg      60
attaaaaaaa taattaaatt tattaatccg cagttaaatg aaatattggt tgaaattgga     120
ccgggattag ctgctatcac tcgacctatt tgtgatttga tagatcattt aattgtgatt     180
gaaattgata aaattttatt agatagatta aaacagttct cattttattc aaaattaaca     240
gtatatcatc aagatgcttt agcatttgat tacataaagt tatttaataa aaaaaataaa     300
ttagttcgaa tttttggtaa tttaccatat catgttccta cgtctttaat attgcattta     360
tttaaaagaa ttaatattat taaagatatg aattttatgc tacaaaaaga agttgctgaa     420
cgtttaattg caactccagg tagtaaaatta tatggtcgtt taagtattat ttctcaatat     480
tattgtaata taaaagtttt attgcatgtg tcttcaaaat gttttaaacc agttcctaaa     540
gtagaatcaa ttttttcttaa tttgacacct tatactgatt atttccctta ttttacttat     600
aatgtaaacg ttcttagtta tattacaaat ttagcttttc aaaaaagaag aaaaatatta     660
cgtcatagtt taggtaaaat attttctgaa aaagttttta taaaattaaa tattaatccc     720
aaattaagac ctgagaatat ttctatatta caatattgtc agttatctaa ttatatgata     780
gaaaataata ttcatcagga acatgtttgt atttaa                              816

<210> SEQ ID NO 12
<211> LENGTH: 1463
<212> TYPE: DNA
<213> ORGANISM: Annandia pinicola

<400> SEQUENCE: 12
agattgaacg ctggcggcat gccttacaca tgcaagtcga acggtaacag gtcttcggac      60
gctgacgagt ggcgaacggg tgagtaatac atcggaacgt gcccagtcgt ggggataac     120 tactcgaaag agtagctaat accgcatacg atctgaggat gaaagcgggg gaccttcggg     180
```

```
cctcgcgcga ttggagcggc cgatggcaga ttaggtagtt ggtgggataa aagcttacca    240
agccgacgat ctgtagctgg tctgagagga cgaccagcca cactggaact gagatacggt    300
ccagactctt acgggaggca gcagtgggga atattgcaca atgggcgcaa gcctgatgca    360
gctatgtcgc gtgtatgaag aagaccttag ggttgtaaag tactttcgat agcataagaa    420
gataatgaga ctaataattt tattgtctga cgttagctat agaagaagca ccggctaact    480
ccgtgccagc agccgcggta atacgggggg tgctagcgtt aatcggaatt actgggcgta    540
aagagcatgt aggtggttta ttaagtcaga tgtgaaatcc ctggacttaa tctaggaact    600
gcatttgaaa ctaataggct agagtttcgt agagggaggt agaattctag gtgtagcggt    660
gaaatgcata gatatctaga ggaatatcag tggcgaaggc gaccttctgg acgataactg    720
acgctaaaat gcgaaagcat gggtagcaaa caggattaga taccctggta gtccatgctg    780
taaacgatgt cgactaagag gttggaggta aacttttaa tctctgtagc taacgcgtta    840
agtcgaccgc ctgggagta cggtcgcaag gctaaaactc aaatgaattg acgggggcct    900
gcacaagcgg tggagcatgt ggtttaattc gatgcaacgc gtaaaacctt acctggtctt    960
gacatccaca gaattttaca gaaatgtaga agtgcaattt gaactgtgag acaggtgctg   1020
catggctgtc gtcagctcgt gttgtgaaat gttgggttaa gtcccgcaac gagcgcaacc   1080
cttgtccttt gttaccataa gatttaagga actcaaagga gactgccggt gataaactgg   1140
aggaaggcgg ggacgacgtc aagtcatcat ggcccttatg accagggcta cacacgtgct   1200
acaatggcat atacaaagag atgcaatatt gcgaaataaa gccaatctta taaaatatgt   1260
cctagttcgg actggagtct gcaactcgac tccacgaagt cggaatcgct agtaatcgtg   1320
gatcagcatg ccacggtgaa tatgttttcca ggccttgtac acaccgcccg tcacaccatg   1380
gaagtggatt gcaaaagaag taagaaaatt aaccttctta caaggaaat aacttaccac   1440 tttgtgactc ataactgggg tga                                            1463

<210> SEQ ID NO 13
<211> LENGTH: 1554
<212> TYPE: DNA
<213> ORGANISM: Moranella endobia

<400> SEQUENCE: 13
tctttttggt aaggaggtga tccaaccgca ggttcccta cggttacctt gttacgactt     60
caccccagtc atgaatcaca aagtggtaag cgccctccta aaaggttagg ctacctactt    120
cttttgcaac ccacttccat ggtgtgacgg gcggtgtgta caaggcccgg gaacgtattc    180
accgtggcat tctgatccac gattactagc gattcctact tcatggagtc gagttgcaga    240
ctccaatccg gactacgacg cactttatga ggtccgctaa ctctcgcgag cttgcttctc    300
tttgtatgcg ccattgtagc acgtgtgtag ccctactcgt aagggccatg atgacttgac    360
gtcatcccca ccttcctccg gtttatcacc ggcagtctcc tttgagttcc gaccgaatc    420 gctggcaaaa aaggataagg gttgcgctcg ttgcgggact aacccaaca tttcacaaca    480 cgagctgacg acagccatgc agcacctgtc tcagagttcc cgaaggtacc aaaacatctc    540
tgctaagttc tctggatgtc aagagtaggt aaggttcttc gcgttgcatc gaattaaacc    600
acatgctcca ccgcttgtgc gggccccgt caattcattt gagttttaac cttgcggccg    660
tactccccag gcggtcgatt taacgcgtta actacgaaag ccacagttca agaccacagc    720
tttcaaatcg acatagttta cggcgtggac taccagggta tctaatcctg tttgctcccc    780
```

| | | |
|---|---|---|
| acgctttcgt acctgagcgt cagtattcgt ccagggggcc gccttcgcca ctggtattcc | 840 |
| tccagatatc tacacatttc accgctacac ctggaattct accccctct acgagactct | 900 |
| agcctatcag tttcaaatgc agttcctagg ttaagcccag ggatttcaca tctgacttaa | 960 |
| taaaccgcct acgtactctt tacgcccagt aattccgatt aacgcttgca ccctccgtat | 1020 |
| taccgcggct gctggcacgg agttagccgg tgcttcttct gtaggtaacg tcaatcaata | 1080 |
| accgtattaa ggatattgcc ttcctcccta ctgaaagtgc tttacaaccc gaaggccttc | 1140 |
| ttcacacacg cggcatggct gcatcagggt ttcccccatt gtgcaatatt ccccactgct | 1200 |
| gcctcccgta ggagtctgga ccgtgtctca gttccagtgt ggctggtcat cctctcagac | 1260 |
| cagctaggga tcgtcgccta ggtaagctat tacctcacct actagctaat cccatctggg | 1320 |
| ttcatctgaa ggtgtgaggc caaaaggtcc cccactttgg tcttacgaca ttatgcggta | 1380 |
| ttagctaccg tttccagcag ttatcccct ccatcaggca gatccccaga ctttactcac | 1440 |
| ccgttcgctg ctcgccggca aaaagtaaa cttttttccg ttgccgctca acttgcatgt | 1500 |
| gttaggcctg ccgccagcgt tcaatctgag ccatgatcaa actcttcaat taaa | 1554 |

<210> SEQ ID NO 14
<211> LENGTH: 1539
<212> TYPE: DNA
<213> ORGANISM: Ishikawaella capsulata Mpkobe

<400> SEQUENCE: 14

| | | |
|---|---|---|
| aaattgaaga gtttgatcat ggctcagatt gaacgctagc ggcaagctta acacatgcaa | 60 |
| gtcgaacggt aacagaaaaa agcttgcttt tttgctgacg agtggcggac gggtgagtaa | 120 |
| tgtctgggga tctacctaat ggcggggat aactactgga aacggtagct aataccgcat | 180 |
| aatgttgtaa aaccaaagtg ggggacctta tggcctcaca ccattagatg aacctagatg | 240 |
| ggattagctt gtaggtgggg taaaggctca cctaggcaac gatccctagc tggtctgaga | 300 |
| ggatgaccag ccacactgga actgagatac ggtccagact cctacgggag gcagcagtgg | 360 |
| ggaatcttgc acaatgggcg caagcctgat gcagctatgt cgcgtgtatg aagaaggcct | 420 |
| tagggttgta aagtactttc atcggggaag aaggatatga gcctaatatt ctcatatatt | 480 |
| gacgttacct gcagaagaag caccggctaa ctccgtgcca gcagccgcgg taacacggag | 540 |
| ggtgcgagcg ttaatcggaa ttactgggcg taaagagcac gtaggtggtt tattaagtca | 600 |
| tatgtgaaat ccctgggctt aacctaggaa ctgcatgtga aactgataaa ctagagtttc | 660 |
| gtagagggag gtggaattcc aggtgtagcg gtgaaatgcg tagatatctg gaggaatatc | 720 |
| agaggcgaag gcgaccttct ggacgaaaac tgacactcag gtgcgaaagc gtggggagca | 780 |
| aacaggatta gataccctgg tagtccacgc tgtaaacaat gtcgactaaa aaactgtgag | 840 |
| cttgacttgt ggttttgta gctaacgcat aagtcgacc gcctggggag tacggccgca | 900 |
| aggttaaaac tcaaatgaat tgacggggt ccgcacaagc ggtggagcat gtggtttaat | 960 |
| tcgatgcaac gcgaaaaacc ttacctggtc ttgacatcca gcgaattata tagaaatata | 1020 |
| taagtgcctt tcggggaact ctgagacgct gcatggctgt cgtcagctcg tgttgtgaaa | 1080 |
| tgttgggtta agtcccgcaa cgagcgccct tatcctctgt tgccagcggc atggccggga | 1140 |
| actcagagga gactgccagt attaaactgg aggaaggtgg ggatgacgtc aagtcatcat | 1200 |
| ggcccttatg accagggcta cacacgtgct acaatggtgt atacaaagag aagcaatctc | 1260 |
| gcaagagtaa gcaaaactca aaagtacat cgtagtccgg attagagtct gcaactcgac | 1320 |
| tctatgaagt aggaatcgct agtaatcgtg gatcagaatg ccacggtgaa tacgttctct | 1380 |

```
ggccttgtac acaccgcccg tcacaccatg ggagtaagtt gcaaagaag taggtagctt    1440 aacctttata ggagggcgct taccactttg tgatttatga ctggggtgaa gtcgtaacaa   1500
ggtaactgta ggggaacctg tggttggatt acctcctta                          1539
```

<210> SEQ ID NO 15
<211> LENGTH: 1561
<212> TYPE: DNA
<213> ORGANISM: Baumannia cicadellinicola

<400> SEQUENCE: 15

```
ttcaattgaa gagtttgatc atggctcaga ttgaacgctg gcggtaagct taacacatgc     60
aagtcgagcg gcatcggaaa gtaaattaat tactttgccg gcaagcggcg aacgggtgag    120
taatatctgg ggatctacct tatggagagg gataactatt ggaaacgata gctaacaccg    180
cataatgtcg tcagaccaaa atgggggacc taatttaggc ctcatgccat aagatgaacc    240
cagatgagat tagctagtag gtgagataat agctcaccta gcaacgatc tctagttggt     300 ctgagaggat gaccagccac actggaactg agacacggtc cagactccta cgggaggcag    360
cagtggggaa tcttgcacaa tgggggaaac cctgatgcag ctataccgcg tgtgtgaaga    420
aggccttcgg gttgtaaagc actttcagcg gggaagaaaa tgaagttact aataataatt    480
gtcaattgac gttacccgca aaagaagcac cggctaactc cgtgccagca gccgcggtaa    540
gacggagggt gcaagcgtta atcggaatta ctgggcgtaa agcgtatgta ggcggtttat    600
ttagtcaggt gtgaaagccc taggcttaac ctaggaattg catttgaaac tggtaagcta    660
gagtctcgta gagggggga gaattccagg tgtagcggtg aaatgcgtag agatctggaa    720
gaataccagt ggcgaaggcg ccccctgga cgaaaactga cgctcaagta cgaaagcgtg     780
gggagcaaac aggattagat accctggtag tccacgctgt aaacgatgtc gatttgaagg    840
ttgtagcctt gagctatagc tttcgaagct aacgcattaa atcgaccgcc tggggagtac    900
gaccgcaagg ttaaaactca aatgaattga cgggggcccg cacaagcggt ggagcatgtg    960
gtttaattcg atacaacgcg aaaaaccttta cctactcttg acatccagag tataaagcag   1020
aaaagcttta gtgccttcgg gaactctgag acaggtgctg catggctgtc gtcagctcgt    1080
gttgtgaaat gttgggttaa gtcccgcaac gagcgcaacc cttatccttt gttgccaacg    1140
attaagtcgg gaactcaaag gagactgccg gtgataaacc ggaggaaggt gaggataacg    1200
tcaagtcatc atggccctta cgagtagggc tacacacgtg ctacaatggt gcatacaaag    1260
agaagcaatc tcgtaagagt tagcaaacct cataaagtgc atcgtagtcc ggattagagt    1320
ctgcaactcg actctatgaa gtcggaatcg ctagtaatcg tggatcagaa tgccacggtg    1380
aatacgttcc cgggccttgt acacaccgcc cgtcacacca tggagtgta ttgcaaaaga    1440 agttagtagc ttaactcata atacgagagg gcgcttacca cttgtgatt cataactggg    1500 gtgaagtcgt aacaaggtaa ccgtagggga acctgcggtt ggatcacctc cttacactaa    1560
a                                                                    1561
```

<210> SEQ ID NO 16
<211> LENGTH: 1464
<212> TYPE: DNA
<213> ORGANISM: Unknown
<220> FEATURE:
<223> OTHER INFORMATION: Sodalis like gamma proteobacterium

<400> SEQUENCE: 16

| | |
|---|---|
| attgaacgct ggcggcaggc ctaacacatg caagtcgagc ggcagcggga agaagcttgc | 60 |
| ttctttgccg gcgagcggcg gacgggtgag taatgtctgg ggatctgccc gatggagggg | 120 |
| gataactact ggaaacggta gctaataccg cataacgtcg caagaccaaa gtggggggacc | 180 |
| ttcgggcctc acaccatcgg atgaacccag gtgggattag ctagtaggtg gggtaatggc | 240 |
| tcacctaggc gacgatccct agctggtctg agaggatgac cagtcacact ggaactgaga | 300 |
| cacggtccag actcctacgg gaggcagcag tggggaatat tgcacaatgg gggaaaccct | 360 |
| gatgcagcca tgccgcgtgt gtgaagaagg ccttcgggtt gtaaagcact ttcagcgggg | 420 |
| aggaaggcga tggcgttaat agcgctatcg attgacgtta cccgcagaag aagcaccggc | 480 |
| taactccgtg ccagcagccg cggtaatacg gagggtgcga gcgttaatcg gaattactgg | 540 |
| gcgtaaagcg tacgcaggcg gtctgttaag tcagatgtga atccccgggc tcaacctgg | 600 |
| gaactgcatt tgaaactggc aggctagagt ctcgtagagg ggggtagaat tccaggtgta | 660 |
| gcggtgaaat gcgtagagat ctggaggaat accggtggcg aaggcggccc cctggacgaa | 720 |
| gactgacgct caggtacgaa agcgtgggga gcaaacagga ttagatacccc tggtagtcca | 780 |
| cgctgtaaac gatgtcgatt tgaaggttgt ggccttgagc cgtggctttc ggagctaacg | 840 |
| tgttaaatcg accgcctggg gagtacggcc gcaaggttaa aactcaaatg aattgacggg | 900 |
| ggcccgcaca agcggtggag catgtggttt aattcgatgc aacgcgaaga accttaccta | 960 |
| ctcttgacat ccagagaact tggcagagat gctttggtgc cttcgggaac tctgagacag | 1020 |
| gtgctgcatg gctgtcgtca gctcgtgttg tgaaatgttg ggttaagtcc cgcaacgagc | 1080 |
| gcaacccttg tcctttattg ccagcgattc ggtcgggaac tcaaaggaga ctgccggtga | 1140 |
| taaaccggag gaaggtgggg atgacgtcaa gtcatcatgg cccttacgag tagggctaca | 1200 |
| cacgtgctac aatggcgcat acaaagagaa gcgatctcgc gagagtcagc ggacctcata | 1260 |
| aagtgcgtcg tagtccggat tggagtctgc aactcgactc catgaagtcg gaatcgctag | 1320 |
| taatcgtgga tcagaatgcc acggtgaata cgttcccggg ccttgtacac accgcccgtc | 1380 |
| acaccatggg agtgggttgc aaaagaagta ggtagcttaa ccttcgggag ggcgcttacc | 1440 |
| actttgtgat tcatgactgg ggtg | 1464 |

<210> SEQ ID NO 17
<211> LENGTH: 1465
<212> TYPE: DNA
<213> ORGANISM: Hartigia pinicola

<400> SEQUENCE: 17

| | |
|---|---|
| agatttaacg ctggcggcag gcctaacaca tgcaagtcga gcggtaccag aagaagcttg | 60 |
| cttcttgctg acgagcggcg gacgggtgag taatgtatgg ggatctgccc gacagagggg | 120 |
| gataactatt ggaaacggta gctaataccg cataatctct gaggagcaaa gcagggggaac | 180 |
| ttcggtcctt gcgctatcgg atgaacccat atgggattag ctagtaggtg aggtaatggc | 240 |
| tcccctaggc aacgatccct agctggtctg agaggatgat cagccacact gggactgaga | 300 |
| cacggcccag actcctacgg gaggcagcag tggggaatat tgcacaatgg gcgaaagcct | 360 |
| gatgcagcca tgccgcgtgt atgaagaagg ctttagggtt gtaaagtact ttcagtcgag | 420 |
| aggaaaacat tgatgctaat atcatcaatt attgacgttt ccgacagaag aagcaccggc | 480 |
| taactccgtg ccagcagccg cggtaatacg gagggtgcaa gcgttaatcg gaattactgg | 540 |
| gcgtaaagcg cacgcaggcg gttaattaag ttagatgtga agcccccggg cttaacccag | 600 |
| gaatagcata taaaactggt caactagagt attgtagagg ggggtagaat tccatgtgta | 660 |

```
gcggtgaaat gcgtagagat gtggaggaat accagtggcg aaggcggccc cctggacaaa      720
aactgacgct caaatgcgaa agcgtgggga gcaaacagga ttagataccc tggtagtcca      780
tgctgtaaac gatgtcgatt tggaggttgt tcccttgagg agtagcttcc gtagctaacg      840
cgttaaatcg accgcctggg ggagtacgac tgcaaggtta aaactcaaat gaattgacgg      900
gggcccgcac aagcggtgga gcatgtggtt taattcgatg caacgcgaaa aaccttacct      960
actcttgaca tccagataat ttagcagaaa tgctttagta ccttcgggaa atctgagaca     1020
ggtgctgcat ggctgtcgtc agctcgtgtt gtgaaatgtt gggttaagtc cgcaacgag      1080 cgcaacccct tatcctttgt tgccagcgat taggtcggga ctcaaaggag actgccggtg     1140
ataaaccgga ggaaggtggg gatgacgtca agtcatcatg gcccttacga gtagggctac     1200
acacgtgcta caatggcata caaagggga gcaacctcg cgagagcaag cgaaactcat       1260
aaattatgtc gtagttcaga ttggagtctg caactcgact ccatgaagtc ggaatcgcta     1320
gtaatcgtag atcagaatgc tacggtgaat acgttcccgg gccttgtaca ccgcccgt      1380 cacaccatgg gagtgggttg caaaagaagt aggtaactta accttatgga aagcgcttac     1440
cactttgtga ttcataactg gggtg                                            1465

<210> SEQ ID NO 18
<211> LENGTH: 1571
<212> TYPE: DNA
<213> ORGANISM: Tremblaya phenacola

<400> SEQUENCE: 18
aggtaatcca gccacacctt ccagtacggc taccttgtta cgacttcacc ccagtcacaa        60
cccttacctt cggaactgcc ctcctcacaa ctcaaaccac caaacacttt taaatcaggt       120
tgagagaggt taggcctgtt acttctggca agaattattt ccatggtgtg acgggcggtg       180
tgtacaagac ccgagaacat attcaccgtg gcatgctgat ccacgattac tagcaattcc       240
aacttcatgc actcgagttt cagagtacaa tccgaactga ggccggcttt gtgagattag       300
ctcccttttg caagttggca actctttggt ccggccattg tatgatgtgt gaagccccac       360
ccataaaggc catgaggact tgacgtcatc cccaccttcc tccaacttat cgctggcagt       420
ctctttaagg taactgacta atccagtagc aattaaagac aggggttgcg ctcgttacag       480
gacttaaccc aacatctcac gacacgagct gacgacagcc atgcagcacc tgtgcactaa       540 ttctcttttca agcactcccg cttctcaaca ggatcttagc catatcaaag gtaggtaagg      600 ttttttcgcgt tgcatcgaat taatccacat catccactgc ttgtgcgggt ccccgtcaat     660
tcctttgagt tttaaccttg cggccgtact ccccaggcgg tcgacttgtg cgttagctgc      720
accactgaaa aggaaaactg cccaatggtt agtcaacatc gtttagggca tggactacca     780
gggtatctaa tcctgtttgc tccccatgct ttagtgtctg agcgtcagta acgaaccagg     840
aggctgccta cgctttcggt attcctccac atctctacac atttcactgc tacatgcgga     900
attctacctc cccctctcgt actccagcct gccagtaact gccgcattct gaggttaagc     960
ctcagccttt cacagcaatc ttaacaggca gcctgcacac cctttacgcc caataaatct    1020
gattaacgct cgcaccctac gtattaccgc ggctgctggc acgtagtttg ccggtgctta    1080
ttctttcggt acagtcacac caccaaattg ttagttgggt ggctttcttt ccgaacaaaa    1140 gtgcttttaca acccaaaggc cttcttcaca cacgcggcat tgctggatca ggcttccgcc     1200
cattgtccaa gattcctcac tgctgccttc ctcagaagtc tgggccgtgt ctcagtccca    1260
```

```
gtgtggctgg ccgtcctctc agaccagcta ccgatcattg ccttgggaag ccattacctt     1320
tccaacaagc taatcagaca tcagccaatc tcagagcgca aggcaattgg tcccctgctt     1380
tcattctgct tggtagagaa ctttatgcgg tattaattag gctttcacct agctgtcccc     1440
cactctgagg catgttctga tgcattactc acccgtttgc cacttgccac caagcctaag     1500
cccgtgttgc cgttcgactt gcatgtgtaa ggcatgccgc tagcgttcaa tctgagccag     1560
gatcaaactc t                                                          1571

<210> SEQ ID NO 19
<211> LENGTH: 1535
<212> TYPE: DNA
<213> ORGANISM: Tremblaya princeps

<400> SEQUENCE: 19
agagtttgat cctggctcag attgaacgct agcggcatgc attacacatg caagtcgtac       60
ggcagcacgg gcttaggcct ggtggcgagt ggcgaacggg tgagtaacgc ctcggaacgt      120
gccttgtagt gggggatagc ctggcgaaag ccagattaat accgcatgaa gccgcacagc      180
atgcgcggtg aaagtggggg attctagcct cacgctactg gatcggccgg ggtctgatta      240
gctagttggc ggggtaatgg cccaccaagg cttagatcag tagctggtct gagaggacga      300
tcagccacac tgggactgag acacggccca gactcctacg ggaggcagca gtggggaatc      360
ttggacaatg ggcgcaagcc tgatccagca atgccgcgtg tgtgaagaag ccttcgggt      420 cgtaaagcac ttttgttcgg gatgaagggg ggcgtgcaaa caccatgccc tcttgacgat      480
accgaaagaa taagcaccgg ctaactacgt gccagcagcc gcggtaatac gtagggtgcg      540
agcgttaatc ggaatcactg ggcgtaaagg gtgcgcgggt ggtttgccaa gaccctgta      600 aaatcctacg gcccaaccgt agtgctgcgg aggttactgg taagcttgag tatggcagag      660
gggggtagaa ttccaggtgt agcggtgaaa tgcgtagata tctggaggaa taccgaaggc      720
gaaggcaacc ccctgggcca tcactgacac tgaggcacga aagcgtgggg agcaaacagg      780
attagatacc ctggtagtcc acgccctaaa ccatgtcgac tagttgtcgg ggggagccct      840
ttttcctcgg tgacgaagct aacgcatgaa gtcgaccgcc tggggagtac gaccgcaagg      900
ttaaaactca aggaattga cggggacccg cacaagcggt ggatgatgtg gattaattcg      960
atgcaacgcg aaaaaccttta cctacccttg acatggcgga gattctgccg agaggcggaa     1020
gtgctcgaaa gagaatccgt gcacaggtgc tgcatggctg tcgtcagctc gtgtcgtgag     1080
atgttgggtt aagtcccata acgagcgcaa ccccgtctt tagttgctac cactgggca     1140 ctctatagag actgccggtg ataaaccgga ggaaggtggg gacgacgtca agtcatcatg     1200
gcctttatgg gtagggcttc acacgtcata caatggctgg agcaaagggt cgccaactcg     1260
agagagggag ctaatcccac aaacccagcc ccagttcgga ttgcactctg caactcgagt     1320
gcatgaagtc ggaatcgcta gtaatcgtgg atcagcatgc cacggtgaat acgttctcgg     1380
gtcttgtaca caccgcccgt cacaccatgg gagtaagccg catcagaagc agcctcccta     1440 acccctatgct gggaaggagg ctgcgaaggt ggggtctatg actggggtga agtcgtaaca     1500
aggtagccgt accggaaggt gcggctggat tacct                                1535

<210> SEQ ID NO 20
<211> LENGTH: 1450
<212> TYPE: DNA
<213> ORGANISM: Nasuia deltocephalinicola

<400> SEQUENCE: 20
```

```
agtttaatcc tggctcagat ttaacgcttg cgacatgcct aacacatgca agttgaacgt    60
tgaaaatatt tcaaagtagc gtataggtga gtataacatt taaacatacc ttaaagttcg   120
gaatacccg atgaaaatcg gtataatacc gtataaaagt atttaagaat taaagcgggg   180
aaaacctcgt gctataagat tgttaaatgc ctgattagtt tgttggtttt taaggtaaaa   240
gcttaccaag actttgatca gtagctattc tgtgaggatg tatagccaca ttgggattga   300
aataatgccc aaacctctac ggagggcagc agtggggaat attggacaat gagcgaaagc   360
ttgatccagc aatgtcgcgt gtgcgattaa gggaaactgt aaagcacttt tttttaagaa   420
taagaaattt taattaataa ttaaaatttt tgaatgtatt aaaagaataa gtaccgacta   480
atcacgtgcc agcagtcgcg gtaatacgtg gggtgcgagc gttaatcgga tttattgggc   540
gtaaagtgta ttcaggctgc ttaaaaagat ttatattaaa tatttaaatt aaatttaaaa   600
aatgtataaa ttactattaa gctagagttt agtataagaa aaagaatttt tatgtgtagc   660
agtgaaatgc gttgatatat aaaggaacgc cgaaagcgaa agcattttc tgtaatagaa   720
ctgacgctta tatcgaaag cgtgggtagc aaacaggatt agataccctg gtagtccacg   780
ccctaaacta tgtcaattaa ctattagaat ttttttagt ggtgtagcta acgcgttaaa   840
ttgaccgcct gggtattacg atcgcaagat taaaactcaa aggaattgac ggggaccagc   900
acaagcggtg gatgatgtgg attaattcga tgatacgcga aaaaccttac ctgcccttga   960
catggttaga attttattga aaaataaaag tgcttggaaa agagctaaca cacaggtgct  1020
gcatggctgt cgtcagctcg tgtcgtgaga gtttgggta agtcccgcaa cgagcgcaac  1080
ccctactctt agttgctaat taaagaactt taagagaaca gctaacaata agtttagagg  1140
aaggagggga tgacttcaag tcctcatggc ccttatgggc agggcttcac acgtcataca  1200
atggttaata caaaaagttg caatatcgta agattgagct aatctttaaa attaatctta  1260
gttcggattg tactctgcaa ctcgagtaca tgaagtggga atcgctagta atcgcggatc  1320
agcatgccgc ggtgaatagt ttaactggtc ttgtacacac cgcccgtcac accatggaaa  1380
taaatcttgt tttaaatgaa gtaatatatt ttatcaaaac aggttttgta accggggtga  1440
agtcgtaaca                                                          1450
```

<210> SEQ ID NO 21
<211> LENGTH: 1536
<212> TYPE: DNA
<213> ORGANISM: Zinderia insecticola CARI

<400> SEQUENCE: 21

```
atataaataa gagtttgatc ctggctcaga ttgaacgcta gcggtatgct ttacacatgc    60
aagtcgaacg acaatattaa agcttgcttt aatataaagt ggcgaacggg tgagtaatat   120
atcaaaacgt acccttaaagt gggggataac taattgaaaa attagataat accgcatatt   180
aatcttagga tgaaatagg ataatatct tatgctttta gatcggttga tatctgatta   240
gctagttggt agggtaaatg cttaccaagg caatgatcag tagctggttt tagcgaatga   300
tcagccacac tggaactgag acacggtcca gacttctacg gaaggcagca gtggggaata   360
ttggacaatg ggagaaatcc tgatccagca ataccgcgtg agtgatgaag ccttagggt   420
cgtaaaactc ttttgttagg aaagaaataa tttaaataa tatttaaaat tgatgacggt   480
acctaaagaa taagcaccgg ctaactacgt gccagcagcc gcggtaatac gtagggtgca   540
agcgttaatc ggaattattg ggcgtaaaga gtgcgtaggc tgttatataa gatagatgtg   600
```

| | |
|---|---|
| aaatacttaa gcttaacttq agaactgcat ttattactgt ttaactagag tttattagag | 660 |
| agaagtggaa ttttatgtgt agcagtgaaa tgcgtagata tataaaggaa tatcgatggc | 720 |
| gaaggcagct tcttggaata atactgacgc tgaggcacga aagcgtgggg agcaaacagg | 780 |
| attagatacc ctggtagtcc acgccctaaa ctatgtctac tagttattaa attaaaaata | 840 |
| aaatttagta acgtagctaa cgcattaagt agaccgcctg gggagtacga tcgcaagatt | 900 |
| aaaactcaaa ggaattgacg gggacccgca caagcggtgg atgatgtgga ttaattcgat | 960 |
| gcaacacgaa aaaccttacc tactcttgac atgtttggaa ttttaaagaa atttaaaagt | 1020 |
| gcttgaaaaa gaaccaaaac acaggtgctg catggctgtc gtcagctcgt gtcgtgagat | 1080 |
| gttgggttaa gtcccgcaac gagcgcaacc cttgttatta tttgctaata aaaagaactt | 1140 |
| taataagact gccaatgaca aattggagga aggtggggat gacgtcaagt cctcatggcc | 1200 |
| cttatgagta gggcttcaca cgtcatacaa tgatatatac aatgggtagc aaatttgtga | 1260 |
| aaatgagcca atccttaaag tatatcttag ttcggattgt agtctgcaac tcgactacat | 1320 |
| gaagttggaa tcgctagtaa tcgcggatca gcatgccgcg gtgaatacgt tctcgggtct | 1380 |
| tgtacacacc gcccgtcaca ccatggaagt gattttttacc agaaattatt tgtttaacct | 1440 |
| ttattggaaa aaataatta aggtagaatt catgactggg gtgaagtcgt aacaaggtag | 1500 |
| cagtatcgga aggtgcggct ggattacatt ttaaat | 1536 |

<210> SEQ ID NO 22
<211> LENGTH: 1423
<212> TYPE: DNA
<213> ORGANISM: Hodgkinia

<400> SEQUENCE: 22

| | |
|---|---|
| aatgctggcg gcaggcctaa cacatgcaag tcgagcggac aacgttcaaa cgttgttagc | 60 |
| ggcgaacggg tgagtaatac gtgagaatct acccatccca acgtgataac atagtcaaca | 120 |
| ccatgtcaat aacgtatgat tcctgcaaca ggtaaagatt ttatcgggga tggatgagct | 180 |
| cacgctagat tagctagttg gtgagataaa agcccaccaa ggccaagatc tatagctggt | 240 |
| ctggaaggat ggacagccac attgggactg agacaaggcc caaccctcta aggagggcag | 300 |
| cagtgaggaa tattggacaa tgggcgtaag cctgatccag ccatgccgca tgagtgattg | 360 |
| aaggtccaac ggactgtaaa actcttttct ccagagatca taaatgatag tatctggtga | 420 |
| tataagctcc ggccaacttc gtgccagcag ccgcggtaat acgaggggag cgagtattgt | 480 |
| tcggttttat tgggcgtaaa gggtgtccag gttgctaagt aagttaacaa caaaatcttg | 540 |
| agattcaacc tcataacgtt cggttaatac tactaagctc gagcttggat agagacaaac | 600 |
| ggaattccga gtgtagaggt gaaattcgtt gatacttgga ggaacaccag aggcgaaggc | 660 |
| ggtttgtcat accaagctga cactgaagac acgaaagcat ggggagcaaa caggattaga | 720 |
| taccctggta gtccatgccc taaacgttga gtgctaacag ttcgatcaag ccacatgcta | 780 |
| tgatccagga ttgtacagct aacgcgttaa gcactccgcc tggtattac gaccgcaagg | 840 |
| ttaaaactca aggaattga cggagacccg cacaagcggt ggagcatgtg gtttaattcg | 900 |
| aagctacacg aagaaccttt ccagcccttg acataccatg ccaaccatc ctggaaacag | 960 |
| gatgttgttc aagttaaacc cttgaaatgc caggaacagg tgctgcatgg ctgttgtcag | 1020 |
| ttcgtgtcgt gagatgtatg gttaagtccc aaaacgaaca caaccctcac ccatagttgc | 1080 |
| cataaacaca attgggttct ctatgggtac tgctaacgta agttagagga aggtgaggac | 1140 |
| cacaacaagt catcatggcc cttatgggct gggccacaca catgctacaa tggtggttac | 1200 |

| aaagagccgc aacgttgtga gaccgagcaa atctccaaag accatctcag tccggattgt | 1260 |
| actctgcaac ccgagtacat gaagtaggaa tcgctagtaa tcgtggatca gcatgccacg | 1320 |
| gtgaatacgt tctcgggtct tgtacacgcc gcccgtcaca ccatgggagc ttcgctccga | 1380 |
| tcgaagtcaa gttacccttg accacatctt ggcaagtgac cga | 1423 |

<210> SEQ ID NO 23
<211> LENGTH: 1504
<212> TYPE: DNA
<213> ORGANISM: Wolbachia sp. wPip

<400> SEQUENCE: 23

| aaatttgaga gtttgatcct ggctcagaat gaacgctggc ggcaggccta acacatgcaa | 60 |
| gtcgaacgga gttatattgt agcttgctat ggtataactt agtggcagac gggtgagtaa | 120 |
| tgtataggaa tctacctagt agtacggaat aattgttgga acgacaact aataccgtat | 180 |
| acgccctacg ggggaaaaat ttattgctat tagatgagcc tatattagat tagctagttg | 240 |
| gtggggtaat agcctaccaa ggtaatgatc tatagctgat ctgagaggat gatcagccac | 300 |
| actggaactg agatacggtc cagactccta cgggaggcag cagtggggaa tattggacaa | 360 |
| tgggcgaaag cctgatccag ccatgccgca tgagtgaaga aggcctttgg ttgtaaagc | 420 |
| tcttttagtg aggaagataa tgacggtact cacagaagaa gtcctggcta actccgtgcc | 480 |
| agcagccgcg gtaatacgga gagggctagc gttattcgga attattgggc gtaaagggcg | 540 |
| cgtaggctgg ttaataagtt aaaagtgaaa tcccgaggct taaccttgga attgcttta | 600 |
| aaactattaa tctagagatt gaaagaggat agaggaattc ctgatgtaga ggtaaaattc | 660 |
| gtaaatatta ggaggaacac cagtggcgaa ggcgtctatc tggttcaaat ctgacgctga | 720 |
| agcgcgaagg cgtggggagc aaacaggatt agataccctg gtagtccacg ctgtaaacga | 780 |
| tgaatgttaa atatggggag tttactttct gtattacagc taacgcgtta aacattccgc | 840 |
| ctggggacta cggtcgcaag attaaaactc aaaggaattg acggggaccc gcacaagcgg | 900 |
| tggagcatgt ggtttaattc gatgcaacgc gaaaaacctt accacttctt gacatgaaaa | 960 |
| tcatacctat tcgaagggat agggtcggtt cggccggatt ttacacaagt gttgcatggc | 1020 |
| tgtcgtcagc tcgtgtcgtg agatgttggg ttaagtcccg caacgagcgc aaccctcatc | 1080 |
| cttagttgcc atcaggtaat gctgagtact ttaaggaaac tgccagtgat aagctggagg | 1140 |
| aaggtgggga tgatgtcaag tcatcatggc ctttatggag tgggctacac acgtgctaca | 1200 |
| atggtgtcta caatgggctg caaggtgcgc aagcctaagc taatccctaa agacatctc | 1260 |
| agttcggatt gtactctgca actcgagtac atgaagttgg aatcgctagt aatcgtggat | 1320 |
| cagcatgcca cggtgaatac gttctcgggt cttgtacaca ctgcccgtca cgccatggga | 1380 |
| attggtttca ctcgaagcta atggcctaac cgcaaggaag gagttattta agtgggatc | 1440 |
| agtgactggg gtgaagtcgt aacaaggtag cagtagggga atctgcagct ggattacctc | 1500 |
| ctta | 1504 |

<210> SEQ ID NO 24
<211> LENGTH: 1532
<212> TYPE: DNA
<213> ORGANISM: Uzinura diaspidicola

<400> SEQUENCE: 24

| aaaggagata ttccaaccac accttccggt acggttacct tgttacgact tagccctagt | 60 |

```
catcaagttt accttaggca gaccactgaa ggattactga cttcaggtac ccccgactcc      120
catggcttga cgggcggtgt gtacaaggtt cgagaacata ttcaccgcgc cattgctgat      180
gcgcgattac tagcgattcc tgcttcatag agtcgaattg cagactccaa tccgaactga      240
gactggtttt agagattagc tcctgatcac ccagtggctg ccctttgtaa ccagccattg      300
tagcacgtgt gtagcccaag gcatagaggc catgatgatt tgacatcatc cccaccttcc      360
tcacagttta caccggcagt tttgttagag tccccggctt tacccgatgg caactaacaa      420 tagggghttgc gctcgttata ggacttaacc aaacacttca cagcacgaac tgaagacaac      480
catgcagcac cttgtaatac gtcgtataga ctaagctgtt tccagcttat tcgtaataca      540
tttaagcctt ggtaaggttc ctcgcgtatc atcgaattaa accacatgct ccaccgcttg      600
tgcgaacccc cgtcaattcc tttgagtttc aatcttgcga ctgtacttcc caggtggatc      660
acttatcgct ttcgctaagc cactgaatat cgttttcca atagctagtg atcatcgttt      720
agggcgtgga ctaccagggt atctaatcct gtttgctccc cacgctttcg tgcactgagc      780
gtcagtaaag atttagcaac ctgccttcgc tatcggtgtt ctgtatgata tctatgcatt      840
tcaccgctac accatacatt ccagatgctc aatcttact caagtttacc agtatcaata      900
gcaattttac agttaagctg taagcttca ctactgactt aataaacagc ctacacaccc      960
tttaaaccca ataaatccga ataacgcttg tgtcatccgt attgccgcgg ctgctggcac     1020
ggaattagcc gacacttatt cgtatagtac cttcaatctc ctatcacgta agatatttta     1080
tttctataca aaagcagttt acaacctaaa agaccttcat cctgcacgcg acgtagctgg     1140
ttcagagttt cctccattga ccaatattcc tcactgctgc ctcccgtagg agtctggtcc     1200
gtgtctcagt accagtgtgg aggtacaccc tcttaggccc cctactgatc atagtcttgg     1260
tagagccatt acctcaccaa ctaactaatc aaacgcaggc tcatcttttg ccacctaagt     1320
tttaataaag gctccatgca gaaactttat attatggggg attaatcaga atttcttctg     1380 gctataccc agcaaaaggt agattgcata cgtgttactc acccattcgc cggtcgccga      1440
caaattaaaa attttcgat gccoctcgac ttgcatgtgt taagctcgcc gctagcgtta     1500
attctgagcc aggatcaaac tcttcgttgt ag                                 1532
```

<210> SEQ ID NO 25
<211> LENGTH: 1470
<212> TYPE: DNA
<213> ORGANISM: Carsonella ruddii

<400> SEQUENCE: 25

```
ctcaggataa acgctagcgg agggcttaac acatgcaagt cgaggggcag caaaaataat       60 tattttggc gaccggcaaa cgggtgagta atacatacg aactttcctt atgctgagga       120
atagcctgag gaaacttgga ttaataccte ataatacaat tttttagaaa gaaaaattgt      180 taaagttta ttatggcata agataggcgt atgtccaatt agttagttgg taaggtaatg       240
gcttaccaag acgatgattg gtaggggggcc tgagaggggc gttccccac attggtactg      300 agacacggac caaacttcta cggaaggctg cagtgaggaa tattggtcaa tggaggaaac      360
tctgaaccag ccactccgcg tgcaggatga agaaagcct tattggttgt aaactgcttt       420
tgtatatgaa taaaaaattc taattataga ataattgaa ggtaatatac gataagtat       480 cgactaactc tgtgccagca gtcgcggtaa gacagaggat acaagcgtta tccggattta      540 ttgggttaa agggtgcgta ggcggttttt aaagtcagta gtgaaatctt aaagcttaac      600
tttaaaagtg ctattgatac tgaaaaacta gagtaaggtt ggagtaactg gaatgtgtgg      660
```

```
tgtagcggtg aaatgcatag atatcacaca gaacaccgat agcgaaagca agttactaac      720
cctatactga cgctgagtca cgaaagcatg gggagcaaac aggattagat accctggtag      780
tccatgccgt aaacgatgat cactaactat tgggttttat acgttgtaat tcagtggtga      840
agcgaaagtg ttaagtgatc cacctgagga gtacgaccgc aaggttgaaa ctcaaaggaa      900
ttgacggggg cccgcacaat cggtggagca tgtggtttaa ttcgatgata cacgaggaac      960
cttaccaaga cttaaatgta ctacgaataa attggaaaca atttagtcaa gcgacggagt     1020
acaaggtgct gcatggttgt cgtcagctcg tgccgtgagg tgtaaggtta agtcctttaa     1080
acgagcgcaa cccttattat tagttgccat cgagtaatgt cagggactc taataagact      1140 gccggcgcaa gccgagagga aggtggggat gacgtcaaat catcacggcc cttacgtctt     1200
gggccacaca cgtgctacaa tgatcggtac aaaagggagc gactgggtga ccaggagcaa     1260
atccagaaag ccgatctaag ttcggattgg agtctgaaac tcgactccat gaagctggaa     1320
tcgctagtaa tcgtgcatca gccatggcac ggtgaatatg ttcccgggcc ttgtacacac     1380
cgcccgtcaa gccatggaag ttggaagtac ctaaagttgg ttcgctacct aaggtaagtc     1440
taataactgg ggctaagtcg taacaaggta                                      1470

<210> SEQ ID NO 26
<211> LENGTH: 1761
<212> TYPE: DNA
<213> ORGANISM: Symbiotaphrina buchneri voucher JCM9740
<220> FEATURE:
<221> NAME/KEY: misc_feature
<222> LOCATION: (30)..(30)
<223> OTHER INFORMATION: n is a, g, c, or t
<220> FEATURE:
<221> NAME/KEY: misc_feature
<222> LOCATION: (40)..(40)
<223> OTHER INFORMATION: n is a, g, c, or t

<400> SEQUENCE: 26
agattaagcc atgcaagtct aagtataagn aatctatacn gtgaaactgc gaatggctca       60
ttaaatcagt tatcgtttat ttgatagtac cttactacat ggataaccgt ggtaattcta      120
gagctaatac atgctaaaaa ccccgacttc ggaagggggtg tatttattag ataaaaaacc     180 aatgccttc ggggctcctt ggtgattcat gataacttaa cgaatcgcat ggccttgcgc       240
cggcgatggt tcattcaaat ttctgcccta tcaactttcg atggtaggat agtggcctac      300
catggtttta acgggtaacg gggaattagg gttcgattcc ggagagggag cctgagaaac      360
ggctaccaca tccaaggaag gcagcaggcg cgcaaattac ccaatcccga cacggggagg     420
tagtgacaat aaatactgat acagggctct tttgggtctt gtaattggaa tgagtacaat      480
ttaaatccct taacgaggaa caattggagg gcaagtctgg tgccagcagc cgcggtaatt     540
ccagctccaa tagcgtatat taaagttgtt gcagttaaaa agctcgtagt tgaaccttgg     600
gcctggctgg ccggtccgcc taaccgcgtg tactggtccg gccgggcctt tccttctggg     660
gagccgcatg cccttcactg ggtgtgtcgg ggaaccagga cttttacttt gaaaaaatta     720
gagtgttcaa agcaggccta tgctcgaata cattagcatg gaataataga ataggacgtg     780
cggttctatt ttgttggttt ctaggaccgc cgtaatgatt aatagggata gtcggggca      840 tcagtattca attgtcagag gtgaaattct tggatttatt gaagactaac tactgcgaaa     900
gcatttgcca aggatgtttt cattaatcag tgaacgaaag ttaggggatc gaagacgatc      960
agataccgtc gtagtcttaa ccataaacta tgccgactag ggatcgggcg atgttattat     1020
```

| | |
|---|---|
| tttgactcgc tcggcacctt acgagaaatc aaagtctttg ggttctgggg ggagtatggt | 1080 |
| cgcaaggctg aaacttaaag aaattgacgg aagggcacca ccaggagtgg agcctgcggc | 1140 |
| ttaatttgac tcaacacggg gaaactcacc aggtccagac acattaagga ttgacagatt | 1200 |
| gagagctctt tcttgattat gtgggtggtg gtgcatggcc gttcttagtt ggtggagtga | 1260 |
| tttgtctgct taattgcgat aacgaacgag accttaacct gctaaatagc ccggtccgct | 1320 |
| ttggcgggcc gctggcttct tagagggact atcggctcaa gccgatggaa gtttgaggca | 1380 |
| ataacaggtc tgtgatgccc ttagatgttc tgggccgcac gcgcgctaca ctgacagagc | 1440 |
| caacgagtaa atcaccttgg ccggaaggtc tgggtaatct tgttaaactc tgtcgtgctg | 1500 |
| gggatagagc attgcaatta ttgctcttca acgaggaatt cctagtaagc gcaagtcatc | 1560 |
| agcttgcgct gattacgtcc ctgcccttttg tacacaccgc ccgtcgctac taccgattga | 1620 |
| atggctcagt gaggccttcg gactggcaca gggacgttgg caacgacgac ccagtgccgg | 1680 |
| aaagttggtc aaacttggtc atttagagga agtaaaagtc gtaacaaggt ttccgtaggt | 1740 |
| gaacctgcgg aaggatcatt a | 1761 |

<210> SEQ ID NO 27
<211> LENGTH: 1801
<212> TYPE: DNA
<213> ORGANISM: Symbiotaphrina kochii voucher CBS 589.63
<220> FEATURE:
<221> NAME/KEY: misc_feature
<222> LOCATION: (1753)..(1755)
<223> OTHER INFORMATION: n is a, g, c, or t

<400> SEQUENCE: 27

| | |
|---|---|
| tacctggttg attctgccag tagtcatatg cttgtctcaa agattaagcc atgcaagtct | 60 |
| aagtataagc aatctatacg gtgaaactgc gaatggctca ttaaatcagt tatcgtttat | 120 |
| ttgatagtac cttactacat ggataaccgt ggtaattcta gagctaatac atgctaaaaa | 180 |
| cctcgacttc ggaaggggtg tatttattag ataaaaaacc aatgcccttc ggggctcctt | 240 |
| ggtgattcat gataacttaa cgaatcgcat ggccttgcgc cggcgatggt tcattcaaat | 300 |
| ttctgcccta tcaactttcg atggtaggat agtggcctac catggtttca acgggtaacg | 360 |
| gggaattagg gttcgattcc ggagagggag cctgagaaac ggctaccaca tccaaggaag | 420 |
| gcagcaggcg cgcaaattac ccaatcccga cacggggagg tagtgacaat aaatactgat | 480 |
| acagggctct tttgggtctt gtaattggaa tgagtacaat ttaaatccct taacgaggaa | 540 |
| caattggagg gcaagtctgg tgccagcagc cgcggtaatt ccagctccaa tagcgtatat | 600 |
| taaagttgtt gcagttaaaa agctcgtagt tgaaccttgg gcctggctgg ccggtccgcc | 660 |
| taaccgcgtg tactggtccg gccgggcctt tccttctggg gagccgcatg cccttcactg | 720 |
| ggtgtgtcgg ggaaccagga cttttacttt gaaaaaatta gagtgttcaa agcaggccta | 780 |
| tgctcgaata cattagcatg gaataataga ataggacgtg tggttctatt ttgttggttt | 840 |
| ctaggaccgc cgtaatgatt aatagggata gtcggggca tcagtattca attgtcagag | 900 |
| gtgaaattct tggatttatt gaagactaac tactgcgaaa gcatttgcca aggatgtttt | 960 |
| cattaatcag tgaacgaaag ttaggggatc gaagacgatc agataccgtc gtagtcttaa | 1020 |
| ccataaacta tgccgactag ggatcgggcg atgttattat tttgactcgc tcggcacctt | 1080 |
| acgagaaatc aaagtctttg ggttctgggg ggagtatggt cgcaaggctg aaacttaaag | 1140 |
| aaattgacgg aagggcacca ccaggagtgg agcctgcggc ttaatttgac tcaacacggg | 1200 |
| gaaactcacc aggtccagac acattaagga ttgacagatt gagagctctt tcttgattat | 1260 |

```
gtgggtggtg gtgcatggcc gttcttagtt ggtggagtga tttgtctgct taattgcgat   1320
aacgaacgag accttaacct gctaaatagc ccggtccgct tggcgggcc gctggcttct    1380 tagagggact atcggctcaa gccgatggaa gtttgaggca ataacaggtc tgtgatgccc   1440
ttagatgttc tgggccgcac gcgcgctaca ctgacagagc caacgagtac atcaccttgg   1500
ccggaaggtc tgggtaatct tgttaaactc tgtcgtgctg ggatagagc attgcaatta    1560 ttgctcttca acgaggaatt cctagtaagc gcaagtcatc agcttgcgct gattacgtcc   1620 ctgcccttttg tacacaccgc ccgtcgctac taccgattga atggctcagt gaggccttcg  1680
gactggcaca gggacgttgg caacgacgac ccagtgccgg aaagttcgtc aaacttggtc   1740
atttagagga agnnnaagtc gtaacaaggt ttccgtaggt gaacctgcgg aaggatcatt   1800
a                                                                   1801
```

<210> SEQ ID NO 28
<211> LENGTH: 1490
<212> TYPE: DNA
<213> ORGANISM: Burkholderia sp. SFA1

<400> SEQUENCE: 28

```
agtttgatcc tggctcagat tgaacgctgg cggcatgcct tacacatgca agtcgaacgg   60
cagcacgggg gcaaccctgg tggcgagtgg cgaacgggtg agtaatacat cggaacgtgt   120
cctgtagtgg gggatagccc ggcgaaagcc ggattaatac cgcatacgac ctaagggaga   180
aagcggggga tcttcggacc tcgcgctata ggggcggccg atggcagatt agctagttgg   240
tggggtaaag gcctaccaag cgacgatct gtagctggtc tgagaggacg accagccaca   300
ctgggactga gacacggccc agactcctac gggaggcagc agtggggaat tttggacaat   360 ggggcaacc ctgatccagc aatgccgcgt gtgtgaagaa ggcttcgggt tgtaaagcac   420
ttttgtccgg aaagaaaact tcgtccctaa tatggatgga ggatgacggt accggaagaa   480
taagcaccgg ctaactacgt gccagcagcc gcggtaatac gtagggtgcg agcgttaatc   540
ggaattactg ggcgtaaagc gtgcgcaggc ggtctgttaa gaccgatgtg aaatccccgg   600
gcttaacctg ggaactgcat tggtgactgg caggctttga gtgtggcaga ggggggtaga   660
attccacgtg tagcagtgaa atgcgtagag atgtggagga ataccgatgg cgaaggcagc   720
cccctgggcc aactactgac gctcatgcac gaaagcgtgg ggagcaaaca ggattagata   780
ccctggtagt ccacgcccta aacgatgtca actagttgtt ggggattcat tccttagta    840 acgtagctaa cgcgtgaagt tgaccgcctg gggagtacgg tcgcaagatt aaaactcaaa   900
ggaattgacg gggacccgca caagcggtgg atgatgtgga ttaattcgat gcaacgcgaa   960
aaaccttacc tacccttgac atggtcgaa ccctgctgaa aggtggggt gctcgaaaga    1020 gaaccggcgc acaggtgctg catggctgtc gtcagctcgt gtcgtgagat gttgggttaa   1080
gtcccgcaac gagcgcaacc cttgtccttta gttgctacgc aagagcactc taaggagact   1140
gccggtgaca aaccggagga aggtggggat gacgtcaagt cctcatggcc cttatgggta   1200
gggcttcaca cgtcatacaa tggtcggaac agagggttgc caagccgcga ggtggagcca   1260
atcccagaaa accgatcgta gtccggatcg cagtctgcaa ctcgactgcg tgaagctgga   1320
atcgctagta atcgcggatc agcatgccgc ggtgaatacg ttcccgggtc ttgtacacac   1380
cgcccgtcac accatgggag tgggtttcac cagaagtagg tagcctaacc gcaaggaggg   1440
cgcttaccac ggtgggattc atgactgggg tgaagtcgta acaaggtagc              1490
```

<210> SEQ ID NO 29
<211> LENGTH: 1408
<212> TYPE: DNA
<213> ORGANISM: Burkholderia sp. KM-A

<400> SEQUENCE: 29

| | | | | |
|---|---|---|---|---|
| gcaaccctgg | tggcgagtgg | cgaacgggtg | agtaatacat | cggaacgtgt | cctgtagtgg | 60 |
| gggatagccc | ggcgaaagcc | ggattaatac | cgcatacgat | ctacggaaga | aagcggggga | 120 |
| tccttcggga | cctcgcgcta | tagggcggc | cgatggcaga | ttagctagtt | ggtggggtaa | 180 |
| aggcctacca | aggcgacgat | ctgtagctgg | tctgagagga | cgaccagcca | cactgggact | 240 |
| gagacacggc | ccagactcct | acgggaggca | gcagtgggga | attttggaca | atggggggcaa | 300 |
| ccctgatcca | gcaatgccgc | gtgtgtgaag | aaggccttcg | ggttgtaaag | cacttttgtc | 360 |
| cggaaagaaa | acgtcttggt | taatacctga | ggcgatgac | ggtaccggaa | gaataagcac | 420 |
| cggctaacta | cgtgccagca | gccgcggtaa | tacgtagggt | gcgagcgtta | atcggaatta | 480 |
| ctgggcgtaa | agcgtgcgca | ggcggtctgt | taagaccgat | gtgaaatccc | cgggcttaac | 540 |
| ctggaactg | cattggtgac | tggcaggctt | tgagtgtggc | agaggggggt | agaattccac | 600 |
| gtgtagcagt | gaaatgcgta | gagatgtgga | ggaataccga | tggcgaaggc | agccccctgg | 660 |
| gccaacactg | acgctcatgc | acgaaagcgt | ggggagcaaa | caggattaga | taccctggta | 720 |
| gtccacgccc | taaacgatgt | caactagttg | ttggggattc | atttccttag | taacgtagct | 780 |
| aacgcgtgaa | gttgaccgcc | tggggagtac | ggtcgcaaga | ttaaaactca | aaggaattga | 840 |
| cggggacccg | cacaagcggt | ggatgatgtg | gattaattcg | atgcaacgcg | aaaaaccta | 900 |
| cctacccttg | acatggtcgg | aagtctgctg | agaggtggac | gtgctcgaaa | gagaaccggc | 960 |
| gcacaggtgc | tgcatggctg | tcgtcagctc | gtgtcgtgag | atgttgggtt | aagtcccgca | 1020 |
| acgagcgcaa | cccttgtcct | tagttgctac | gcaagagcac | tctaaggaga | ctgccggtga | 1080 |
| caaaccggag | gaaggtgggg | atgacgtcaa | gtcctcatgg | cccttatggg | tagggcttca | 1140 |
| cacgtcatac | aatggtcgga | acagagggtt | gccaagccgc | gaggtggagc | caatcccaga | 1200 |
| aaaccgatcg | tagtccggat | cgcagtctgc | aactcgactg | cgtgaagctg | gaatcgctag | 1260 |
| taatcgcgga | tcagcatgcc | gcggtgaata | cgttcccggg | tcttgtacac | accgcccgtc | 1320 |
| acaccatggg | agtgggttc | accagaagta | ggtagcctaa | ccgcaaggag | ggcgcttacc | 1380 |
| acggtgggat | tcatgactgg | ggtgaagt | | | | 1408 |

<210> SEQ ID NO 30
<211> LENGTH: 1383
<212> TYPE: DNA
<213> ORGANISM: Burkholderia sp. KM-G

<400> SEQUENCE: 30

| | | | | |
|---|---|---|---|---|
| gcaaccctgg | tggcgagtgg | cgaacgggtg | agtaatacat | cggaacgtgt | cctgtagtgg | 60 |
| gggatagccc | ggcgaaagcc | ggattaatac | cgcatacgac | ctaagggaga | aagcggggga | 120 |
| tcttcggacc | tcgcgctata | ggggcggccg | atggcagatt | agctagttgg | tgggtaaag | 180 |
| gcctaccaag | gcgacgatct | gtagctggtc | tgagaggacg | accagccaca | ctgggactga | 240 |
| gacacggccc | agactcctac | gggaggcagc | agtggggaat | tttggacaat | ggggggcaacc | 300 |
| ctgatccagc | aatgccgcgt | gtgtgaagaa | ggccttcggg | ttgtaaagca | cttttgtccg | 360 |
| gaaagaaaac | ttcgaggtta | ataccctttgg | aggatgacgg | taccggaaga | ataagcaccg | 420 |
| gctaactacg | tgccagcagc | cgcggtaata | cgtagggtgc | gagcgttaat | cggaattact | 480 |

-continued

```
gggcgtaaag cgtgcgcagg cggtctgtta agaccgatgt gaaatccccg ggcttaacct    540
gggaactgca ttggtgactg gcaggctttg agtgtggcag agggggggtag aattccacgt    600
gtagcagtga aatgcgtaga gatgtggagg aataccgatg gcgaaggcag ccccctgggc    660
caacactgac gctcatgcac gaaagcgtgg ggagcaaaca ggattagata ccctggtagt    720
ccacgcccta aacgatgtca actagttgtt ggggattcat ttccttagta acgtagctaa    780
cgcgtgaagt tgaccgcctg gggagtacgg tcgcaagatt aaaactcaaa ggaattgacg    840
gggacccgca caagcggtgg atgatgtgga ttaattcgat gcaacgcgaa aaaccttacc    900
taccctttgac atggtcggaa gtctgctgag aggtggacgt gctcgaaaga gaaccggcgc    960
acaggtgctg catggctgtc gtcagctcgt gtcgtgagat gttgggttaa gtcccgcaac   1020
gagcgcaacc cttgtcctta gttgctacgc aagagcactc taaggagact gccggtgaca   1080
aaccggagga aggtggggat gacgtcaagt cctcatggcc cttatgggta gggcttcaca   1140
cgtcatacaa tggtcggaac agagggttgc caagccgcga ggtggagcca atcccagaaa   1200
accgatcgta gtccggatcg cagtctgcaa ctcgactgcg tgaagctgga atcgctagta   1260
atcgcggatc agcatgccgc ggtgaatacg ttcccgggtc ttgtacacac cgcccgtcac   1320
accatgggag tgggtttcac cagaagtagg tagcctaacc tgcaaaggag ggcgcttacc   1380
acg                                                                  1383
```

<210> SEQ ID NO 31

<400> SEQUENCE: 31

000

<210> SEQ ID NO 32

<400> SEQUENCE: 32

000

<210> SEQ ID NO 33
<211> LENGTH: 1505
<212> TYPE: DNA
<213> ORGANISM: Snodgrassella alvi

<400> SEQUENCE: 33

```
gagagtttga tcctggctca gattgaacgc tggcggcatg ccttacacat gcaagtcgaa     60
cggcagcacg gagagcttgc tctctggtgg cgagtgcga acgggtgagt aatgcatcgg    120
aacgtaccga gtaatggggg ataactgtcc gaaaggatgg ctaataccgc atacgccctg    180
aggggggaaag cggggatcg aaagacctcg cgttatttga gcggccgatg ttggattagc    240
tagttggtgg ggtaaaggcc taccaaggcg acgatccata gcgggtctga gaggatgatc    300
cgccacattg ggactgagac acggcccaaa ctcctacggg aggcagcagt gggaatttt    360
ggacaatggg gggaaccctg atccagccat gccgcgtgtc tgaagaaggc cttcgggttg    420
taaaggactt tgttaggga agaaaagccg ggtgttaata ccatctggtg ctgacggtac    480
ctaaagaata agcaccggct aactacgtgc cagcagccgc ggtaatacgt agggtgcgag    540
cgttaatcgg aattactggg cgtaaagcga gcgcagacgg ttaattaagt cagatgtgaa    600
atccccgagc tcaacttggg acgtgcattt gaaactggtt aactagagtg tgtcagaggg    660
aggtagaatt ccacgtgtag cagtgaaatg cgtagagatg tggaggaata ccgatggcga    720
```

```
aggcagcctc ctgggataac actgacgttc atgctcgaaa gcgtgggtag caaacaggat      780 tagatacccct ggtagtccac gccctaaacg atgacaatta gctgttggga cactagatgt     840
cttagtagcg aagctaacgc gtgaaattgt ccgcctgggg agtacggtcg caagattaaa      900
actcaaagga attgacgggg acccgcacaa gcggtggatg atgtggatta attcgatgca      960
acgcgaagaa ccttacctgg tcttgacatg tacggaatct cttagagata ggagagtgcc     1020
ttcgggaacc gtaacacagg tgctgcatgg ctgtcgtcag ctcgtgtcgt gagatgttgg     1080
gttaagtccc gcaacgagcg caaccccttgt cattagttgc catcattaag ttgggcactc    1140
taatgagact gccggtgaca aaccggagga aggtggggat gacgtcaagt cctcatggcc     1200
cttatgacca gggcttcaca cgtcatacaa tggtcggtac agagggtagc gaagccgcga     1260
ggtgaagcca atctcagaaa gccgatcgta gtccggattg cactctgcaa ctcgagtgca     1320
tgaagtcgga atcgctagta atcgcaggtc agcatactgc ggtgaatacg ttcccgggtc     1380
ttgtacacac cgcccgtcac accatgggag tggggatac cagaattggg tagactaacc      1440
gcaaggaggt cgcttaacac ggtatgcttc atgactgggg tgaagtcgta acaaggtagc     1500
cgtag                                                                  1505

<210> SEQ ID NO 34
<211> LENGTH: 1541
<212> TYPE: DNA
<213> ORGANISM: Gilliamella apicola

<400> SEQUENCE: 34
ttaaattgaa gagtttgatc atggctcaga ttgaacgctg gcggcaggct taacacatgc       60
aagtcgaacg gtaacatgag tgcttgcact tgatgacgag tggcggacgg gtgagtaaag      120
tatggggatc tgccgaatgg aggggggacaa cagttggaaa cgactgctaa taccgcataa     180
agttgagaga ccaaagcatg ggaccttcgg gccatgcgcc atttgatgaa cccatatggg      240
attagctagt tggtagggta atggcttacc aaggcgacga tctctagctg gtctgagagg      300
atgaccagcc acactggaac tgagacacgg tccagactcc tacgggaggc agcagtgggg      360
aatattgcac aatgggggaa accctgatgc agccatgccg cgtgtatgaa gaaggccttc      420
gggttgtaaa gtactttcgg tgatgaggaa ggtggtgtat ctaataggtg catcaattga      480
cgttaattac agaagaagca ccggctaact ccgtgccagc agccgcggta atacggaggg     540
tgcgagcgtt aatcggaatg actgggcgta aagggcatgt aggcggataa ttaagttagg     600
tgtgaaagcc ctgggctcaa cctaggaatt gcacttaaaa ctggttaact agagtattgt     660
agaggaaggt agaattccac gtgtagcggt gaaatgcgta gagatgtgga ggaataccgg     720
tggcgaaggc ggccttctgg acagatactg acgctgagat gcgaaagcgt ggggagcaaa     780
caggattaga taccctggta gtccacgctg taaacgatgt cgatttggag tttgttgcct     840
agagtgatgg gctccgaagc taacgcgata aatcgaccgc ctgggagta cggccgcaag     900 gttaaaactc aaatgaattg acggggggccc gcacaagcgg tggagcatgt ggtttaattc     960
gatgcaacgc gaagaacctt acctggtctt gacatccaca gaatcttgca gagatgcggg    1020
agtgccttcg ggaactgtga cacaggtgct gcatggctgt cgtcagctcg tgttgtgaaa    1080
tgttgggtta agtcccgcaa cgagcgcaac ccttatcctt gttgccatc ggttaggccg      1140 ggaactcaaa ggagactgcc gttgataaag cggaggaagg tgggacgac gtcaagtcat      1200 catgccctt acgaccaggg ctacacacgt gctacaatgg cgtatacaaa gggaggcgac     1260
ctcgcgagag caagcggacc tcataaagta cgtctaagtc cggattggag tctgcaactc    1320
```

```
gactccatga agtcggaatc gctagtaatc gtgaatcaga atgtcacggt gaatacgttc       1380
ccgggccttg tacacaccgc ccgtcacacc atgggagtgg gttgcaccag aagtagatag       1440
cttaaccttc ggagggcgt ttaccacggt gtggtccatg actggggtga agtcgtaaca        1500
aggtaaccgt aggggaacct gcggttggat cacctcctta c                           1541

<210> SEQ ID NO 35
<211> LENGTH: 1528
<212> TYPE: DNA
<213> ORGANISM: Bartonella apis

<400> SEQUENCE: 35
aagccaaaat caaattttca acttgagagt ttgatcctgg ctcagaacga acgctggcgg        60
caggcttaac acatgcaagt cgaacgcact tttcggagtg agtggcagac gggtgagtaa       120
cgcgtgggaa tctacctatt tctacggaat aacgcagaga aatttgtgct aataccgtat       180
acgtccttcg ggagaaagat ttatcggaga tagatgagcc cgcgttggat tagctagttg       240
gtgaggtaat ggcccaccaa ggcgacgatc catagctggt ctgagaggat gaccagccac       300
attgggactg agacacggcc cagactccta cgggaggcag cagtggggaa tattggacaa       360
tgggcgcaag cctgatccag ccatgccgcg tgagtgatga aggccctagg gttgtaaagc       420
tctttcaccg gtgaagataa tgacggtaac cggagaagaa gccccggcta acttcgtgcc       480
agcagccgcg gtaatacgaa gggggctagc gttgttcgga tttactgggc gtaaagcgca       540
cgtaggcgga tatttaagtc aggggtgaaa tcccggggct caaccccgga actgcctttg       600
atactggata tcttgagtat ggaagaggta agtggaattc cgagtgtaga ggtgaaattc       660
gtagatattc ggaggaacac cagtggcgaa ggcggcttac tggtccatta ctgacgctga       720
ggtgcgaaag cgtggggagc aaacaggatt agataccctg gtagtccacg ctgtaaacga       780
tgaatgttag ccgttggaca gtttactgtt cggtggcgca gctaacgcat taaacattcc       840
gcctggggag tacggtcgca agattaaaac tcaaaggaat tgacggggggc ccgcacaagc       900 ggtggagcat gtggtttaat tcgaagcaac gcgcagaacc ttaccagccc ttgacatccc       960
gatcgcggat ggtggagaca ccgtctttca gttcggctgg atcggtgaca ggtgctgcat      1020
ggctgtcgtc agctcgtgtc gtgagatgtt gggttaagtc cgcaacgag cgcaaccctc       1080 gcccttagtt gccatcattt agttgggcac tctaagggga ctgccggtga taagccgaga      1140
ggaaggtggg gatgacgtca agtcctcatg gcccttacgg gctgggctac acacgtgcta      1200
caatggtggt gacagtgggc agcgagaccg cgaggtcgca ctaatctcca aaagccatct      1260
cagttcggat tgcactctgc aactcgagtg catgaagttg gaatcgctag taatcgtgga      1320
tcagcatgcc acggtgaata cgttcccggg ccttgtacac accgcccgtc acaccatggg      1380
agttggtttt acccgaaggt gctgtgctaa ccgcaaggag gcaggcaacc acggtagggt      1440
cagcgactgg ggtgaagtcg taacaaggta gccgtagggg aacctgcggc tggatcacct      1500
cctttctaag gaagatgaag aattggaa                                         1528

<210> SEQ ID NO 36
<211> LENGTH: 1390
<212> TYPE: DNA
<213> ORGANISM: Parasaccharibacter apium
<220> FEATURE:
<221> NAME/KEY: misc_feature
<222> LOCATION: (643)..(756)
<223> OTHER INFORMATION: n is a, g, c, or t
```

<400> SEQUENCE: 36

```
ctaccatgca agtcgcacga aacctttcgg ggttagtggc ggacgggtga gtaacgcgtt      60
aggaacctat ctggaggtgg gggataacat cgggaaactg gtgctaatac cgcatgatgc     120
ctgagggcca aaggagagat ccgccattgg aggggcctgc gttcgattag ctagttggtt     180
gggtaaaggc tgaccaaggc gatgatcgat agctggtttg agaggatgat cagccacact     240
gggactgaga cacggcccag actcctacga gaggcagcag tggggaatat tggacaatgg     300
gggcaaccct gatccagcaa tgccgcgtgt gtgaagaagg tcttcggatt gtaaagcact     360
ttcactaggg aagatgatga cggtacctag agaagaagcc ccggctaact tcgtgccagc     420
agccgcggta atacgaaggg ggctagcgtt gctcggaatg actgggcgta aagggcgcgt     480
aggctgtttg tacagtcaga tgtgaaatcc ccgggcttaa cctgggaact gcatttgata     540
cgtgcagact agagtccgag agagggttgt ggaattccca gtgtagaggt gaaattcgta     600
gatattggga agaacaccgg ttgcgaaggc ggcaacctgg ctnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnngagc taacgcgtta agcacaccgc     780
ctggggagta cggccgcaag gttgaaactc aaaggaattg acgggggccc gcacaagcgg     840
tggagcatgt ggtttaattc gaagcaacgc gcagaacctt accagggctt gcatggggag     900
gctgtattca gagatggata tttcttcgga cctcccgcac aggtgctgca tggctgtcgt     960
cagctcgtgt cgtgagatgt tgggttaagt cccgcaacga gcgcaaccct tgtctttagt    1020
tgccatcacg tctgggtggg cactctagag agactgccgg tgacaagccg gaggaaggtg    1080
gggatgacgt caagtcctca tggcccttat gtcctgggct acacacgtgc tacaatggcg    1140
gtgacagagg gatgctacat ggtgacatgg tgctgatctc aaaaaaccgt ctcagttcgg    1200
attgtactct gcaactcgag tgcatgaagg tggaatcgct agtaatcgcg gatcagcatg    1260
ccgcggtgaa tacgttcccg ggccttgtac acaccgcccg tcacaccatg ggagttggtt    1320
tgaccttaag ccggtgagcg aaccgcaagg aacgcagccg accaccggtt cgggttcagc    1380
gactggggga                                                           1390
```

<210> SEQ ID NO 37
<211> LENGTH: 1583
<212> TYPE: DNA
<213> ORGANISM: Lactobacillus kunkeei

<400> SEQUENCE: 37

```
ttccttagaa aggaggtgat ccagccgcag gttctcctac ggctaccttg ttacgacttc      60
accctaatca tctgtcccac cttagacgac tagctcctaa aaggttaccc catcgtcttt     120
gggtgttaca aactctcatg gtgtgacggg cggtgtgtac aaggcccggg aacgtattca     180
ccgtggcatg ctgatccacg attactagtg attccaactt catgcaggcg agttgcagcc     240
tgcaatccga actgagaatg gctttaagag attagcttga cctcgcggtt tcgcgactcg     300
ttgtaccatc cattgtagca cgtgtgtagc ccagctcata aggggcatga tgatttgacg     360
tcgtccccac cttcctccgg tttatcaccg gcagtctcac tagagtgccc aactaaatgc     420
tggcaactaa taataagggt tgcgctcgtt gcgggactta acccaacatc tcacgacacg     480
agctgacgac aaccatgcac cacctgtcat tctgtcccg aagggaacgc ccaatctctt     540
gggttggcag aagatgtcaa gagctggtaa ggttcttcgc gtagcatcga attaaaccac     600
atgctccacc acttgtgcgg gcccccgtca attcctttga gtttcaacct tgcggtcgta     660
```

```
ctccccaggc ggaatactta atgcgttagc tgcggcactg aagggcggaa accctccaac        720
acctagtatt catcgtttac ggcatggact accagggtat ctaatcctgt tcgctaccca        780
tgctttcgag cctcagcgtc agtaacagac cagaaagccg ccttcgccac tggtgttctt        840
ccatatatct acgcatttca ccgctacaca tggagttcca ctttcctctt ctgtactcaa        900
gttttgtagt ttccactgca cttcctcagt tgagctgagg ctttcacag cagacttaca         960 aaaccgcctg cgctcgcttt acgcccaata aatccggaca acgcttgcca cctacgtatt       1020
accgcggctg ctggcacgta gttagccgtg gctttctggt aaataccgt caaagtgtta       1080 acagttactc taaacttgt tcttctttaa caacagagtt ttacgatccg aaaaccttca        1140
tcactcacgc ggcgttgctc catcagactt cgtccattg tggaagattc cctactgctg        1200
cctcccgtag gagtctgggc cgtgtctcag tcccaatgtg gccgattacc ctctcaggtc       1260
ggctacgtat catcgtcttg gtgggctttt atctcaccaa ctaactaata cggcgcgggt       1320
ccatcccaaa gtgatagcaa agccatcttt caagttggaa ccatgcggtt ccaactaatt       1380
atgcggtatt agcacttgtt tccaaatgtt atccccgct tcggggcagg ttacccacgt        1440
gttactcacc agtcgccac tcgctccgaa tccaaaaatc atttatgcaa gcataaaatc        1500
aatttgggag aactcgttcg acttgcatgt attaggcacg ccgccagcgt tcgtcctgag       1560
ccaggatcaa actctcatct taa                                              1583

<210> SEQ ID NO 38
<211> LENGTH: 1395
<212> TYPE: DNA
<213> ORGANISM: Lactobacillus Firm-4

<400> SEQUENCE: 38
acgaacgctg gcggcgtgcc taatacatgc aagtcgagcg cgggaagtca gggaagcctt         60
cgggtggaac tggtggaacg agcggcggat gggtgagtaa cacgtaggta acctgcccta        120
aagcggggga taccatctgg aaacaggtgc taataccgca taaacccagc agtcacatga        180
gtgctggttg aaagacggct tcggctgtca ctttaggatg gacctgcggc gtattagcta        240
gttggtggag taacggttca ccaaggcaat gatacgtagc cgacctgaga gggtaatcgg        300
ccacattggg actgagacac ggcccaaact cctacgggag gcagcagtag ggaatcttcc        360
acaatggacg caagtctgat ggagcaacgc cgcgtggatg aagaaggtct tcggatcgta        420
aaatcctgtt gttgaagaag aacggttgtg agagtaactg ctcataacgt gacggtaatc        480
aaccagaaag tcacggctaa ctacgtgcca gcagccgcgg taatacgtag gtggcaagcg        540
ttgtccggat ttattgggcg taagggagc gcaggcggtc ttttaagtct gaatgtgaaa         600
gccctcagct taactgagga agagcatcgg aaactgagag acttgagtgc agaagaggag        660
agtggaactc catgtgtagc ggtgaaatgc gtagatatat ggaagaacac cagtggcgaa        720
ggcggctctc tggtctgtta ctgacgctga ggctcgaaag catgggtagc gaacaggatt        780
agataccctg gtagtccatg ccgtaaacga tgagtgctaa gtgttgggag gtttccgcct        840
ctcagtgctg cagctaacgc attaagcact ccgcctgggg agtacgaccg caaggttgaa        900
actcaaagga attgacgggg gcccgcacaa gcggtggagc atgtggttta attcgaagca        960
acgcgaagaa ccttaccagg tcttgacatc tcctgcaagc ctaagagatt aggggttccc       1020
ttcggggaca ggaagacagg tggtgcatgg ttgtcgtcag ctcgtgtcgt gagatgttgg       1080
gttaagtccc gcaacgagcg caacccttgt tactagttgc cagcattaag ttgggcactc       1140
```

| | |
|---|---|
| tagtgagact gccggtgaca aaccggagga aggtggggac gacgtcaaat catcatgccc | 1200 |
| cttatgacct gggctacaca cgtgctacaa tggatggtac aatgagaagc gaactcgcga | 1260 |
| ggggaagctg atctctgaaa accattctca gttcggattg caggctgcaa ctcgcctgca | 1320 |
| tgaagctgga atcgctagta atcgcggatc agcatgccgc ggtgaatacg ttcccgggcc | 1380 |
| ttgtacacac cgccc | 1395 |

<210> SEQ ID NO 39
<211> LENGTH: 1549
<212> TYPE: DNA
<213> ORGANISM: Enterococcus

<400> SEQUENCE: 39

| | |
|---|---|
| aggtgatcca gccgcacctt ccgatacggc taccttgtta cgacttcacc ccaatcatct | 60 |
| atcccacctt aggcggctgg ctccaaaaag gttacctcac cgacttcggg tgttacaaac | 120 |
| tctcgtggtg tgacgggcgg tgtgtacaag gcccgggaac gtattcaccg cggcgtgctg | 180 |
| atccgcgatt actagcgatt ccggcttcat gcaggcgagt tgcagcctgc aatccgaact | 240 |
| gagagaagct ttaagagatt tgcatgacct cgcggtctag cgactcgttg tacttcccat | 300 |
| tgtagcacgt gtgtagccca ggtcataagg gcatgatga tttgacgtca tccccacctt | 360 |
| cctccggttt gtcaccggca gtctcgctag agtgcccaac taaatgatgg caactaacaa | 420 |
| taagggttgc gctcgttgcg ggacttaacc caacatctca cgacacgagc tgacgacaac | 480 |
| catgcaccac ctgtcacttt gtccccgaag ggaaagctct atctctagag tggtcaaagg | 540 |
| atgtcaagac ctggtaaggt tcttcgcgtt gcttcgaatt aaaccacatg ctccaccgct | 600 |
| tgtgcgggcc cccgtcaatt cctttgagtt tcaaccttgc ggtcgtactc cccaggcgga | 660 |
| gtgcttaatg cgtttgctgc agcactgaag ggcggaaacc ctccaacact tagcactcat | 720 |
| cgtttacggc gtggactacc agggtatcta atcctgtttg ctccccacgc tttcgagcct | 780 |
| cagcgtcagt tacagaccag agagccgcct tcgccactgg tgttcctcca tatatctacg | 840 |
| catttcaccg ctacacatgg aattccactc tcctcttctg cactcaagtc tcccagtttc | 900 |
| caatgacccc tcccggttga ccgggggct tcacatcag acttaagaaa ccgcctgcgc | 960 |
| tcgctttacg cccaataaat ccggacaacg cttgccacct acgtattacc gcggctgctg | 1020 |
| gcacgtagtt agccgtggct ttctggttag ataccgtcag gggacgttca gttactaacg | 1080 |
| tccttgttct tctctaacaa cagagtttta cgatccgaaa accttcttca ctcacgcggc | 1140 |
| gttgctcggt cagactttcg tccattgccg aagattccct actgctgcct cccgtaggag | 1200 |
| tctgggccgt gtctcagtcc cagtgtggcc gatcaccctc tcaggtcggc tatgcatcgt | 1260 |
| ggccttggtg agccgttacc tcaccaacta gctaatgcac cgcgggtcca tccatcagcg | 1320 |
| acacccgaaa gcgcctttca ctcttatgcc atgcggcata aactgttatg cggtattagc | 1380 |
| acctgttccc aagtgttatc cccctctgat gggtaggtta cccacgtgtt actcacccgt | 1440 |
| ccgccactcc tctttccaat tgagtgcaag cactcgggag gaaagaagcg ttcgacttgc | 1500 |
| atgtattagg cacgccgcca gcgttcgtcc tgagccagga tcaaactct | 1549 |

<210> SEQ ID NO 40
<211> LENGTH: 1541
<212> TYPE: DNA
<213> ORGANISM: Delftia

<400> SEQUENCE: 40

| | |
|---|---|
| cagaaaggag gtgatccagc cgcaccttcc gatacggcta ccttgttacg acttcacccc | 60 |

```
agtcacgaac cccgccgtgg taagcgccct ccttgcggtt aggctaccta cttctggcga    120
gacccgctcc catggtgtga cgggcggtgt gtacaagacc cgggaacgta ttcaccgcgg    180
catgctgatc cgcgattact agcgattccg acttcacgca gtcgagttgc agactgcgat    240
ccggactacg actggtttta tgggattagc tccccctcgc gggttggcaa ccctctgtac    300
cagccattgt atgacgtgtg tagccccacc tataagggcc atgaggactt gacgtcatcc    360
ccaccttcct ccggtttgtc accggcagtc tcattagagt gctcaactga atgtagcaac    420
taatgacaag ggttgcgctc gttgcgggac ttaacccaac atctcacgac acgagctgac    480
gacagccatg cagcacctgt gtgcaggttc tctttcgagc acgaatccat ctctggaaac    540
ttcctgccat gtcaaaggtg ggtaaggttt tcgcgttgc atcgaattaa accacatcat    600
ccaccgcttg tgcgggtccc cgtcaattcc tttgagtttc aaccttgcgg ccgtactccc    660
caggcggtca acttcacgcg ttagcttcgt tactgagaaa actaattccc aacaaccagt    720
tgacatcgtt tagggcgtgg actaccaggg tatctaatcc tgtttgctcc ccacgctttc    780
gtgcatgagc gtcagtacag gtccagggga ttgccttcgc catcggtgtt cctccgcata    840
tctacgcatt tcactgctac acgcggaatt ccatcccct ctaccgtact ctagccatgc    900
agtcacaaat gcagttccca ggttgagccc ggggatttca catctgtctt acataaccgc    960
ctgcgcacgc tttacgccca gtaattccga ttaacgctcg caccctacgt attaccgcgg   1020
ctgctggcac gtagttagcc ggtgcttatt cttacggtac cgtcatgggc ccctgtatt   1080 agaaggagct ttttcgttcc gtacaaaagc agtttacaac ccgaaggcct tcatcctgca   1140
cgcggcattg ctggatcagg ctttcgccca ttgtccaaaa ttccccactg ctgcctcccg   1200
taggagtctg ggccgtgtct cagtcccagt gtggctggtc gtcctctcag accagctaca   1260
gatcgtcggc ttggtaagct tttatcccac caactaccta atctgccatc ggccgctcca   1320
atcgcgcgag gcccgaaggg cccccgcttt catcctcaga tcgtatgcgg tattagctac   1380
tctttcgagt agttatcccc cacgactggg cacgttccga tgtattactc acccgttcgc   1440
cactcgtcag cgtccgaaga cctgttaccg ttcgacttgc atgtgtaagg catgccgcca   1500
gcgttcaatc tgagccagga tcaaactcta cagttcgatc t                       1541
```

<210> SEQ ID NO 41
<211> LENGTH: 1502
<212> TYPE: DNA
<213> ORGANISM: Pelomonas
<220> FEATURE:
<221> NAME/KEY: misc_feature
<222> LOCATION: (192)..(193)
<223> OTHER INFORMATION: n is a, g, c, or t
<220> FEATURE:
<221> NAME/KEY: misc_feature
<222> LOCATION: (832)..(833)
<223> OTHER INFORMATION: n is a, g, c, or t

<400> SEQUENCE: 41

```
atcctggctc agattgaacg ctggcggcat gccttacaca tgcaagtcga acggtaacag    60
gttaagctga cgagtggcga acgggtgagt aatatatcgg aacgtgccca gtcgtggggg   120
ataactgctc gaaagagcag ctaataccgc atacgacctg agggtgaaag cggggggatcg   180 caagacctcg cnngattgga gcggccgata tcagattagg tagttggtgg ggtaaaggcc   240
caccaagcca acgatctgta gctggtctga gaggacgacc agccacactg ggactgagac   300
acggcccaga ctcctacggg aggcagcagt ggggaatttt ggacaatggg cgcaagcctg   360
```

```
atccagccat gccgcgtgcg ggaagaaggc cttcgggttg taaaccgctt ttgtcaggga    420
agaaaaggtt ctggttaata cctgggactc atgacggtac ctgaagaata agcaccggct    480
aactacgtgc cagcagccgc ggtaatacgt agggtgcaag cgttaatcgg aattactggg    540
cgtaaagcgt gcgcaggcgg ttatgcaaga cagaggtgaa atccccgggc tcaacctggg    600
aactgccttt gtgactgcat agctagagta cggtagaggg ggatggaatt ccgcgtgtag    660
cagtgaaatg cgtagatatg cggaggaaca ccgatggcga aggcaatccc ctggacctgt    720
actgacgctc atgcacgaaa gcgtggggag caaacaggat tagataccct ggtagtccac    780
gccctaaacg atgtcaactg gttgttggga gggtttcttc tcagtaacgt anntaacgcg    840
tgaagttgac cgcctgggga gtacggccgc aaggttgaaa ctcaaaggaa ttgacgggga    900
cccgcacaag cggtggatga tgtggtttaa ttcgatgcaa cgcgaaaaac cttacctacc    960
cttgacatgc caggaatcct gaagagattt gggagtgctc gaaagagaac ctggacacag   1020
gtgctgcatg gccgtcgtca gctcgtgtcg tgagatgttg ggttaagtcc cgcaacgagc   1080
gcaacccttg tcattagttg ctacgaaagg gcactctaat gagactgccg gtgacaaacc   1140
ggaggaaggt ggggatgacg tcaggtcatc atggccctta tgggtagggc tacacacgtc   1200
atacaatggc cggacagag ggctgccaac ccgcgagggg gagctaatcc cagaaacccg    1260
gtcgtagtcc ggatcgtagt ctgcaactcg actgcgtgaa gtcggaatcg ctagtaatcg   1320
cggatcagct tgccgcggtg aatacgttcc cgggtcttgt acacaccgcc cgtcacacca   1380
tgggagcggg ttctgccaga agtagttagc ctaaccgcaa ggagggcgat taccacggca   1440
gggttcgtga ctggggtgaa gtcgtaacaa ggtagccgta tcggaaggtg cggctggatc   1500
ac                                                                  1502
```

<210> SEQ ID NO 42
<211> LENGTH: 34
<212> TYPE: PRT
<213> ORGANISM: Lactococcus lactis

<400> SEQUENCE: 42

Ile Thr Ser Ile Ser Leu Cys Thr Pro Gly Cys Lys Thr Gly Ala Leu
1               5                   10                  15

Met Gly Cys Asn Met Lys Thr Ala Thr Cys His Cys Ser Ile His Val
            20                  25                  30

Ser Lys

<210> SEQ ID NO 43
<211> LENGTH: 22
<212> TYPE: PRT
<213> ORGANISM: Staphylococcus epidermis

<400> SEQUENCE: 43

Ile Ala Ser Lys Phe Ile Cys Thr Pro Gly Cys Ala Lys Thr Gly Ser
1               5                   10                  15

Phe Asn Ser Tyr Cys Cys
            20

<210> SEQ ID NO 44
<211> LENGTH: 44
<212> TYPE: PRT
<213> ORGANISM: Pediococcus acidilactici

<400> SEQUENCE: 44

Lys Tyr Tyr Gly Asn Gly Val Thr Cys Gly Lys His Ser Cys Ser Val

```
                1               5                   10                  15
Asp Trp Gly Lys Ala Thr Thr Cys Ile Ile Asn Asn Gly Ala Met Ala
                    20                  25                  30

Trp Ala Thr Gly Gly His Gln Gly Asn His Lys Cys
            35                  40

<210> SEQ ID NO 45
<211> LENGTH: 44
<212> TYPE: PRT
<213> ORGANISM: Enterococcus faecium

<400> SEQUENCE: 45

Ala Thr Arg Ser Tyr Gly Asn Gly Val Tyr Cys Asn Asn Ser Lys Cys
1               5                   10                  15

Trp Val Asn Trp Gly Glu Ala Lys Glu Asn Ile Ala Gly Ile Val Ile
            20                  25                  30

Ser Gly Trp Ala Ser Gly Leu Ala Gly Met Gly His
            35                  40

<210> SEQ ID NO 46
<211> LENGTH: 39
<212> TYPE: PRT
<213> ORGANISM: Streptococcus lactis

<400> SEQUENCE: 46

Gly Thr Trp Asp Asp Ile Gly Gln Gly Ile Gly Arg Val Ala Tyr Trp
1               5                   10                  15

Val Gly Lys Ala Met Gly Asn Met Ser Asp Val Asn Gln Ala Ser Arg
            20                  25                  30

Ile Asn Arg Lys Lys Lys His
            35

<210> SEQ ID NO 47
<211> LENGTH: 48
<212> TYPE: PRT
<213> ORGANISM: Lactobacillus johnsonii

<400> SEQUENCE: 47

Asn Arg Trp Gly Asp Thr Val Leu Ser Ala Ala Ser Gly Ala Gly Thr
1               5                   10                  15

Gly Ile Lys Ala Cys Lys Ser Phe Gly Pro Trp Gly Met Ala Ile Cys
            20                  25                  30

Gly Val Gly Gly Ala Ala Ile Gly Gly Tyr Phe Gly Tyr Thr His Asn
            35                  40                  45

<210> SEQ ID NO 48
<211> LENGTH: 70
<212> TYPE: PRT
<213> ORGANISM: Enterococcus faecalis

<400> SEQUENCE: 48

Met Ala Lys Glu Phe Gly Ile Pro Ala Ala Val Ala Gly Thr Val Leu
1               5                   10                  15

Asn Val Val Glu Ala Gly Gly Trp Val Thr Thr Ile Val Ser Ile Leu
            20                  25                  30

Thr Ala Val Gly Ser Gly Gly Leu Ser Leu Leu Ala Ala Ala Gly Arg
            35                  40                  45

Glu Ser Ile Lys Ala Tyr Leu Lys Lys Glu Ile Lys Lys Lys Gly Lys
            50                  55                  60
```

Arg Ala Val Ile Ala Trp
 65                  70

<210> SEQ ID NO 49
<211> LENGTH: 51
<212> TYPE: PRT
<213> ORGANISM: Staphylococcus aureus

<400> SEQUENCE: 49

Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
        35                  40                  45

Ala Gly Leu
    50

<210> SEQ ID NO 50
<211> LENGTH: 43
<212> TYPE: PRT
<213> ORGANISM: Lactococcus garvieae

<400> SEQUENCE: 50

Ile Gly Gly Ala Leu Gly Asn Ala Leu Asn Gly Leu Gly Thr Trp Ala
1               5                   10                  15

Asn Met Met Asn Gly Gly Gly Phe Val Asn Gln Trp Gln Val Tyr Ala
            20                  25                  30

Asn Lys Gly Lys Ile Asn Gln Tyr Arg Pro Tyr
        35                  40

<210> SEQ ID NO 51
<211> LENGTH: 103
<212> TYPE: PRT
<213> ORGANISM: Escherichia coli

<400> SEQUENCE: 51

Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
            20                  25                  30

Val Ala Gly Gly Ile Gly Ala Ala Ala Gly Gly Val Ala Gly Gly Ala
        35                  40                  45

Ile Tyr Asp Tyr Ala Ser Thr His Lys Pro Asn Pro Ala Met Ser Pro
    50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100

<210> SEQ ID NO 52
<211> LENGTH: 339
<212> TYPE: PRT
<213> ORGANISM: Streptococcus phage Cp1

<400> SEQUENCE: 52

Met Val Lys Lys Asn Asp Leu Phe Val Asp Val Ser Ser His Asn Gly
1               5                   10                  15

```
Tyr Asp Ile Thr Gly Ile Leu Glu Gln Met Gly Thr Asn Thr Ile
            20                  25                  30

Ile Lys Ile Ser Glu Ser Thr Thr Tyr Leu Asn Pro Cys Leu Ser Ala
        35                  40                  45

Gln Val Glu Gln Ser Asn Pro Ile Gly Phe Tyr His Phe Ala Arg Phe
50                  55                  60

Gly Gly Asp Val Ala Glu Ala Glu Arg Glu Ala Gln Phe Phe Leu Asp
65                  70                  75                  80

Asn Val Pro Met Gln Val Lys Tyr Leu Val Leu Asp Tyr Glu Asp Asp
                85                  90                  95

Pro Ser Gly Asp Ala Gln Ala Asn Thr Asn Ala Cys Leu Arg Phe Met
            100                 105                 110

Gln Met Ile Ala Asp Ala Gly Tyr Lys Pro Ile Tyr Tyr Ser Tyr Lys
        115                 120                 125

Pro Phe Thr His Asp Asn Val Asp Tyr Gln Gln Ile Leu Ala Gln Phe
130                 135                 140

Pro Asn Ser Leu Trp Ile Ala Gly Tyr Gly Leu Asn Asp Gly Thr Ala
145                 150                 155                 160

Asn Phe Glu Tyr Phe Pro Ser Met Asp Gly Ile Arg Trp Trp Gln Tyr
                165                 170                 175

Ser Ser Asn Pro Phe Asp Lys Asn Ile Val Leu Leu Asp Asp Glu Glu
            180                 185                 190

Asp Asp Lys Pro Lys Thr Ala Gly Thr Trp Lys Gln Asp Ser Lys Gly
        195                 200                 205

Trp Trp Phe Arg Arg Asn Asn Gly Ser Phe Pro Tyr Asn Lys Trp Glu
210                 215                 220

Lys Ile Gly Gly Val Trp Tyr Tyr Phe Asp Ser Lys Gly Tyr Cys Leu
225                 230                 235                 240

Thr Ser Glu Trp Leu Lys Asp Asn Glu Lys Trp Tyr Tyr Leu Lys Asp
                245                 250                 255

Asn Gly Ala Met Ala Thr Gly Trp Val Leu Val Gly Ser Glu Trp Tyr
            260                 265                 270

Tyr Met Asp Asp Ser Gly Ala Met Val Thr Gly Trp Val Lys Tyr Lys
        275                 280                 285

Asn Asn Trp Tyr Tyr Met Thr Asn Glu Arg Gly Asn Met Val Ser Asn
290                 295                 300

Glu Phe Ile Lys Ser Gly Lys Gly Trp Tyr Phe Met Asn Thr Asn Gly
305                 310                 315                 320

Glu Leu Ala Asp Asn Pro Ser Phe Thr Lys Glu Pro Asp Gly Leu Ile
                325                 330                 335

Thr Val Ala

<210> SEQ ID NO 53
<211> LENGTH: 296
<212> TYPE: PRT
<213> ORGANISM: Streptococcus phage Dp-1

<400> SEQUENCE: 53

Met Gly Val Asp Ile Glu Lys Gly Val Ala Trp Met Gln Ala Arg Lys
1               5                   10                  15

Gly Arg Val Ser Tyr Ser Met Asp Phe Arg Asp Gly Pro Asp Ser Tyr
            20                  25                  30

Asp Cys Ser Ser Ser Met Tyr Tyr Ala Leu Arg Ser Ala Gly Ala Ser
        35                  40                  45
```

```
Ser Ala Gly Trp Ala Val Asn Thr Glu Tyr Met His Ala Trp Leu Ile
 50                  55                  60

Glu Asn Gly Tyr Glu Leu Ile Ser Glu Asn Ala Pro Trp Asp Ala Lys
 65                  70                  75                  80

Arg Gly Asp Ile Phe Ile Trp Gly Arg Lys Gly Ala Ser Ala Gly Ala
                 85                  90                  95

Gly Gly His Thr Gly Met Phe Ile Asp Ser Asp Asn Ile Ile His Cys
                100                 105                 110

Asn Tyr Ala Tyr Asp Gly Ile Ser Val Asn Asp His Asp Glu Arg Trp
                115                 120                 125

Tyr Tyr Ala Gly Gln Pro Tyr Tyr Val Tyr Arg Leu Thr Asn Ala
130                 135                 140

Asn Ala Gln Pro Ala Glu Lys Lys Leu Gly Trp Gln Lys Asp Ala Thr
145                 150                 155                 160

Gly Phe Trp Tyr Ala Arg Ala Asn Gly Thr Tyr Pro Lys Asp Glu Phe
                165                 170                 175

Glu Tyr Ile Glu Glu Asn Lys Ser Trp Phe Tyr Phe Asp Asp Gln Gly
                180                 185                 190

Tyr Met Leu Ala Glu Lys Trp Leu Lys His Thr Asp Gly Asn Trp Tyr
                195                 200                 205

Trp Phe Asp Arg Asp Gly Tyr Met Ala Thr Ser Trp Lys Arg Ile Gly
210                 215                 220

Glu Ser Trp Tyr Tyr Phe Asn Arg Asp Gly Ser Met Val Thr Gly Trp
225                 230                 235                 240

Ile Lys Tyr Tyr Asp Asn Trp Tyr Tyr Cys Asp Ala Thr Asn Gly Asp
                245                 250                 255

Met Lys Ser Asn Ala Phe Ile Arg Tyr Asn Asp Gly Trp Tyr Leu Leu
                260                 265                 270

Leu Pro Asp Gly Arg Leu Ala Asp Lys Pro Gln Phe Thr Val Glu Pro
                275                 280                 285

Asp Gly Leu Ile Thr Ala Lys Val
                290                 295

<210> SEQ ID NO 54
<211> LENGTH: 233
<212> TYPE: PRT
<213> ORGANISM: Bacillus phage gamma

<400> SEQUENCE: 54

Met Glu Ile Gln Lys Lys Leu Val Asp Pro Ser Lys Tyr Gly Thr Lys
 1                   5                  10                  15

Cys Pro Tyr Thr Met Lys Pro Lys Tyr Ile Thr Val His Asn Thr Tyr
                 20                  25                  30

Asn Asp Ala Pro Ala Glu Asn Glu Val Ser Tyr Met Ile Ser Asn Asn
                 35                  40                  45

Asn Glu Val Ser Phe His Ile Ala Val Asp Asp Lys Lys Ala Ile Gln
 50                  55                  60

Gly Ile Pro Leu Glu Arg Asn Ala Trp Ala Cys Gly Asp Gly Asn Gly
 65                  70                  75                  80

Ser Gly Asn Arg Gln Ser Ile Ser Val Glu Ile Cys Tyr Ser Lys Ser
                 85                  90                  95

Gly Gly Asp Arg Tyr Tyr Lys Ala Glu Asp Asn Ala Val Asp Val Val
                100                 105                 110

Arg Gln Leu Met Ser Met Tyr Asn Ile Pro Ile Glu Asn Val Arg Thr
```

```
                115                 120                 125
His Gln Ser Trp Ser Gly Lys Tyr Cys Pro His Arg Met Leu Ala Glu
        130                 135                 140

Gly Arg Trp Gly Ala Phe Ile Gln Lys Val Lys Asn Gly Asn Val Ala
145                 150                 155                 160

Thr Thr Ser Pro Thr Lys Gln Asn Ile Ile Gln Ser Gly Ala Phe Ser
                165                 170                 175

Pro Tyr Glu Thr Pro Asp Val Met Gly Ala Leu Thr Ser Leu Lys Met
            180                 185                 190

Thr Ala Asp Phe Ile Leu Gln Ser Asp Gly Leu Thr Tyr Phe Ile Ser
        195                 200                 205

Lys Pro Thr Ser Asp Ala Gln Leu Lys Ala Met Lys Glu Tyr Leu Asp
    210                 215                 220

Arg Lys Gly Trp Trp Tyr Glu Val Lys
225                 230

<210> SEQ ID NO 55
<211> LENGTH: 481
<212> TYPE: PRT
<213> ORGANISM: Staphylococcus phage phi MR11

<400> SEQUENCE: 55

Met Gln Ala Lys Leu Thr Lys Lys Glu Phe Ile Glu Trp Leu Lys Thr
1               5                   10                  15

Ser Glu Gly Lys Gln Phe Asn Val Asp Leu Trp Tyr Gly Phe Gln Cys
                20                  25                  30

Phe Asp Tyr Ala Asn Ala Gly Trp Lys Val Leu Phe Gly Leu Leu Leu
            35                  40                  45

Lys Gly Leu Gly Ala Lys Asp Ile Pro Phe Ala Asn Asn Phe Asp Gly
50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Ile Val Tyr Glu Gln
            100                 105                 110

Asn Trp Leu Gly Gly Gly Trp Thr Asp Arg Ile Glu Gln Pro Gly Trp
        115                 120                 125

Gly Trp Glu Lys Val Thr Arg Arg Gln His Ala Tyr Asp Phe Pro Met
    130                 135                 140

Trp Phe Ile Arg Pro Asn Phe Lys Ser Glu Thr Ala Pro Arg Ser Ile
145                 150                 155                 160

Gln Ser Pro Thr Gln Ala Ser Lys Glu Thr Ala Lys Pro Gln Pro
                165                 170                 175

Lys Ala Val Glu Leu Lys Ile Ile Lys Asp Val Val Lys Gly Tyr Asp
            180                 185                 190

Leu Pro Lys Arg Gly Gly Asn Pro Lys Gly Ile Val Ile His Asn Asp
        195                 200                 205

Ala Gly Ser Lys Gly Ala Thr Ala Glu Ala Tyr Arg Asn Gly Leu Val
    210                 215                 220

Asn Ala Pro Leu Ser Arg Leu Glu Ala Gly Ile Ala His Ser Tyr Val
225                 230                 235                 240

Ser Gly Asn Thr Val Trp Gln Ala Leu Asp Glu Ser Gln Val Gly Trp
                245                 250                 255
```

His Thr Ala Asn Gln Leu Gly Asn Lys Tyr Tyr Gly Ile Glu Val
            260                 265                 270

Cys Gln Ser Met Gly Ala Asp Asn Ala Thr Phe Leu Lys Asn Glu Gln
        275                 280                 285

Ala Thr Phe Gln Glu Cys Ala Arg Leu Leu Lys Lys Trp Gly Leu Pro
    290                 295                 300

Ala Asn Arg Asn Thr Ile Arg Leu His Asn Glu Phe Thr Ser Thr Ser
305                 310                 315                 320

Cys Pro His Arg Ser Ser Val Leu His Thr Gly Phe Asp Pro Val Thr
                325                 330                 335

Arg Gly Leu Leu Pro Glu Asp Lys Gln Leu Gln Leu Lys Asp Tyr Phe
            340                 345                 350

Ile Lys Gln Ile Arg Val Tyr Met Asp Gly Lys Ile Pro Val Ala Thr
        355                 360                 365

Val Ser Asn Glu Ser Ser Ala Ser Ser Asn Thr Val Lys Pro Val Ala
    370                 375                 380

Ser Ala Trp Lys Arg Asn Lys Tyr Gly Thr Tyr Tyr Met Glu Glu Asn
385                 390                 395                 400

Ala Arg Phe Thr Asn Gly Asn Gln Pro Ile Thr Val Arg Lys Ile Gly
                405                 410                 415

Pro Phe Leu Ser Cys Pro Val Ala Tyr Gln Phe Gln Pro Gly Gly Tyr
            420                 425                 430

Cys Asp Tyr Thr Glu Val Met Leu Gln Asp Gly His Val Trp Val Gly
        435                 440                 445

Tyr Thr Trp Glu Gly Gln Arg Tyr Tyr Leu Pro Ile Arg Thr Trp Asn
    450                 455                 460

Gly Ser Ala Pro Pro Asn Gln Ile Leu Gly Asp Leu Trp Gly Glu Ile
465                 470                 475                 480

Ser

<210> SEQ ID NO 56
<211> LENGTH: 239
<212> TYPE: PRT
<213> ORGANISM: Streptococcus phage B30

<400> SEQUENCE: 56

Met Val Ile Asn Ile Glu Gln Ala Ile Ala Trp Met Ala Ser Arg Lys
1               5                   10                  15

Gly Lys Val Thr Tyr Ser Met Asp Tyr Arg Asn Gly Pro Ser Ser Tyr
            20                  25                  30

Asp Cys Ser Ser Ser Val Tyr Phe Ala Leu Arg Ser Ala Gly Ala Ser
        35                  40                  45

Asp Asn Gly Trp Ala Val Asn Thr Glu Tyr Glu His Asp Trp Leu Ile
    50                  55                  60

Lys Asn Gly Tyr Val Leu Ile Ala Glu Asn Thr Asn Trp Asn Ala Gln
65                  70                  75                  80

Arg Gly Asp Ile Phe Ile Trp Gly Lys Arg Gly Ala Ser Ala Gly Ala
                85                  90                  95

Phe Gly His Thr Gly Met Phe Val Asp Pro Asp Asn Ile Ile His Cys
            100                 105                 110

Asn Tyr Gly Tyr Asn Ser Ile Thr Val Asn Asn His Asp Glu Ile Trp
        115                 120                 125

Gly Tyr Asn Gly Gln Pro Tyr Val Tyr Ala Tyr Arg Tyr Ser Gly Lys
    130                 135                 140

```
Gln Ser Asn Ala Lys Val Asp Asn Lys Ser Val Ser Lys Phe Glu
145                 150                 155                 160

Lys Glu Leu Asp Val Asn Thr Pro Leu Ser Asn Ser Asn Met Pro Tyr
                165                 170                 175

Tyr Glu Ala Thr Ile Ser Glu Asp Tyr Tyr Val Glu Ser Lys Pro Asp
            180                 185                 190

Val Asn Ser Thr Asp Lys Glu Leu Leu Val Ala Gly Thr Arg Val Arg
        195                 200                 205

Val Tyr Glu Lys Val Lys Gly Trp Ala Arg Ile Gly Ala Pro Gln Ser
        210                 215                 220

Asn Gln Trp Val Glu Asp Ala Tyr Leu Ile Asp Ala Thr Asp Met
225                 230                 235
```

<210> SEQ ID NO 57
<211> LENGTH: 495
<212> TYPE: PRT
<213> ORGANISM: Staphylococcus phage K

<400> SEQUENCE: 57

```
Met Ala Lys Thr Gln Ala Glu Ile Asn Lys Arg Leu Asp Ala Tyr Ala
1               5                   10                  15

Lys Gly Thr Val Asp Ser Pro Tyr Arg Val Lys Lys Ala Thr Ser Tyr
                20                  25                  30

Asp Pro Ser Phe Gly Val Met Glu Ala Gly Ala Ile Asp Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95

Thr Val Pro Lys Lys Gly Trp Ile Ala Val Phe Thr Ser Gly Ser Tyr
            100                 105                 110

Glu Gln Trp Gly His Ile Gly Ile Val Tyr Asp Gly Gly Asn Thr Ser
        115                 120                 125

Thr Phe Thr Ile Leu Glu Gln Asn Trp Asn Gly Tyr Ala Asn Lys Lys
130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285
```

```
Ala Ser Asp Ala Gln Phe Leu Lys Asn Glu Gln Ala Val Phe Gln Phe
        290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Thr Val Val Lys Asp Gly
370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
        435                 440                 445

Tyr Asp Glu Val Cys Ile Gln Ala Gly His Ile Trp Ile Gly Tyr Asn
450                 455                 460

Ala Tyr Asn Gly Asn Arg Val Tyr Cys Pro Val Arg Thr Cys Gln Gly
465                 470                 475                 480

Val Pro Pro Asn Gln Ile Pro Gly Val Ala Trp Gly Val Phe Lys
                485                 490                 495

<210> SEQ ID NO 58
<211> LENGTH: 281
<212> TYPE: PRT
<213> ORGANISM: Listeria phage A118

<400> SEQUENCE: 58

Met Thr Ser Tyr Tyr Ser Arg Ser Leu Ala Asn Val Asn Lys Leu
1               5                   10                  15

Ala Asp Asn Thr Lys Ala Ala Arg Lys Leu Leu Asp Trp Ser Glu
            20                  25                  30

Ser Asn Gly Ile Glu Val Leu Ile Tyr Glu Thr Ile Arg Thr Lys Glu
        35                  40                  45

Gln Gln Ala Ala Asn Val Asn Ser Gly Ala Ser Gln Thr Met Arg Ser
    50                  55                  60

Tyr His Leu Val Gly Gln Ala Leu Asp Phe Val Met Ala Lys Gly Lys
65                  70                  75                  80

Thr Val Asp Trp Gly Ala Tyr Arg Ser Asp Lys Gly Lys Lys Phe Val
                85                  90                  95

Ala Lys Ala Lys Ser Leu Gly Phe Glu Trp Gly Gly Asp Trp Ser Gly
            100                 105                 110

Phe Val Asp Asn Pro His Leu Gln Phe Asn Tyr Lys Gly Tyr Gly Thr
        115                 120                 125

Asp Thr Phe Gly Lys Gly Ala Ser Thr Ser Asn Ser Ser Lys Pro Ser
130                 135                 140

Ala Asp Thr Asn Thr Asn Ser Leu Gly Leu Val Asp Tyr Met Asn Leu
145                 150                 155                 160

Asn Lys Leu Asp Ser Ser Phe Ala Asn Arg Lys Lys Leu Ala Thr Ser
```

```
            165                 170                 175
Tyr Gly Ile Lys Asn Tyr Ser Gly Thr Ala Thr Gln Asn Thr Thr Leu
            180                 185                 190

Leu Ala Lys Leu Lys Ala Gly Lys Pro His Thr Pro Ala Ser Lys Asn
            195                 200                 205

Thr Tyr Tyr Thr Glu Asn Pro Arg Lys Val Lys Thr Leu Val Gln Cys
        210                 215                 220

Asp Leu Tyr Lys Ser Val Asp Phe Thr Thr Lys Asn Gln Thr Gly Gly
225                 230                 235                 240

Thr Phe Pro Pro Gly Thr Val Phe Thr Ile Ser Gly Met Gly Lys Thr
                245                 250                 255

Lys Gly Gly Thr Pro Arg Leu Lys Thr Lys Ser Gly Tyr Tyr Leu Thr
                260                 265                 270

Ala Asn Thr Lys Phe Val Lys Lys Ile
                275                 280

<210> SEQ ID NO 59
<211> LENGTH: 341
<212> TYPE: PRT
<213> ORGANISM: Listeria phage A511

<400> SEQUENCE: 59

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
            20                  25                  30

Ser Lys Ser Thr Ile Asp Asn Glu Val Ser Tyr Met Thr Arg Asn Trp
        35                  40                  45

Lys Asn Ala Phe Val Thr His Phe Val Gly Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
            100                 105                 110

Leu Ala Lys Lys Ala Gly Ile Pro Ile Thr Leu Asp Ser Gly Ser Lys
        115                 120                 125

Thr Ser Asp Lys Gly Ile Lys Ser His Lys Trp Val Ala Asp Lys Leu
    130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ala Pro Lys
            180                 185                 190

Pro Ser Thr Pro Ser Thr Asn Leu Asp Lys Leu Gly Leu Val Asp Tyr
        195                 200                 205

Met Asn Ala Lys Lys Met Asp Ser Ser Tyr Ser Asn Arg Asp Lys Leu
    210                 215                 220

Ala Lys Gln Tyr Gly Ile Ala Asn Tyr Ser Gly Thr Ala Ser Gln Asn
225                 230                 235                 240

Thr Thr Leu Leu Ser Lys Ile Lys Gly Gly Ala Pro Lys Pro Ser Thr
                245                 250                 255
```

```
Pro Ala Pro Lys Pro Ser Thr Ser Thr Ala Lys Lys Ile Tyr Phe Pro
            260                 265                 270

Pro Asn Lys Gly Asn Trp Ser Val Tyr Pro Thr Asn Lys Ala Pro Val
            275                 280                 285

Lys Ala Asn Ala Ile Gly Ala Ile Asn Pro Thr Lys Phe Gly Gly Leu
            290                 295                 300

Thr Tyr Thr Ile Gln Lys Asp Arg Gly Asn Gly Val Tyr Glu Ile Gln
305                 310                 315                 320

Thr Asp Gln Phe Gly Arg Val Gln Val Tyr Gly Ala Pro Ser Thr Gly
                    325                 330                 335

Ala Val Ile Lys Lys
            340

<210> SEQ ID NO 60
<211> LENGTH: 289
<212> TYPE: PRT
<213> ORGANISM: Listeria phage A500

<400> SEQUENCE: 60

Met Ala Leu Thr Glu Ala Trp Leu Ile Glu Lys Ala Asn Arg Lys Leu
1               5                   10                  15

Asn Ala Gly Gly Met Tyr Lys Ile Thr Ser Asp Lys Thr Arg Asn Val
            20                  25                  30

Ile Lys Lys Met Ala Lys Glu Gly Ile Tyr Leu Cys Val Ala Gln Gly
            35                  40                  45

Tyr Arg Ser Thr Ala Glu Gln Asn Ala Leu Tyr Ala Gln Gly Arg Thr
        50                  55                  60

Lys Pro Gly Ala Ile Val Thr Asn Ala Lys Gly Gly Gln Ser Asn His
65                  70                  75                  80

Asn Tyr Gly Val Ala Val Asp Leu Cys Leu Tyr Thr Asn Asp Gly Lys
                85                  90                  95

Asp Val Ile Trp Glu Ser Thr Thr Ser Arg Trp Lys Lys Val Val Ala
            100                 105                 110

Ala Met Lys Ala Glu Gly Phe Lys Trp Gly Gly Asp Trp Lys Ser Phe
            115                 120                 125

Lys Asp Tyr Pro His Phe Glu Leu Cys Asp Ala Val Ser Gly Glu Lys
        130                 135                 140

Ile Pro Ala Ala Thr Gln Asn Thr Asn Thr Asn Ser Asn Arg Tyr Glu
145                 150                 155                 160

Gly Lys Val Ile Asp Ser Ala Pro Leu Leu Pro Lys Met Asp Phe Lys
                165                 170                 175

Ser Ser Pro Phe Arg Met Tyr Lys Val Gly Thr Glu Phe Leu Val Tyr
            180                 185                 190

Asp His Asn Gln Tyr Trp Tyr Lys Thr Tyr Ile Asp Asp Lys Leu Tyr
            195                 200                 205

Tyr Met Tyr Lys Ser Phe Cys Asp Val Ala Lys Lys Asp Ala Lys
        210                 215                 220

Gly Arg Ile Lys Val Arg Ile Lys Ser Ala Lys Asp Leu Arg Ile Pro
225                 230                 235                 240

Val Trp Asn Asn Ile Lys Leu Asn Ser Gly Lys Ile Lys Trp Tyr Ala
                245                 250                 255

Pro Asn Val Lys Leu Ala Trp Tyr Asn Tyr Arg Arg Gly Tyr Leu Glu
            260                 265                 270

Leu Trp Tyr Pro Asn Asp Gly Trp Tyr Tyr Thr Ala Glu Tyr Phe Leu
            275                 280                 285
```

Lys

<210> SEQ ID NO 61
<211> LENGTH: 239
<212> TYPE: PRT
<213> ORGANISM: Streptococcus prophage LambdaSa1

<400> SEQUENCE: 61

Met Val Ile Asn Ile Glu Gln Ala Ile Ala Trp Met Ala Ser Arg Lys
1               5                   10                  15

Gly Lys Val Thr Tyr Ser Met Asp Tyr Arg Asn Gly Pro Ser Ser Tyr
            20                  25                  30

Asp Cys Ser Ser Val Tyr Phe Ala Leu Arg Ser Ala Gly Ala Ser
        35                  40                  45

Asp Asn Gly Trp Ala Val Asn Thr Glu Tyr Glu His Asp Trp Leu Ile
    50                  55                  60

Lys Asn Gly Tyr Val Leu Ile Ala Glu Asn Thr Asn Trp Asn Ala Gln
65                  70                  75                  80

Arg Gly Asp Ile Phe Ile Trp Gly Lys Arg Gly Ala Ser Ala Gly Ala
                85                  90                  95

Phe Gly His Thr Gly Met Phe Val Asp Pro Asp Asn Ile Ile His Cys
            100                 105                 110

Asn Tyr Gly Tyr Asn Ser Ile Thr Val Asn Asn His Asp Glu Ile Trp
        115                 120                 125

Gly Tyr Asn Gly Gln Pro Tyr Val Tyr Ala Tyr Arg Tyr Ala Arg Lys
    130                 135                 140

Gln Ser Asn Ala Lys Val Asp Asn Gln Ser Val Val Ser Lys Phe Glu
145                 150                 155                 160

Lys Glu Leu Asp Val Asn Thr Pro Leu Ser Asn Ser Asn Met Pro Tyr
                165                 170                 175

Tyr Glu Ala Thr Ile Ser Glu Asp Tyr Tyr Val Glu Ser Lys Pro Asp
            180                 185                 190

Val Asn Ser Thr Asp Lys Glu Leu Leu Val Ala Gly Thr Arg Val Arg
        195                 200                 205

Val Tyr Glu Lys Val Lys Gly Trp Ala Arg Ile Gly Ala Pro Gln Ser
    210                 215                 220

Asn Gln Trp Val Glu Asp Ala Tyr Leu Ile Asp Ala Thr Asp Met
225                 230                 235

<210> SEQ ID NO 62
<211> LENGTH: 468
<212> TYPE: PRT
<213> ORGANISM: Streptococcus prophage LambdaSa2

<400> SEQUENCE: 62

Met Glu Ile Asn Thr Glu Ile Ala Ile Ala Trp Met Ser Ala Arg Gln
1               5                   10                  15

Gly Lys Val Ser Tyr Ser Met Asp Tyr Arg Asp Gly Pro Asn Ser Tyr
            20                  25                  30

Asp Cys Ser Ser Val Tyr Tyr Ala Leu Arg Ser Ala Gly Ala Ser
        35                  40                  45

Ser Ala Gly Trp Ala Val Asn Thr Glu Tyr Met His Asp Trp Leu Ile
    50                  55                  60

Lys Asn Gly Tyr Glu Leu Ile Ala Glu Asn Val Asp Trp Asn Ala Val
65                  70                  75                  80

```
Arg Gly Asp Ile Ala Ile Trp Gly Met Arg Gly His Ser Ser Gly Ala
                 85                  90                  95
Gly Gly His Val Val Met Phe Ile Asp Pro Glu Asn Ile Ile His Cys
            100                 105                 110
Asn Trp Ala Asn Asn Gly Ile Thr Val Asn Asn Tyr Asn Gln Thr Ala
        115                 120                 125
Ala Ala Ser Gly Trp Met Tyr Cys Tyr Val Tyr Arg Leu Lys Ser Gly
130                 135                 140
Ala Ser Thr Gln Gly Lys Ser Leu Asp Thr Leu Val Lys Glu Thr Leu
145                 150                 155                 160
Ala Gly Asn Tyr Gly Asn Gly Glu Ala Arg Lys Ala Val Leu Gly Asn
                165                 170                 175
Gln Tyr Glu Ala Val Met Ser Val Ile Asn Gly Lys Thr Thr Thr Asn
            180                 185                 190
Gln Lys Thr Val Asp Gln Leu Val Gln Glu Val Ile Ala Gly Lys His
        195                 200                 205
Gly Asn Gly Glu Ala Arg Lys Lys Ser Leu Gly Ser Gln Tyr Asp Ala
210                 215                 220
Val Gln Lys Arg Val Thr Glu Leu Leu Lys Lys Gln Pro Ser Glu Pro
225                 230                 235                 240
Phe Lys Ala Gln Glu Val Asn Lys Pro Thr Glu Thr Lys Thr Ser Gln
                245                 250                 255
Thr Glu Leu Thr Gly Gln Ala Thr Ala Thr Lys Glu Glu Gly Asp Leu
            260                 265                 270
Ser Phe Asn Gly Thr Ile Leu Lys Lys Ala Val Leu Asp Lys Ile Leu
        275                 280                 285
Gly Asn Cys Lys Lys His Asp Ile Leu Pro Ser Tyr Ala Leu Thr Ile
290                 295                 300
Leu His Tyr Glu Gly Leu Trp Gly Thr Ser Ala Val Gly Lys Ala Asp
305                 310                 315                 320
Asn Asn Trp Gly Gly Met Thr Trp Thr Gly Gln Gly Asn Arg Pro Ser
                325                 330                 335
Gly Val Thr Val Thr Gln Gly Ser Ala Arg Pro Ser Asn Glu Gly Gly
            340                 345                 350
His Tyr Met His Tyr Ala Ser Val Asp Asp Phe Leu Thr Asp Trp Phe
        355                 360                 365
Tyr Leu Leu Arg Ala Gly Gly Ser Tyr Lys Val Ser Gly Ala Lys Thr
370                 375                 380
Phe Ser Glu Ala Ile Lys Gly Met Phe Lys Val Gly Gly Ala Val Tyr
385                 390                 395                 400
Asp Tyr Ala Ala Ser Gly Phe Asp Ser Tyr Ile Val Gly Ala Ser Ser
                405                 410                 415
Arg Leu Lys Ala Ile Glu Ala Glu Asn Gly Ser Leu Asp Lys Phe Asp
            420                 425                 430
Lys Ala Thr Asp Ile Gly Asp Gly Ser Lys Asp Lys Ile Asp Ile Thr
        435                 440                 445
Ile Glu Gly Ile Glu Val Thr Ile Asn Gly Ile Thr Tyr Glu Leu Thr
450                 455                 460
Lys Lys Pro Val
465

<210> SEQ ID NO 63
<211> LENGTH: 236
<212> TYPE: PRT
```

<213> ORGANISM: Artificial Sequence
<220> FEATURE:
<223> OTHER INFORMATION: Prophage identified in Streptococcus uberis (ATCC 700407)

<400> SEQUENCE: 63

```
Met Thr Asp Ser Ile Gln Glu Met Arg Lys Leu Gln Ser Ile Pro Val
1               5                   10                  15

Arg Tyr Asp Met Gly Asp Arg Tyr Gly Asn Asp Ala Asp Arg Asp Gly
            20                  25                  30

Arg Ile Glu Met Asp Cys Ser Ser Ala Val Ser Lys Ala Leu Gly Ile
        35                  40                  45

Ser Met Thr Asn Asn Thr Glu Thr Leu Gln Gln Ala Leu Pro Ala Ile
50                  55                  60

Gly Tyr Gly Lys Ile His Asp Ala Val Asp Gly Thr Phe Asp Met Gln
65                  70                  75                  80

Ala Tyr Asp Val Ile Ile Trp Ala Pro Arg Asp Gly Ser Ser Ser Leu
                85                  90                  95

Gly Ala Phe Gly His Val Leu Ile Ala Thr Ser Pro Thr Thr Ala Ile
            100                 105                 110

His Cys Asn Tyr Gly Ser Asp Gly Ile Thr Glu Asn Asp Tyr Asn Tyr
        115                 120                 125

Ile Trp Glu Ile Asn Gly Arg Pro Arg Glu Ile Val Phe Arg Lys Gly
130                 135                 140

Val Thr Gln Thr Gln Ala Thr Val Thr Ser Gln Phe Glu Arg Glu Leu
145                 150                 155                 160

Asp Val Asn Ala Arg Leu Thr Val Ser Asp Lys Pro Tyr Tyr Glu Ala
                165                 170                 175

Thr Leu Ser Glu Asp Tyr Tyr Val Glu Ala Gly Pro Arg Ile Asp Ser
            180                 185                 190

Gln Asp Lys Glu Leu Ile Lys Ala Gly Thr Arg Val Arg Val Tyr Glu
        195                 200                 205

Lys Leu Asn Gly Trp Ser Arg Ile Asn His Pro Glu Ser Ala Gln Trp
210                 215                 220

Val Glu Asp Ser Tyr Leu Val Asp Ala Thr Glu Met
225                 230                 235
```

<210> SEQ ID NO 64
<211> LENGTH: 481
<212> TYPE: PRT
<213> ORGANISM: Staphylococcus phage Phi11

<400> SEQUENCE: 64

```
Met Gln Ala Lys Leu Thr Lys Asn Glu Phe Ile Glu Trp Leu Lys Thr
1               5                   10                  15

Ser Glu Gly Lys Gln Phe Asn Val Asp Leu Trp Tyr Gly Phe Gln Cys
            20                  25                  30

Phe Asp Tyr Ala Asn Ala Gly Trp Lys Val Leu Phe Gly Leu Leu Leu
        35                  40                  45

Lys Gly Leu Gly Ala Lys Asp Ile Pro Phe Ala Asn Asn Phe Asp Gly
50                  55                  60

Leu Ala Thr Val Tyr Gln Asn Thr Pro Asp Phe Leu Ala Gln Pro Gly
65                  70                  75                  80

Asp Met Val Val Phe Gly Ser Asn Tyr Gly Ala Gly Tyr Gly His Val
                85                  90                  95

Ala Trp Val Ile Glu Ala Thr Leu Asp Tyr Ile Ile Val Tyr Glu Gln
```

-continued

```
                100               105               110
Asn Trp Leu Gly Gly Gly Trp Thr Asp Gly Ile Glu Gln Pro Gly Trp
            115                 120                 125
Gly Trp Glu Lys Val Thr Arg Arg Gln His Ala Tyr Asp Phe Pro Met
130                 135                 140
Trp Phe Ile Arg Pro Asn Phe Lys Ser Glu Thr Ala Pro Arg Ser Val
145                 150                 155                 160
Gln Ser Pro Thr Gln Ala Pro Lys Lys Glu Thr Ala Lys Pro Gln Pro
                165                 170                 175
Lys Ala Val Glu Leu Lys Ile Ile Lys Asp Val Val Lys Gly Tyr Asp
                180                 185                 190
Leu Pro Lys Arg Gly Ser Asn Pro Lys Gly Ile Val Ile His Asn Asp
                195                 200                 205
Ala Gly Ser Lys Gly Ala Thr Ala Glu Ala Tyr Arg Asn Gly Leu Val
                210                 215                 220
Asn Ala Pro Leu Ser Arg Leu Glu Ala Gly Ile Ala His Ser Tyr Val
225                 230                 235                 240
Ser Gly Asn Thr Val Trp Gln Ala Leu Asp Glu Ser Gln Val Gly Trp
                245                 250                 255
His Thr Ala Asn Gln Ile Gly Asn Lys Tyr Tyr Gly Ile Glu Val
                260                 265                 270
Cys Gln Ser Met Gly Ala Asp Asn Ala Thr Phe Leu Lys Asn Glu Gln
                275                 280                 285
Ala Thr Phe Gln Glu Cys Ala Arg Leu Leu Lys Lys Trp Gly Leu Pro
                290                 295                 300
Ala Asn Arg Asn Thr Ile Arg Leu His Asn Glu Phe Thr Ser Thr Ser
305                 310                 315                 320
Cys Pro His Arg Ser Ser Val Leu His Thr Gly Phe Asp Pro Val Thr
                325                 330                 335
Arg Gly Leu Leu Pro Glu Asp Lys Arg Leu Gln Leu Lys Asp Tyr Phe
                340                 345                 350
Ile Lys Gln Ile Arg Ala Tyr Met Asp Gly Lys Ile Pro Val Ala Thr
                355                 360                 365
Val Ser Asn Glu Ser Ser Ala Ser Ser Asn Thr Val Lys Pro Val Ala
                370                 375                 380
Ser Ala Trp Lys Arg Asn Lys Tyr Gly Thr Tyr Tyr Met Glu Glu Ser
385                 390                 395                 400
Ala Arg Phe Thr Asn Gly Asn Gln Pro Ile Thr Val Arg Lys Val Gly
                405                 410                 415
Pro Phe Leu Ser Cys Pro Val Gly Tyr Gln Phe Gln Pro Gly Gly Tyr
                420                 425                 430
Cys Asp Tyr Thr Glu Val Met Leu Gln Asp Gly His Val Trp Val Gly
                435                 440                 445
Tyr Thr Trp Glu Gly Gln Arg Tyr Tyr Leu Pro Ile Arg Thr Trp Asn
                450                 455                 460
Gly Ser Ala Pro Pro Asn Gln Ile Leu Gly Asp Leu Trp Gly Glu Ile
465                 470                 475                 480
Ser

<210> SEQ ID NO 65
<211> LENGTH: 481
<212> TYPE: PRT
<213> ORGANISM: Staphylococcus phage PhiH5
```

<400> SEQUENCE: 65

```
Met Gln Ala Lys Leu Thr Lys Lys Glu Phe Ile Glu Trp Leu Lys Thr
1               5                   10                  15
Ser Glu Gly Lys Gln Tyr Asn Ala Asp Gly Trp Tyr Gly Phe Gln Cys
                20                  25                  30
Phe Asp Tyr Ala Asn Ala Gly Trp Lys Ala Leu Phe Gly Leu Leu Leu
            35                  40                  45
Lys Gly Val Gly Ala Lys Asp Ile Pro Phe Ala Asn Asn Phe Asp Gly
        50                  55                  60
Leu Ala Thr Val Tyr Gln Asn Thr Pro Asp Phe Leu Ala Gln Pro Gly
65                  70                  75                  80
Asp Met Val Val Phe Gly Ser Asn Tyr Gly Ala Gly Tyr Gly His Val
                85                  90                  95
Ala Trp Val Ile Glu Ala Thr Leu Asp Tyr Ile Ile Val Tyr Glu Gln
            100                 105                 110
Asn Trp Leu Gly Gly Gly Trp Thr Asp Gly Val Gln Gln Pro Gly Ser
        115                 120                 125
Gly Trp Glu Lys Val Thr Arg Arg Gln His Ala Tyr Asp Phe Pro Met
130                 135                 140
Trp Phe Ile Arg Pro Asn Phe Lys Ser Glu Thr Ala Pro Arg Ser Val
145                 150                 155                 160
Gln Ser Pro Thr Gln Ala Ser Lys Lys Glu Thr Ala Lys Pro Gln Pro
                165                 170                 175
Lys Ala Val Glu Leu Lys Ile Ile Lys Asp Val Val Lys Gly Tyr Asp
            180                 185                 190
Leu Pro Lys Arg Gly Ser Asn Pro Asn Phe Ile Val Ile His Asn Asp
        195                 200                 205
Ala Gly Ser Lys Gly Ala Thr Ala Glu Ala Tyr Arg Asn Gly Leu Val
210                 215                 220
Asn Ala Pro Leu Ser Arg Leu Glu Ala Gly Ile Ala His Ser Tyr Val
225                 230                 235                 240
Ser Gly Asn Thr Val Trp Gln Ala Leu Asp Glu Ser Gln Val Gly Trp
                245                 250                 255
His Thr Ala Asn Gln Ile Gly Asn Lys Tyr Gly Tyr Gly Ile Glu Val
            260                 265                 270
Cys Gln Ser Met Gly Ala Asp Asn Ala Thr Phe Leu Lys Asn Glu Gln
        275                 280                 285
Ala Thr Phe Gln Glu Cys Ala Arg Leu Leu Lys Lys Trp Gly Leu Pro
290                 295                 300
Ala Asn Arg Asn Thr Ile Arg Leu His Asn Glu Phe Thr Ser Thr Ser
305                 310                 315                 320
Cys Pro His Arg Ser Ser Val Leu His Thr Gly Phe Asp Pro Val Thr
                325                 330                 335
Arg Gly Leu Leu Pro Glu Asp Lys Arg Leu Gln Leu Lys Asp Tyr Phe
            340                 345                 350
Ile Lys Gln Ile Arg Ala Tyr Met Asp Gly Lys Ile Pro Val Ala Thr
        355                 360                 365
Val Ser Asn Asp Ser Ser Ala Ser Ser Asn Thr Val Lys Pro Val Ala
370                 375                 380
Ser Ala Trp Lys Arg Asn Lys Tyr Gly Thr Tyr Tyr Met Glu Glu Ser
385                 390                 395                 400
Ala Arg Phe Thr Asn Gly Asn Gln Pro Ile Thr Val Arg Lys Val Gly
                405                 410                 415
```

```
Pro Phe Leu Ser Cys Pro Val Gly Tyr Gln Phe Gln Pro Gly Gly Tyr
            420                 425                 430

Cys Asp Tyr Thr Glu Val Met Leu Gln Asp Gly His Val Trp Val Gly
            435                 440                 445

Tyr Thr Trp Glu Gly Gln Arg Tyr Tyr Leu Pro Ile Arg Thr Trp Asn
450                 455                 460

Gly Ser Ala Pro Pro Asn Gln Ile Leu Gly Asp Leu Trp Gly Glu Ile
465                 470                 475                 480

Ser

<210> SEQ ID NO 66
<211> LENGTH: 477
<212> TYPE: PRT
<213> ORGANISM: Staphylococcus phage phiWMY

<400> SEQUENCE: 66

Met Lys Thr Lys Ala Gln Ala Lys Ser Trp Ile Asn Ser Lys Ile Gly
1               5                   10                  15

Lys Gly Ile Asp Trp Asp Gly Met Tyr Gly Tyr Gln Cys Met Asp Glu
            20                  25                  30

Ala Val Asp Tyr Ile His His Val Thr Asp Gly Lys Val Thr Met Trp
            35                  40                  45

Gly Asn Ala Ile Asp Ala Pro Lys Asn Asn Phe Gln Gly Leu Cys Thr
50                  55                  60

Val Tyr Thr Asn Thr Pro Glu Phe Arg Pro Tyr Gly Asp Val Ile
65                  70                  75                  80

Val Trp Ser Tyr Gly Thr Phe Ala Thr Tyr Gly His Ile Ala Ile Val
            85                  90                  95

Val Asn Pro Asp Pro Tyr Gly Asp Leu Gln Tyr Ile Thr Val Leu Glu
            100                 105                 110

Gln Asn Trp Asn Gly Asn Gly Ile Tyr Lys Thr Glu Phe Ala Thr Ile
            115                 120                 125

Arg Thr His Asp Tyr Thr Gly Val Ser His Phe Ile Arg Pro Lys Phe
            130                 135                 140

Ala Asp Glu Val Lys Glu Thr Ala Lys Thr Val Asn Lys Leu Ser Val
145                 150                 155                 160

Gln Lys Lys Ile Val Thr Pro Lys Asn Ser Val Glu Arg Ile Lys Asn
                165                 170                 175

Tyr Val Lys Thr Ser Gly Tyr Ile Asn Gly Glu His Tyr Glu Leu Tyr
            180                 185                 190

Asn Arg Gly His Lys Pro Lys Gly Val Val Ile His Asn Thr Ala Gly
            195                 200                 205

Thr Ala Ser Ala Thr Gln Glu Gly Gln Arg Leu Thr Asn Met Thr Phe
210                 215                 220

Gln Gln Leu Ala Asn Gly Val Ala His Val Tyr Ile Asp Lys Asn Thr
225                 230                 235                 240

Ile Tyr Glu Thr Leu Pro Glu Asp Arg Ile Ala Trp His Val Ala Gln
                245                 250                 255

Gln Tyr Gly Asn Thr Glu Phe Tyr Gly Ile Glu Val Cys Gly Ser Arg
            260                 265                 270

Asn Thr Asp Lys Glu Gln Phe Leu Ala Asn Glu Gln Val Ala Phe Gln
            275                 280                 285

Glu Ala Ala Arg Arg Leu Lys Ser Trp Gly Met Arg Ala Asn Arg Asn
290                 295                 300
```

```
Thr Val Arg Leu His His Thr Phe Ser Ser Thr Glu Cys Pro Asp Met
305                 310                 315                 320

Ser Met Leu Leu His Thr Gly Tyr Ser Met Lys Asn Gly Lys Pro Thr
            325                 330                 335

Gln Asp Ile Thr Asn Lys Cys Ala Asp Tyr Phe Met Lys Gln Ile Asn
        340                 345                 350

Ala Tyr Ile Asp Gly Lys Gln Pro Thr Ser Thr Val Val Gly Ser Ser
            355                 360                 365

Ser Ser Asn Lys Leu Lys Ala Lys Asn Lys Asp Lys Ser Thr Gly Trp
    370                 375                 380

Asn Thr Asn Glu Tyr Gly Thr Leu Trp Lys Lys Glu His Ala Thr Phe
385                 390                 395                 400

Thr Cys Gly Val Arg Gln Gly Ile Val Thr Arg Thr Thr Gly Pro Phe
                405                 410                 415

Thr Ser Cys Pro Gln Ala Gly Val Leu Tyr Tyr Gly Gln Ser Val Asn
            420                 425                 430

Tyr Asp Thr Val Cys Lys Gln Asp Gly Tyr Val Trp Ile Ser Trp Thr
            435                 440                 445

Thr Ser Asp Gly Tyr Asp Val Trp Met Pro Ile Arg Thr Trp Asp Arg
    450                 455                 460

Ser Thr Asp Lys Val Ser Glu Ile Trp Gly Thr Ile Ser
465                 470                 475

<210> SEQ ID NO 67
<211> LENGTH: 443
<212> TYPE: PRT
<213> ORGANISM: Streptococcus phage NCTC 11261

<400> SEQUENCE: 67

Met Ala Thr Tyr Gln Glu Tyr Lys Ser Arg Ser Asn Gly Asn Ala Tyr
1               5                   10                  15

Asp Ile Asp Gly Ser Phe Gly Ala Gln Cys Trp Asp Gly Tyr Ala Asp
            20                  25                  30

Tyr Cys Lys Tyr Leu Gly Leu Pro Tyr Ala Asn Cys Thr Asn Thr Gly
        35                  40                  45

Tyr Ala Arg Asp Ile Trp Glu Gln Arg His Glu Asn Gly Ile Leu Asn
    50                  55                  60

Tyr Phe Asp Glu Val Glu Val Met Gln Ala Gly Asp Val Ala Ile Phe
65                  70                  75                  80

Met Val Val Asp Gly Val Thr Pro Tyr Ser His Val Ala Ile Phe Asp
                85                  90                  95

Ser Asp Ala Gly Gly Gly Tyr Gly Trp Phe Leu Gly Gln Asn Gln Gly
            100                 105                 110

Gly Ala Asn Gly Ala Tyr Asn Ile Val Lys Ile Pro Tyr Ser Ala Thr
        115                 120                 125

Tyr Pro Thr Ala Phe Arg Pro Lys Val Phe Lys Asn Ala Val Thr Val
    130                 135                 140

Thr Gly Asn Ile Gly Leu Asn Lys Gly Asp Tyr Phe Ile Asp Val Ser
145                 150                 155                 160

Ala Tyr Gln Gln Ala Asp Leu Thr Thr Thr Cys Gln Gly Ala Gly Thr
                165                 170                 175

Thr Lys Thr Ile Ile Lys Val Ser Glu Ser Ile Ala Trp Leu Ser Asp
            180                 185                 190

Arg His Gln Gln Gln Ala Asn Thr Ser Asp Pro Ile Gly Tyr Tyr His
```

```
                195                 200                 205
Phe Gly Arg Phe Gly Gly Asp Ser Ala Leu Ala Gln Arg Glu Ala Asp
210                 215                 220

Leu Phe Leu Ser Asn Leu Pro Ser Lys Lys Val Ser Tyr Leu Val Ile
225                 230                 235                 240

Asp Tyr Glu Asp Ser Ala Ser Ala Asp Lys Gln Ala Asn Thr Asn Ala
                245                 250                 255

Val Ile Ala Phe Met Asp Lys Ile Ala Ser Ala Gly Tyr Lys Pro Ile
                260                 265                 270

Tyr Tyr Ser Tyr Lys Pro Phe Thr Leu Asn Asn Ile Asp Tyr Gln Lys
                275                 280                 285

Ile Ile Ala Lys Tyr Pro Asn Ser Ile Trp Ile Ala Gly Tyr Pro Asp
290                 295                 300

Tyr Glu Val Arg Thr Glu Pro Leu Trp Glu Phe Pro Ser Met Asp
305                 310                 315                 320

Gly Val Arg Trp Trp Gln Phe Thr Ser Val Gly Val Ala Gly Gly Leu
                325                 330                 335

Asp Lys Asn Ile Val Leu Leu Ala Asp Asp Ser Ser Lys Met Asp Ile
                340                 345                 350

Pro Lys Val Asp Lys Pro Gln Glu Leu Thr Phe Tyr Gln Lys Leu Ala
                355                 360                 365

Thr Asn Thr Lys Leu Asp Asn Ser Asn Val Pro Tyr Tyr Glu Ala Thr
370                 375                 380

Leu Ser Thr Asp Tyr Tyr Val Glu Ser Lys Pro Asn Ala Ser Ser Ala
385                 390                 395                 400

Asp Lys Glu Phe Ile Lys Ala Gly Thr Arg Val Arg Val Tyr Glu Lys
                405                 410                 415

Val Asn Gly Trp Ser Arg Ile Asn His Pro Glu Ser Ala Gln Trp Val
                420                 425                 430

Glu Asp Ser Tyr Leu Val Asn Ala Thr Asp Met
                435                 440

<210> SEQ ID NO 68
<211> LENGTH: 334
<212> TYPE: PRT
<213> ORGANISM: Listeria phage FWLLm3

<400> SEQUENCE: 68

Met Val Lys Tyr Thr Val Glu Asn Lys Ile Ile Ala Gly Leu Pro Lys
1               5                   10                  15

Gly Lys Leu Lys Gly Ala Asn Phe Val Ile Ala His Glu Thr Ala Asn
                20                  25                  30

Ser Lys Ser Thr Ile Asp Asn Glu Val Ser Tyr Met Thr Arg Asn Trp
            35                  40                  45

Gln Asn Ala Phe Val Thr His Phe Val Gly Gly Gly Arg Val Val
    50                  55                  60

Gln Val Ala Asn Val Asn Tyr Val Ser Trp Gly Ala Gly Gln Tyr Ala
65                  70                  75                  80

Asn Ser Tyr Ser Tyr Ala Gln Val Glu Leu Cys Arg Thr Ser Asn Ala
                85                  90                  95

Thr Thr Phe Lys Lys Asp Tyr Glu Val Tyr Cys Gln Leu Leu Val Asp
                100                 105                 110

Leu Ala Lys Lys Ala Gly Ile Pro Ile Thr Leu Asp Ser Gly Ser Lys
            115                 120                 125
```

```
Thr Ser Asp Lys Gly Ile Lys Ser His Lys Trp Val Ala Asp Lys Leu
        130                 135                 140

Gly Gly Thr Thr His Gln Asp Pro Tyr Ala Tyr Leu Ser Ser Trp Gly
145                 150                 155                 160

Ile Ser Lys Ala Gln Phe Ala Ser Asp Leu Ala Lys Val Ser Gly Gly
                165                 170                 175

Gly Asn Thr Gly Thr Ala Pro Ala Lys Pro Ser Thr Pro Ser Thr Asn
            180                 185                 190

Leu Asp Lys Leu Gly Leu Val Asp Tyr Met Asn Ala Lys Lys Met Asp
        195                 200                 205

Ser Ser Tyr Ser Asn Arg Ala Lys Leu Ala Lys Gln Tyr Gly Ile Ala
    210                 215                 220

Asn Tyr Ser Gly Thr Ala Ser Gln Asn Thr Thr Leu Leu Ser Lys Ile
225                 230                 235                 240

Lys Gly Gly Ala Pro Lys Pro Ser Thr Pro Ala Pro Lys Pro Ser Thr
                245                 250                 255

Ser Thr Ala Lys Lys Ile Tyr Phe Pro Pro Asn Lys Gly Asn Trp Ser
            260                 265                 270

Val Tyr Pro Thr Asn Lys Ala Pro Val Lys Ala Asn Ala Ile Gly Ala
        275                 280                 285

Ile Asn Pro Thr Lys Phe Gly Gly Leu Thr Tyr Thr Ile Gln Lys Asp
    290                 295                 300

Arg Gly Asn Gly Val Tyr Glu Ile Gln Thr Asp Gln Phe Gly Arg Val
305                 310                 315                 320

Gln Val Tyr Gly Ala Pro Ser Thr Gly Ala Val Ile Lys Lys
                325                 330
```

<210> SEQ ID NO 69
<211> LENGTH: 1278
<212> TYPE: PRT
<213> ORGANISM: Bacillus phage BPS13

<400> SEQUENCE: 69

```
Met Ala Lys Arg Glu Lys Tyr Ile Phe Asp Val Glu Ala Glu Val Gly
1               5                   10                  15

Lys Ala Ala Lys Ser Ile Lys Ser Leu Glu Ala Glu Leu Ser Lys Leu
                20                  25                  30

Gln Lys Leu Asn Lys Glu Ile Asp Ala Thr Gly Gly Asp Arg Thr Glu
            35                  40                  45

Lys Glu Met Leu Ala Thr Leu Lys Ala Ala Lys Glu Val Asn Ala Glu
        50                  55                  60

Tyr Gln Lys Met Gln Arg Ile Leu Lys Asp Leu Ser Lys Tyr Ser Gly
65                  70                  75                  80

Lys Val Ser Arg Lys Glu Phe Asn Asp Ser Lys Val Ile Asn Asn Ala
                85                  90                  95

Lys Thr Ser Val Gln Gly Gly Lys Val Thr Asp Ser Phe Gly Gln Met
            100                 105                 110

Leu Lys Asn Met Glu Arg Gln Ile Asn Ser Val Asn Lys Gln Phe Asp
        115                 120                 125

Asn His Arg Lys Ala Met Val Asp Arg Gly Gln Gln Tyr Thr Pro His
    130                 135                 140

Leu Lys Thr Asn Arg Lys Asp Ser Gln Gly Asn Ser Asn Pro Ser Met
145                 150                 155                 160

Met Gly Arg Asn Lys Ser Thr Thr Gln Asp Met Glu Lys Ala Val Asp
                165                 170                 175
```

```
Lys Phe Leu Asn Gly Gln Asn Glu Ala Thr Thr Gly Leu Asn Gln Ala
            180                 185                 190

Leu Tyr Gln Leu Lys Glu Ile Ser Lys Leu Asn Arg Ser Glu Ser
        195                 200                 205

Leu Ser Arg Arg Ala Ser Ala Ser Gly Tyr Met Ser Phe Gln Gln Tyr
    210                 215                 220

Ser Asn Phe Thr Gly Asp Arg Arg Thr Val Gln Gln Thr Tyr Gly Gly
225                 230                 235                 240

Leu Lys Thr Ala Asn Arg Glu Arg Val Leu Glu Leu Ser Gly Gln Ala
                245                 250                 255

Thr Gly Ile Ser Lys Glu Leu Asp Arg Leu Asn Ser Lys Lys Gly Leu
            260                 265                 270

Thr Ala Arg Glu Gly Glu Glu Arg Lys Lys Leu Met Arg Gln Leu Glu
        275                 280                 285

Gly Ile Asp Ala Glu Leu Thr Ala Arg Lys Lys Leu Asn Ser Ser Leu
    290                 295                 300

Asp Glu Thr Thr Ser Asn Met Glu Lys Phe Asn Gln Ser Leu Val Asp
305                 310                 315                 320

Ala Gln Val Ser Val Lys Pro Glu Arg Gly Thr Met Arg Gly Met Met
                325                 330                 335

Tyr Glu Arg Ala Pro Ala Ile Ala Leu Ala Ile Gly Gly Ala Ile Thr
            340                 345                 350

Ala Thr Ile Gly Lys Leu Tyr Ser Glu Gly Gly Asn His Ser Lys Ala
        355                 360                 365

Met Arg Pro Asp Glu Met Tyr Val Gly Gln Gln Thr Gly Ala Val Gly
    370                 375                 380

Ala Asn Trp Arg Pro Asn Arg Thr Ala Thr Met Arg Ser Gly Leu Gly
385                 390                 395                 400

Asn His Leu Gly Phe Thr Gly Gln Glu Met Met Glu Phe Gln Ser Asn
                405                 410                 415

Tyr Leu Ser Ala Asn Gly Tyr His Gly Ala Glu Asp Met Lys Ala Ala
            420                 425                 430

Thr Thr Gly Gln Ala Thr Phe Ala Arg Ala Thr Gly Leu Gly Ser Asp
        435                 440                 445

Glu Val Lys Asp Phe Phe Asn Thr Ala Tyr Arg Ser Gly Gly Ile Asp
    450                 455                 460

Gly Asn Gln Thr Lys Gln Phe Gln Asn Ala Phe Leu Gly Ala Met Lys
465                 470                 475                 480

Gln Ser Gly Ala Val Gly Arg Glu Lys Asp Gln Leu Lys Ala Leu Asn
                485                 490                 495

Gly Ile Leu Ser Ser Met Ser Gln Asn Arg Thr Val Ser Asn Gln Asp
            500                 505                 510

Met Met Arg Thr Val Gly Leu Gln Ser Ala Ile Ser Ser Ser Gly Val
        515                 520                 525

Ala Ser Leu Gln Gly Thr Lys Gly Gly Ala Leu Met Glu Gln Leu Asp
    530                 535                 540

Asn Gly Ile Arg Glu Gly Phe Asn Asp Pro Gln Met Arg Val Leu Phe
545                 550                 555                 560

Gly Gln Gly Thr Lys Tyr Gln Gly Met Gly Gly Arg Ala Ala Leu Arg
                565                 570                 575

Lys Gln Met Glu Lys Gly Ile Ser Asp Pro Asp Asn Leu Asn Thr Leu
            580                 585                 590
```

-continued

```
Ile Asp Ala Ser Lys Ala Ser Ala Gly Gln Asp Pro Ala Glu Gln Ala
            595                 600                 605

Glu Val Leu Ala Thr Leu Ala Ser Lys Met Gly Val Asn Met Ser Ser
610                 615                 620

Asp Gln Ala Arg Gly Leu Ile Asp Leu Gln Pro Ser Gly Lys Leu Thr
625                 630                 635                 640

Lys Glu Asn Ile Asp Lys Val Met Lys Glu Gly Leu Lys Glu Gly Ser
            645                 650                 655

Ile Glu Ser Ala Lys Arg Asp Lys Ala Tyr Ser Glu Ser Lys Ala Ser
            660                 665                 670

Ile Asp Asn Ser Ser Glu Ala Ala Thr Ala Lys Gln Ala Thr Glu Leu
            675                 680                 685

Asn Asp Met Gly Ser Lys Leu Arg Gln Ala Asn Ala Ala Leu Gly Gly
690                 695                 700

Leu Pro Ala Pro Leu Tyr Thr Ala Ile Ala Ala Val Val Ala Phe Thr
705                 710                 715                 720

Ala Ala Val Ala Gly Ser Ala Leu Met Phe Lys Gly Ala Ser Trp Leu
                725                 730                 735

Lys Gly Gly Met Ala Ser Lys Tyr Gly Gly Lys Gly Gly Lys Gly Gly
                740                 745                 750

Lys Gly Gly Gly Thr Gly Gly Gly Gly Ala Gly Gly Ala Ala Ala
                755                 760                 765

Thr Gly Ala Gly Ala Ala Gly Ala Gly Gly Val Gly Ala Ala Ala
770                 775                 780

Ala Gly Glu Val Gly Ala Gly Val Ala Ala Gly Gly Ala Ala Ala Gly
785                 790                 795                 800

Ala Ala Ala Gly Gly Ser Lys Leu Ala Gly Val Gly Lys Gly Phe Met
                805                 810                 815

Lys Gly Ala Gly Lys Leu Met Leu Pro Leu Gly Ile Leu Met Gly Ala
                820                 825                 830

Ser Glu Ile Met Gln Ala Pro Glu Glu Ala Lys Gly Ser Ala Ile Gly
                835                 840                 845

Ser Ala Val Gly Gly Ile Gly Gly Ile Ala Gly Ala Ala Thr
850                 855                 860

Gly Ala Ile Ala Gly Ser Phe Leu Gly Pro Ile Gly Thr Ala Val Gly
865                 870                 875                 880

Gly Ile Ala Gly Gly Ile Ala Gly Gly Phe Ala Gly Ser Ser Leu Gly
                885                 890                 895

Glu Thr Ile Gly Gly Trp Phe Asp Ser Gly Pro Lys Glu Asp Ala Ser
                900                 905                 910

Ala Ala Asp Lys Ala Lys Ala Asp Ala Ser Ala Ala Leu Ala Ala
                915                 920                 925

Ala Ala Gly Thr Ser Gly Ala Val Gly Ser Ser Ala Leu Gln Ser Gln
930                 935                 940

Met Ala Gln Gly Ile Thr Gly Ala Pro Asn Met Ser Gln Val Gly Ser
945                 950                 955                 960

Met Ala Ser Ala Leu Gly Ile Ser Ser Gly Ala Met Ala Ser Ala Leu
                965                 970                 975

Gly Ile Ser Ser Gly Gln Glu Asn Gln Ile Gln Thr Met Thr Asp Lys
                980                 985                 990

Glu Asn Thr Asn Thr Lys Lys Ala Asn Glu Ala Lys Lys Gly Asp Asn
            995                 1000                1005

Leu Ser Tyr Glu Arg Glu Asn Ile Ser Met Tyr Glu Arg Val Leu
```

```
                 1010                1015                1020
Thr Arg Ala Glu Gln Ile Leu Ala Gln Ala Arg Ala Gln Asn Gly
    1025                1030                1035

Ile Met Gly Val Gly Gly Gly Thr Ala Gly Ala Gly Gly Gly
    1040                1045                1050

Ile Asn Gly Phe Thr Gly Gly Lys Leu Gln Phe Leu Ala Ala
    1055                1060                1065

Gly Gln Lys Trp Ser Ser Ser Asn Leu Gln Gln His Asp Leu Gly
    1070                1075                1080

Phe Thr Asp Gln Asn Leu Thr Ala Glu Asp Leu Asp Lys Trp Ile
    1085                1090                1095

Asp Ser Lys Ala Pro Gln Gly Ser Met Met Arg Gly Met Gly Ala
    1100                1105                1110

Thr Phe Leu Lys Ala Gly Gln Glu Tyr Gly Leu Asp Pro Arg Tyr
    1115                1120                1125

Leu Ile Ala His Ala Ala Glu Glu Ser Gly Trp Gly Thr Ser Lys
    1130                1135                1140

Ile Ala Arg Asp Lys Gly Asn Phe Phe Gly Ile Gly Ala Phe Asp
    1145                1150                1155

Asp Ser Pro Tyr Ser Ser Ala Tyr Glu Phe Lys Asp Gly Thr Gly
    1160                1165                1170

Ser Ala Ala Glu Arg Gly Ile Met Gly Gly Ala Lys Trp Ile Ser
    1175                1180                1185

Glu Lys Tyr Tyr Gly Lys Gly Asn Thr Thr Leu Asp Lys Met Lys
    1190                1195                1200

Ala Ala Gly Tyr Ala Thr Asn Ala Ser Trp Ala Pro Asn Ile Ala
    1205                1210                1215

Ser Ile Met Ala Gly Ala Pro Thr Gly Ser Gly Ser Gly Asn Val
    1220                1225                1230

Thr Ala Thr Ile Asn Val Asn Val Lys Gly Asp Glu Lys Val Ser
    1235                1240                1245

Asp Lys Leu Lys Asn Ser Ser Asp Met Lys Lys Ala Gly Lys Asp
    1250                1255                1260

Ile Gly Ser Leu Leu Gly Phe Tyr Ser Arg Glu Met Thr Ile Ala
    1265                1270                1275

<210> SEQ ID NO 70
<211> LENGTH: 495
<212> TYPE: PRT
<213> ORGANISM: Staphylococcus phage GH15

<400> SEQUENCE: 70

Met Ala Lys Thr Gln Ala Glu Ile Asn Lys Arg Leu Asp Ala Tyr Ala
1               5                   10                  15

Lys Gly Thr Val Asp Ser Pro Tyr Arg Ile Lys Lys Ala Thr Ser Tyr
                20                  25                  30

Asp Pro Ser Phe Gly Val Met Glu Ala Gly Ala Ile Ala Asp Gly
            35                  40                  45

Tyr Tyr His Ala Gln Cys Gln Asp Leu Ile Thr Asp Tyr Val Leu Trp
        50                  55                  60

Leu Thr Asp Asn Lys Val Arg Thr Trp Gly Asn Ala Lys Asp Gln Ile
65                  70                  75                  80

Lys Gln Ser Tyr Gly Thr Gly Phe Lys Ile His Glu Asn Lys Pro Ser
                85                  90                  95
```

```
Thr Val Pro Lys Lys Gly Trp Ile Ala Val Phe Thr Ser Gly Ser Tyr
                100                 105                 110

Gln Gln Trp Gly His Ile Gly Ile Val Tyr Asp Gly Gly Asn Thr Ser
            115                 120                 125

Thr Phe Thr Ile Leu Glu Gln Asn Trp Asn Gly Tyr Ala Asn Lys Lys
        130                 135                 140

Pro Thr Lys Arg Val Asp Asn Tyr Tyr Gly Leu Thr His Phe Ile Glu
145                 150                 155                 160

Ile Pro Val Lys Ala Gly Thr Thr Val Lys Glu Thr Ala Lys Lys
                165                 170                 175

Ser Ala Ser Lys Thr Pro Ala Pro Lys Lys Ala Thr Leu Lys Val
            180                 185                 190

Ser Lys Asn His Ile Asn Tyr Thr Met Asp Lys Arg Gly Lys Lys Pro
        195                 200                 205

Glu Gly Met Val Ile His Asn Asp Ala Gly Arg Ser Ser Gly Gln Gln
210                 215                 220

Tyr Glu Asn Ser Leu Ala Asn Ala Gly Tyr Ala Arg Tyr Ala Asn Gly
225                 230                 235                 240

Ile Ala His Tyr Tyr Gly Ser Glu Gly Tyr Val Trp Glu Ala Ile Asp
                245                 250                 255

Ala Lys Asn Gln Ile Ala Trp His Thr Gly Asp Gly Thr Gly Ala Asn
            260                 265                 270

Ser Gly Asn Phe Arg Phe Ala Gly Ile Glu Val Cys Gln Ser Met Ser
        275                 280                 285

Ala Ser Asp Ala Gln Phe Leu Lys Asn Glu Gln Ala Val Phe Gln Phe
290                 295                 300

Thr Ala Glu Lys Phe Lys Glu Trp Gly Leu Thr Pro Asn Arg Lys Thr
305                 310                 315                 320

Val Arg Leu His Met Glu Phe Val Pro Thr Ala Cys Pro His Arg Ser
                325                 330                 335

Met Val Leu His Thr Gly Phe Asn Pro Val Thr Gln Gly Arg Pro Ser
            340                 345                 350

Gln Ala Ile Met Asn Lys Leu Lys Asp Tyr Phe Ile Lys Gln Ile Lys
        355                 360                 365

Asn Tyr Met Asp Lys Gly Thr Ser Ser Thr Val Lys Asp Gly
370                 375                 380

Lys Thr Ser Ser Ala Ser Thr Pro Ala Thr Arg Pro Val Thr Gly Ser
385                 390                 395                 400

Trp Lys Lys Asn Gln Tyr Gly Thr Trp Tyr Lys Pro Glu Asn Ala Thr
                405                 410                 415

Phe Val Asn Gly Asn Gln Pro Ile Val Thr Arg Ile Gly Ser Pro Phe
            420                 425                 430

Leu Asn Ala Pro Val Gly Gly Asn Leu Pro Ala Gly Ala Thr Ile Val
        435                 440                 445

Tyr Asp Glu Val Cys Ile Gln Ala Gly His Ile Trp Ile Gly Tyr Asn
450                 455                 460

Ala Tyr Asn Gly Asp Arg Val Tyr Cys Pro Val Arg Thr Cys Gln Gly
465                 470                 475                 480

Val Pro Pro Asn His Ile Pro Gly Val Ala Trp Gly Val Phe Lys
                485                 490                 495

<210> SEQ ID NO 71
<211> LENGTH: 264
<212> TYPE: PRT
```

<213> ORGANISM: Clostridium phage phi8074-B1

<400> SEQUENCE: 71

| | | | | | | | | | | | | | | | |
|---|---|---|---|---|---|---|---|---|---|---|---|---|---|---|---|
|Met|Lys|Ile|Gly|Ile|Asp|Met|Gly|His|Thr|Leu|Ser|Gly|Ala|Asp|Tyr|
|1| | | |5| | | |10| | | |15| | | |
|Gly|Val|Val|Gly|Leu|Arg|Pro|Glu|Ser|Val|Leu|Thr|Arg|Glu|Val|Gly|
| | | |20| | | |25| | | |30| | | | |
|Thr|Lys|Val|Ile|Tyr|Lys|Leu|Gln|Lys|Leu|Gly|His|Val|Val|Val|Asn|
| | |35| | | |40| | | |45| | | | | |
|Cys|Thr|Val|Asp|Lys|Ala|Ser|Ser|Val|Ser|Glu|Ser|Leu|Tyr|Thr|Arg|
|50| | | | |55| | | |60| | | | | | |
|Tyr|Tyr|Arg|Ala|Asn|Gln|Ala|Asn|Val|Asp|Leu|Phe|Ile|Ser|Ile|His|
|65| | | |70| | | |75| | | |80| | | |
|Phe|Asn|Ala|Thr|Pro|Gly|Gly|Thr|Gly|Thr|Glu|Val|Tyr|Thr|Tyr|Ala|
| | | |85| | | |90| | | |95| | | | |
|Gly|Arg|Gln|Leu|Gly|Glu|Ala|Thr|Arg|Ile|Arg|Gln|Glu|Phe|Lys|Ser|
| | | |100| | | |105| | | |110| | | | |
|Leu|Gly|Leu|Arg|Asp|Arg|Gly|Thr|Lys|Asp|Gly|Ser|Gly|Leu|Ala|Val|
| | |115| | | |120| | | |125| | | | | |
|Ile|Arg|Asn|Thr|Lys|Ala|Lys|Ala|Met|Leu|Val|Glu|Cys|Cys|Phe|Cys|
| |130| | | |135| | | |140| | | | | | |
|Asp|Asn|Pro|Asn|Asp|Met|Lys|Leu|Tyr|Asn|Ser|Glu|Ser|Phe|Ser|Asn|
|145| | | |150| | | |155| | | |160| | | |
|Ala|Ile|Val|Lys|Gly|Ile|Thr|Gly|Lys|Leu|Pro|Asn|Gly|Glu|Ser|Gly|
| | | |165| | | |170| | | |175| | | | |
|Asn|Asn|Asn|Gln|Gly|Gly|Asn|Lys|Val|Lys|Ala|Val|Val|Ile|Tyr|Asn|
| | |180| | | |185| | | |190| | | | | |
|Glu|Gly|Ala|Asp|Arg|Arg|Gly|Ala|Glu|Tyr|Leu|Ala|Asp|Tyr|Leu|Asn|
| |195| | | |200| | | |205| | | | | | |
|Cys|Pro|Thr|Ile|Ser|Asn|Ser|Arg|Thr|Phe|Asp|Tyr|Ser|Cys|Val|Glu|
|210| | | | |215| | | |220| | | | | | |
|His|Val|Tyr|Ala|Val|Gly|Gly|Lys|Lys|Glu|Gln|Tyr|Thr|Lys|Tyr|Leu|
|225| | | |230| | | |235| | | |240| | | |
|Lys|Thr|Leu|Leu|Ser|Gly|Ala|Asn|Arg|Tyr|Asp|Thr|Met|Gln|Gln|Ile|
| | | |245| | | |250| | | |255| | | | |
|Leu|Asn|Phe|Ile|Asn|Gly|Gly|Lys| | | | | | | | |
| | | |260| | | | | | | | | | | | |

<210> SEQ ID NO 72
<211> LENGTH: 209
<212> TYPE: PRT
<213> ORGANISM: Salmonella phage SPN1S

<400> SEQUENCE: 72

| | | | | | | | | | | | | | | | |
|---|---|---|---|---|---|---|---|---|---|---|---|---|---|---|---|
|Met|Asp|Ile|Asn|Gln|Phe|Arg|Arg|Ala|Ser|Gly|Ile|Asn|Glu|Gln|Leu|
|1| | | |5| | | |10| | | |15| | | |
|Ala|Ala|Arg|Trp|Phe|Pro|His|Ile|Thr|Thr|Ala|Met|Asn|Glu|Phe|Gly|
| | | |20| | | |25| | | |30| | | | |
|Ile|Thr|Lys|Pro|Asp|Asp|Gln|Ala|Met|Phe|Ile|Ala|Gln|Val|Gly|His|
| | |35| | | |40| | | |45| | | | | |
|Glu|Ser|Gly|Gly|Phe|Thr|Arg|Leu|Gln|Glu|Asn|Phe|Asn|Tyr|Ser|Val|
| |50| | | |55| | | |60| | | | | | |
|Asn|Gly|Leu|Ser|Gly|Phe|Ile|Arg|Ala|Gly|Arg|Ile|Thr|Pro|Asp|Gln|
|65| | | |70| | | |75| | | |80| | | |
|Ala|Asn|Ala|Leu|Gly|Arg|Lys|Thr|Tyr|Glu|Lys|Ser|Leu|Pro|Leu|Glu|

```
                    85                  90                  95
Arg Gln Arg Ala Ile Ala Asn Leu Val Tyr Ser Lys Arg Met Gly Asn
                100                 105                 110

Asn Gly Pro Gly Asp Gly Trp Asn Tyr Arg Gly Arg Gly Leu Ile Gln
                115                 120                 125

Ile Thr Gly Leu Asn Asn Tyr Arg Asp Cys Gly Asn Gly Leu Lys Val
            130                 135                 140

Asp Leu Val Ala Gln Pro Glu Leu Leu Ala Gln Asp Glu Tyr Ala Ala
145                 150                 155                 160

Arg Ser Ala Ala Trp Phe Phe Ser Ser Lys Gly Cys Met Lys Tyr Thr
                165                 170                 175

Gly Asp Leu Val Arg Val Thr Gln Ile Ile Asn Gly Gly Gln Asn Gly
                180                 185                 190

Ile Asp Asp Arg Arg Thr Arg Tyr Ala Ala Ala Arg Lys Val Leu Ala
            195                 200                 205

Leu

<210> SEQ ID NO 73
<211> LENGTH: 290
<212> TYPE: PRT
<213> ORGANISM: Clavibacter phage CN77

<400> SEQUENCE: 73

Met Gly Tyr Trp Gly Tyr Pro Asn Gly Gln Ile Pro Asn Asp Lys Met
1               5                   10                  15

Ala Leu Tyr Arg Gly Cys Leu Leu Arg Ala Asp Ala Ala Gln Ala
                20                  25                  30

Tyr Ala Leu Gln Asp Ala Tyr Thr Arg Ala Thr Gly Lys Pro Leu Val
            35                  40                  45

Ile Leu Glu Gly Tyr Arg Asp Leu Thr Arg Gln Lys Tyr Leu Arg Asn
        50                  55                  60

Leu Tyr Leu Ser Gly Arg Gly Asn Ile Ala Ala Val Pro Gly Leu Ser
65                  70                  75                  80

Asn His Gly Trp Gly Leu Ala Cys Asp Phe Ala Ala Pro Leu Asn Ser
                85                  90                  95

Ser Gly Ser Glu Glu His Arg Trp Met Arg Gln Asn Ala Pro Leu Phe
                100                 105                 110

Gly Phe Asp Trp Ala Arg Gly Lys Ala Asp Asn Glu Pro Trp His Trp
            115                 120                 125

Glu Tyr Gly Asn Val Pro Val Ser Arg Trp Ala Ser Leu Asp Val Thr
            130                 135                 140

Pro Ile Asp Arg Asn Asp Met Ala Asp Ile Thr Glu Gly Gln Met Gln
145                 150                 155                 160

Arg Ile Ala Val Ile Leu Leu Asp Thr Glu Ile Gln Thr Pro Leu Gly
                165                 170                 175

Pro Arg Leu Val Lys His Ala Leu Gly Asp Ala Leu Leu Leu Gly Gln
                180                 185                 190

Ala Asn Ala Asn Ser Ile Ala Glu Val Pro Asp Lys Thr Trp Asp Val
            195                 200                 205

Leu Val Asp His Pro Leu Ala Lys Asn Glu Asp Gly Thr Pro Leu Lys
            210                 215                 220

Val Arg Leu Gly Asp Val Ala Lys Tyr Glu Pro Leu Glu His Gln Asn
225                 230                 235                 240

Thr Arg Asp Ala Ile Ala Lys Leu Gly Thr Leu Gln Phe Thr Asp Lys
```

```
                    245                 250                 255
Gln Leu Ala Thr Ile Gly Ala Gly Val Lys Pro Ile Asp Glu Ala Ser
                260                 265                 270

Leu Val Lys Lys Ile Val Asp Gly Val Arg Ala Leu Phe Gly Arg Ala
            275                 280                 285

Ala Ala
    290

<210> SEQ ID NO 74
<211> LENGTH: 185
<212> TYPE: PRT
<213> ORGANISM: Acinetobacter phage phiAB2

<400> SEQUENCE: 74

Met Ile Leu Thr Lys Asp Gly Phe Ser Ile Ile Arg Asn Glu Leu Phe
1               5                   10                  15

Gly Gly Lys Leu Asp Gln Thr Gln Val Asp Ala Ile Asn Phe Ile Val
            20                  25                  30

Ala Lys Ala Thr Glu Ser Gly Leu Thr Tyr Pro Glu Ala Ala Tyr Leu
        35                  40                  45

Leu Ala Thr Ile Tyr His Glu Thr Gly Leu Pro Ser Gly Tyr Arg Thr
    50                  55                  60

Met Gln Pro Ile Lys Glu Ala Gly Ser Asp Ser Tyr Leu Arg Ser Lys
65                  70                  75                  80

Lys Tyr Tyr Pro Tyr Ile Gly Tyr Gly Tyr Val Gln Leu Thr Trp Lys
                85                  90                  95

Glu Asn Tyr Glu Arg Ile Gly Lys Leu Ile Gly Val Asp Leu Ile Lys
            100                 105                 110

Asn Pro Glu Lys Ala Leu Glu Pro Leu Ile Ala Ile Gln Ile Ala Ile
        115                 120                 125

Lys Gly Met Leu Asn Gly Trp Phe Thr Gly Val Gly Phe Arg Arg Lys
    130                 135                 140

Arg Pro Val Ser Lys Tyr Asn Lys Gln Gln Tyr Val Ala Ala Arg Asn
145                 150                 155                 160

Ile Ile Asn Gly Lys Asp Lys Ala Glu Leu Ile Ala Lys Tyr Ala Ile
                165                 170                 175

Ile Phe Glu Arg Ala Leu Arg Ser Leu
            180                 185

<210> SEQ ID NO 75
<211> LENGTH: 262
<212> TYPE: PRT
<213> ORGANISM: Bacillus phage B4

<400> SEQUENCE: 75

Met Ala Met Ala Leu Gln Thr Leu Ile Asp Lys Ala Asn Arg Lys Leu
1               5                   10                  15

Asn Val Ser Gly Met Arg Lys Asp Val Ala Asp Arg Thr Arg Ala Val
            20                  25                  30

Ile Thr Gln Met His Ala Gln Gly Ile Tyr Ile Cys Val Ala Gln Gly
        35                  40                  45

Phe Arg Ser Phe Ala Glu Gln Asn Ala Leu Tyr Ala Gln Gly Arg Thr
    50                  55                  60

Lys Pro Gly Ser Ile Val Thr Asn Ala Arg Gly Gly Gln Ser Asn His
65                  70                  75                  80

Asn Tyr Gly Val Ala Val Asp Leu Cys Leu Tyr Thr Gln Asp Gly Ser
```

```
                85                  90                  95
Asp Val Ile Trp Thr Val Glu Gly Asn Phe Arg Lys Val Ile Ala Ala
            100                 105                 110
Met Lys Ala Gln Gly Phe Lys Trp Gly Gly Asp Trp Val Ser Phe Lys
            115                 120                 125
Asp Tyr Pro His Phe Glu Leu Tyr Asp Val Val Gly Gln Lys Pro
        130                 135                 140
Pro Ala Asp Asn Gly Gly Ala Val Asp Asn Gly Gly Ser Gly Ser
145                 150                 155                 160
Thr Gly Gly Ser Gly Gly Gly Ser Thr Gly Gly Ser Thr Gly Gly
                165                 170                 175
Gly Tyr Asp Ser Ser Trp Phe Thr Lys Glu Thr Gly Thr Phe Val Thr
            180                 185                 190
Asn Thr Ser Ile Lys Leu Arg Thr Ala Pro Phe Thr Ser Ala Asp Val
                195                 200                 205
Ile Ala Thr Leu Pro Ala Gly Ser Pro Val Asn Tyr Asn Gly Phe Gly
        210                 215                 220
Ile Glu Tyr Asp Gly Tyr Val Trp Ile Arg Gln Pro Arg Ser Asn Gly
225                 230                 235                 240
Tyr Gly Tyr Leu Ala Thr Gly Glu Ser Lys Gly Gly Lys Arg Gln Asn
                245                 250                 255
Tyr Trp Gly Thr Phe Lys
            260
```

<210> SEQ ID NO 76
<211> LENGTH: 274
<212> TYPE: PRT
<213> ORGANISM: Clostridium phage phiCTP1

<400> SEQUENCE: 76

```
Met Lys Lys Ile Ala Asp Ile Ser Asn Leu Asn Gly Asn Val Asp Val
1               5                   10                  15
Lys Leu Leu Phe Asn Leu Gly Tyr Ile Gly Ile Ile Ala Lys Ala Ser
            20                  25                  30
Glu Gly Gly Thr Phe Val Asp Lys Tyr Tyr Lys Gln Asn Tyr Thr Asn
        35                  40                  45
Thr Lys Ala Gln Gly Lys Ile Thr Gly Ala Tyr His Phe Ala Asn Phe
    50                  55                  60
Ser Thr Ile Ala Lys Ala Gln Gln Glu Ala Asn Phe Phe Leu Asn Cys
65                  70                  75                  80
Ile Ala Gly Thr Thr Pro Asp Phe Val Val Leu Asp Leu Glu Gln Gln
                85                  90                  95
Cys Thr Gly Asp Ile Thr Asp Ala Cys Leu Ala Phe Leu Asn Ile Val
            100                 105                 110
Ala Lys Lys Phe Lys Cys Val Val Tyr Cys Asn Ser Ser Phe Ile Lys
        115                 120                 125
Glu His Leu Asn Ser Lys Ile Cys Ala Tyr Pro Leu Trp Ile Ala Asn
    130                 135                 140
Tyr Gly Val Ala Thr Pro Ala Phe Thr Leu Trp Thr Lys Tyr Ala Met
145                 150                 155                 160
Trp Gln Phe Thr Glu Lys Gly Gln Val Ser Gly Ile Ser Gly Tyr Ile
                165                 170                 175
Asp Phe Ser Tyr Ile Thr Asp Glu Phe Ile Lys Tyr Ile Lys Gly Glu
            180                 185                 190
```

Asp Glu Val Glu Asn Leu Val Val Tyr Asn Asp Gly Ala Asp Gln Arg
            195                 200                 205

Ala Ala Glu Tyr Leu Ala Asp Arg Leu Ala Cys Pro Thr Ile Asn Asn
        210                 215                 220

Ala Arg Lys Phe Asp Tyr Ser Asn Val Lys Asn Val Tyr Ala Val Gly
225                 230                 235                 240

Gly Asn Lys Glu Gln Tyr Thr Ser Tyr Leu Thr Thr Leu Ile Ala Gly
            245                 250                 255

Ser Thr Arg Tyr Thr Thr Met Gln Ala Val Leu Asp Tyr Ile Lys Asn
                260                 265                 270

Leu Lys

<210> SEQ ID NO 77
<211> LENGTH: 628
<212> TYPE: PRT
<213> ORGANISM: Staphylococcus virus 187

<400> SEQUENCE: 77

Met Ala Leu Pro Lys Thr Gly Lys Pro Thr Ala Lys Gln Val Val Asp
1               5                   10                  15

Trp Ala Ile Asn Leu Ile Gly Ser Gly Val Asp Val Asp Gly Tyr Tyr
            20                  25                  30

Gly Arg Gln Cys Trp Asp Leu Pro Asn Tyr Ile Phe Asn Arg Tyr Trp
        35                  40                  45

Asn Phe Lys Thr Pro Gly Asn Ala Arg Asp Met Ala Trp Tyr Arg Tyr
    50                  55                  60

Pro Glu Gly Phe Lys Val Phe Arg Asn Thr Ser Asp Phe Val Pro Lys
65                  70                  75                  80

Pro Gly Asp Ile Ala Val Trp Thr Gly Gly Asn Tyr Asn Trp Asn Thr
                85                  90                  95

Trp Gly His Thr Gly Ile Val Val Gly Pro Ser Thr Lys Ser Tyr Phe
            100                 105                 110

Tyr Ser Val Asp Gln Asn Trp Asn Asn Ser Asn Ser Tyr Val Gly Ser
        115                 120                 125

Pro Ala Ala Lys Ile Lys His Ser Tyr Phe Gly Val Thr His Phe Val
    130                 135                 140

Arg Pro Ala Tyr Lys Ala Glu Pro Lys Pro Thr Pro Ala Gln Asn
145                 150                 155                 160

Asn Pro Ala Pro Lys Asp Pro Glu Pro Ser Lys Lys Pro Glu Ser Asn
                165                 170                 175

Lys Pro Ile Tyr Lys Val Val Thr Lys Ile Leu Phe Thr Thr Ala His
            180                 185                 190

Ile Glu His Val Lys Ala Asn Arg Phe Val His Tyr Ile Thr Lys Ser
        195                 200                 205

Asp Asn His Asn Asn Lys Pro Asn Lys Ile Val Ile Lys Asn Thr Asn
    210                 215                 220

Thr Ala Leu Ser Thr Ile Asp Val Tyr Arg Tyr Arg Asp Glu Leu Asp
225                 230                 235                 240

Lys Asp Glu Ile Pro His Phe Phe Val Asp Arg Leu Asn Val Trp Ala
                245                 250                 255

Cys Arg Pro Ile Glu Asp Ser Ile Asn Gly Tyr His Asp Ser Val Val
            260                 265                 270

Leu Ser Ile Thr Glu Thr Arg Thr Ala Leu Ser Asp Asn Phe Lys Met
        275                 280                 285

```
Asn Glu Ile Glu Cys Leu Ser Leu Ala Glu Ser Ile Leu Lys Ala Asn
    290                 295                 300

Asn Lys Lys Met Ser Ala Ser Asn Ile Ile Val Asp Asn Lys Ala Trp
305                 310                 315                 320

Arg Thr Phe Lys Leu His Thr Gly Lys Asp Ser Leu Lys Ser Ser Ser
                325                 330                 335

Phe Thr Ser Lys Asp Tyr Gln Lys Ala Val Asn Glu Leu Ile Lys Leu
            340                 345                 350

Phe Asn Asp Lys Asp Lys Leu Leu Asn Asn Lys Pro Lys Asp Val Val
        355                 360                 365

Glu Arg Ile Arg Ile Arg Thr Ile Val Lys Glu Asn Thr Lys Phe Val
370                 375                 380

Pro Ser Glu Leu Lys Pro Arg Asn Asn Ile Arg Asp Lys Gln Asp Ser
385                 390                 395                 400

Lys Ile Asp Arg Val Ile Asn Asn Tyr Thr Leu Lys Gln Ala Leu Asn
                405                 410                 415

Ile Gln Tyr Lys Leu Asn Pro Lys Pro Gln Thr Ser Asn Gly Val Ser
            420                 425                 430

Trp Tyr Asn Ala Ser Val Asn Gln Ile Lys Ser Ala Met Asp Thr Thr
        435                 440                 445

Lys Ile Phe Asn Asn Asn Val Gln Val Tyr Gln Phe Leu Lys Leu Asn
450                 455                 460

Gln Tyr Gln Gly Ile Pro Val Asp Lys Leu Asn Lys Leu Leu Val Gly
465                 470                 475                 480

Lys Gly Thr Leu Ala Asn Gln Gly His Ala Phe Ala Asp Gly Cys Lys
                485                 490                 495

Lys Tyr Asn Ile Asn Glu Ile Tyr Leu Ile Ala His Arg Phe Leu Glu
            500                 505                 510

Ser Ala Asn Gly Thr Ser Phe Phe Ala Ser Gly Lys Thr Gly Val Tyr
        515                 520                 525

Asn Tyr Phe Gly Ile Gly Ala Phe Asp Asn Asn Pro Asn Asn Ala Met
    530                 535                 540

Ala Phe Ala Arg Ser His Gly Trp Thr Ser Pro Thr Lys Ala Ile Ile
545                 550                 555                 560

Gly Gly Ala Glu Phe Val Gly Lys Gly Tyr Phe Asn Val Gly Gln Asn
                565                 570                 575

Thr Leu Tyr Arg Met Arg Trp Asn Pro Gln Lys Pro Gly Thr His Gln
            580                 585                 590

Tyr Ala Thr Asp Ile Ser Trp Ala Lys Val Gln Ala Gln Met Ile Ser
        595                 600                 605

Ala Met Tyr Lys Glu Ile Gly Leu Thr Gly Asp Tyr Phe Ile Tyr Asp
    610                 615                 620

Gln Tyr Lys Lys
625

<210> SEQ ID NO 78
<211> LENGTH: 291
<212> TYPE: PRT
<213> ORGANISM: Listeria phage phiP35

<400> SEQUENCE: 78

Met Ala Arg Lys Phe Thr Lys Ala Glu Leu Val Ala Lys Ala Glu Lys
1               5                   10                  15

Lys Val Gly Gly Leu Lys Pro Asp Val Lys Lys Ala Val Leu Ser Ala
            20                  25                  30
```

Val Lys Glu Ala Tyr Asp Arg Tyr Gly Ile Gly Ile Ile Val Ser Gln
         35                  40                  45

Gly Tyr Arg Ser Ile Ala Glu Gln Asn Gly Leu Tyr Ala Gln Gly Arg
     50                  55                  60

Thr Lys Pro Gly Asn Ile Val Thr Asn Ala Lys Gly Gly Gln Ser Asn
 65                  70                  75                  80

His Asn Phe Gly Val Ala Val Asp Phe Ala Ile Asp Leu Ile Asp Asp
                 85                  90                  95

Gly Lys Ile Asp Ser Trp Gln Pro Ser Ala Thr Ile Val Asn Met Met
            100                 105                 110

Lys Arg Arg Gly Phe Lys Trp Gly Gly Asp Trp Lys Ser Phe Thr Asp
            115                 120                 125

Leu Pro His Phe Glu Ala Cys Asp Trp Tyr Arg Gly Glu Arg Lys Tyr
        130                 135                 140

Lys Val Asp Thr Ser Glu Trp Lys Lys Lys Glu Asn Ile Asn Ile Val
145                 150                 155                 160

Ile Lys Asp Val Gly Tyr Phe Gln Asp Lys Pro Gln Phe Leu Asn Ser
                165                 170                 175

Lys Ser Val Arg Gln Trp Lys His Gly Thr Lys Val Lys Leu Thr Lys
            180                 185                 190

His Asn Ser His Trp Tyr Thr Gly Val Val Lys Asp Gly Asn Lys Ser
        195                 200                 205

Val Arg Gly Tyr Ile Tyr His Ser Met Ala Lys Val Thr Ser Lys Asn
    210                 215                 220

Ser Asp Gly Ser Val Asn Ala Thr Ile Asn Ala His Ala Phe Cys Trp
225                 230                 235                 240

Asp Asn Lys Lys Leu Asn Gly Gly Asp Phe Ile Asn Leu Lys Arg Gly
                245                 250                 255

Phe Lys Gly Ile Thr His Pro Ala Ser Asp Gly Phe Tyr Pro Leu Tyr
            260                 265                 270

Phe Ala Ser Arg Lys Lys Thr Phe Tyr Ile Pro Arg Tyr Met Phe Asp
        275                 280                 285

Ile Lys Lys
    290

<210> SEQ ID NO 79
<211> LENGTH: 342
<212> TYPE: PRT
<213> ORGANISM: Streptococcus phage CP-7

<400> SEQUENCE: 79

Met Val Lys Lys Asn Asp Leu Phe Val Asp Val Ala Ser His Gln Gly
 1               5                  10                  15

Tyr Asp Ile Ser Gly Ile Leu Glu Glu Ala Gly Thr Thr Asn Thr Ile
             20                  25                  30

Ile Lys Val Ser Glu Ser Thr Ser Tyr Leu Asn Pro Cys Leu Ser Ala
         35                  40                  45

Gln Val Ser Gln Ser Asn Pro Ile Gly Phe Tyr His Phe Ala Trp Phe
     50                  55                  60

Gly Gly Asn Glu Glu Ala Glu Ala Glu Arg Tyr Phe Leu Asp
 65                  70                  75                  80

Asn Val Pro Thr Gln Val Lys Tyr Leu Val Leu Asp Tyr Glu Asp His
                 85                  90                  95

Ala Ser Ala Ser Val Gln Arg Asn Thr Thr Ala Cys Leu Arg Phe Met

```
            100                 105                 110
Gln Ile Ile Ala Glu Ala Gly Tyr Thr Pro Ile Tyr Tyr Ser Tyr Lys
        115                 120                 125
Pro Phe Thr Leu Asp Asn Val Asp Tyr Gln Gln Ile Leu Ala Gln Phe
        130                 135                 140
Pro Asn Ser Leu Trp Ile Ala Gly Tyr Gly Leu Asn Asp Gly Thr Ala
145                 150                 155                 160
Asn Phe Glu Tyr Phe Pro Ser Met Asp Gly Ile Arg Trp Trp Gln Tyr
                165                 170                 175
Ser Ser Asn Pro Phe Asp Lys Asn Ile Val Leu Leu Asp Asp Glu Lys
            180                 185                 190
Glu Asp Asn Ile Asn Asn Glu Asn Thr Leu Lys Ser Leu Thr Thr Val
            195                 200                 205
Ala Asn Glu Val Ile Gln Gly Leu Trp Gly Asn Gly Gln Glu Arg Tyr
            210                 215                 220
Asp Ser Leu Ala Asn Ala Gly Tyr Asp Pro Gln Ala Val Gln Asp Lys
225                 230                 235                 240
Val Asn Glu Ile Leu Asn Ala Arg Glu Ile Ala Asp Leu Thr Thr Val
                245                 250                 255
Ala Asn Glu Val Ile Gln Gly Leu Trp Gly Asn Gly Gln Glu Arg Tyr
                260                 265                 270
Asp Ser Leu Ala Asn Ala Gly Tyr Asp Pro Gln Ala Val Gln Asp Lys
            275                 280                 285
Val Asn Glu Ile Leu Asn Ala Arg Glu Ile Ala Asp Leu Thr Thr Val
            290                 295                 300
Ala Asn Glu Val Ile Gln Gly Leu Trp Gly Asn Gly Gln Glu Arg Tyr
305                 310                 315                 320
Asp Ser Leu Ala Asn Ala Gly Tyr Asp Pro Gln Ala Val Gln Asp Lys
                325                 330                 335
Val Asn Glu Leu Leu Ser
            340

<210> SEQ ID NO 80
<211> LENGTH: 328
<212> TYPE: PRT
<213> ORGANISM: Enterococcus phage EFAP-1

<400> SEQUENCE: 80

Met Lys Leu Lys Gly Ile Leu Leu Ser Val Val Thr Thr Phe Gly Leu
1               5                   10                  15
Leu Phe Gly Ala Thr Asn Val Gln Ala Tyr Glu Val Asn Asn Glu Phe
            20                  25                  30
Asn Leu Gln Pro Trp Glu Gly Ser Gln Gln Leu Ala Tyr Pro Asn Lys
        35                  40                  45
Ile Ile Leu His Glu Thr Ala Asn Pro Arg Ala Thr Gly Arg Asn Glu
    50                  55                  60
Ala Thr Tyr Met Lys Asn Asn Trp Phe Asn Ala His Thr Thr Ala Ile
65                  70                  75                  80
Val Gly Asp Gly Gly Ile Val Tyr Lys Val Ala Pro Glu Gly Asn Val
                85                  90                  95
Ser Trp Gly Ala Gly Asn Ala Asn Pro Tyr Ala Pro Val Gln Ile Glu
            100                 105                 110
Leu Gln His Thr Asn Asp Pro Glu Leu Phe Lys Ala Asn Tyr Lys Ala
        115                 120                 125
```

```
Tyr Val Asp Tyr Thr Arg Asp Met Gly Lys Lys Phe Gly Ile Pro Met
    130                 135                 140

Thr Leu Asp Gln Gly Gly Ser Leu Trp Glu Lys Gly Val Val Ser His
145                 150                 155                 160

Gln Trp Val Thr Asp Phe Val Trp Gly Asp His Thr Asp Pro Tyr Gly
                165                 170                 175

Tyr Leu Ala Lys Met Gly Ile Ser Lys Ala Gln Leu Ala His Asp Leu
            180                 185                 190

Ala Asn Gly Val Ser Gly Asn Thr Ala Thr Pro Thr Pro Lys Pro Asp
            195                 200                 205

Lys Pro Lys Pro Thr Gln Pro Ser Lys Pro Ser Asn Lys Lys Arg Phe
210                 215                 220

Asn Tyr Arg Val Asp Gly Leu Glu Tyr Val Asn Gly Met Trp Gln Ile
225                 230                 235                 240

Tyr Asn Glu His Leu Gly Lys Ile Asp Phe Asn Trp Thr Glu Asn Gly
                245                 250                 255

Ile Pro Val Glu Val Val Asp Lys Val Asn Pro Ala Thr Gly Gln Pro
            260                 265                 270

Thr Lys Asp Gln Val Leu Lys Val Gly Asp Tyr Phe Asn Phe Gln Glu
        275                 280                 285

Asn Ser Thr Gly Val Val Gln Glu Gln Thr Pro Tyr Met Gly Tyr Thr
290                 295                 300

Leu Ser His Val Gln Leu Pro Asn Glu Phe Ile Trp Leu Phe Thr Asp
305                 310                 315                 320

Ser Lys Gln Ala Leu Met Tyr Gln
                325

<210> SEQ ID NO 81
<211> LENGTH: 48
<212> TYPE: PRT
<213> ORGANISM: Homo sapiens

<400> SEQUENCE: 81

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45

<210> SEQ ID NO 82
<211> LENGTH: 37
<212> TYPE: PRT
<213> ORGANISM: Hyalophora cecropia

<400> SEQUENCE: 82

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 83
<211> LENGTH: 62
<212> TYPE: PRT
<213> ORGANISM: Drosophila teissieri
```

-continued

```
<400> SEQUENCE: 83

Met Lys Tyr Phe Ser Val Leu Val Val Leu Thr Leu Ile Leu Ala Ile
1               5                   10                  15

Val Asp Gln Ser Asp Ala Phe Ile Asn Leu Leu Asp Lys Val Glu Asp
            20                  25                  30

Ala Leu His Thr Gly Ala Gln Ala Gly Phe Lys Leu Ile Arg Pro Val
        35                  40                  45

Glu Arg Gly Ala Thr Pro Lys Lys Ser Glu Lys Pro Glu Lys
    50                  55                  60

<210> SEQ ID NO 84
<211> LENGTH: 66
<212> TYPE: PRT
<213> ORGANISM: Bombyz mori

<400> SEQUENCE: 84

Met Asn Ile Leu Lys Phe Phe Val Phe Ile Val Ala Met Ser Leu
1               5                   10                  15

Val Ser Cys Ser Thr Ala Ala Pro Ala Lys Ile Pro Ile Lys Ala Ile
            20                  25                  30

Lys Thr Val Gly Lys Ala Val Gly Lys Gly Leu Arg Ala Ile Asn Ile
        35                  40                  45

Ala Ser Thr Ala Asn Asp Val Phe Asn Phe Leu Lys Pro Lys Lys Arg
    50                  55                  60

Lys His
65

<210> SEQ ID NO 85
<211> LENGTH: 71
<212> TYPE: PRT
<213> ORGANISM: Ceratitis capitata

<400> SEQUENCE: 85

Met Ala Asn Leu Lys Ala Val Phe Leu Ile Cys Ile Val Ala Phe Ile
1               5                   10                  15

Ala Leu Gln Cys Val Val Ala Glu Pro Ala Ala Glu Asp Ser Val Val
            20                  25                  30

Val Lys Arg Ser Ile Gly Ser Ala Leu Lys Lys Ala Leu Pro Val Ala
        35                  40                  45

Lys Lys Ile Gly Lys Ile Ala Leu Pro Ile Ala Lys Ala Ala Leu Pro
    50                  55                  60

Val Ala Ala Gly Leu Val Gly
65                  70

<210> SEQ ID NO 86
<211> LENGTH: 53
<212> TYPE: PRT
<213> ORGANISM: Apis mellifera

<400> SEQUENCE: 86

Met Lys Val Val Ile Phe Ile Phe Ala Leu Leu Ala Thr Ile Cys Ala
1               5                   10                  15

Ala Phe Ala Tyr Val Pro Leu Pro Asn Val Pro Gln Pro Gly Arg Arg
            20                  25                  30

Pro Phe Pro Thr Phe Pro Gly Gln Gly Pro Phe Asn Pro Lys Ile Lys
        35                  40                  45

Trp Pro Gln Gly Tyr
    50
```

<210> SEQ ID NO 87
<211> LENGTH: 283
<212> TYPE: PRT
<213> ORGANISM: Apis mellifera

<400> SEQUENCE: 87

```
Lys Asn Phe Ala Leu Ala Ile Leu Val Val Thr Phe Val Ala Val
1               5                   10                  15

Phe Gly Asn Thr Asn Leu Asp Pro Pro Thr Arg Pro Thr Arg Leu Arg
            20                  25                  30

Arg Glu Ala Lys Pro Glu Ala Glu Pro Gly Asn Asn Arg Pro Val Tyr
            35                  40                  45

Ile Pro Gln Pro Arg Pro Pro His Pro Arg Leu Arg Arg Glu Ala Glu
        50                  55                  60

Pro Glu Ala Glu Pro Gly Asn Asn Arg Pro Val Tyr Ile Pro Gln Pro
65                  70                  75                  80

Arg Pro Pro His Pro Arg Leu Arg Arg Glu Ala Glu Leu Glu Ala Glu
                85                  90                  95

Pro Gly Asn Asn Arg Pro Val Tyr Ile Ser Gln Pro Arg Pro Pro His
            100                 105                 110

Pro Arg Leu Arg Arg Glu Ala Glu Pro Glu Ala Glu Pro Gly Asn Asn
        115                 120                 125

Arg Pro Val Tyr Ile Pro Gln Pro Arg Pro Pro His Pro Arg Leu Arg
    130                 135                 140

Arg Glu Ala Glu Leu Glu Ala Glu Pro Gly Asn Asn Arg Pro Val Tyr
145                 150                 155                 160

Ile Ser Gln Pro Arg Pro Pro His Pro Arg Leu Arg Arg Glu Ala Glu
                165                 170                 175

Pro Glu Ala Glu Pro Gly Asn Asn Arg Pro Val Tyr Ile Pro Gln Pro
            180                 185                 190

Arg Pro Pro His Pro Arg Leu Arg Arg Glu Ala Glu Pro Glu Ala Glu
        195                 200                 205

Pro Gly Asn Asn Arg Pro Val Tyr Ile Pro Gln Pro Arg Pro Pro His
    210                 215                 220

Pro Arg Leu Arg Arg Glu Ala Glu Pro Glu Ala Glu Pro Gly Asn Asn
225                 230                 235                 240

Arg Pro Val Tyr Ile Pro Gln Pro Arg Pro Pro His Pro Arg Leu Arg
                245                 250                 255

Arg Glu Ala Lys Pro Glu Ala Lys Pro Gly Asn Asn Arg Pro Val Tyr
            260                 265                 270

Ile Pro Gln Pro Arg Pro Pro His Pro Arg Ile
            275                 280
```

<210> SEQ ID NO 88
<211> LENGTH: 228
<212> TYPE: PRT
<213> ORGANISM: Sus scrofa

<400> SEQUENCE: 88

```
Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
            35                  40                  45
```

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Arg Pro Pro Glu Leu Cys
                85                  90                  95

Asp Phe Lys Glu Asn Gly Arg Val Lys Gln Cys Val Gly Thr Val Thr
                100                 105                 110

Leu Asp Gln Ile Lys Asp Pro Leu Asp Ile Thr Cys Asn Glu Gly Val
                115                 120                 125

Arg Arg Phe Pro Trp Trp Trp Pro Phe Leu Arg Arg Pro Arg Leu Arg
130                 135                 140

Arg Gln Ala Phe Pro Pro Asn Val Pro Gly Pro Arg Phe Pro Pro
145                 150                 155                 160

Pro Asn Val Pro Gly Pro Arg Phe Pro Pro Asn Phe Pro Gly Pro
                165                 170                 175

Arg Phe Pro Pro Pro Asn Phe Pro Gly Pro Arg Phe Pro Pro Asn
                180                 185                 190

Phe Pro Gly Pro Pro Phe Pro Pro Pro Ile Phe Pro Gly Pro Trp Phe
                195                 200                 205

Pro Pro Pro Pro Pro Phe Arg Pro Pro Pro Phe Gly Pro Pro Arg Phe
210                 215                 220

Pro Gly Arg Arg
225

<210> SEQ ID NO 89
<211> LENGTH: 144
<212> TYPE: PRT
<213> ORGANISM: Bos taurus

<400> SEQUENCE: 89

Met Gln Thr Gln Arg Ala Ser Leu Ser Leu Gly Arg Trp Ser Leu Trp
1               5                   10                  15

Leu Leu Leu Leu Gly Leu Val Val Pro Ser Ala Ser Ala Gln Ala Leu
                20                  25                  30

Ser Tyr Arg Glu Ala Val Leu Arg Ala Val Asp Gln Leu Asn Glu Leu
            35                  40                  45

Ser Ser Glu Ala Asn Leu Tyr Arg Leu Leu Glu Leu Asp Pro Pro Pro
    50                  55                  60

Lys Asp Asn Glu Asp Leu Gly Thr Arg Lys Pro Val Ser Phe Thr Val
65                  70                  75                  80

Lys Glu Thr Val Cys Pro Arg Thr Ile Gln Gln Pro Ala Glu Gln Cys
                85                  90                  95

Asp Phe Lys Glu Lys Gly Arg Val Lys Gln Cys Val Gly Thr Val Thr
                100                 105                 110

Leu Asp Pro Ser Asn Asp Gln Phe Asp Leu Asn Cys Asn Glu Leu Gln
                115                 120                 125

Ser Val Ile Leu Pro Trp Lys Trp Pro Trp Trp Pro Trp Arg Arg Gly
130                 135                 140

<210> SEQ ID NO 90
<211> LENGTH: 149
<212> TYPE: PRT
<213> ORGANISM: Sus scrofa

<400> SEQUENCE: 90

```
Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
50                      55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asp Gln Ile Lys Asp Pro Leu Asp Ile Thr Cys Asn Glu Val Gln
            115                 120                 125

Gly Val Arg Gly Gly Arg Leu Cys Tyr Cys Arg Arg Phe Cys Val
130                 135                 140

Cys Val Gly Arg Gly
145

<210> SEQ ID NO 91
<211> LENGTH: 17
<212> TYPE: PRT
<213> ORGANISM: Tachypleus gigas

<400> SEQUENCE: 91

Lys Trp Cys Phe Arg Val Cys Tyr Arg Gly Ile Cys Tyr Arg Arg Cys
1               5                   10                  15

Arg

<210> SEQ ID NO 92
<211> LENGTH: 102
<212> TYPE: PRT
<213> ORGANISM: Anopheles gambiae

<400> SEQUENCE: 92

Met Lys Cys Ala Thr Ile Val Cys Thr Ile Ala Val Val Leu Ala Ala
1               5                   10                  15

Thr Leu Leu Asn Gly Ser Val Gln Ala Ala Pro Gln Glu Glu Ala Ala
            20                  25                  30

Leu Ser Gly Gly Ala Asn Leu Asn Thr Leu Leu Asp Glu Leu Pro Glu
        35                  40                  45

Glu Thr His His Ala Ala Leu Glu Asn Tyr Arg Ala Lys Arg Ala Thr
50                      55                  60

Cys Asp Leu Ala Ser Gly Phe Gly Val Gly Ser Ser Leu Cys Ala Ala
65                  70                  75                  80

His Cys Ile Ala Arg Arg Tyr Arg Gly Gly Tyr Cys Asn Ser Lys Ala
                85                  90                  95

Val Cys Val Cys Arg Asn
            100

<210> SEQ ID NO 93
<211> LENGTH: 70
<212> TYPE: PRT
<213> ORGANISM: Drosophila melanogaster
```

-continued

<400> SEQUENCE: 93

Met Met Gln Ile Lys Tyr Leu Phe Ala Leu Phe Ala Val Leu Met Leu
1               5                   10                  15

Val Val Leu Gly Ala Asn Glu Ala Asp Ala Asp Cys Leu Ser Gly Arg
            20                  25                  30

Tyr Lys Gly Pro Cys Ala Val Trp Asp Asn Glu Thr Cys Arg Arg Val
        35                  40                  45

Cys Lys Glu Glu Gly Arg Ser Ser Gly His Cys Ser Pro Ser Leu Lys
    50                  55                  60

Cys Trp Cys Glu Gly Cys
65              70

<210> SEQ ID NO 94
<211> LENGTH: 63
<212> TYPE: PRT
<213> ORGANISM: Medicago truncatula

<400> SEQUENCE: 94

Met Thr Lys Ile Val Val Phe Ile Tyr Val Val Ile Leu Leu Leu Thr
1               5                   10                  15

Ile Phe His Val Ser Ala Lys Lys Lys Arg Tyr Ile Glu Cys Glu Thr
            20                  25                  30

His Glu Asp Cys Ser Gln Val Phe Met Pro Pro Phe Val Met Arg Cys
        35                  40                  45

Val Ile His Glu Cys Lys Ile Phe Asn Gly Glu His Leu Arg Tyr
    50                  55                  60

<210> SEQ ID NO 95
<211> LENGTH: 76
<212> TYPE: PRT
<213> ORGANISM: Medicago truncatula

<400> SEQUENCE: 95

Met Ala Lys Ile Met Lys Phe Val Tyr Asn Met Ile Pro Phe Leu Ser
1               5                   10                  15

Ile Phe Ile Ile Thr Leu Gln Val Asn Val Val Cys Glu Ile Asp
            20                  25                  30

Ala Asp Cys Pro Gln Ile Cys Met Pro Pro Tyr Glu Val Arg Cys Val
        35                  40                  45

Asn His Arg Cys Gly Trp Val Asn Thr Asp Ser Leu Phe Leu Thr
    50                  55                  60

Gln Glu Phe Thr Arg Ser Lys Gln Tyr Ile Ile Ser
65                  70                  75

<210> SEQ ID NO 96
<211> LENGTH: 76
<212> TYPE: PRT
<213> ORGANISM: Medicago truncatula

<400> SEQUENCE: 96

Met Tyr Lys Val Val Glu Ser Ile Phe Ile Arg Tyr Met His Arg Lys
1               5                   10                  15

Pro Asn Met Thr Lys Phe Phe Lys Phe Val Tyr Thr Met Phe Ile Leu
            20                  25                  30

Ile Ser Leu Phe Leu Val Val Thr Asn Ala Asn Ala His Asn Cys Thr
        35                  40                  45

Asp Ile Ser Asp Cys Ser Ser Asn His Cys Ser Tyr Glu Gly Val Ser
    50                  55                  60

Leu Cys Met Asn Gly Gln Cys Ile Cys Ile Tyr Glu
65                  70              75

<210> SEQ ID NO 97
<211> LENGTH: 64
<212> TYPE: PRT
<213> ORGANISM: Medicago truncatula

<400> SEQUENCE: 97

Met Val Glu Thr Leu Arg Leu Phe Tyr Ile Met Ile Leu Phe Val Ser
1               5                   10                  15

Leu Cys Leu Val Val Val Asp Gly Glu Ser Lys Leu Glu Gln Thr Cys
            20                  25                  30

Ser Glu Asp Phe Glu Cys Tyr Ile Lys Asn Pro His Val Pro Phe Gly
        35                  40                  45

His Leu Arg Cys Phe Glu Gly Phe Cys Gln Gln Leu Asn Gly Pro Ala
    50                  55                  60

<210> SEQ ID NO 98
<211> LENGTH: 67
<212> TYPE: PRT
<213> ORGANISM: Medicago truncatula

<400> SEQUENCE: 98

Met Ala Lys Ile Val Asn Phe Val Tyr Ser Met Ile Val Phe Leu Phe
1               5                   10                  15

Leu Phe Leu Val Ala Thr Lys Ala Ala Arg Gly Tyr Leu Cys Val Thr
            20                  25                  30

Asp Ser His Cys Pro Pro His Met Cys Pro Pro Gly Met Glu Pro Arg
        35                  40                  45

Cys Val Arg Arg Met Cys Lys Cys Leu Pro Ile Gly Trp Arg Lys Tyr
    50                  55                  60

Phe Val Pro
65

<210> SEQ ID NO 99
<211> LENGTH: 96
<212> TYPE: PRT
<213> ORGANISM: Medicago truncatula

<400> SEQUENCE: 99

Met Gln Ile Gly Lys Asn Met Val Glu Thr Pro Lys Leu Asp Tyr Val
1               5                   10                  15

Ile Ile Phe Phe Phe Leu Tyr Phe Phe Arg Gln Met Ile Ile Leu
            20                  25                  30

Arg Leu Asn Thr Thr Phe Arg Pro Leu Asn Phe Lys Met Leu Arg Phe
        35                  40                  45

Trp Gly Gln Asn Arg Asn Ile Met Lys His Arg Gly Gln Lys Val His
    50                  55                  60

Phe Ser Leu Ile Leu Ser Asp Cys Lys Thr Asn Lys Asp Cys Pro Lys
65                  70                  75                  80

Leu Arg Arg Ala Asn Val Arg Cys Arg Lys Ser Tyr Cys Val Pro Ile
                85                  90                  95

<210> SEQ ID NO 100
<211> LENGTH: 65
<212> TYPE: PRT
<213> ORGANISM: Medicago truncatula

```
<400> SEQUENCE: 100

Met Leu Arg Leu Tyr Leu Val Ser Tyr Phe Leu Lys Arg Thr Leu
1               5                   10                  15

Leu Val Ser Tyr Phe Ser Tyr Phe Ser Thr Tyr Ile Ile Glu Cys Lys
                20                  25                  30

Thr Asp Asn Asp Cys Pro Ile Ser Gln Leu Lys Ile Tyr Ala Trp Lys
            35                  40                  45

Cys Val Lys Asn Gly Cys His Leu Phe Asp Val Ile Pro Met Met Tyr
50                  55                  60

Glu
65

<210> SEQ ID NO 101
<211> LENGTH: 79
<212> TYPE: PRT
<213> ORGANISM: Medicago truncatula

<400> SEQUENCE: 101

Met Ala Glu Ile Leu Lys Phe Val Tyr Ile Val Ile Leu Phe Val Ser
1               5                   10                  15

Leu Leu Leu Ile Val Val Ala Ser Glu Arg Glu Cys Val Thr Asp Asp
                20                  25                  30

Asp Cys Glu Lys Leu Tyr Pro Thr Asn Glu Tyr Arg Met Met Cys Asp
            35                  40                  45

Ser Gly Tyr Cys Met Asn Leu Leu Asn Gly Lys Ile Ile Tyr Leu Leu
50                  55                  60

Cys Leu Lys Lys Lys Phe Leu Ile Ile Ile Ser Val Leu Leu
65                  70                  75

<210> SEQ ID NO 102
<211> LENGTH: 95
<212> TYPE: PRT
<213> ORGANISM: Medicago truncatula

<400> SEQUENCE: 102

Met Ala Glu Ile Ile Lys Phe Val Tyr Ile Met Ile Leu Cys Val Ser
1               5                   10                  15

Leu Leu Leu Ile Glu Val Ala Gly Glu Glu Cys Val Thr Asp Ala Asp
                20                  25                  30

Cys Asp Lys Leu Tyr Pro Asp Ile Arg Lys Pro Leu Met Cys Ser Ile
            35                  40                  45

Gly Glu Cys Tyr Ser Leu Tyr Lys Gly Lys Phe Ser Leu Ser Ile Ile
50                  55                  60

Ser Lys Thr Ser Phe Ser Leu Met Val Tyr Asn Val Val Thr Leu Val
65                  70                  75                  80

Ile Cys Leu Arg Leu Ala Tyr Ile Ser Leu Leu Leu Lys Phe Leu
                85                  90                  95

<210> SEQ ID NO 103
<211> LENGTH: 100
<212> TYPE: PRT
<213> ORGANISM: Medicago truncatula

<400> SEQUENCE: 103

Met Ala Glu Ile Leu Lys Asp Phe Tyr Ala Met Asn Leu Phe Ile Phe
1               5                   10                  15

Leu Ile Ile Leu Pro Ala Lys Ile Arg Gly Glu Thr Leu Ser Leu Thr
                20                  25                  30
```

```
His Pro Lys Cys His His Ile Met Leu Pro Ser Leu Phe Ile Thr Glu
            35                  40                  45

Val Phe Gln Arg Val Thr Asp Asp Gly Cys Pro Lys Pro Val Asn His
        50                  55                  60

Leu Arg Val Val Lys Cys Ile Glu His Ile Cys Glu Tyr Gly Tyr Asn
65                  70                  75                  80

Tyr Arg Pro Asp Phe Ala Ser Gln Ile Pro Glu Ser Thr Lys Met Pro
                85                  90                  95

Arg Lys Arg Glu
            100

<210> SEQ ID NO 104
<211> LENGTH: 78
<212> TYPE: PRT
<213> ORGANISM: Medicago truncatula

<400> SEQUENCE: 104

Met Val Glu Ile Leu Lys Asn Phe Tyr Ala Met Asn Leu Phe Ile Phe
1               5                   10                  15

Leu Ile Ile Leu Ala Val Lys Ile Arg Gly Ala His Phe Pro Cys Val
            20                  25                  30

Thr Asp Asp Asp Cys Pro Lys Pro Val Asn Lys Leu Arg Val Ile Lys
            35                  40                  45

Cys Ile Asp His Ile Cys Gln Tyr Ala Arg Asn Leu Pro Asp Phe Ala
        50                  55                  60

Ser Glu Ile Ser Glu Ser Thr Lys Met Pro Cys Lys Gly Glu
65                  70                  75

<210> SEQ ID NO 105
<211> LENGTH: 72
<212> TYPE: PRT
<213> ORGANISM: Medicago truncatula

<400> SEQUENCE: 105

Met Phe His Ala Gln Ala Glu Asn Met Ala Lys Val Ser Asn Phe Val
1               5                   10                  15

Cys Ile Met Ile Leu Phe Leu Ala Leu Phe Phe Ile Thr Met Asn Asp
            20                  25                  30

Ala Ala Arg Phe Glu Cys Arg Glu Asp Ser His Cys Val Thr Arg Ile
            35                  40                  45

Lys Cys Val Leu Pro Arg Lys Pro Glu Cys Arg Asn Tyr Ala Cys Gly
        50                  55                  60

Cys Tyr Asp Ser Asn Lys Tyr Arg
65                  70

<210> SEQ ID NO 106
<211> LENGTH: 78
<212> TYPE: PRT
<213> ORGANISM: Medicago truncatula

<400> SEQUENCE: 106

Met Gln Met Arg Gln Asn Met Ala Thr Ile Leu Asn Phe Val Phe Val
1               5                   10                  15

Ile Ile Leu Phe Ile Ser Leu Leu Val Val Thr Lys Gly Tyr Arg
            20                  25                  30

Glu Pro Phe Ser Ser Phe Thr Glu Gly Pro Thr Cys Lys Glu Asp Ile
            35                  40                  45
```

```
Asp Cys Pro Ser Ile Ser Cys Val Asn Pro Gln Val Pro Lys Cys Ile
    50                  55                  60

Met Phe Glu Cys His Cys Lys Tyr Ile Pro Thr Thr Leu Lys
65                  70                  75
```

<210> SEQ ID NO 107
<211> LENGTH: 71
<212> TYPE: PRT
<213> ORGANISM: Medicago truncatula

<400> SEQUENCE: 107

```
Met Ala Thr Ile Leu Met Tyr Val Tyr Ile Thr Ile Leu Phe Ile Ser
1               5                   10                  15

Ile Leu Thr Val Leu Thr Glu Gly Leu Tyr Glu Pro Leu Tyr Asn Phe
                20                  25                  30

Arg Arg Asp Pro Asp Cys Arg Arg Asn Ile Asp Cys Pro Ser Tyr Leu
            35                  40                  45

Cys Val Ala Pro Lys Val Pro Arg Cys Ile Met Phe Glu Cys His Cys
    50                  55                  60

Lys Asp Ile Pro Ser Asp His
65                  70
```

<210> SEQ ID NO 108
<211> LENGTH: 57
<212> TYPE: PRT
<213> ORGANISM: Medicago truncatula

<400> SEQUENCE: 108

```
Met Thr Thr Ser Leu Lys Phe Val Tyr Val Ala Ile Leu Phe Leu Ser
1               5                   10                  15

Leu Leu Leu Val Val Met Gly Gly Ile Arg Arg Phe Glu Cys Arg Gln
                20                  25                  30

Asp Ser Asp Cys Pro Ser Tyr Phe Cys Glu Lys Leu Thr Val Pro Lys
            35                  40                  45

Cys Phe Trp Ser Lys Cys Tyr Cys Lys
    50                  55
```

<210> SEQ ID NO 109
<211> LENGTH: 57
<212> TYPE: PRT
<213> ORGANISM: Medicago truncatula

<400> SEQUENCE: 109

```
Met Thr Thr Ser Leu Lys Phe Val Tyr Val Ala Ile Leu Phe Leu Ser
1               5                   10                  15

Leu Leu Leu Val Val Met Gly Gly Ile Arg Lys Lys Glu Cys Arg Gln
                20                  25                  30

Asp Ser Asp Cys Pro Ser Tyr Phe Cys Glu Lys Leu Thr Ile Ala Lys
            35                  40                  45

Cys Ile His Ser Thr Cys Leu Cys Lys
    50                  55
```

<210> SEQ ID NO 110
<211> LENGTH: 66
<212> TYPE: PRT
<213> ORGANISM: Medicago truncatula

<400> SEQUENCE: 110

```
Met Gln Ile Gly Lys Asn Met Val Glu Thr Pro Lys Leu Val Tyr Phe
1               5                   10                  15
```

```
Ile Ile Leu Phe Leu Ser Ile Phe Leu Cys Ile Thr Val Ser Asn Ser
            20                  25                  30

Ser Phe Ser Gln Ile Phe Asn Ser Ala Cys Lys Thr Asp Lys Asp Cys
        35                  40                  45

Pro Lys Phe Gly Arg Val Asn Val Arg Cys Arg Lys Gly Asn Cys Val
 50                  55                  60

Pro Ile
 65

<210> SEQ ID NO 111
<211> LENGTH: 57
<212> TYPE: PRT
<213> ORGANISM: Medicago truncatula

<400> SEQUENCE: 111

Met Thr Ala Ile Leu Lys Lys Phe Ile Asn Ala Val Phe Leu Phe Ile
 1               5                  10                  15

Val Leu Phe Leu Ala Thr Thr Asn Val Glu Asp Phe Val Gly Gly Ser
            20                  25                  30

Asn Asp Glu Cys Val Tyr Pro Asp Val Phe Gln Cys Ile Asn Asn Ile
        35                  40                  45

Cys Lys Cys Val Ser His His Arg Thr
 50                  55

<210> SEQ ID NO 112
<211> LENGTH: 74
<212> TYPE: PRT
<213> ORGANISM: Medicago truncatula

<400> SEQUENCE: 112

Met Gln Lys Arg Lys Asn Met Ala Gln Ile Ile Phe Tyr Val Tyr Ala
 1               5                  10                  15

Leu Ile Ile Leu Phe Ser Pro Phe Leu Ala Ala Arg Leu Val Phe Val
            20                  25                  30

Asn Pro Glu Lys Pro Cys Val Thr Asp Ala Asp Cys Asp Arg Tyr Arg
        35                  40                  45

His Glu Ser Ala Ile Tyr Ser Asp Met Phe Cys Lys Asp Gly Tyr Cys
 50                  55                  60

Phe Ile Asp Tyr His Asp Pro Tyr Pro
 65                  70

<210> SEQ ID NO 113
<211> LENGTH: 76
<212> TYPE: PRT
<213> ORGANISM: Medicago truncatula

<400> SEQUENCE: 113

Met Gln Met Arg Lys Asn Met Ala Gln Ile Leu Phe Tyr Val Tyr Ala
 1               5                  10                  15

Leu Leu Ile Leu Phe Thr Pro Phe Leu Val Ala Arg Ile Met Val Val
            20                  25                  30

Asn Pro Asn Asn Pro Cys Val Thr Asp Ala Asp Cys Gln Arg Tyr Arg
        35                  40                  45

His Lys Leu Ala Thr Arg Met Ile Cys Asn Gln Gly Phe Cys Leu Met
 50                  55                  60

Asp Phe Thr His Asp Pro Tyr Ala Pro Ser Leu Pro
 65                  70                  75
```

<210> SEQ ID NO 114
<211> LENGTH: 64
<212> TYPE: PRT
<213> ORGANISM: Medicago truncatula

<400> SEQUENCE: 114

Met Asn His Ile Ser Lys Phe Val Tyr Ala Leu Ile Ile Phe Leu Ser
1               5                   10                  15

Ile Tyr Leu Val Val Leu Asp Gly Leu Pro Ile Ser Cys Lys Asp His
            20                  25                  30

Phe Glu Cys Arg Arg Lys Ile Asn Ile Leu Arg Cys Ile Tyr Arg Gln
        35                  40                  45

Glu Lys Pro Met Cys Ile Asn Ser Ile Cys Thr Cys Val Lys Leu Leu
    50                  55                  60

<210> SEQ ID NO 115
<211> LENGTH: 67
<212> TYPE: PRT
<213> ORGANISM: Medicago truncatula

<400> SEQUENCE: 115

Met Gln Arg Glu Lys Asn Met Ala Lys Ile Phe Glu Phe Val Tyr Ala
1               5                   10                  15

Met Ile Ile Phe Ile Leu Leu Phe Leu Val Glu Lys Asn Val Val Ala
            20                  25                  30

Tyr Leu Lys Phe Glu Cys Lys Thr Asp Asp Cys Gln Lys Ser Leu
        35                  40                  45

Leu Lys Thr Tyr Val Trp Lys Cys Val Lys Asn Glu Cys Tyr Phe Phe
    50                  55                  60

Ala Lys Lys
65

<210> SEQ ID NO 116
<211> LENGTH: 61
<212> TYPE: PRT
<213> ORGANISM: Medicago truncatula

<400> SEQUENCE: 116

Met Ala Gly Ile Ile Lys Phe Val His Val Leu Ile Ile Phe Leu Ser
1               5                   10                  15

Leu Phe His Val Val Lys Asn Asp Asp Gly Ser Phe Cys Phe Lys Asp
            20                  25                  30

Ser Asp Cys Pro Asp Glu Met Cys Pro Ser Pro Leu Lys Glu Met Cys
        35                  40                  45

Tyr Phe Leu Gln Cys Lys Cys Gly Val Asp Thr Ile Ala
    50                  55                  60

<210> SEQ ID NO 117
<211> LENGTH: 59
<212> TYPE: PRT
<213> ORGANISM: Medicago truncatula

<400> SEQUENCE: 117

Met Ala Asn Thr His Lys Leu Val Ser Met Ile Leu Phe Ile Phe Leu
1               5                   10                  15

Phe Leu Ala Ser Asn Asn Val Glu Gly Tyr Val Asn Cys Glu Thr Asp
            20                  25                  30

Ala Asp Cys Pro Pro Ser Thr Arg Val Lys Arg Phe Lys Cys Val Lys
        35                  40                  45

```
Gly Glu Cys Arg Trp Thr Arg Met Ser Tyr Ala
    50                  55

<210> SEQ ID NO 118
<211> LENGTH: 63
<212> TYPE: PRT
<213> ORGANISM: Medicago truncatula

<400> SEQUENCE: 118

Met Gln Arg Arg Lys Lys Lys Ala Gln Val Val Met Phe Val His Asp
1               5                   10                  15

Leu Ile Ile Cys Ile Tyr Leu Phe Ile Val Ile Thr Thr Arg Lys Thr
            20                  25                  30

Asp Ile Arg Cys Arg Phe Tyr Tyr Asp Cys Pro Arg Leu Glu Tyr His
        35                  40                  45

Phe Cys Glu Cys Ile Glu Asp Phe Cys Ala Tyr Ile Arg Leu Asn
    50                  55                  60

<210> SEQ ID NO 119
<211> LENGTH: 57
<212> TYPE: PRT
<213> ORGANISM: Medicago truncatula

<400> SEQUENCE: 119

Met Ala Lys Val Tyr Met Phe Val Tyr Ala Leu Ile Ile Phe Val Ser
1               5                   10                  15

Pro Phe Leu Leu Ala Thr Phe Arg Thr Arg Leu Pro Cys Glu Lys Asp
            20                  25                  30

Asp Asp Cys Pro Glu Ala Phe Leu Pro Pro Val Met Lys Cys Val Asn
        35                  40                  45

Arg Phe Cys Gln Tyr Glu Ile Leu Glu
    50                  55

<210> SEQ ID NO 120
<211> LENGTH: 77
<212> TYPE: PRT
<213> ORGANISM: Medicago truncatula

<400> SEQUENCE: 120

Met Ile Lys Gln Phe Ser Val Cys Tyr Ile Gln Met Arg Arg Asn Met
1               5                   10                  15

Thr Thr Ile Leu Lys Phe Pro Tyr Ile Met Val Ile Cys Leu Leu Leu
            20                  25                  30

Leu His Val Ala Ala Tyr Glu Asp Phe Glu Lys Glu Ile Phe Asp Cys
        35                  40                  45

Lys Lys Asp Gly Asp Cys Asp His Met Cys Val Thr Pro Gly Ile Pro
    50                  55                  60

Lys Cys Thr Gly Tyr Val Cys Phe Cys Phe Glu Asn Leu
65                  70                  75

<210> SEQ ID NO 121
<211> LENGTH: 73
<212> TYPE: PRT
<213> ORGANISM: Medicago truncatula

<400> SEQUENCE: 121

Met Gln Arg Ser Arg Asn Met Thr Thr Ile Phe Lys Phe Ala Tyr Ile
1               5                   10                  15

Met Ile Ile Cys Val Phe Leu Leu Asn Ile Ala Ala Gln Glu Ile Glu
```

```
                20                  25                  30
Asn Gly Ile His Pro Cys Lys Lys Asn Glu Asp Cys Asn His Met Cys
                35                  40                  45

Val Met Pro Gly Leu Pro Trp Cys His Glu Asn Asn Leu Cys Phe Cys
        50                  55                  60

Tyr Glu Asn Ala Tyr Gly Asn Thr Arg
65                  70

<210> SEQ ID NO 122
<211> LENGTH: 85
<212> TYPE: PRT
<213> ORGANISM: Medicago truncatula

<400> SEQUENCE: 122

Met Thr Ile Ile Ile Lys Phe Val Asn Val Leu Ile Ile Phe Leu Ser
1               5                   10                  15

Leu Phe His Val Ala Lys Asn Asp Asp Asn Lys Leu Leu Leu Ser Phe
                20                  25                  30

Ile Glu Glu Gly Phe Leu Cys Phe Lys Asp Ser Asp Cys Pro Tyr Asn
            35                  40                  45

Met Cys Pro Ser Pro Leu Lys Glu Met Cys Tyr Phe Ile Lys Cys Val
        50                  55                  60

Cys Gly Val Tyr Gly Pro Ile Arg Glu Arg Leu Tyr Gln Ser His
65                  70                  75                  80

Asn Pro Met Ile Gln
                85

<210> SEQ ID NO 123
<211> LENGTH: 69
<212> TYPE: PRT
<213> ORGANISM: Medicago truncatula

<400> SEQUENCE: 123

Met Arg Lys Asn Met Thr Lys Ile Leu Met Ile Gly Tyr Ala Leu Met
1               5                   10                  15

Ile Phe Ile Phe Leu Ser Ile Ala Val Ser Ile Thr Gly Asn Leu Ala
                20                  25                  30

Arg Ala Ser Arg Lys Lys Pro Val Asp Val Ile Pro Cys Ile Tyr Asp
            35                  40                  45

His Asp Cys Pro Arg Lys Leu Tyr Phe Leu Glu Arg Cys Val Gly Arg
        50                  55                  60

Val Cys Lys Tyr Leu
65

<210> SEQ ID NO 124
<211> LENGTH: 58
<212> TYPE: PRT
<213> ORGANISM: Medicago truncatula

<400> SEQUENCE: 124

Met Ala His Lys Leu Val Tyr Ala Ile Thr Leu Phe Ile Phe Leu Phe
1               5                   10                  15

Leu Ile Ala Asn Asn Ile Glu Asp Asp Ile Phe Cys Ile Thr Asp Asn
                20                  25                  30

Asp Cys Pro Pro Asn Thr Leu Val Gln Arg Tyr Arg Cys Ile Asn Gly
            35                  40                  45

Lys Cys Asn Leu Ser Phe Val Ser Tyr Gly
        50                  55
```

-continued

<210> SEQ ID NO 125
<211> LENGTH: 61
<212> TYPE: PRT
<213> ORGANISM: Medicago truncatula

<400> SEQUENCE: 125

Met Asp Glu Thr Leu Lys Phe Val Tyr Ile Leu Ile Leu Phe Val Ser
1               5                   10                  15

Leu Cys Leu Val Val Ala Asp Gly Val Lys Asn Ile Asn Arg Glu Cys
            20                  25                  30

Thr Gln Thr Ser Asp Cys Tyr Lys Lys Tyr Pro Phe Ile Pro Trp Gly
        35                  40                  45

Lys Val Arg Cys Val Lys Gly Arg Cys Arg Leu Asp Met
    50                  55                  60

<210> SEQ ID NO 126
<211> LENGTH: 62
<212> TYPE: PRT
<213> ORGANISM: Medicago truncatula

<400> SEQUENCE: 126

Met Ala Lys Ile Ile Lys Phe Val Tyr Val Leu Ala Ile Phe Phe Ser
1               5                   10                  15

Leu Phe Leu Val Ala Lys Asn Val Asn Gly Trp Thr Cys Val Glu Asp
            20                  25                  30

Ser Asp Cys Pro Ala Asn Ile Cys Gln Pro Pro Met Gln Arg Met Cys
        35                  40                  45

Phe Tyr Gly Glu Cys Ala Cys Val Arg Ser Lys Phe Cys Thr
    50                  55                  60

<210> SEQ ID NO 127
<211> LENGTH: 61
<212> TYPE: PRT
<213> ORGANISM: Medicago truncatula

<400> SEQUENCE: 127

Met Val Lys Ile Ile Lys Phe Val Tyr Phe Met Thr Leu Phe Leu Ser
1               5                   10                  15

Met Leu Leu Val Thr Thr Lys Glu Asp Gly Ser Val Glu Cys Ile Ala
            20                  25                  30

Asn Ile Asp Cys Pro Gln Ile Phe Met Leu Pro Phe Val Met Arg Cys
        35                  40                  45

Ile Asn Phe Arg Cys Gln Ile Val Asn Ser Glu Asp Thr
    50                  55                  60

<210> SEQ ID NO 128
<211> LENGTH: 67
<212> TYPE: PRT
<213> ORGANISM: Medicago truncatula

<400> SEQUENCE: 128

Met Asp Glu Ile Leu Lys Phe Val Tyr Thr Leu Ile Ile Phe Phe Ser
1               5                   10                  15

Leu Phe Phe Ala Ala Asn Asn Val Asp Ala Asn Ile Met Asn Cys Gln
            20                  25                  30

Ser Thr Phe Asp Cys Pro Arg Asp Met Cys Ser His Ile Arg Asp Val
        35                  40                  45

Ile Cys Ile Phe Lys Lys Cys Lys Cys Ala Gly Gly Arg Tyr Met Pro

Gln Val Pro
65

<210> SEQ ID NO 129
<211> LENGTH: 62
<212> TYPE: PRT
<213> ORGANISM: Medicago truncatula

<400> SEQUENCE: 129

Met Gln Arg Arg Lys Asn Met Ala Asn Asn His Met Leu Ile Tyr Ala
1               5                   10                  15

Met Ile Ile Cys Leu Phe Pro Tyr Leu Val Val Thr Phe Lys Thr Ala
                20                  25                  30

Ile Thr Cys Asp Cys Asn Glu Asp Cys Leu Asn Phe Phe Thr Pro Leu
            35                  40                  45

Asp Asn Leu Lys Cys Ile Asp Asn Val Cys Glu Val Phe Met
        50                  55                  60

<210> SEQ ID NO 130
<211> LENGTH: 65
<212> TYPE: PRT
<213> ORGANISM: Medicago truncatula

<400> SEQUENCE: 130

Met Val Asn Ile Leu Lys Phe Ile Tyr Val Ile Phe Phe Ile Leu
1               5                   10                  15

Met Phe Phe Val Leu Ile Asp Val Asp Gly His Val Leu Val Glu Cys
                20                  25                  30

Ile Glu Asn Arg Asp Cys Glu Lys Gly Met Cys Lys Phe Pro Phe Ile
            35                  40                  45

Val Arg Cys Leu Met Asp Gln Cys Lys Cys Val Arg Ile His Asn Leu
        50                  55                  60

Ile
65

<210> SEQ ID NO 131
<211> LENGTH: 74
<212> TYPE: PRT
<213> ORGANISM: Medicago truncatula

<400> SEQUENCE: 131

Met Ile Ile Gln Phe Ser Ile Tyr Tyr Met Gln Arg Arg Lys Leu Asn
1               5                   10                  15

Met Val Glu Ile Leu Lys Phe Ser His Ala Leu Ile Ile Phe Leu Phe
                20                  25                  30

Leu Ser Ala Leu Val Thr Asn Ala Asn Ile Phe Phe Cys Ser Thr Asp
            35                  40                  45

Glu Asp Cys Thr Trp Asn Leu Cys Arg Gln Pro Trp Val Gln Lys Cys
        50                  55                  60

Arg Leu His Met Cys Ser Cys Glu Lys Asn
65                  70

<210> SEQ ID NO 132
<211> LENGTH: 58
<212> TYPE: PRT
<213> ORGANISM: Medicago truncatula

<400> SEQUENCE: 132

```
Met Asp Glu Val Phe Lys Phe Val Tyr Val Met Ile Ile Phe Pro Phe
1               5                   10                  15

Leu Ile Leu Asp Val Ala Thr Asn Ala Glu Lys Ile Arg Arg Cys Phe
            20                  25                  30

Asn Asp Ala His Cys Pro Pro Asp Met Cys Thr Leu Gly Val Ile Pro
            35                  40                  45

Lys Cys Ser Arg Phe Thr Ile Cys Ile Cys
50                  55
```

<210> SEQ ID NO 133
<211> LENGTH: 64
<212> TYPE: PRT
<213> ORGANISM: Medicago truncatula

<400> SEQUENCE: 133

```
Met His Arg Lys Pro Asn Met Thr Lys Phe Phe Lys Phe Val Tyr Thr
1               5                   10                  15

Met Phe Ile Leu Ile Ser Leu Phe Leu Val Val Thr Asn Ala Asn Ala
            20                  25                  30

Asn Asn Cys Thr Asp Thr Ser Asp Cys Ser Ser Asn His Cys Ser Tyr
            35                  40                  45

Glu Gly Val Ser Leu Cys Met Asn Gly Gln Cys Ile Cys Ile Tyr Glu
50                  55                  60
```

<210> SEQ ID NO 134
<211> LENGTH: 69
<212> TYPE: PRT
<213> ORGANISM: Medicago truncatula

<400> SEQUENCE: 134

```
Met Gln Met Lys Lys Met Ala Thr Ile Leu Lys Phe Val Tyr Leu Ile
1               5                   10                  15

Ile Leu Leu Ile Tyr Pro Leu Leu Val Val Thr Glu Glu Ser His Tyr
            20                  25                  30

Met Lys Phe Ser Ile Cys Lys Asp Asp Thr Asp Cys Pro Thr Leu Phe
            35                  40                  45

Cys Val Leu Pro Asn Val Pro Lys Cys Ile Gly Ser Lys Cys His Cys
50                  55                  60

Lys Leu Met Val Asn
65
```

<210> SEQ ID NO 135
<211> LENGTH: 64
<212> TYPE: PRT
<213> ORGANISM: Medicago truncatula

<400> SEQUENCE: 135

```
Met Val Glu Thr Leu Arg Leu Phe Tyr Ile Met Ile Leu Phe Val Ser
1               5                   10                  15

Leu Tyr Leu Val Val Val Asp Gly Val Ser Lys Leu Ala Gln Ser Cys
            20                  25                  30

Ser Glu Asp Phe Glu Cys Tyr Ile Lys Asn Pro His Ala Pro Phe Gly
            35                  40                  45

Gln Leu Arg Cys Phe Glu Gly Tyr Cys Gln Arg Leu Asp Lys Pro Thr
50                  55                  60
```

<210> SEQ ID NO 136
<211> LENGTH: 63
<212> TYPE: PRT

<213> ORGANISM: Medicago truncatula

<400> SEQUENCE: 136

Met Thr Thr Phe Leu Lys Val Ala Tyr Ile Met Ile Cys Val Phe
1               5                   10                  15

Val Leu His Leu Ala Ala Gln Val Asp Ser Gln Lys Arg Leu His Gly
                20                  25                  30

Cys Lys Glu Asp Arg Asp Cys Asp Asn Ile Cys Ser Val His Ala Val
            35                  40                  45

Thr Lys Cys Ile Gly Asn Met Cys Arg Cys Leu Ala Asn Val Lys
        50                  55                  60

<210> SEQ ID NO 137
<211> LENGTH: 61
<212> TYPE: PRT
<213> ORGANISM: Medicago truncatula

<400> SEQUENCE: 137

Met Arg Ile Asn Arg Thr Pro Ala Ile Phe Lys Phe Val Tyr Thr Ile
1               5                   10                  15

Ile Ile Tyr Leu Phe Leu Leu Arg Val Val Ala Lys Asp Leu Pro Phe
                20                  25                  30

Asn Ile Cys Glu Lys Asp Glu Asp Cys Leu Glu Phe Cys Ala His Asp
            35                  40                  45

Lys Val Ala Lys Cys Met Leu Asn Ile Cys Phe Cys Phe
        50                  55                  60

<210> SEQ ID NO 138
<211> LENGTH: 54
<212> TYPE: PRT
<213> ORGANISM: Medicago truncatula

<400> SEQUENCE: 138

Met Ala Glu Ile Leu Lys Ile Leu Tyr Val Phe Ile Ile Phe Leu Ser
1               5                   10                  15

Leu Ile Leu Ala Val Ile Ser Gln His Pro Phe Thr Pro Cys Glu Thr
                20                  25                  30

Asn Ala Asp Cys Lys Cys Arg Asn His Lys Arg Pro Asp Cys Leu Trp
            35                  40                  45

His Lys Cys Tyr Cys Tyr
        50

<210> SEQ ID NO 139
<211> LENGTH: 65
<212> TYPE: PRT
<213> ORGANISM: Medicago truncatula

<400> SEQUENCE: 139

Met Arg Lys Ser Met Ala Thr Ile Leu Lys Phe Val Tyr Val Ile Met
1               5                   10                  15

Leu Phe Ile Tyr Ser Leu Phe Val Ile Glu Ser Phe Gly His Arg Phe
                20                  25                  30

Leu Ile Tyr Asn Asn Cys Lys Asn Asp Thr Glu Cys Pro Asn Asp Cys
            35                  40                  45

Gly Pro His Glu Gln Ala Lys Cys Ile Leu Tyr Ala Cys Tyr Cys Val
        50                  55                  60

Glu
65

<210> SEQ ID NO 140
<211> LENGTH: 58
<212> TYPE: PRT
<213> ORGANISM: Medicago truncatula

<400> SEQUENCE: 140

Met Asn Thr Ile Leu Lys Phe Ile Phe Val Phe Leu Phe Leu Ser
1               5                   10                  15

Ile Phe Leu Ser Ala Gly Asn Ser Lys Ser Tyr Gly Pro Cys Thr Thr
            20                  25                  30

Leu Gln Asp Cys Glu Thr His Asn Trp Phe Glu Val Cys Ser Cys Ile
        35                  40                  45

Asp Phe Glu Cys Lys Cys Trp Ser Leu Leu
    50                  55

<210> SEQ ID NO 141
<211> LENGTH: 64
<212> TYPE: PRT
<213> ORGANISM: Medicago truncatula

<400> SEQUENCE: 141

Met Ala Glu Ile Ile Lys Phe Val Tyr Ile Met Ile Leu Cys Val Ser
1               5                   10                  15

Leu Leu Leu Ile Ala Glu Ala Ser Gly Lys Glu Cys Val Thr Asp Ala
            20                  25                  30

Asp Cys Glu Asn Leu Tyr Pro Gly Asn Lys Lys Pro Met Phe Cys Asn
        35                  40                  45

Asn Thr Gly Tyr Cys Met Ser Leu Tyr Lys Glu Pro Ser Arg Tyr Met
    50                  55                  60

<210> SEQ ID NO 142
<211> LENGTH: 64
<212> TYPE: PRT
<213> ORGANISM: Medicago truncatula

<400> SEQUENCE: 142

Met Ala Lys Ile Ile Lys Phe Val Tyr Ile Met Ile Leu Cys Val Ser
1               5                   10                  15

Leu Leu Leu Ile Val Glu Ala Gly Lys Glu Cys Val Thr Asp Val
            20                  25                  30

Asp Cys Glu Lys Ile Tyr Pro Gly Asn Lys Lys Pro Leu Ile Cys Ser
        35                  40                  45

Thr Gly Tyr Cys Tyr Ser Leu Tyr Glu Glu Pro Pro Arg Tyr His Lys
    50                  55                  60

<210> SEQ ID NO 143
<211> LENGTH: 64
<212> TYPE: PRT
<213> ORGANISM: Medicago truncatula

<400> SEQUENCE: 143

Met Ala Lys Val Thr Lys Phe Gly Tyr Ile Ile His Phe Leu Ser
1               5                   10                  15

Leu Phe Phe Leu Ala Met Asn Val Ala Gly Gly Arg Glu Cys His Ala
            20                  25                  30

Asn Ser His Cys Val Gly Lys Ile Thr Cys Val Leu Pro Gln Lys Pro
        35                  40                  45

Glu Cys Trp Asn Tyr Ala Cys Val Cys Tyr Asp Ser Asn Lys Tyr Arg
    50                  55                  60

<210> SEQ ID NO 144
<211> LENGTH: 55
<212> TYPE: PRT
<213> ORGANISM: Medicago truncatula

<400> SEQUENCE: 144

Met Ala Lys Ile Phe Asn Tyr Val Tyr Ala Leu Ile Met Phe Leu Ser
1               5                   10                  15

Leu Phe Leu Met Gly Thr Ser Gly Met Lys Asn Gly Cys Lys His Thr
            20                  25                  30

Gly His Cys Pro Arg Lys Met Cys Gly Ala Lys Thr Thr Lys Cys Arg
        35                  40                  45

Asn Asn Lys Cys Gln Cys Val
    50                  55

<210> SEQ ID NO 145
<211> LENGTH: 69
<212> TYPE: PRT
<213> ORGANISM: Medicago truncatula

<400> SEQUENCE: 145

Met Thr Glu Ile Leu Lys Phe Val Cys Val Met Ile Ile Phe Ile Ser
1               5                   10                  15

Ser Phe Ile Val Ser Lys Ser Leu Asn Gly Gly Gly Lys Asp Lys Cys
            20                  25                  30

Phe Arg Asp Ser Asp Cys Pro Lys His Met Cys Pro Ser Ser Leu Val
        35                  40                  45

Ala Lys Cys Ile Asn Arg Leu Cys Arg Cys Arg Arg Pro Glu Leu Gln
    50                  55                  60

Val Gln Leu Asn Pro
65

<210> SEQ ID NO 146
<211> LENGTH: 69
<212> TYPE: PRT
<213> ORGANISM: Medicago truncatula

<400> SEQUENCE: 146

Met Ala His Ile Ile Met Phe Val Tyr Ala Leu Ile Tyr Ala Leu Ile
1               5                   10                  15

Ile Phe Ser Ser Leu Phe Val Arg Asp Gly Ile Pro Cys Leu Ser Asp
            20                  25                  30

Asp Glu Cys Pro Glu Met Ser His Tyr Ser Phe Lys Cys Asn Asn Lys
        35                  40                  45

Ile Cys Glu Tyr Asp Leu Gly Glu Met Ser Asp Asp Tyr Tyr Leu
    50                  55                  60

Glu Met Ser Arg Glu
65

<210> SEQ ID NO 147
<211> LENGTH: 77
<212> TYPE: PRT
<213> ORGANISM: Medicago truncatula

<400> SEQUENCE: 147

Met Tyr Arg Glu Lys Asn Met Ala Lys Thr Leu Lys Phe Val Tyr Val
1               5                   10                  15

Ile Val Leu Phe Leu Ser Leu Phe Leu Ala Ala Lys Asn Ile Asp Gly

```
                    20                  25                  30

Arg Val Ser Tyr Asn Ser Phe Ile Ala Leu Pro Val Cys Gln Thr Ala
            35                  40                  45

Ala Asp Cys Pro Glu Gly Thr Arg Gly Arg Thr Tyr Lys Cys Ile Asn
        50                  55                  60

Asn Lys Cys Arg Tyr Pro Lys Leu Leu Lys Pro Ile Gln
65                  70                  75

<210> SEQ ID NO 148
<211> LENGTH: 56
<212> TYPE: PRT
<213> ORGANISM: Medicago truncatula

<400> SEQUENCE: 148

Met Ala His Ile Phe Asn Tyr Val Tyr Ala Leu Leu Val Phe Leu Ser
1               5                   10                  15

Leu Phe Leu Met Val Thr Asn Gly Ile His Ile Gly Cys Asp Lys Asp
                20                  25                  30

Arg Asp Cys Pro Lys Gln Met Cys His Leu Asn Gln Thr Pro Lys Cys
            35                  40                  45

Leu Lys Asn Ile Cys Lys Cys Val
        50                  55

<210> SEQ ID NO 149
<211> LENGTH: 77
<212> TYPE: PRT
<213> ORGANISM: Medicago truncatula

<400> SEQUENCE: 149

Met Ala Glu Ile Leu Lys Cys Phe Tyr Thr Met Asn Leu Phe Ile Phe
1               5                   10                  15

Leu Ile Ile Leu Pro Ala Lys Ile Arg Glu His Ile Gln Cys Val Ile
                20                  25                  30

Asp Asp Asp Cys Pro Lys Ser Leu Asn Lys Leu Ile Ile Lys Cys
            35                  40                  45

Ile Asn His Val Cys Gln Tyr Val Gly Asn Leu Pro Asp Phe Ala Ser
        50                  55                  60

Gln Ile Pro Lys Ser Thr Lys Met Pro Tyr Lys Gly Glu
65                  70                  75

<210> SEQ ID NO 150
<211> LENGTH: 70
<212> TYPE: PRT
<213> ORGANISM: Medicago truncatula

<400> SEQUENCE: 150

Met Ala Tyr Ile Ser Arg Ile Phe Tyr Val Leu Ile Ile Phe Leu Ser
1               5                   10                  15

Leu Phe Phe Val Val Ile Asn Gly Val Lys Ser Leu Leu Leu Ile Lys
                20                  25                  30

Val Arg Ser Phe Ile Pro Cys Gln Arg Ser Asp Asp Cys Pro Arg Asn
            35                  40                  45

Leu Cys Val Asp Gln Ile Ile Pro Thr Cys Val Trp Ala Lys Cys Lys
        50                  55                  60

Cys Lys Asn Tyr Asn Asp
65                  70

<210> SEQ ID NO 151
```

```
<211> LENGTH: 64
<212> TYPE: PRT
<213> ORGANISM: Medicago truncatula

<400> SEQUENCE: 151

Met Ala Asn Val Thr Lys Phe Val Tyr Ile Ala Ile Tyr Phe Leu Ser
1               5                   10                  15

Leu Phe Phe Ile Ala Lys Asn Asp Ala Thr Ala Thr Phe Cys His Asp
                20                  25                  30

Asp Ser His Cys Val Thr Lys Ile Lys Cys Val Leu Pro Arg Thr Pro
            35                  40                  45

Gln Cys Arg Asn Glu Ala Cys Gly Cys Tyr His Ser Asn Lys Phe Arg
        50                  55                  60

<210> SEQ ID NO 152
<211> LENGTH: 62
<212> TYPE: PRT
<213> ORGANISM: Medicago truncatula

<400> SEQUENCE: 152

Met Gly Glu Ile Met Lys Phe Val Tyr Val Met Ile Ile Tyr Leu Phe
1               5                   10                  15

Met Phe Asn Val Ala Thr Gly Ser Glu Phe Ile Phe Thr Lys Lys Leu
                20                  25                  30

Thr Ser Cys Asp Ser Ser Lys Asp Cys Arg Ser Phe Leu Cys Tyr Ser
            35                  40                  45

Pro Lys Phe Pro Val Cys Lys Arg Gly Ile Cys Glu Cys Ile
        50                  55                  60

<210> SEQ ID NO 153
<211> LENGTH: 61
<212> TYPE: PRT
<213> ORGANISM: Medicago truncatula

<400> SEQUENCE: 153

Met Gly Glu Met Phe Lys Phe Ile Tyr Thr Phe Ile Leu Phe Val His
1               5                   10                  15

Leu Phe Leu Val Val Ile Phe Glu Asp Ile Gly His Ile Lys Tyr Cys
                20                  25                  30

Gly Ile Val Asp Asp Cys Tyr Lys Ser Lys Lys Pro Leu Phe Lys Ile
            35                  40                  45

Trp Lys Cys Val Glu Asn Val Cys Val Leu Trp Tyr Lys
        50                  55                  60

<210> SEQ ID NO 154
<211> LENGTH: 63
<212> TYPE: PRT
<213> ORGANISM: Medicago truncatula

<400> SEQUENCE: 154

Met Ala Arg Thr Leu Lys Phe Val Tyr Ser Met Ile Leu Phe Leu Ser
1               5                   10                  15

Leu Phe Leu Val Ala Asn Gly Leu Lys Ile Phe Cys Ile Asp Val Ala
                20                  25                  30

Asp Cys Pro Lys Asp Leu Tyr Pro Leu Leu Tyr Lys Cys Ile Tyr Asn
            35                  40                  45

Lys Cys Ile Val Phe Thr Arg Ile Pro Phe Pro Phe Asp Trp Ile
        50                  55                  60
```

<210> SEQ ID NO 155
<211> LENGTH: 66
<212> TYPE: PRT
<213> ORGANISM: Medicago truncatula

<400> SEQUENCE: 155

Met Ala Asn Ile Thr Lys Phe Val Tyr Ile Ala Ile Leu Phe Leu Ser
1               5                   10                  15

Leu Phe Phe Ile Gly Met Asn Asp Ala Ala Ile Leu Glu Cys Arg Glu
            20                  25                  30

Asp Ser His Cys Val Thr Lys Ile Lys Cys Val Leu Pro Arg Lys Pro
        35                  40                  45

Glu Cys Arg Asn Asn Ala Cys Thr Cys Tyr Lys Gly Gly Phe Ser Phe
    50                  55                  60

His His
65

<210> SEQ ID NO 156
<211> LENGTH: 68
<212> TYPE: PRT
<213> ORGANISM: Medicago truncatula

<400> SEQUENCE: 156

Met Gln Arg Val Lys Lys Met Ser Glu Thr Leu Lys Phe Val Tyr Val
1               5                   10                  15

Leu Ile Leu Phe Ile Ser Ile Phe His Val Val Ile Val Cys Asp Ser
            20                  25                  30

Ile Tyr Phe Pro Val Ser Arg Pro Cys Ile Thr Asp Lys Asp Cys Pro
        35                  40                  45

Asn Met Lys His Tyr Lys Ala Lys Cys Arg Lys Gly Phe Cys Ile Ser
    50                  55                  60

Ser Arg Val Arg
65

<210> SEQ ID NO 157
<211> LENGTH: 72
<212> TYPE: PRT
<213> ORGANISM: Medicago truncatula

<400> SEQUENCE: 157

Met Gln Ile Arg Lys Ile Met Ser Gly Val Leu Lys Phe Val Tyr Ala
1               5                   10                  15

Ile Ile Leu Phe Leu Phe Leu Phe Leu Val Ala Arg Glu Val Gly Gly
            20                  25                  30

Leu Glu Thr Ile Glu Cys Glu Thr Asp Gly Asp Cys Pro Arg Ser Met
        35                  40                  45

Ile Lys Met Trp Asn Lys Asn Tyr Arg His Lys Cys Ile Asp Gly Lys
    50                  55                  60

Cys Glu Trp Ile Lys Lys Leu Pro
65                  70

<210> SEQ ID NO 158
<211> LENGTH: 54
<212> TYPE: PRT
<213> ORGANISM: Medicago truncatula

<400> SEQUENCE: 158

Met Phe Val Tyr Asp Leu Ile Leu Phe Ile Ser Leu Ile Leu Val Val
1               5                   10                  15

Thr Gly Ile Asn Ala Glu Ala Asp Thr Ser Cys His Ser Phe Asp Asp
                20                  25                  30

Cys Pro Trp Val Ala His His Tyr Arg Glu Cys Ile Glu Gly Leu Cys
            35                  40                  45

Ala Tyr Arg Ile Leu Tyr
        50

<210> SEQ ID NO 159
<211> LENGTH: 69
<212> TYPE: PRT
<213> ORGANISM: Medicago truncatula

<400> SEQUENCE: 159

Met Gln Arg Arg Lys Ser Met Ala Lys Met Leu Lys Phe Phe Phe
1               5                   10                  15

Ala Ile Ile Leu Leu Leu Ser Leu Phe Leu Val Ala Thr Glu Val Gly
                20                  25                  30

Gly Ala Tyr Ile Glu Cys Glu Val Asp Asp Asp Cys Pro Lys Pro Met
            35                  40                  45

Lys Asn Ser His Pro Asp Thr Tyr Tyr Lys Cys Val Lys His Arg Cys
    50                  55                  60

Gln Trp Ala Trp Lys
65

<210> SEQ ID NO 160
<211> LENGTH: 140
<212> TYPE: PRT
<213> ORGANISM: Medicago truncatula

<400> SEQUENCE: 160

Met Phe Val Tyr Thr Leu Ile Ile Phe Leu Phe Pro Ser His Val Ile
1               5                   10                  15

Thr Asn Lys Ile Ala Ile Tyr Cys Val Ser Asp Asp Asp Cys Leu Lys
                20                  25                  30

Thr Phe Thr Pro Leu Asp Leu Lys Cys Val Asp Asn Val Cys Glu Phe
            35                  40                  45

Asn Leu Arg Cys Lys Gly Lys Cys Gly Glu Arg Asp Glu Lys Phe Val
    50                  55                  60

Phe Leu Lys Ala Leu Lys Lys Met Asp Gln Lys Leu Val Leu Glu Glu
65                  70                  75                  80

Gln Gly Asn Ala Arg Glu Val Lys Ile Pro Lys Lys Leu Leu Phe Asp
                85                  90                  95

Arg Ile Gln Val Pro Thr Pro Ala Thr Lys Asp Gln Val Glu Glu Asp
            100                 105                 110

Asp Tyr Asp Asp Asp Glu Glu Glu Glu Glu Glu Asp Asp Val
            115                 120                 125

Asp Met Trp Phe His Leu Pro Asp Val Val Cys His
    130                 135                 140

<210> SEQ ID NO 161
<211> LENGTH: 60
<212> TYPE: PRT
<213> ORGANISM: Medicago truncatula

<400> SEQUENCE: 161

Met Ala Lys Phe Ser Met Phe Val Tyr Ala Leu Ile Asn Phe Leu Ser
1               5                   10                  15

Leu Phe Leu Val Glu Thr Ala Ile Thr Asn Ile Arg Cys Val Ser Asp

```
                    20                  25                  30
Asp Asp Cys Pro Lys Val Ile Lys Pro Leu Val Met Lys Cys Ile Gly
            35                  40                  45

Asn Tyr Cys Tyr Phe Phe Met Ile Tyr Glu Gly Pro
        50                  55                  60

<210> SEQ ID NO 162
<211> LENGTH: 58
<212> TYPE: PRT
<213> ORGANISM: Medicago truncatula

<400> SEQUENCE: 162

Met Ala His Lys Phe Val Tyr Ala Ile Ile Leu Phe Ile Phe Leu Phe
1               5                   10                  15

Leu Val Ala Lys Asn Val Lys Gly Tyr Val Val Cys Arg Thr Val Asp
                20                  25                  30

Asp Cys Pro Pro Asp Thr Arg Asp Leu Arg Tyr Arg Cys Leu Asn Gly
            35                  40                  45

Lys Cys Lys Ser Tyr Arg Leu Ser Tyr Gly
        50                  55

<210> SEQ ID NO 163
<211> LENGTH: 61
<212> TYPE: PRT
<213> ORGANISM: Medicago truncatula

<400> SEQUENCE: 163

Met Gln Arg Lys Lys Asn Met Gly Gln Ile Leu Ile Phe Val Phe Ala
1               5                   10                  15

Leu Ile Asn Phe Leu Ser Pro Ile Leu Val Glu Met Thr Thr Thr Thr
                20                  25                  30

Ile Pro Cys Thr Phe Ile Asp Asp Cys Pro Lys Met Pro Leu Val Val
            35                  40                  45

Lys Cys Ile Asp Asn Phe Cys Asn Tyr Phe Glu Ile Lys
        50                  55                  60

<210> SEQ ID NO 164
<211> LENGTH: 57
<212> TYPE: PRT
<213> ORGANISM: Medicago truncatula

<400> SEQUENCE: 164

Met Ala Gln Thr Leu Met Leu Val Tyr Ala Leu Ile Ile Phe Thr Ser
1               5                   10                  15

Leu Phe Leu Val Val Ile Ser Arg Gln Thr Asp Ile Pro Cys Lys Ser
                20                  25                  30

Asp Asp Ala Cys Pro Arg Val Ser Ser His His Ile Glu Cys Val Lys
            35                  40                  45

Gly Phe Cys Thr Tyr Trp Lys Leu Asp
        50                  55

<210> SEQ ID NO 165
<211> LENGTH: 77
<212> TYPE: PRT
<213> ORGANISM: Medicago truncatula

<400> SEQUENCE: 165

Met Leu Arg Arg Lys Asn Thr Val Gln Ile Leu Met Phe Val Ser Ala
1               5                   10                  15
```

```
Leu Leu Ile Tyr Ile Phe Leu Phe Leu Val Ile Thr Ser Ser Ala Asn
            20                  25                  30

Ile Pro Cys Asn Ser Asp Ser Asp Cys Pro Trp Lys Ile Tyr Tyr Thr
        35                  40                  45

Tyr Arg Cys Asn Asp Gly Phe Cys Val Tyr Lys Ser Ile Asp Pro Ser
    50                  55                  60

Thr Ile Pro Gln Tyr Met Thr Asp Leu Ile Phe Pro Arg
65                  70                  75
```

<210> SEQ ID NO 166
<211> LENGTH: 59
<212> TYPE: PRT
<213> ORGANISM: Medicago truncatula

<400> SEQUENCE: 166

```
Met Ala Val Ile Leu Lys Phe Val Tyr Ile Met Ile Ile Phe Leu Phe
1               5                   10                  15

Leu Leu Tyr Val Val Asn Gly Thr Arg Cys Asn Arg Asp Glu Asp Cys
            20                  25                  30

Pro Phe Ile Cys Thr Gly Pro Gln Ile Pro Lys Cys Val Ser His Ile
        35                  40                  45

Cys Phe Cys Leu Ser Ser Gly Lys Glu Ala Tyr
    50                  55
```

<210> SEQ ID NO 167
<211> LENGTH: 62
<212> TYPE: PRT
<213> ORGANISM: Medicago truncatula

<400> SEQUENCE: 167

```
Met Asp Ala Ile Leu Lys Phe Ile Tyr Ala Met Phe Leu Phe Leu Phe
1               5                   10                  15

Leu Phe Val Thr Thr Arg Asn Val Glu Ala Leu Phe Glu Cys Asn Arg
            20                  25                  30

Asp Phe Val Cys Gly Asn Asp Asp Glu Cys Val Tyr Pro Tyr Ala Val
        35                  40                  45

Gln Cys Ile His Arg Tyr Cys Lys Cys Leu Lys Ser Arg Asn
    50                  55                  60
```

<210> SEQ ID NO 168
<211> LENGTH: 67
<212> TYPE: PRT
<213> ORGANISM: Medicago truncatula

<400> SEQUENCE: 168

```
Met Gln Ile Gly Arg Lys Lys Met Gly Glu Thr Pro Lys Leu Val Tyr
1               5                   10                  15

Val Ile Ile Leu Phe Leu Ser Ile Phe Leu Cys Thr Asn Ser Ser Phe
            20                  25                  30

Ser Gln Met Ile Asn Phe Arg Gly Cys Lys Arg Asp Lys Asp Cys Pro
        35                  40                  45

Gln Phe Arg Gly Val Asn Ile Arg Cys Arg Ser Gly Phe Cys Thr Pro
    50                  55                  60

Ile Asp Ser
65
```

<210> SEQ ID NO 169
<211> LENGTH: 76
<212> TYPE: PRT

<213> ORGANISM: Medicago truncatula

<400> SEQUENCE: 169

Met Gln Met Arg Lys Asn Met Ala Gln Ile Leu Phe Tyr Val Tyr Ala
1               5                   10                  15

Leu Leu Ile Leu Phe Ser Pro Phe Leu Val Ala Arg Ile Met Val Val
            20                  25                  30

Asn Pro Asn Pro Cys Val Thr Asp Ala Asp Cys Gln Arg Tyr Arg
        35                  40                  45

His Lys Leu Ala Thr Arg Met Val Cys Asn Ile Gly Phe Cys Leu Met
    50                  55                  60

Asp Phe Thr His Asp Pro Tyr Ala Pro Ser Leu Pro
65                  70                  75

<210> SEQ ID NO 170
<211> LENGTH: 77
<212> TYPE: PRT
<213> ORGANISM: Medicago truncatula

<400> SEQUENCE: 170

Met Tyr Val Tyr Tyr Ile Gln Met Gly Lys Asn Met Ala Gln Arg Phe
1               5                   10                  15

Met Phe Ile Tyr Ala Leu Ile Ile Phe Leu Ser Gln Phe Phe Val Val
            20                  25                  30

Ile Asn Thr Ser Asp Ile Pro Asn Asn Ser Asn Arg Asn Ser Pro Lys
        35                  40                  45

Glu Asp Val Phe Cys Asn Ser Asn Asp Cys Pro Thr Ile Leu Tyr
    50                  55                  60

Tyr Val Ser Lys Cys Val Tyr Asn Phe Cys Glu Tyr Trp
65                  70                  75

<210> SEQ ID NO 171
<211> LENGTH: 67
<212> TYPE: PRT
<213> ORGANISM: Medicago truncatula

<400> SEQUENCE: 171

Met Ala Lys Ile Val Asn Phe Val Tyr Ser Met Ile Ile Phe Val Ser
1               5                   10                  15

Leu Phe Leu Val Ala Thr Lys Gly Gly Ser Lys Pro Phe Leu Thr Arg
            20                  25                  30

Pro Tyr Pro Cys Asn Thr Gly Ser Asp Cys Pro Gln Asn Met Cys Pro
        35                  40                  45

Pro Gly Tyr Lys Pro Gly Cys Glu Asp Gly Tyr Cys Asn His Cys Tyr
    50                  55                  60

Lys Arg Trp
65

<210> SEQ ID NO 172
<211> LENGTH: 62
<212> TYPE: PRT
<213> ORGANISM: Medicago truncatula

<400> SEQUENCE: 172

Met Val Arg Thr Leu Lys Phe Val Tyr Val Ile Ile Leu Ile Leu Ser
1               5                   10                  15

Leu Phe Leu Val Ala Lys Gly Gly Lys Lys Ile Tyr Cys Glu Asn
            20                  25                  30

```
Ala Ala Ser Cys Pro Arg Leu Met Tyr Pro Leu Val Tyr Lys Cys Leu
         35                  40                  45

Asp Asn Lys Cys Val Lys Phe Met Met Lys Ser Arg Phe Val
 50                  55                  60
```

<210> SEQ ID NO 173
<211> LENGTH: 62
<212> TYPE: PRT
<213> ORGANISM: Medicago truncatula

<400> SEQUENCE: 173

```
Met Ala Arg Thr Leu Lys Phe Val Tyr Ala Val Ile Leu Phe Leu Ser
 1               5                  10                  15

Leu Phe Leu Val Ala Lys Gly Asp Asp Val Lys Ile Lys Cys Val Val
             20                  25                  30

Ala Ala Asn Cys Pro Asp Leu Met Tyr Pro Leu Val Tyr Lys Cys Leu
         35                  40                  45

Asn Gly Ile Cys Val Gln Phe Thr Leu Thr Phe Pro Phe Val
 50                  55                  60
```

<210> SEQ ID NO 174
<211> LENGTH: 65
<212> TYPE: PRT
<213> ORGANISM: Medicago truncatula

<400> SEQUENCE: 174

```
Met Ser Asn Thr Leu Met Phe Val Ile Thr Phe Ile Val Leu Val Thr
 1               5                  10                  15

Leu Phe Leu Gly Pro Lys Asn Val Tyr Ala Phe Gln Pro Cys Val Thr
             20                  25                  30

Thr Ala Asp Cys Met Lys Thr Leu Lys Thr Asp Glu Asn Ile Trp Tyr
         35                  40                  45

Glu Cys Ile Asn Asp Phe Cys Ile Pro Phe Pro Ile Pro Lys Gly Arg
 50                  55                  60

Lys
65
```

<210> SEQ ID NO 175
<211> LENGTH: 76
<212> TYPE: PRT
<213> ORGANISM: Medicago truncatula

<400> SEQUENCE: 175

```
Met Lys Arg Val Val Asn Met Ala Lys Ile Val Lys Tyr Val Tyr Val
 1               5                  10                  15

Ile Ile Ile Phe Leu Ser Leu Phe Leu Val Ala Thr Lys Ile Glu Gly
             20                  25                  30

Tyr Tyr Tyr Lys Cys Phe Lys Asp Ser Asp Cys Val Lys Leu Leu Cys
         35                  40                  45

Arg Ile Pro Leu Arg Pro Lys Cys Met Tyr Arg His Ile Cys Lys Cys
 50                  55                  60

Lys Val Val Leu Thr Gln Asn Asn Tyr Val Leu Thr
65                  70                  75
```

<210> SEQ ID NO 176
<211> LENGTH: 66
<212> TYPE: PRT
<213> ORGANISM: Medicago truncatula

<400> SEQUENCE: 176

```
Met Lys Arg Gly Lys Asn Met Ser Lys Ile Leu Lys Phe Ile Tyr Ala
1               5                   10                  15

Thr Leu Val Leu Tyr Leu Phe Leu Val Val Thr Lys Ala Ser Asp Asp
                20                  25                  30

Glu Cys Lys Ile Asp Gly Asp Cys Pro Ile Ser Trp Gln Lys Phe His
                35                  40                  45

Thr Tyr Lys Cys Ile Asn Gln Lys Cys Lys Trp Val Leu Arg Phe His
        50                  55                  60

Glu Tyr
65

<210> SEQ ID NO 177
<211> LENGTH: 64
<212> TYPE: PRT
<213> ORGANISM: Medicago truncatula

<400> SEQUENCE: 177

Met Ala Lys Thr Leu Asn Phe Met Phe Ala Leu Ile Leu Phe Ile Ser
1               5                   10                  15

Leu Phe Leu Val Ser Lys Asn Val Ala Ile Asp Ile Phe Val Cys Gln
                20                  25                  30

Thr Asp Ala Asp Cys Pro Lys Ser Glu Leu Ser Met Tyr Thr Trp Lys
                35                  40                  45

Cys Ile Asp Asn Glu Cys Asn Leu Phe Lys Val Met Gln Gln Met Val
        50                  55                  60

<210> SEQ ID NO 178
<211> LENGTH: 59
<212> TYPE: PRT
<213> ORGANISM: Medicago truncatula

<400> SEQUENCE: 178

Met Ala Asn Thr His Lys Leu Val Ser Met Ile Leu Phe Ile Phe Leu
1               5                   10                  15

Phe Leu Val Ala Asn Asn Val Glu Gly Tyr Val Asn Cys Glu Thr Asp
                20                  25                  30

Ala Asp Cys Pro Pro Ser Thr Arg Val Lys Arg Phe Lys Cys Val Lys
                35                  40                  45

Gly Glu Cys Arg Trp Thr Arg Met Ser Tyr Ala
        50                  55

<210> SEQ ID NO 179
<211> LENGTH: 59
<212> TYPE: PRT
<213> ORGANISM: Medicago truncatula

<400> SEQUENCE: 179

Met Ala His Phe Leu Met Phe Val Tyr Ala Leu Ile Thr Cys Leu Ser
1               5                   10                  15

Leu Phe Leu Val Glu Met Gly His Leu Ser Ile His Cys Val Ser Val
                20                  25                  30

Asp Asp Cys Pro Lys Val Glu Lys Pro Ile Thr Met Lys Cys Ile Asn
                35                  40                  45

Asn Tyr Cys Lys Tyr Phe Val Asp His Lys Leu
        50                  55

<210> SEQ ID NO 180
<211> LENGTH: 66
```

<212> TYPE: PRT
<213> ORGANISM: Medicago truncatula

<400> SEQUENCE: 180

Met Asn Gln Ile Pro Met Phe Gly Tyr Thr Leu Ile Ile Phe Phe Ser
1               5                   10                  15

Leu Phe Pro Val Ile Thr Asn Gly Asp Arg Ile Pro Cys Val Thr Asn
            20                  25                  30

Gly Asp Cys Pro Val Met Arg Leu Pro Leu Tyr Met Arg Cys Ile Thr
        35                  40                  45

Tyr Ser Cys Glu Leu Phe Phe Asp Gly Pro Asn Leu Cys Ala Val Glu
    50                  55                  60

Arg Ile
65

<210> SEQ ID NO 181
<211> LENGTH: 61
<212> TYPE: PRT
<213> ORGANISM: Medicago truncatula

<400> SEQUENCE: 181

Met Arg Lys Asp Met Ala Arg Ile Ser Leu Phe Val Tyr Ala Leu Ile
1               5                   10                  15

Ile Phe Phe Ser Leu Phe Phe Val Leu Thr Asn Gly Glu Leu Glu Ile
            20                  25                  30

Arg Cys Val Ser Asp Ala Asp Cys Pro Leu Phe Pro Leu Pro Leu His
        35                  40                  45

Asn Arg Cys Ile Asp Asp Val Cys His Leu Phe Thr Ser
    50                  55                  60

<210> SEQ ID NO 182
<211> LENGTH: 60
<212> TYPE: PRT
<213> ORGANISM: Medicago truncatula

<400> SEQUENCE: 182

Met Ala Gln Ile Leu Met Phe Val Tyr Phe Leu Ile Ile Phe Leu Ser
1               5                   10                  15

Leu Phe Leu Val Glu Ser Ile Lys Ile Phe Thr Glu His Arg Cys Arg
            20                  25                  30

Thr Asp Ala Asp Cys Pro Ala Arg Glu Leu Pro Glu Tyr Leu Lys Cys
        35                  40                  45

Gln Gly Gly Met Cys Arg Leu Leu Ile Lys Lys Asp
    50                  55                  60

<210> SEQ ID NO 183
<211> LENGTH: 56
<212> TYPE: PRT
<213> ORGANISM: Medicago truncatula

<400> SEQUENCE: 183

Met Ala Arg Val Ile Ser Leu Phe Tyr Ala Leu Ile Ile Phe Leu Phe
1               5                   10                  15

Leu Phe Leu Val Ala Thr Asn Gly Asp Leu Ser Pro Cys Leu Arg Ser
            20                  25                  30

Gly Asp Cys Ser Lys Asp Glu Cys Pro Ser His Leu Val Pro Lys Cys
        35                  40                  45

Ile Gly Leu Thr Cys Tyr Cys Ile
    50                  55

<210> SEQ ID NO 184
<211> LENGTH: 62
<212> TYPE: PRT
<213> ORGANISM: Medicago truncatula

<400> SEQUENCE: 184

Met Gln Arg Arg Lys Asn Met Ala Gln Ile Leu Leu Phe Ala Tyr Val
1               5                   10                  15

Phe Ile Ile Ser Ile Ser Leu Phe Val Val Thr Asn Gly Val Lys
            20                  25                  30

Ile Pro Cys Val Lys Asp Thr Asp Cys Pro Thr Leu Pro Cys Pro Leu
            35                  40                  45

Tyr Ser Lys Cys Val Asp Gly Phe Cys Lys Met Leu Ser Ile
            50                  55                  60

<210> SEQ ID NO 185
<211> LENGTH: 66
<212> TYPE: PRT
<213> ORGANISM: Medicago truncatula

<400> SEQUENCE: 185

Met Asn His Ile Ser Lys Phe Val Tyr Ala Leu Ile Ile Phe Leu Ser
1               5                   10                  15

Val Tyr Leu Val Val Leu Asp Gly Arg Pro Val Ser Cys Lys Asp His
            20                  25                  30

Tyr Asp Cys Arg Arg Lys Val Lys Ile Val Gly Cys Ile Phe Pro Gln
            35                  40                  45

Glu Lys Pro Met Cys Ile Asn Ser Met Cys Thr Cys Ile Arg Glu Ile
            50                  55                  60

Val Pro
65

<210> SEQ ID NO 186
<211> LENGTH: 86
<212> TYPE: PRT
<213> ORGANISM: Medicago truncatula

<400> SEQUENCE: 186

Met Lys Ser Gln Asn His Ala Lys Phe Ile Ser Phe Tyr Lys Asn Asp
1               5                   10                  15

Leu Phe Lys Ile Phe Gln Asn Asn Asp Ser His Phe Lys Val Phe Phe
            20                  25                  30

Ala Leu Ile Ile Phe Leu Tyr Thr Tyr Leu His Val Thr Asn Gly Val
            35                  40                  45

Phe Val Ser Cys Asn Ser His Ile His Cys Arg Val Asn Asn His Lys
            50                  55                  60

Ile Gly Cys Asn Ile Pro Glu Gln Tyr Leu Leu Cys Val Asn Leu Phe
65                  70                  75                  80

Cys Leu Trp Leu Asp Tyr
                85

<210> SEQ ID NO 187
<211> LENGTH: 62
<212> TYPE: PRT
<213> ORGANISM: Medicago truncatula

<400> SEQUENCE: 187

Met Thr Tyr Ile Ser Lys Val Val Tyr Ala Leu Ile Ile Phe Leu Ser

```
                1               5                   10                  15
Ile Tyr Val Gly Val Asn Asp Cys Met Leu Val Thr Cys Glu Asp His
                20                  25                  30

Phe Asp Cys Arg Gln Asn Val Gln Gln Val Gly Cys Ser Phe Arg Glu
                35                  40                  45

Ile Pro Gln Cys Ile Asn Ser Ile Cys Lys Cys Met Lys Gly
    50                  55                  60

<210> SEQ ID NO 188
<211> LENGTH: 63
<212> TYPE: PRT
<213> ORGANISM: Medicago truncatula

<400> SEQUENCE: 188

Met Thr His Ile Ser Lys Phe Val Phe Ala Leu Ile Ile Phe Leu Ser
1               5                   10                  15

Ile Tyr Val Gly Val Asn Asp Cys Lys Arg Ile Pro Cys Lys Asp Asn
                20                  25                  30

Asn Asp Cys Asn Asn Asn Trp Gln Leu Leu Ala Cys Arg Phe Glu Arg
                35                  40                  45

Glu Val Pro Arg Cys Ile Asn Ser Ile Cys Lys Cys Met Pro Met
    50                  55                  60

<210> SEQ ID NO 189
<211> LENGTH: 60
<212> TYPE: PRT
<213> ORGANISM: Medicago truncatula

<400> SEQUENCE: 189

Met Val Gln Thr Pro Lys Leu Val Tyr Val Ile Val Leu Leu Leu Ser
1               5                   10                  15

Ile Phe Leu Gly Met Thr Ile Cys Asn Ser Ser Phe Ser His Phe Phe
                20                  25                  30

Glu Gly Ala Cys Lys Ser Asp Lys Asp Cys Pro Lys Leu His Arg Ser
                35                  40                  45

Asn Val Arg Cys Arg Lys Gly Gln Cys Val Gln Ile
    50                  55                  60

<210> SEQ ID NO 190
<211> LENGTH: 77
<212> TYPE: PRT
<213> ORGANISM: Medicago truncatula

<400> SEQUENCE: 190

Met Thr Lys Ile Leu Met Leu Phe Tyr Ala Met Ile Val Phe His Ser
1               5                   10                  15

Ile Phe Leu Val Ala Ser Tyr Thr Asp Glu Cys Ser Thr Asp Ala Asp
                20                  25                  30

Cys Glu Tyr Ile Leu Cys Leu Phe Pro Ile Ile Lys Arg Cys Ile His
                35                  40                  45

Asn His Cys Lys Cys Val Pro Met Gly Ser Ile Glu Pro Met Ser Thr
    50                  55                  60

Ile Pro Asn Gly Val His Lys Phe His Ile Ile Asn Asn
65                  70                  75

<210> SEQ ID NO 191
<211> LENGTH: 64
<212> TYPE: PRT
<213> ORGANISM: Medicago truncatula
```

<400> SEQUENCE: 191

Met Ala Lys Thr Leu Asn Phe Val Cys Ala Met Ile Leu Phe Ile Ser
1               5                   10                  15

Leu Phe Leu Val Ser Lys Asn Val Ala Leu Tyr Ile Ile Glu Cys Lys
            20                  25                  30

Thr Asp Ala Asp Cys Pro Ile Ser Lys Leu Asn Met Tyr Asn Trp Arg
        35                  40                  45

Cys Ile Lys Ser Ser Cys His Leu Tyr Lys Val Ile Gln Phe Met Val
    50                  55                  60

<210> SEQ ID NO 192
<211> LENGTH: 72
<212> TYPE: PRT
<213> ORGANISM: Medicago truncatula

<400> SEQUENCE: 192

Met Gln Lys Glu Lys Asn Met Ala Lys Thr Phe Glu Phe Val Tyr Ala
1               5                   10                  15

Met Ile Ile Phe Ile Leu Leu Phe Leu Val Glu Asn Asn Phe Ala Ala
            20                  25                  30

Tyr Ile Ile Glu Cys Gln Thr Asp Asp Cys Pro Lys Ser Gln Leu
        35                  40                  45

Glu Met Phe Ala Trp Lys Cys Val Lys Asn Gly Cys His Leu Phe Gly
    50                  55                  60

Met Tyr Glu Asp Asp Asp Pro
65                  70

<210> SEQ ID NO 193
<211> LENGTH: 57
<212> TYPE: PRT
<213> ORGANISM: Medicago truncatula

<400> SEQUENCE: 193

Met Ala Ala Thr Arg Lys Phe Ile Tyr Val Leu Ser His Phe Leu Phe
1               5                   10                  15

Leu Phe Leu Val Thr Lys Ile Thr Asp Ala Arg Val Cys Lys Ser Asp
            20                  25                  30

Lys Asp Cys Lys Asp Ile Ile Ile Tyr Arg Tyr Ile Leu Lys Cys Arg
        35                  40                  45

Asn Gly Glu Cys Val Lys Ile Lys Ile
    50                  55

<210> SEQ ID NO 194
<211> LENGTH: 75
<212> TYPE: PRT
<213> ORGANISM: Medicago truncatula

<400> SEQUENCE: 194

Met Gln Arg Leu Asp Asn Met Ala Lys Asn Val Lys Phe Ile Tyr Val
1               5                   10                  15

Ile Ile Leu Leu Leu Phe Ile Phe Leu Val Ile Ile Val Cys Asp Ser
            20                  25                  30

Ala Phe Val Pro Asn Ser Gly Pro Cys Thr Thr Asp Lys Asp Cys Lys
        35                  40                  45

Gln Val Lys Gly Tyr Ile Ala Arg Cys Arg Lys Gly Tyr Cys Met Gln
    50                  55                  60

Ser Val Lys Arg Thr Trp Ser Ser Tyr Ser Arg

```
65                  70                  75

<210> SEQ ID NO 195
<211> LENGTH: 102
<212> TYPE: PRT
<213> ORGANISM: Medicago truncatula

<400> SEQUENCE: 195

Met Lys Phe Ile Tyr Ile Met Ile Leu Phe Leu Ser Leu Phe Leu Val
1               5                   10                  15

Gln Phe Leu Thr Cys Lys Gly Leu Thr Val Pro Cys Glu Asn Pro Thr
            20                  25                  30

Thr Cys Pro Glu Asp Phe Cys Thr Pro Pro Met Ile Thr Arg Cys Ile
        35                  40                  45

Asn Phe Ile Cys Leu Cys Asp Gly Pro Glu Tyr Ala Glu Pro Glu Tyr
    50                  55                  60

Asp Gly Pro Glu Pro Glu Tyr Asp His Lys Gly Asp Phe Leu Ser Val
65                  70                  75                  80

Lys Pro Lys Ile Ile Asn Glu Asn Met Met Arg Glu Arg His Met
                85                  90                  95

Met Lys Glu Ile Glu Val
            100

<210> SEQ ID NO 196
<211> LENGTH: 59
<212> TYPE: PRT
<213> ORGANISM: Medicago truncatula

<400> SEQUENCE: 196

Met Ala Gln Phe Leu Met Phe Ile Tyr Val Leu Ile Ile Phe Leu Tyr
1               5                   10                  15

Leu Phe Tyr Val Glu Ala Ala Met Phe Glu Leu Thr Lys Ser Thr Ile
            20                  25                  30

Arg Cys Val Thr Asp Ala Asp Cys Pro Asn Val Val Lys Pro Leu Lys
        35                  40                  45

Pro Lys Cys Val Asp Gly Phe Cys Glu Tyr Thr
    50                  55

<210> SEQ ID NO 197
<211> LENGTH: 70
<212> TYPE: PRT
<213> ORGANISM: Medicago truncatula

<400> SEQUENCE: 197

Met Lys Met Arg Ile His Met Ala Gln Ile Ile Met Phe Phe Tyr Ala
1               5                   10                  15

Leu Ile Ile Phe Leu Ser Pro Phe Leu Val Asp Arg Arg Ser Phe Pro
            20                  25                  30

Ser Ser Phe Val Ser Pro Lys Ser Tyr Thr Ser Glu Ile Pro Cys Lys
        35                  40                  45

Ala Thr Arg Asp Cys Pro Tyr Glu Leu Tyr Tyr Glu Thr Lys Cys Val
    50                  55                  60

Asp Ser Leu Cys Thr Tyr
65                  70

<210> SEQ ID NO 198
<211> LENGTH: 41
<212> TYPE: PRT
<213> ORGANISM: Medicago truncatula
```

<400> SEQUENCE: 198

Thr Arg Met Leu Thr Ile Pro Cys Thr Ser Asp Asp Asn Cys Pro Lys
1               5                   10                  15

Val Ile Ser Pro Cys His Thr Lys Cys Phe Asp Gly Phe Cys Gly Trp
                20                  25                  30

Tyr Ile Glu Gly Ser Tyr Glu Gly Pro
            35                  40

<210> SEQ ID NO 199
<211> LENGTH: 69
<212> TYPE: PRT
<213> ORGANISM: Medicago truncatula

<400> SEQUENCE: 199

Met Ala Gln Phe Leu Leu Phe Val Tyr Ser Leu Ile Ile Phe Leu Ser
1               5                   10                  15

Leu Phe Phe Gly Glu Ala Ala Phe Glu Arg Thr Glu Thr Arg Met Leu
                20                  25                  30

Thr Ile Pro Cys Thr Ser Asp Asp Asn Cys Pro Lys Val Ile Ser Pro
            35                  40                  45

Cys His Thr Lys Cys Phe Asp Gly Phe Cys Gly Trp Tyr Ile Glu Gly
        50                  55                  60

Ser Tyr Glu Gly Pro
65

<210> SEQ ID NO 200
<211> LENGTH: 78
<212> TYPE: PRT
<213> ORGANISM: Buchnera aphidicola

<400> SEQUENCE: 200

Met Lys Leu Leu His Gly Phe Leu Ile Ile Met Leu Thr Met His Leu
1               5                   10                  15

Ser Ile Gln Tyr Ala Tyr Gly Gly Pro Phe Leu Thr Lys Tyr Leu Cys
                20                  25                  30

Asp Arg Val Cys His Lys Leu Cys Gly Asp Glu Phe Val Cys Ser Cys
            35                  40                  45

Ile Gln Tyr Lys Ser Leu Lys Gly Leu Trp Phe Pro His Cys Pro Thr
        50                  55                  60

Gly Lys Ala Ser Val Val Leu His Asn Phe Leu Thr Ser Pro
65                  70                  75

<210> SEQ ID NO 201
<211> LENGTH: 77
<212> TYPE: PRT
<213> ORGANISM: Buchnera aphidicola

<400> SEQUENCE: 201

Met Lys Leu Leu Tyr Gly Phe Leu Ile Ile Met Leu Thr Ile His Leu
1               5                   10                  15

Ser Val Gln Tyr Phe Glu Ser Pro Phe Glu Thr Lys Tyr Asn Cys Asp
                20                  25                  30

Thr His Cys Asn Lys Leu Cys Gly Lys Ile Asp His Ser Cys Ile
            35                  40                  45

Gln Tyr His Ser Met Glu Gly Leu Trp Phe Pro His Cys Arg Thr Gly
        50                  55                  60

Ser Ala Ala Gln Met Leu His Asp Phe Leu Ser Asn Pro

```
65                  70                  75

<210> SEQ ID NO 202
<211> LENGTH: 86
<212> TYPE: PRT
<213> ORGANISM: Buchnera aphidicola

<400> SEQUENCE: 202

Met Ser Val Arg Lys Asn Val Leu Pro Thr Met Phe Val Val Leu Leu
1               5                   10                  15

Ile Met Ser Pro Val Thr Pro Thr Ser Val Phe Ile Ser Ala Val Cys
            20                  25                  30

Tyr Ser Gly Cys Gly Ser Leu Ala Leu Val Cys Phe Val Ser Asn Gly
        35                  40                  45

Ile Thr Asn Gly Leu Asp Tyr Phe Lys Ser Ser Ala Pro Leu Ser Thr
    50                  55                  60

Ser Glu Thr Ser Cys Gly Glu Ala Phe Asp Thr Cys Thr Asp His Cys
65                  70                  75                  80

Leu Ala Asn Phe Lys Phe
                85

<210> SEQ ID NO 203
<211> LENGTH: 69
<212> TYPE: PRT
<213> ORGANISM: Buchnera aphidicola

<400> SEQUENCE: 203

Met Arg Leu Leu Tyr Gly Phe Leu Ile Ile Met Leu Thr Ile Tyr Leu
1               5                   10                  15

Ser Val Gln Asp Phe Asp Pro Thr Glu Phe Lys Gly Pro Phe Pro Thr
            20                  25                  30

Ile Glu Ile Cys Ser Lys Tyr Cys Ala Val Val Cys Asn Tyr Thr Ser
        35                  40                  45

Arg Pro Cys Tyr Cys Val Glu Ala Ala Lys Glu Arg Asp Gln Trp Phe
    50                  55                  60

Pro Tyr Cys Tyr Asp
65

<210> SEQ ID NO 204
<211> LENGTH: 77
<212> TYPE: PRT
<213> ORGANISM: Buchnera aphidicola

<400> SEQUENCE: 204

Met Arg Leu Leu Tyr Gly Phe Leu Ile Ile Met Leu Thr Ile His Leu
1               5                   10                  15

Ser Val Gln Asp Ile Asp Pro Asn Thr Leu Arg Gly Pro Tyr Pro Thr
            20                  25                  30

Lys Glu Ile Cys Ser Lys Tyr Cys Glu Tyr Asn Val Val Cys Gly Ala
        35                  40                  45

Ser Leu Pro Cys Ile Cys Val Gln Asp Ala Arg Gln Leu Asp His Trp
    50                  55                  60

Phe Ala Cys Cys Tyr Asp Gly Gly Pro Glu Met Leu Met
65                  70                  75

<210> SEQ ID NO 205
<211> LENGTH: 108
<212> TYPE: PRT
<213> ORGANISM: Buchnera aphidicola
```

<400> SEQUENCE: 205

Met Lys Leu Phe Val Val Val Leu Val Ala Val Gly Ile Met Phe
1               5                   10                  15

Val Phe Ala Ser Asp Thr Ala Ala Pro Thr Asp Tyr Glu Asp Thr
            20                  25                  30

Asn Asp Met Ile Ser Leu Ser Ser Leu Val Gly Asp Asn Ser Pro Tyr
        35                  40                  45

Val Arg Val Ser Ser Ala Asp Ser Gly Gly Ser Lys Thr Ser Ser
    50                  55                  60

Lys Asn Pro Ile Leu Gly Leu Leu Lys Ser Val Ile Lys Leu Leu Thr
65                  70                  75                  80

Lys Ile Phe Gly Thr Tyr Ser Asp Ala Ala Pro Ala Met Pro Pro Ile
                85                  90                  95

Pro Pro Ala Leu Arg Lys Asn Arg Gly Met Leu Ala
            100                 105

<210> SEQ ID NO 206
<211> LENGTH: 178
<212> TYPE: PRT
<213> ORGANISM: Buchnera aphidicola

<400> SEQUENCE: 206

Met Val Ala Cys Lys Val Ile Leu Ala Val Ala Val Phe Val Ala
1               5                   10                  15

Ala Val Gln Gly Arg Pro Gly Gly Glu Pro Glu Trp Ala Ala Pro Ile
            20                  25                  30

Phe Ala Glu Leu Lys Ser Val Ser Asp Asn Ile Thr Asn Leu Val Gly
        35                  40                  45

Leu Asp Asn Ala Gly Glu Tyr Ala Thr Ala Ala Lys Asn Asn Leu Asn
    50                  55                  60

Ala Phe Ala Glu Ser Leu Lys Thr Glu Ala Ala Val Phe Ser Lys Ser
65                  70                  75                  80

Phe Glu Gly Lys Ala Ser Ala Ser Asp Val Phe Lys Glu Ser Thr Lys
                85                  90                  95

Asn Phe Gln Ala Val Val Asp Thr Tyr Ile Lys Asn Leu Pro Lys Asp
            100                 105                 110

Leu Thr Leu Lys Asp Phe Thr Glu Lys Ser Glu Gln Ala Leu Lys Tyr
        115                 120                 125

Met Val Glu His Gly Thr Glu Ile Thr Lys Lys Ala Gln Gly Asn Thr
    130                 135                 140

Glu Thr Glu Lys Glu Ile Lys Glu Phe Phe Lys Lys Gln Ile Glu Asn
145                 150                 155                 160

Leu Ile Gly Gln Gly Lys Ala Leu Gln Ala Lys Ile Ala Glu Ala Lys
                165                 170                 175

Lys Ala

<210> SEQ ID NO 207
<211> LENGTH: 311
<212> TYPE: PRT
<213> ORGANISM: Buchnera aphidicola

<400> SEQUENCE: 207

Met Lys Thr Ser Ser Ser Lys Val Phe Ala Ser Cys Val Ala Ile Val
1               5                   10                  15

Cys Leu Ala Ser Val Ala Asn Ala Leu Pro Val Gln Lys Ser Val Ala

```
                    20                  25                  30
Ala Thr Thr Glu Asn Pro Ile Val Glu Lys His Gly Cys Arg Ala His
                35                  40                  45

Lys Asn Leu Val Arg Gln Asn Val Val Asp Leu Lys Thr Tyr Asp Ser
            50                  55                  60

Met Leu Ile Thr Asn Glu Val Val Gln Lys Gln Ser Asn Glu Val Gln
 65                  70                  75                  80

Ser Ser Glu Gln Ser Asn Glu Gly Gln Asn Ser Glu Gln Ser Asn Glu
                85                  90                  95

Gly Gln Asn Ser Glu Gln Ser Asn Glu Val Gln Ser Ser Glu His Ser
                100                 105                 110

Asn Glu Gly Gln Asn Ser Lys Gln Ser Asn Glu Gly Gln Asn Ser Glu
            115                 120                 125

Gln Ser Asn Glu Val Gln Ser Ser Glu His Ser Asn Glu Gly Gln Asn
            130                 135                 140

Ser Glu Gln Ser Asn Glu Val Gln Ser Ser Glu His Ser Asn Glu Gly
145                 150                 155                 160

Gln Asn Ser Lys Gln Ser Asn Glu Gly Gln Asn Ser Lys Gln Ser Asn
                165                 170                 175

Glu Val Gln Ser Ser Glu His Trp Asn Glu Gly Gln Asn Ser Lys Gln
                180                 185                 190

Ser Asn Glu Asp Gln Asn Ser Glu Gln Ser Asn Glu Gly Gln Asn Ser
            195                 200                 205

Lys Gln Ser Asn Glu Gly Gln Asn Ser Lys Gln Ser Asn Glu Asp Gln
        210                 215                 220

Asn Ser Glu Gln Ser Asn Glu Gly Gln Asn Ser Lys Gln Ser Asn Glu
225                 230                 235                 240

Val Gln Ser Ser Glu Gln Ser Asn Glu Gly Gln Asn Ser Lys Gln Ser
                245                 250                 255

Asn Glu Gly Gln Ser Ser Glu Gln Ser Asn Gly Gln Asn Ser Lys
            260                 265                 270

Gln Ser Asn Glu Val Gln Ser Pro Glu Glu His Tyr Asp Leu Pro Asp
            275                 280                 285

Pro Glu Ser Ser Tyr Glu Ser Glu Thr Lys Gly Ser His Glu Ser
        290                 295                 300

Gly Asp Asp Ser Glu His Arg
305                 310

<210> SEQ ID NO 208
<211> LENGTH: 431
<212> TYPE: PRT
<213> ORGANISM: Buchnera aphidicola

<400> SEQUENCE: 208

Met Lys Thr Ile Ile Leu Gly Leu Cys Leu Phe Gly Ala Leu Phe Trp
 1               5                  10                  15

Ser Thr Gln Ser Met Pro Val Gly Glu Val Ala Pro Ala Val Pro Ala
                20                  25                  30

Val Pro Ser Glu Ala Val Pro Gln Lys Gln Val Glu Ala Lys Pro Glu
            35                  40                  45

Thr Asn Ala Ala Ser Pro Val Ser Asp Ala Lys Pro Glu Ser Asp Ser
        50                  55                  60

Lys Pro Val Asp Ala Glu Val Lys Pro Thr Val Ser Glu Val Lys Ala
 65                  70                  75                  80
```

```
Glu Ser Glu Gln Lys Pro Ser Gly Glu Pro Lys Pro Glu Ser Asp Ala
            85                  90                  95

Lys Pro Val Val Ala Ser Glu Ser Lys Pro Glu Ser Asp Pro Lys Pro
            100                 105                 110

Ala Ala Val Val Glu Ser Lys Pro Glu Asn Asp Ala Val Ala Pro Glu
            115                 120                 125

Thr Asn Asn Asp Ala Lys Pro Glu Asn Ala Ala Pro Val Ser Glu
            130                 135                 140

Asn Lys Pro Ala Thr Asp Ala Lys Ala Glu Thr Glu Leu Ile Ala Gln
145                 150                 155                 160

Ala Lys Pro Glu Ser Lys Pro Ala Ser Asp Leu Lys Ala Glu Pro Glu
            165                 170                 175

Ala Ala Lys Pro Asn Ser Glu Val Pro Val Ala Leu Pro Leu Asn Pro
            180                 185                 190

Thr Glu Thr Lys Ala Thr Gln Gln Ser Val Glu Thr Asn Gln Val Glu
            195                 200                 205

Gln Ala Ala Pro Ala Ala Gln Ala Asp Pro Ala Ala Pro Ala
            210                 215                 220

Ala Asp Pro Ala Pro Ala Pro Ala Ala Pro Val Ala Ala Glu Glu
225                 230                 235                 240

Ala Lys Leu Ser Glu Ser Ala Pro Ser Thr Glu Asn Lys Ala Ala Glu
            245                 250                 255

Glu Pro Ser Lys Pro Ala Glu Gln Gln Ser Ala Lys Pro Val Glu Asp
            260                 265                 270

Ala Val Pro Ala Ala Ser Glu Ile Ser Glu Thr Lys Val Ser Pro Ala
            275                 280                 285

Val Pro Ala Val Pro Glu Val Pro Ala Ser Pro Ser Ala Pro Ala Val
            290                 295                 300

Ala Asp Pro Val Ser Ala Pro Glu Ala Glu Lys Asn Ala Glu Pro Ala
305                 310                 315                 320

Lys Ala Ala Asn Ser Ala Glu Pro Ala Val Gln Ser Glu Ala Lys Pro
            325                 330                 335

Ala Glu Asp Ile Gln Lys Ser Gly Ala Val Ser Ala Glu Asn Pro
            340                 345                 350

Lys Pro Val Glu Glu Lys Pro Ala Glu Val Ala Lys Pro Ala Glu
            355                 360                 365

Gln Ser Lys Ser Glu Ala Pro Ala Glu Ala Pro Lys Pro Thr Glu Gln
            370                 375                 380

Ser Ala Glu Glu Pro Lys Lys Pro Glu Ser Ala Asn Asp Glu Lys
385                 390                 395                 400

Lys Glu Gln His Ser Val Asn Lys Arg Asp Ala Thr Lys Glu Lys Lys
            405                 410                 415

Pro Thr Asp Ser Ile Met Lys Lys Gln Lys Gln Lys Ala Asn
            420                 425                 430

<210> SEQ ID NO 209
<211> LENGTH: 160
<212> TYPE: PRT
<213> ORGANISM: Buchnera aphidicola

<400> SEQUENCE: 209

Met Asn Gly Lys Ile Val Leu Cys Phe Ala Val Val Phe Ile Gly Gln
1               5                   10                  15

Ala Met Ser Ala Ala Thr Gly Thr Thr Pro Glu Val Glu Asp Ile Lys
            20                  25                  30
```

```
Lys Val Ala Glu Gln Met Ser Gln Thr Phe Met Ser Val Ala Asn His
             35                  40                  45

Leu Val Gly Ile Thr Pro Asn Ser Ala Asp Ala Gln Lys Ser Ile Glu
 50                  55                  60

Lys Ile Arg Thr Ile Met Asn Lys Gly Phe Thr Asp Met Glu Thr Glu
 65                  70                  75                  80

Ala Asn Lys Met Lys Asp Ile Val Arg Lys Asn Ala Asp Pro Lys Leu
                 85                  90                  95

Val Glu Lys Tyr Asp Glu Leu Glu Lys Leu Lys Lys His Leu Ser
                100                 105                 110

Thr Ala Lys Asp Met Phe Glu Asp Lys Val Val Lys Pro Ile Gly Glu
                115                 120                 125

Lys Val Glu Leu Lys Lys Ile Thr Glu Asn Val Ile Lys Thr Thr Lys
130                 135                 140

Asp Met Glu Ala Thr Met Asn Lys Ala Ile Asp Gly Phe Lys Lys Gln
145                 150                 155                 160

<210> SEQ ID NO 210
<211> LENGTH: 415
<212> TYPE: PRT
<213> ORGANISM: Buchnera aphidicola

<400> SEQUENCE: 210

Met His Leu Phe Leu Ala Leu Gly Leu Phe Ile Val Cys Gly Met Val
 1               5                  10                  15

Asp Ala Thr Phe Tyr Asn Pro Arg Ser Gln Thr Phe Asn Gln Leu Met
                 20                  25                  30

Glu Arg Arg Gln Arg Ser Ile Pro Ile Pro Tyr Ser Tyr Gly Tyr His
             35                  40                  45

Tyr Asn Pro Ile Glu Pro Ser Ile Asn Val Leu Asp Ser Leu Ser Glu
 50                  55                  60

Gly Leu Asp Ser Arg Ile Asn Thr Phe Lys Pro Ile Tyr Gln Asn Val
 65                  70                  75                  80

Lys Met Ser Thr Gln Asp Val Asn Ser Val Pro Arg Thr Gln Tyr Gln
                 85                  90                  95

Pro Lys Asn Ser Leu Tyr Asp Ser Glu Tyr Ile Ser Ala Lys Asp Ile
                100                 105                 110

Pro Ser Leu Phe Pro Glu Glu Asp Ser Tyr Asp Tyr Lys Tyr Leu Gly
                115                 120                 125

Ser Pro Leu Asn Lys Tyr Leu Thr Arg Pro Ser Thr Gln Glu Ser Gly
                130                 135                 140

Ile Ala Ile Asn Leu Val Ala Ile Lys Glu Thr Ser Val Phe Asp Tyr
145                 150                 155                 160

Gly Phe Pro Thr Tyr Lys Ser Pro Tyr Ser Ser Asp Ser Val Trp Asn
                165                 170                 175

Phe Gly Ser Lys Ile Pro Asn Thr Val Phe Glu Asp Pro Gln Ser Val
                180                 185                 190

Glu Ser Asp Pro Asn Thr Phe Lys Val Ser Ser Pro Thr Ile Lys Ile
                195                 200                 205

Val Lys Leu Leu Pro Glu Thr Pro Glu Gln Ser Ile Ile Thr Thr
                210                 215                 220

Thr Lys Asn Tyr Glu Leu Asn Tyr Lys Thr Thr Gln Glu Thr Pro Thr
225                 230                 235                 240

Glu Ala Glu Leu Tyr Pro Ile Thr Ser Glu Glu Phe Gln Thr Glu Asp
```

```
                        245                 250                 255
Glu Trp His Pro Met Val Pro Lys Glu Asn Thr Thr Lys Asp Glu Ser
            260                 265                 270
Ser Phe Ile Thr Thr Glu Glu Pro Leu Thr Glu Asp Lys Ser Asn Ser
        275                 280                 285
Ile Thr Ile Glu Lys Thr Gln Thr Glu Asp Glu Ser Asn Ser Ile Glu
    290                 295                 300
Phe Asn Ser Ile Arg Thr Glu Glu Lys Ser Asn Ser Ile Thr Thr Glu
305                 310                 315                 320
Glu Asn Gln Lys Glu Asp Asp Glu Ser Met Ser Thr Thr Ser Gln Glu
                325                 330                 335
Thr Thr Thr Ala Phe Asn Leu Asn Asp Thr Phe Asp Thr Asn Arg Tyr
            340                 345                 350
Ser Ser Ser His Glu Ser Leu Met Leu Arg Ile Arg Glu Leu Met Lys
        355                 360                 365
Asn Ile Ala Asp Gln Gln Asn Lys Ser Gln Phe Arg Thr Val Asp Asn
    370                 375                 380
Ile Pro Ala Lys Ser Gln Ser Asn Leu Ser Ser Asp Glu Ser Thr Asn
385                 390                 395                 400
Gln Gln Phe Glu Pro Gln Leu Val Asn Gly Ala Asp Thr Tyr Lys
                405                 410                 415

<210> SEQ ID NO 211
<211> LENGTH: 126
<212> TYPE: PRT
<213> ORGANISM: Sitophilus zeamais

<400> SEQUENCE: 211

Met Thr Arg Thr Met Leu Phe Leu Ala Cys Val Ala Ala Leu Tyr Val
1               5                   10                  15
Cys Ile Ser Ala Thr Ala Gly Lys Pro Glu Glu Phe Ala Lys Leu Ser
            20                  25                  30
Asp Glu Ala Pro Ser Asn Asp Gln Ala Met Tyr Glu Ser Ile Gln Arg
        35                  40                  45
Tyr Arg Arg Phe Val Asp Gly Asn Arg Tyr Asn Gly Gly Gln Gln Gln
    50                  55                  60
Gln Gln Gln Pro Lys Gln Trp Glu Val Arg Pro Asp Leu Ser Arg Asp
65                  70                  75                  80
Gln Arg Gly Asn Thr Lys Ala Gln Val Glu Ile Asn Lys Lys Gly Asp
                85                  90                  95
Asn His Asp Ile Asn Ala Gly Trp Gly Lys Asn Ile Asn Gly Pro Asp
            100                 105                 110
Ser His Lys Asp Thr Trp His Val Gly Ser Val Arg Trp
        115                 120                 125

<210> SEQ ID NO 212
<211> LENGTH: 220
<212> TYPE: PRT
<213> ORGANISM: Acyrthosiphon pisum

<400> SEQUENCE: 212

Met Lys Glu Thr Thr Val Val Trp Ala Lys Leu Phe Leu Ile Leu Ile
1               5                   10                  15
Ile Leu Ala Lys Pro Leu Gly Leu Lys Ala Val Asn Glu Cys Lys Arg
            20                  25                  30
Leu Gly Asn Asn Ser Cys Arg Ser His Gly Glu Cys Cys Ser Gly Phe
```

-continued

```
                35                  40                  45
Cys Phe Ile Glu Pro Gly Trp Ala Leu Gly Val Cys Lys Arg Leu Gly
 50                  55                  60
Thr Pro Lys Lys Ser Asp Asp Ser Asn Asn Gly Lys Asn Ile Glu Lys
 65                  70                  75                  80
Asn Asn Gly Val His Glu Arg Ile Asp Asp Val Phe Glu Arg Gly Val
                 85                  90                  95
Cys Ser Tyr Tyr Lys Gly Pro Ser Ile Thr Ala Asn Gly Asp Val Phe
                100                 105                 110
Asp Glu Asn Glu Met Thr Ala Ala His Arg Thr Leu Pro Phe Asn Thr
            115                 120                 125
Met Val Lys Val Glu Gly Met Gly Thr Ser Val Val Lys Ile Asn
 130                 135                 140
Asp Arg Lys Thr Ala Ala Asp Gly Lys Val Met Leu Leu Ser Arg Ala
 145                 150                 155                 160
Ala Ala Glu Ser Leu Asn Ile Asp Glu Asn Thr Gly Pro Val Gln Cys
                165                 170                 175
Gln Leu Lys Phe Val Leu Asp Gly Ser Gly Cys Thr Pro Asp Tyr Gly
                180                 185                 190
Asp Thr Cys Val Leu His His Glu Cys Cys Ser Gln Asn Cys Phe Arg
            195                 200                 205
Glu Met Phe Ser Asp Lys Gly Phe Cys Leu Pro Lys
            210                 215                 220

<210> SEQ ID NO 213
<211> LENGTH: 16
<212> TYPE: PRT
<213> ORGANISM: Artificial Sequence
<220> FEATURE:
<223> OTHER INFORMATION: Penetratin

<400> SEQUENCE: 213

Arg Gln Ile Lys Ile Trp Phe Gln Asn Arg Arg Met Lys Trp Lys Lys
 1               5                  10                  15

<210> SEQ ID NO 214
<211> LENGTH: 13
<212> TYPE: PRT
<213> ORGANISM: Human immunodeficiency virus 1

<400> SEQUENCE: 214

Gly Arg Lys Lys Arg Arg Gln Arg Arg Arg Pro Pro Gln
 1               5                  10

<210> SEQ ID NO 215
<211> LENGTH: 18
<212> TYPE: PRT
<213> ORGANISM: Artificial Sequence
<220> FEATURE:
<223> OTHER INFORMATION: pVEC

<400> SEQUENCE: 215

Leu Leu Ile Ile Leu Arg Arg Arg Ile Arg Lys Gln Ala His Ala His
 1               5                  10                  15

Ser Lys

<210> SEQ ID NO 216
<211> LENGTH: 27
<212> TYPE: PRT
<213> ORGANISM: Artificial Sequence
```

<220> FEATURE:
<223> OTHER INFORMATION: Transportan

<400> SEQUENCE: 216

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 217
<211> LENGTH: 27
<212> TYPE: PRT
<213> ORGANISM: Artificial Sequence
<220> FEATURE:
<223> OTHER INFORMATION: MPG

<400> SEQUENCE: 217

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 218
<211> LENGTH: 21
<212> TYPE: PRT
<213> ORGANISM: Artificial Sequence
<220> FEATURE:
<223> OTHER INFORMATION: Pep-1

<400> SEQUENCE: 218

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 219
<211> LENGTH: 18
<212> TYPE: PRT
<213> ORGANISM: Artificial Sequence
<220> FEATURE:
<223> OTHER INFORMATION: MAP

<400> SEQUENCE: 219

Lys Leu Ala Leu Lys Leu Ala Leu Lys Ala Leu Lys Ala Ala Leu Lys
1               5                   10                  15

Leu Ala

<210> SEQ ID NO 220
<211> LENGTH: 9
<212> TYPE: PRT
<213> ORGANISM: Artificial Sequence
<220> FEATURE:
<223> OTHER INFORMATION: R6W3

<400> SEQUENCE: 220

Arg Arg Trp Trp Arg Arg Trp Arg Arg
1               5

<210> SEQ ID NO 221
<211> LENGTH: 13
<212> TYPE: PRT
<213> ORGANISM: Pandinum imperator

<400> SEQUENCE: 221

```
Phe Leu Ser Thr Ile Trp Asn Gly Ile Lys Gly Leu Leu
1               5                   10
```

<210> SEQ ID NO 222
<211> LENGTH: 13
<212> TYPE: PRT
<213> ORGANISM: Urodacus yaschenkoi

<400> SEQUENCE: 222

```
Ile Leu Ser Ala Ile Trp Ser Gly Ile Lys Ser Leu Phe
1               5                   10
```

<210> SEQ ID NO 223
<211> LENGTH: 13
<212> TYPE: PRT
<213> ORGANISM: Scorpiops tibetanus

<400> SEQUENCE: 223

```
Leu Trp Gly Lys Leu Trp Glu Gly Val Lys Ser Leu Ile
1               5                   10
```

<210> SEQ ID NO 224
<211> LENGTH: 22
<212> TYPE: PRT
<213> ORGANISM: Apostichopus japonicus

<400> SEQUENCE: 224

```
Phe Pro Phe Leu Lys Leu Ser Leu Lys Ile Pro Lys Ser Ala Ile Lys
1               5                   10                  15

Ser Ala Ile Lys Arg Leu
            20
```

<210> SEQ ID NO 225
<211> LENGTH: 13
<212> TYPE: PRT
<213> ORGANISM: Urodacus yaschenkoi

<400> SEQUENCE: 225

```
Ile Leu Ser Ala Ile Trp Ser Gly Ile Lys Gly Leu Leu
1               5                   10
```

<210> SEQ ID NO 226
<211> LENGTH: 27
<212> TYPE: PRT
<213> ORGANISM: Artificial Sequence
<220> FEATURE:
<223> OTHER INFORMATION: Uy192 + cell penetrating peptide

<400> SEQUENCE: 226

```
Tyr Gly Arg Lys Lys Arg Arg Gln Arg Arg Phe Leu Ser Thr Ile
1               5                   10                  15

Trp Asn Gly Ile Lys Gly Leu Leu Phe Ala Met
            20                  25
```

<210> SEQ ID NO 227
<211> LENGTH: 20
<212> TYPE: DNA
<213> ORGANISM: Artificial Sequence
<220> FEATURE:
<223> OTHER INFORMATION: Universal bacterial primer 27F

<400> SEQUENCE: 227
agagtttgat cmtggctcag                                           20

```
<210> SEQ ID NO 228
<211> LENGTH: 16
<212> TYPE: DNA
<213> ORGANISM: Artificial Sequence
<220> FEATURE:
<223> OTHER INFORMATION: Universal bacterial primer 1492R

<400> SEQUENCE: 228
taccttgtta cgactt                                                    16
```

METHODS AND RELATED COMPOSITIONS FOR MANUFACTURING FOOD AND FEED

CROSS-REFERENCE TO RELATED APPLICATIONS

This application claims priority to U.S. Provisional Application No. 62/450,038, filed on Jan. 24, 2017, and U.S. Provisional Application No. 62/584,011, filed on Nov. 9, 2017, the contents of which are hereby incorporated herein by reference in their entireties.

SEQUENCE LISTING

The instant application contains a Sequence Listing which has been submitted electronically in ASCII format and is hereby incorporated by reference in its entirety. Said ASCII copy, created Sep. 6, 2019, is named 51215-007003 Sequence Listing 09.06.19 ST25 and is 285,568 bytes in size.

BACKGROUND

Arthropods, such as crickets, cicadas, grasshoppers, ants, insect larvae, caterpillars, and scorpions, have many traditional and potential new uses in the production of food and feed for humans and animals, respectively. Insects as food and feed emerge as an especially relevant issue due to the rising cost of animal protein, food and feed insecurity, environmental pressures, population growth, and increasing demand for affordable and sustainable sources of nutrients for humans and animals (e.g., livestock). To cultivate beneficial arthropods for use in the food and feed industries, there is a need in the art for ways to promote the growth and fitness of such arthropods.

SUMMARY OF THE INVENTION

Disclosed herein are compositions and methods for modulating the fitness of insects for food and feed manufacturing. The composition includes an agent that alters a level, activity, or metabolism of one or more microorganisms resident in a host, the alteration resulting in a modulation in the host's fitness.

In one aspect, provided herein is a method for increasing a nutritional profile of an insect, the method including delivering an effective amount of methionine-producing bacteria to the insect.

In some embodiments, the insect is a cricket, a grasshopper, or a locust.

In some embodiments, the insect may be developmentally an embryo, larva, pupa, or adult.

In some embodiments, the delivery may include delivering the composition to at least one habitat where the insect grows, lives, reproduces, or feeds.

In some embodiments, the methionine-producing bacteria may be delivered in an insect comestible composition for ingestion by the insect.

In some embodiments, the methionine-producing bacteria may be formulated with an agriculturally acceptable carrier as a liquid, a solid, an aerosol, a paste, a gel, or a gas composition.

In some embodiments, the carrier may be a seed coating.

In a second aspect, provided herein is a modified insect comprising exogenous methionine-producing bacteria resident in the insect.

In some embodiments of the second aspect, the insect is developmentally an embryo, a larva, a pupa, or an adult.

In some embodiments of the second aspect, the methionine-producing bacteria alters microbiota in a gut and/or haemocoel of the insect.

In yet another aspect, the composition includes an agent that alters a level, activity, or metabolism of one or more microorganisms resident in an insect host, the alteration resulting in an increase in the insect host's fitness.

In some embodiments of any of the above compositions, the one or more microorganisms may be a bacterium or fungus resident in the host. In some embodiments, the bacterium resident in the host is at least one selected from the group consisting of *Candidatus* spp, *Buchenera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp. In some embodiments, the fungus resident in the host is at least one selected from the group consisting of *Candida, Metschnikowia, Debaromyces, Starmerella, Pichia, Cryptococcus, Pseudozyma, Symbiotaphrina bucneri, Symbiotaphrina Scheffersomyces shehatae, Scheffersomyces stipites, Cryptococcus, Trichosporon, Amylostereum areolatum, Epichloe* spp, *Pichia pinus, Hansenula capsulate, Daldinia decipien, Ceratocytis* spp, *Ophiostoma* spp, and *Attamyces bromatificus*. In certain instances, the bacteria is a naturally occurring bacteria that is capable of producing nutrients (e.g., amino acids, e.g., methionine).

In any of the above compositions, the agent, which hereinafter may also be referred to as a modulating agent, may alter the growth, division, viability, metabolism, and/or longevity of the microorganism resident in the host. In any of the above embodiments, the modulating agent may decrease the viability of the one or more microorganisms resident in the host. In some embodiments, the modulating agent increases growth or viability of the one or more microorganisms resident in the host.

In any of the above embodiments, the modulating agent is a phage, a polypeptide, a small molecule, an antibiotic, a bacterium, or any combination thereof.

In some embodiments, the phage binds a cell surface protein on a bacterium resident in the host. In some embodiments, the phage is virulent to a bacterium resident in the host. In some embodiments, the phage is at least one selected from the group consisting of Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Glubolovirdae, Guttaviridae, Inoviridae, Leviviridae, Microviridae, Plasmaviridae, and Tectiviridae.

In some embodiments, the polypeptide is at least one of a bacteriocin, R-type bacteriocin, nodule C-rich peptide, antimicrobial peptide, lysin, or bacteriocyte regulatory peptide.

In some embodiments, the small molecule is a metabolite.

In some embodiments, the antibiotic is a broad-spectrum antibiotic.

In some embodiments, the modulating agent is a naturally occurring bacteria. In some embodiments, the bacteria is at least one selected from the group consisting of *Bartonella apis*, *Parasaccharibacter apium*, *Frischella perrara*, *Snodgrassella alvi*, *Gilliamela apicola*, *Bifidobacterium* spp, and *Lactobacillus* spp. In some embodiments, the bacterium is at least one selected from the group consisting of *Candidatus* spp, *Buchenera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp.

In any of the above compositions, host fitness may be measured by survival, reproduction, or metabolism of the host. In some embodiments, the modulating agent modulates the host's fitness by decreasing pesticidal susceptibility of the host (e.g., susceptibility to a pesticide listed in Table 12). In some embodiments, the pesticidal susceptibility is bactericidal or fungicidal susceptibility. In some embodiments, the pesticidal susceptibility is insecticidal susceptibility.

In any of the above compositions, the composition may include a plurality of different modulating agents. In some embodiments, the composition includes a modulating agent and a pesticidal agent (e.g., a pesticide listed in Table 12). In some embodiments, the pesticidal agent is a bactericidal or fungicidal agent. In some embodiments, the pesticidal agent is an insecticidal agent.

In any of the above compositions, modulating agent may be linked to a second moiety. In some embodiments, the second moiety is a modulating agent.

In any of the above compositions, the modulating agent may be linked to a targeting domain. In some embodiments, the targeting domain targets the modulating agent to a target site in the host. In some embodiments, the targeting domain targets the modulating agent to the one or more microorganisms resident in the host.

In any of the above compositions, the modulating agent may include an inactivating pre- or pro-sequence, thereby forming a precursor modulating agent. In some embodiments, the precursor modulating agent is converted to an active form in the host.

In any of the above compositions, the modulating agent may include a linker. In some embodiments, the linker is a cleavable linker.

In any of the above compositions, the composition may further include a carrier. In some instances, the carrier may be an agriculturally acceptable carrier.

In any of the above compositions, the composition may further include a host bait, a sticky agent, or a combination thereof. In some embodiments, the host bait is a comestible agent and/or a chemoattractant.

In any of the above compositions, the composition may be at a dose effective to modulate host fitness.

In any of the above embodiments, the modulating agent of the composition may be effective to increase production of a nutrient in the host relative to a reference level. In some embodiments, the modulating agent is a microorganism that produces the nutrient. In some embodiments, the microorganism is a bacterium. In some embodiments, the nutrient is a vitamin, a carbohydrate, an amino acid, or a polypeptide. In certain embodiments, the amino acid is methionine.

In any of the above compositions, the composition may be formulated for delivery to a microorganism inhabiting the gut of the host.

In any of the above compositions, the composition may be formulated for delivery to a microorganism inhabiting a bacteriocyte of the host and/or the gut of the host. In some embodiments, the composition may be formulated for delivery to a plant. In some embodiments, the composition may be formulated for use in a host feeding station.

In any of the above compositions, the composition may be formulated as a liquid, a powder, granules, or nanoparticles. In some embodiments, the composition is formulated as one selected from the group consisting of a liposome, polymer, bacteria secreting peptide, and synthetic nanocapsule. In some embodiments, the synthetic nanocapsule delivers the composition to a target site in the host. In some embodiments, the target site is the gut of the host. In some embodiments, the target site is a bacteriocyte in the host.

In a further aspect, also provided herein are hosts that include any of the above compositions. In some embodiments, the host is an insect. In some embodiments, the insect is a species belonging to the order *Anoplura*, Araneae, Blattodea, *Coleoptera*, *Dermaptera*, *Dictyoptera*, *Diplura*, *Diptera*, *Embioptera*, *Ephemeroptera*, *Grylloblatodea*, *Hemiptera*, *Homoptera*, *Hymenoptera*, *Isoptera*, *Lepidoptera*, *Mantodea*, *Mecoptera*, *Neuroptera*, *Odonata*, *Orthoptera*, *Phasmida*, *Plecoptera*, *Protura*, *Psocoptera*, *Siphonaptera*, *Siphunculata*, *Thysanura*, *Strepsiptera*, *Thysanoptera*, *Trichoptera*, or *Zoraptera*. In certain embodiments, the insect is a cricket. In certain embodiments, the insect is a grasshopper. In certain embodiments, the insect is a locust.

In yet a further aspect, also provided herein is a system for modulating a host's fitness comprising a modulating agent that targets a microorganism that is required for a host's fitness, wherein the system is effective to modulate the host's fitness, and wherein the host is an insect. The modulating agent may include any of the compositions described herein. In some embodiments, the modulating agent is formulated as a powder. In some embodiments, the modulating agent is formulated as a solvent. In some embodiments, the modulating agent is formulated as a concentrate. In some embodiments, the modulating agent is formulated as a diluent. In some embodiments, the modulating agent is prepared for delivery by combining any of the previous compositions with a carrier.

In another aspect, also provided herein are methods for modulating the fitness of an insect using any of the compositions described herein. In one instance, the method of modulating the fitness of an insect host includes delivering the composition of any one of the previous claims to the host, wherein the modulating agent targets the one or more microorganisms resident in the host, and thereby modulates the host's fitness. In another instance, the method of modulating microbial diversity in an insect host includes delivering the composition of any one of the previous claims to the host, wherein the modulating agent targets the one or more microorganisms resident in the host, and thereby modulates microbial diversity in the host.

In some embodiments of any of the above methods, the modulating agent may alter the levels of the one or more microorganisms resident in the host. In some embodiments of any of the above methods, the modulating agent may alter the function of the one or more microorganisms resident in the host. In some embodiments, the one or more microorganisms may be a bacterium and/or fungus. In some embodiments, the one or more microorganisms are required for host fitness. In some embodiments, the one or more microorganisms are required for host survival.

In some embodiments of any of the above methods, the delivering step may include providing the modulating agent at a dose and time sufficient to effect the one or more microorganisms, thereby modulating microbial diversity in the host. In some embodiments, the delivering step includes topical application of any of the previous compositions to a plant. In some embodiments, the delivering step includes providing the modulating agent through a genetically engineered plant. In some embodiments, the delivering step includes providing the modulating agent to the host as a comestible. In some embodiments, the delivering step includes providing a host carrying the modulating agent. In some embodiments the host carrying the modulating agent can transmit the modulating agent to one or more additional hosts.

In some embodiments of any of the above methods, the composition is effective to increase health and/or survival of the host. In some embodiments, the composition is effective to increase host fitness, increase host lifespan, increase effective pollination, increase generation of a host product, increase host reproduction, or a combination thereof. In some embodiments, the composition is effective to decrease the host's sensitivity to a pesticidal agent (e.g., a pesticide listed in Table 12). In some embodiments, the pesticidal agent is a neonicotinoid. In some embodiments, the composition is effective to increase the host's resistance to an allelochemical agent produced by a plant. In some embodiments, the allelochemical agent is toxic to the host prior to delivery of the composition. In some embodiments, the allelochemical agent is caffeine, soyacystatin N, monoterpenes, diterpene acids, or phenolic compounds. In some embodiments, the composition is effective to increase nutrient production in the host, thereby increasing the nutrient content in the product derived from the host. In some embodiments, the nutrient is a vitamin, a carbohydrate, an amino acid, or a polypeptide.

In some embodiments of any of the above methods, at least one part of the host may be used in the manufacture of a consumable product. In some embodiments of any of the above methods, the host is an insect. In some embodiments, the insect is a species belonging to the order *Anoplura, Araneae, Blattodea, Coleoptera, Dermaptera, Dictyoptera, Diplura, Diptera, Embioptera, Ephemeroptera, Grylloblatodea, Hemiptera, Homoptera, Hymenoptera, Isoptera, Lepidoptera, Mantodea, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera,* or *Zoraptera*. In certain embodiments, the insect is a cricket. In certain embodiments, the insect is a grasshopper. In certain embodiments, the insect is a locust. In some embodiments, the product includes a food product for humans. In some embodiments, the product includes a nutritional supplement that supplements an animal feed or human food product. In some embodiments, the product includes feed for animals. In some embodiments, the animals are livestock or farm animals.

In another aspect, provided herein is a method of making a human or animal food product, includes (a) providing a plurality (e.g., 2, >2, >5, >10, >100, >1000, >5,000, >10,000, >50,000, >100,000) of host insects, (b) delivering an ingestible composition described herein to the plurality of host insects, in an amount effective to modulate one or more microorganisms resident in the plurality, and (c) processing the plurality (e.g., grinding, optionally admixing with a carrier or another food component) into a food, food additive or food supplement. In some embodiments, the ingestible composition comprises a microorganism. In some embodiments, the microorganism produces a nutrient, and the microorganism is effective to increase nutrient production in the host relative to a reference level. In some embodiments, the microorganism is a bacterium. In some embodiments, the nutrient is a vitamin, a carbohydrate, an amino acid, or a polypeptide. In some embodiments, the amino acid is methionine.

In some embodiments of any of the above methods, the delivering step includes delivering any of the previous compositions to a plant. In some embodiments, the plant is an agricultural crop. In some embodiments, the crop is an unharvested crop at the time of delivery. In some embodiments, the crop is a harvested crop at the time of delivery. The some embodiments, the crop comprises harvested fruits or vegetables. In some embodiments, the composition is delivered in an amount and for a duration effective to increase growth of the crop. In some embodiments, the crop includes corn, soybean, or wheat plants.

In another aspect, also provided herein are screening assays to identify modulating agent that modulate the fitness of a host. In one instance, the screening assay to identify a modulating agent that modulates the fitness of a host, includes the steps of (a) exposing a microorganism that can be resident in the host to one or more candidate modulating agents and (b) identifying a modulating agent that increases or decreases the fitness of the host.

In some embodiments of the screening assay, the modulating agent is a microorganism resident in the host. In some embodiments, the microorganism is a bacterium. In some embodiments, the bacterium, when resident in the host, increases host fitness. In some embodiments, the bacterium degrades a pesticide (e.g., a pesticide listed in Table 12). In some embodiments, the pesticide is a neonicotinoid. In some embodiments, the bacterium secretes an amino acid. In some embodiments, wherein the amino acid is methionine.

In some embodiments of the screening assay, the modulating agent affects an allelochemical-degrading microorganism. In some embodiments, the modulating agent is a phage, an antibiotic, or a test compound. In some embodiments, the antibiotic is timentin or azithromycin.

In some embodiments of the screening assay, the host may be an invertebrate. In some embodiments, the invertebrate is an insect. In some embodiments, the insect is a cricket. In certain embodiments, the insect is a grasshopper. In certain embodiments, the insect is a locust.

In any of the above embodiments of the screening assay, host fitness may be modulated by modulating the host microbiota.

Definitions

As used herein, the term "bacteriocin" refers to a peptide or polypeptide that possesses anti-microbial properties. Naturally occurring bacteriocins are produced by certain prokaryotes and act against organisms related to the producer strain, but not against the producer strain itself. Bacteriocins contemplated herein include, but are not limited to, naturally occurring bacteriocins, such as bacteriocins produced by bacteria, and derivatives thereof, such as engineered bacteriocins, recombinantly expressed bacteriocins, and chemically synthesized bacteriocins. In some instances, the bacteriocin is a functionally active variant of the bacteriocins described herein. In some instances, the variant of the bacteriocin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a bacteriocin described herein or a naturally occurring bacteriocin.

As used herein, the term "bacteriocyte" refers to a specialized cell found in certain insects where intracellular bacteria reside with symbiotic bacterial properties.

As used herein, the term "effective amount" refers to an amount of a modulating agent (e.g., a phage, lysin, bacteriocin, small molecule, or antibiotic) or composition including said agent sufficient to effect the recited result, e.g., to increase or promote the fitness of a host organism (e.g., insect); to reach a target level (e.g., a predetermined or threshold level) of a modulating agent concentration inside a target host; to reach a target level (e.g., a predetermined or threshold level) of a modulating agent concentration inside a target host gut; to reach a target level (e.g., a predetermined or threshold level) of a modulating agent concentration inside a target host bacteriocyte; to modulate the level, or an activity, of one or more microorganism (e.g., endosymbiont) in the target host.

As used herein, the term "fitness" refers to the ability of a host organism to survive, and/or to produce surviving offspring. Fitness of an organism may be measured by one or more parameters, including, but not limited to, life span, nutrient production, reproductive rate, mobility, body weight, and metabolic rate. Fitness may additionally be measured based on measures of activity or product output.

As used herein, the term "gut" refers to any portion of a host's gut, including, the foregut, midgut, or hindgut of the host.

As used herein, the term "host" refers to an organism (e.g., insect) carrying resident microorganisms (e.g., endogenous microorganisms, endosymbiotic microorganisms (e.g., primary or secondary endosymbionts), commensal organisms, and/or pathogenic microorganisms).

As used herein "increasing host fitness" or "promoting host fitness" refers to any favorable alteration in host physiology, or any activity carried out by said host, as a consequence of administration of a modulating agent, including, but not limited to, any one or more of the following desired effects: (1) increasing a population of a host by about 10%, 20%, 30%, 40%, 50%, 60%, 70%, 80%, 90%, 95%, 99%, 100% or more; (2) increasing the reproductive rate of a host (e.g., insect) by about 10%, 20%, 30%, 40%, 50%, 60%, 70%, 80%, 90%, 95%, 99%, 100% or more; (3) increasing the mobility of a host (e.g., insect) by about 10%, 20%, 30%, 40%, 50%, 60%, 70%, 80%, 90%, 95%, 99%, 100% or more; (4) increasing the body weight of a host (e.g., insect) by about 10%, 20%, 30%, 40%, 50%, 60%, 70%, 80%, 90%, 95%, 99%, 100% or more; (5) increasing the metabolic rate or activity of a host (e.g., insect) by about 10%, 20%, 30%, 40%, 50%, 60%, 70%, 80%, 90%, 95%, 99%, 100% or more; (6) increasing production of host byproducts by about 10%, 20%, 30%, 40%, 50%, 60%, 70%, 80%, 90%, 95%, 99%, 100% or more; (7) increasing nutrient content of the host (e.g., insect) (e.g., protein, fatty acids, or amino acids) by about 10%, 20%, 30%, 40%, 50%, 60%, 70%, 80%, 90%, 95%, 99%, 100% or more; or (8) increasing host resistance to pesticides by about 10%, 20%, 30%, 40%, 50%, 60%, 70%, 80%, 90%, 95%, 99%, 100% or more. An increase in host fitness can be determined in comparison to a host organism to which the modulating agent has not been administered.

The term "insect" includes any organism belonging to the phylum Arthropoda and to the class Insecta or the class Arachnida, in any stage of development, i.e., immature and adult insects.

As used herein, "lysin" also known as endolysin, autolysin, murein hydrolase, peptidoglycan hydrolase, or cell wall hydrolase refers to a hydrolytic enzyme that can lyse a bacterium by cleaving peptidoglycan in the cell wall of the bacterium. Lysins contemplated herein include, but are not limited to, naturally occurring lysins, such as lysins produced by phages, lysins produced by bacteria, and derivatives thereof, such as engineered lysins, recombinantly expressed lysins, and chemically synthesized lysins. A functionally active variant of the bacteriocin may have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a synthetic, recombinant, or naturally derived bacteriocin, including any described herein.

As used herein, the term "microorganism" refers to bacteria or fungi. Microorganisms may refer to microorganisms resident in a host organism (e.g., endogenous microorganisms, endosymbiotic microorganisms (e.g., primary or secondary endosymbionts)) or microorganisms exogenous to the host, including those that may act as modulating agents. As used herein, the term "target microorganism" refers to a microorganism that is resident in the host and impacted by a modulating agent, either directly or indirectly.

As used herein, the term "modulating agent" or "agent" refers to an agent that is capable of altering the levels and/or functioning of microorganisms resident in a host organism (e.g., insect), and thereby modulate (e.g., increase) the fitness of the host organism (e.g., insect).

As used herein, "increasing a nutritional profile of an insect" refers to increased production of a nutrient that may increase protein content, body mass, and/or overall nutritional value of the insect.

As used herein, the term "pesticide" or "pesticidal agent" refers to a substance that can be used in the control of agricultural, environmental, or domestic/household pests, such as insects, fungi, bacteria, or viruses. The term "pesticide" is understood to encompass naturally occurring or synthetic insecticides (larvicides or adulticides), insect growth regulators, acaricides (miticides), nematicides, ectoparasiticides, bactericides, fungicides, or herbicides (substance which can be used in agriculture to control or modify plant growth). Further examples of pesticides or pesticidal agents are listed in Table 12. In some instances, the pesticide is an allelochemical. As used herein, "allelochemical" or "allelochemical agent" is a substance produced by an organism that can effect a physiological function (e.g., the germination, growth, survival, or reproduction) of another organism (e.g., a host insect).

As used herein, the term "peptide," "protein," or "polypeptide" encompasses any chain of naturally or non-naturally occurring amino acids (either D- or L-amino acids), regardless of length (e.g., at least 2, 3, 4, 5, 6, 7, 10, 12, 14, 16, 18, 20, 25, 30, 40, 50, 100, or more amino acids), the presence or absence of post-translational modifications (e.g., glycosylation or phosphorylation), or the presence of, e.g., one or more non-amino acyl groups (for example, sugar, lipid, etc.) covalently linked to the peptide, and includes, for example, natural proteins, synthetic, or recombinant polypeptides and peptides, hybrid molecules, peptoids, or peptidomimetics.

As used herein, "percent identity" between two sequences is determined by the BLAST 2.0 algorithm, which is described in Altschul et al., (1990) J. Mol. Biol. 215:403-410. Software for performing BLAST analyses is publicly available through the National Center for Biotechnology Information.

As used herein, the term "bacteriophage" or "phage" refers to a virus that infects and replicates in bacteria. Bacteriophages replicate within bacteria following the injection of their genome into the cytoplasm and do so using either a lytic cycle, which results in bacterial cell lysis, or a lysogenic (non-lytic) cycle, which leaves the bacterial cell intact. The phage may be a naturally occurring phage isolate, or an engineered phage, including vectors, or nucleic acids that encode either a partial phage genome (e.g., including at least all essential genes necessary to carry out the life cycle of the phage inside a host bacterium) or the full phage genome.

As used herein, the term "plant" refers to whole plants, plant organs, plant tissues, seeds, plant cells, seeds, or progeny of the same. Plant cells include, without limitation, cells from seeds, suspension cultures, embryos, meristematic regions, callus tissue, leaves, roots, shoots, gametophytes, sporophytes, pollen, or microspores. Plant parts include differentiated or undifferentiated tissues including, but not limited to the following: roots, stems, shoots, leaves, pollen, seeds, tumor tissue, and various forms of cells and culture (e.g., single cells, protoplasts, embryos, or callus tissue). The plant tissue may be in a plant or in a plant organ, tissue, or cell culture. In addition, a plant may be genetically engineered to produce a heterologous protein or RNA, for example, of any of the modulating agents in the methods or compositions described herein.

The terms "obtainable by", "producible by" or the like are used to indicate that a claim or embodiment refers to compound, composition, product, etc. per se, i.e. that the compound, composition, product, etc. can be obtained or produced by a method which is described for manufacture of the compound, composition, product, etc., but that the compound, composition, product, etc. may be obtained or produced by other methods than the described one as well. The terms "obtained by," "produced by," or the like indicate that the compound, composition, product, is obtained or produced by a recited specific method. It is to be understood that the terms "obtainable by," "producible by" and the like also disclose the terms "obtained by", "produced by" and the like as a preferred embodiment of "obtainable by", "producible by" and the like.

Other features and advantages of the invention will be apparent from the following Detailed Description and the Claims.

BRIEF DESCRIPTION OF THE FIGURES

The figures are meant to be illustrative of one or more features, aspects, or embodiments of the invention and are not intended to be limiting.

DETAILED DESCRIPTION

Figure 1:
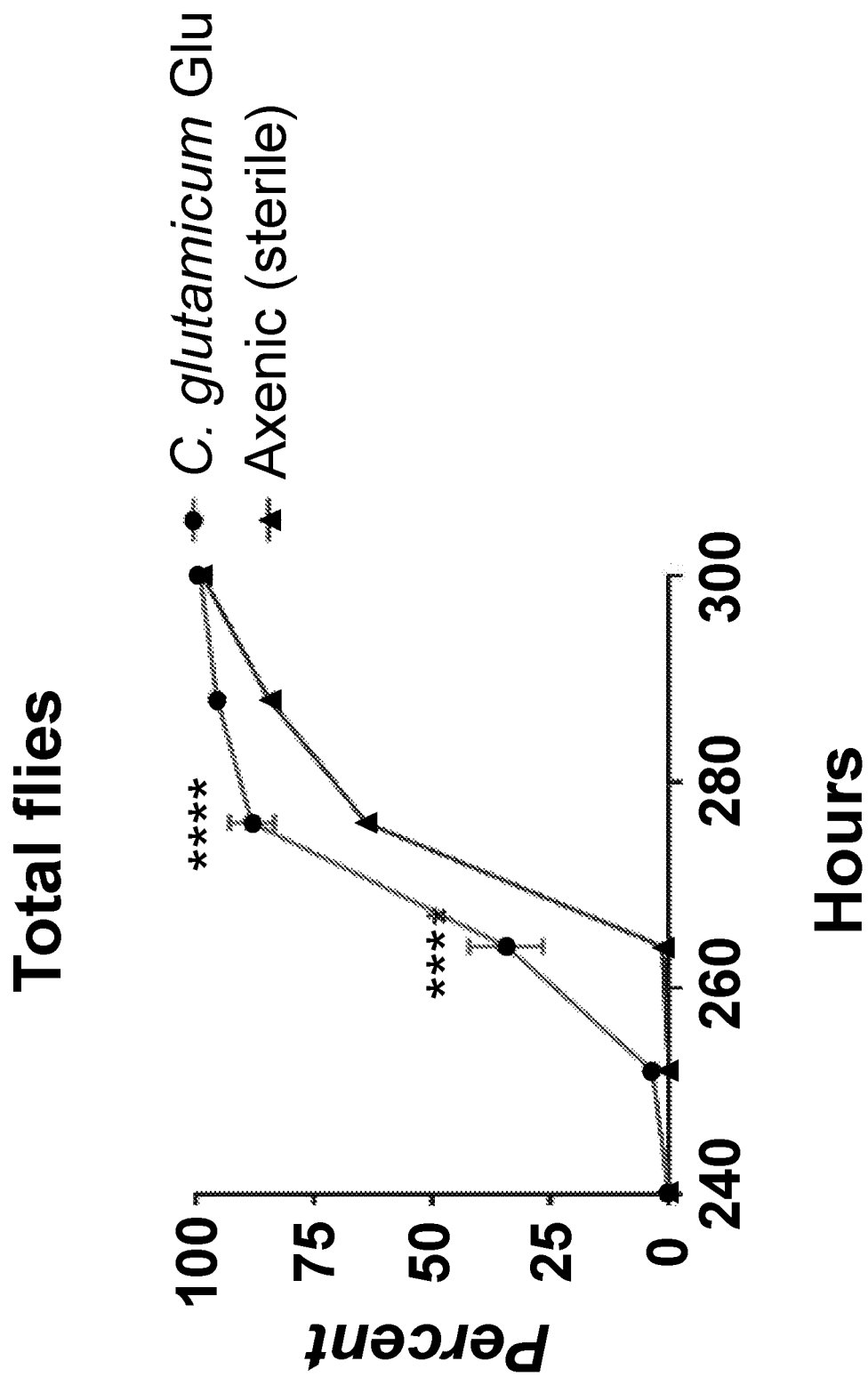
FIG. 1 is a graph showing the time to reach adulthood from embryos in Drosophila melanogaster. Embryos of Drosophila melanogaster were either raised on diet seeded with Corynebacterium glutamicum (a strain that produces glutamate—C. glutamicum Glu) or on axenic diet without any bacteria. The percentage of adults emerging from their pupa was measured every 12 hours from the time of the emergence of the first adult. The organisms raised on bacteria supplemented diet reach adulthood faster than their bacteria free counterparts.

Provided herein are methods and compositions for food and feed applications, e.g., for altering a level, activity, or metabolism of one or more microorganisms resident in a host insect, the alteration resulting in an increase in the fitness of the host. The invention features a composition that includes a modulating agent (e.g., phage, peptide, small molecule, antibiotic, or combinations thereof) that can alter the host's microbiota in a manner that is beneficial to the host. By promoting favorable microbial levels, microbial activity, microbial metabolism, and/or microbial diversity, the modulating agent described herein may be used to increase the fitness of a variety of insects utilized in human food and animal feed industries.

The methods and compositions described herein are based, in part, on the examples which illustrate how different agents, for example methionine-producing microorganisms, can be used in insect hosts such as a cricket, a fly, a grasshopper, or a locust, to indirectly improve the health (e.g., increase methionine content, body mass, development rate, and/or survival) of these hosts by altering the level, activity or metabolism of microorganisms within these hosts. Methionine-producing microorganisms are a representative example of amino acid-producing microorganisms and more generally are representative of nutrient-producing microorganisms, and other microorganisms of this type may be useful in the invention. On this basis, the present disclosure describes a variety of different approaches for the use of agents that alter a level, activity, or metabolism of one or more microorganisms resident in a host, the alteration resulting in a modulation in the host's fitness.

I. Hosts i. Insects

The host of any of the compositions or methods described herein may be any organism belonging to the phylum Arthropoda (e.g., insects), including any arthropods described herein. In some instances, the host may be an insect or an arachnid that may be cultivated for a consumable product (e.g., food or feed). For example, the host may be a moth, butterfly, fly, cricket, grasshopper, locust, spider, or beetle. In some instances, the host is in the order *Anoplura, Araneae,* Blattodea, *Coleoptera, Dermaptera, Dictyoptera, Diplura, Diptera, Embioptera, Ephemeroptera, Grylloblatodea, Hemiptera, Homoptera, Hymenoptera, Isoptera, Lepidoptera, Mantodea, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera,* or *Zoraptera.*

In some examples, the host is a black soldier fly (*Hermetia illucens*), a common house fly, a lesser mealworm, a weaver ant, a silkworm (*Bombyx mori*), a grasshopper, a Chinese grasshopper (*Acrida cinerea*), a yellow mealworm (*Clarias gariepinns*), a moth (*Anaphe infracta* or *Bombyx mori*), *Spodoptera littoralis*, a house cricket, a termite, a palm weevil (*Rhynchophorus ferruginens*), a giant water bug (*Lethocerus indicus*), a water beetle, a termite (*Macrotermes subhyalinus*), a drugstore beetle (*Stegobium paniceum*), *Imbrasia belina, Rhynchophorus phoenicis, Oryctes rhinoceros, Macrotermes bellicosus, Ruspolia differens, Oryctes Monoceros,* or *Oecophylla smaragdina.*

In particular instances, the modulating agents disclosed herein may be used to increase the fitness of crickets, grasshoppers, or locusts.

The host may be at any stage developmentally. For instance, the host may be an embryo, a larva, a pupa, or an adult.

ii. Host Fitness

The methods and compositions provided herein may be used to increase the fitness of any of the hosts described herein. The increase in fitness may arise from any alterations in microorganisms resident in the host, wherein the alterations are a consequence of administration of a modulating agent and have beneficial or advantageous effects on the host.

In some instances, the increase in host fitness may manifest as an improvement in the physiology of the host (e.g., improved health or survival) as a consequence of administration of a modulating agent. In some instances, the fitness of an organism may be measured by one or more parameters, including, but not limited to, reproductive rate, lifespan, mobility, fecundity, body weight, metabolic rate or activity, or survival in comparison to a host organism to which the modulating agent has not been administered. For example, the methods or compositions provided herein may be effective to improve the overall health of the host or to improve the overall survival of the host in comparison to a host organism to which the modulating agent has not been administered. In some instances, the improved survival of the host is about 2%, 5%, 10%, 20%, 30%, 40%, 50%, 60%, 70%, 80%, 90%, 100%, or greater than 100% greater relative to a reference level (e.g., a level found in a host that does not receive a modulating agent). In some instances, the methods and compositions are effective to increase host reproduction (e.g., reproductive rate) in comparison to a host organism to which the modulating agent has not been administered. In some instances, the methods and compositions are effective to increase other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as an increase in the production of one or more nutrients in the host (e.g., vitamins, carbohydrates, amino acids, or polypeptides) in comparison to a host organism to which the modulating agent has not been administered. In some instances, the methods or compositions provided herein may be effective to increase the production of nutrients in the host (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the methods or compositions provided herein may increase nutrients in the host by increasing the production of nutrients by one or more microorganisms (e.g., endosymbiont) in the host in comparison to a host organism to which the modulating agent has not been administered.

In some instances, the increase in host fitness may manifest as a decrease in the host's sensitivity to a pesticidal agent (e.g., a pesticide listed in Table 12) and/or an increase in the host's resistance to a pesticidal agent (e.g., a pesticide listed in Table 12) in comparison to a host organism to which the modulating agent has not been administered. In some instances, the methods or compositions provided herein may be effective to decrease the host's sensitivity to a pesticidal agent by about 2%, 5%, 10%, 20%, 30%, 40%, 50%, 60%, 70%, 80%, 90%, 100%, or greater than 100% relative to a reference level (e.g., a level found in a host that does not receive a modulating agent). The pesticidal agent may be any pesticidal agent known in the art, including insecticidal agents. In some instances, the pesticidal agent is a neonicotinoid. In some instances, the methods or compositions provided herein may decrease the host's sensitivity to a pesticidal agent (e.g., a pesticide listed in Table 12) by increasing the host's ability to metabolize or degrade the pesticidal agent into usable substrates in comparison to a host organism to which the modulating agent has not been administered.

In some instances, the increase in host fitness may manifest as a decrease in the host's sensitivity to an allelochemical agent and/or an increase in the host's resistance to an allelochemical agent in comparison to a host organism to which the modulating agent has not been administered. In some instances, the methods or compositions provided herein may be effective to increase the host's resistance to an allelochemical agent by about 2%, 5%, 10%, 20%, 30%, 40%, 50%, 60%, 70%, 80%, 90%, 100%, or greater than 100% relative to a reference level (e.g., a level found in a host that does not receive a modulating agent). In some instances, the allelochemical agent is caffeine, soyacystatin N, monoterpenes, diterpene acids, or phenolic compounds in comparison to a host organism to which the modulating agent has not been administered. In some instances, the methods or compositions provided herein may decrease the host's sensitivity to an allelochemical agent by increasing the host's ability to metabolize or degrade the allelochemical agent into usable substrates in comparison to a host organism to which the modulating agent has not been administered.

In some instances, the methods or compositions provided herein may be effective to increase the host's resistance to parasites or pathogens (e.g., fungal, bacterial, or viral pathogens; or parasitic mites) in comparison to a host organism to which the modulating agent has not been administered. In some instances, the methods or compositions provided herein may be effective to increase the host's resistance to a pathogen or parasite (e.g., fungal, bacterial, or viral pathogens; or parasitic mites) by about 2%, 5%, 10%, 20%, 30%, 40%, 50%, 60%, 70%, 80%, 90%, 100%, or greater than 100% relative to a reference level (e.g., a level found in a host that does not receive a modulating agent).

In some instances, the increase in host fitness may manifest as other fitness advantages, such as improved tolerance to certain environmental factors (e.g., a high or low temperature tolerance), improved ability to survive in certain habitats, or an improved ability to sustain a certain diet (e.g., an improved ability to metabolize soy vs corn) in comparison to a host organism to which the modulating agent has not been administered. In some instances, the methods or compositions provided herein may be effective to increase host fitness in any plurality of ways described herein. Further, the modulating agent may increase host fitness in any number of host classes, orders, families, genera, or species (e.g., 1 host species, 2, 3, 4, 5, 6, 7, 8, 9, 10, 15, 20, 30, 40, 50, 60, 70, 80, 90, 100, 150, 200, 200, 250, 500, or more host species). In some instances, the modulating agent acts on a single host class, order, family, genus, or species.

Host fitness may be evaluated using any standard methods in the art. In some instances, host fitness may be evaluated by assessing an individual host. Alternatively, host fitness may be evaluated by assessing a host population. For example, an increase in host fitness may manifest as an increase in successful competition against other insects, thereby leading to an increase in the size of the host population.

iii. Host Insects in Feed/Food Production

Upon reaching a desired life stage, the host may be harvested and, if desired, processed for use in the manufacture of a consumable product. In some instances, the harvested insect may be distributed in a whole form (e.g., as the whole, unprocessed insect) as a consumable product. In some instances, the whole harvested insect is processed (e.g., ground up) and distributed as a consumable product. Alternatively, one or more parts of the insect (e.g., one or more body parts or one or more substances) may be extracted from the insect for use in the manufacture of a consumable product.

The consumable product may be any product safe for human or animal consumption (e.g., ingestion). In some instances, the host may be used in the manufacture of a feed for an animal. In some instances, the animal is livestock or a farm animal (e.g., chicken, cow, horse, or pig). In some instances, the animal is a bird, reptile, amphibian, mammal, or fish. In some instances, the host may be used in the manufacture of a product that replaces the normal feed of an animal. Alternatively, the host may be used in the manufacture of a product that supplements the normal feed of an animal. The host may also be used in the manufacture of a food, food additive, or food ingredient for humans. In some instances, the host is used in the manufacture of a nutritional supplement (e.g., protein supplement) for humans.

The host may be a wild or domesticated insect. Additionally, the host may be at any developmental stage at the time of delivering or applying the compositions described herein. Further, the host may be at any developmental stage at the time of harvesting the host for use in the manufacture of a consumable product. In some instances, the host is a larva, pupa, or adult insect at the time of harvesting, using, processing, or manufacturing. The delivery of the modulating agent and the harvesting steps may occur at the same time or different times.

In some instances, an insect species is selected based upon their natural nutritional profile. In some instances, the modulating agent is used to improve the nutritional profile of the insect, wherein the modulating agent leads to an increased production of a nutrient in comparison to a host organism to which the modulating agent has not been administered. Examples of nutrients include vitamins, carbohydrates, amino acids, polypeptides, or fatty acids. In some instances, the increased production may arise from increased production of a nutrient by a microorganism resident in the host. Alternatively, the increased production may arise from increased production of a nutrient by the host insect itself, wherein the host has increased fitness following delivery or administration of a modulating agent.

In some instances, in final processing, a first insect species is combined with a second insect species whose nutritional profile provides a complementary benefit to the overall nutritional value of the food or feed product. For example, a species containing a high protein profile could be combined with a species containing a high omega ⅜ fatty acid profile. In this manner, insect protein meal may be custom blended to suit the needs of humans or different species of animals.

II. Target Microorganisms

The microorganisms targeted by the modulating agent described herein may include any microorganism resident in or on the host, including, but not limited to, any bacteria and/or fungi described herein. Microorganisms resident in the host may include, for example, symbiotic (e.g., endosymbiotic microorganisms that provide beneficial nutrients or enzymes to the host), commensal, pathogenic, or parasitic microorganisms. A symbiotic microorganism (e.g., bacteria or fungi) may be an obligate symbiont of the host or a facultative symbiont of the host. Microorganisms resident in the host may be acquired by any mode of transmission, including vertical, horizontal, or multiple origins of transmission.

i. Bacteria

Exemplary bacteria that may be targeted in accordance with the methods and compositions provided herein, include, but are not limited to, *Xenorhabdus* spp, *Photorhabdus* spp, *Candidatus* spp, *Buchnera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, and *Escherichia* spp. Non-limiting examples of bacteria that may be targeted by the methods and compositions provided herein are shown in Table 1.

TABLE 1

| Examples of Target Bacteria and Host Insects | | | |
|---|---|---|---|
| Primary endosymbiont | Host | Location | 16S rRNA |
| Gamma proteobacteria | | | |
| Carsonella ruddii | Psyllids (Psylloidea) | bacteriocytes | TATCCAGCCACAGGTTCCCCTA CAGCTACCTTGTTACGACTTCA CCCCAGTTACAAATCATACCGTT GTAATAGTAAAATTACTTATGAT ACAATTTACTTCCATGGTGTGAC GGGCGGTGTGTACAAGGCTCG AGAACGTATTCACCGTAACATTC TGATTTACGATTACTAGCGATTC CAACTTCATGAAATCGAGTTACA GATTTCAATCCGAACTAAGAATA TTTTTTAAGATTAGCATTATGTT GCCATATAGCATATAACTTTTTG TAATACTCATTGTAGCACGTGTG TAGCCCTACTTATAAGGGCCAT GATGACTTGACGTCGTCCTCAC CTTCCTCCAATTTATCATTGGCA GTTTCTTATTAGTTCTAATATATT TTTAGTAAAATAAGATAAGGGTT GCGCTCGTTATAGGACTTAACC CAACATTTCACAACACGAGCTG ACGACAGCCATGCAGCACCTGT CTCAAAGCTAAAAAAGCTTTATT ATTTCTAATAAATTCTTTGGATG TCAAAAGTAGGTAAGATTTTTCG TGTTGTATCGAATTAAACCACAT GCTCCACCGCTTGTGCGAGCCC CCGTCAATTCATTTGAGTTTTAA CCTTGCGGTCGTAATCCCCAGG CGGTCAACTTAACGCGTTAGCT TTTTCACTAAAAATATATAACTTT TTTTCATAAAACAAAATTACAATT ATAATATTTAATAAATAGTTGAC ATCGTTTACTGCATGGACTACC AGGGTATCTAATCCTGTTTGCTC CCCATGCTTTCGTGTATTAGTGT CAGTATTAAAATAGAAATACGCC TTCGCCACTAGTATTCTTTCAGA TATCTAAGCATTTCACTGCTACT CCTGAAATTCTAATTTCTTCTTTT ATACTCAAGTTTATAAGTATTAA TTTCAATATTAAATTACTTTAATA AATTTAAAAATTAATTTTTAAAAA CAACCTGCACACCCTTTACGCC CAATAATTCCGATTAACGCTTGC ACCCCTCGTATTACCGCGGCTG CTGGCACGAAGTTAGCCGGTGC TTCTTTTACAAATAACGTCAAAG ATAATATTTTTTATTATAAAATC TCTTCTTACTTTGTTGAAAGTGT TTTACAACCCTAAGGCCTTCTTC ACACACGCGATATAGCTGGATC AAGCTTTCGCTCATTGTCCAATA TCCCCCACTGCTGCCTTCCGTA AAAGTTTGGGCCGTGTCTCAGT CCCAATGTGGTTGTTCATCCTCT AAGATCAACTACGAATCATAGTC TTGTTAAGCTTTTACTTTAACAA CTAACTAATTCGATATAAGCTCT TCTATTAGCGAACGACATTCTC GTTCTTTATCCATTAGGATACAT ATTGAATTACTATACATTTCTATA TACTTTTCTAATACTAATAGGTA GATTCTTATATATTACTCACCCG TTCGCTGCTAATTATTTTTTTAAT AATTCGCACAACTTGCATGTGTT AAGCTTATCGCTAGCGTTCAAT CTGAGCTATGATCAAACTCA (SEQ ID NO: 1) |
| Portiera aleyrodidarum BT-B | whiteflyes (Aleyrodoidea) | bacteriocytes | AAGAGTTTGATCATGGCTCAGA TTGAACGCTAGCGGCAGACATA ACACATGCAAGTCGAGCGGCAT CATACAGGTTGGCAAGCGGCG CACGGGTGAGTAATACATGTAA |

TABLE 1-continued

Examples of Target Bacteria and Host Insects

|   |   |   | ATATACCTAAAAGTGGGGAATA |
|---|---|---|---|
|   |   |   | ACGTACGGAAACGTACGCTAAT |
|   |   |   | ACCGCATAATTATTACGAGATAA |
|   |   |   | AGCAGGGGCTTGATAAAAAAAA |
|   |   |   | TCAACCTTGCGCTTTTAGAAAAT |
|   |   |   | TACATGCCGGATTAGCTAGTTG |
|   |   |   | GTAGAGTAAAAGCCTACCAAGG |
|   |   |   | TAACGATCCGTAGCTGGTCTGA |
|   |   |   | GAGGATGATCAGCCACACTGGG |
|   |   |   | ACTGAGAAAAGGCCCAGACTCC |
|   |   |   | TACGGGAGGCAGCAGTGGGGA |
|   |   |   | ATATTGGACAATGGGGGGAACC |
|   |   |   | CTGATCCAGTCATGCCGCGTGT |
|   |   |   | GTGAAGAAGGCCTTTGGGTTGT |
|   |   |   | AAAGCACTTTCAGCGAAGAAGA |
|   |   |   | AAAGTTAGAAAATAAAAAGTTAT |
|   |   |   | AACTATGACGGTACTCGCAGAA |
|   |   |   | GAAGCACCGGCTAACTCCGTGC |
|   |   |   | CAGCAGCCGCGGTAAGACGGA |
|   |   |   | GGGTGCAAGCGTTAATCAGAAT |
|   |   |   | TACTGGGCGTAAAGGGCATGTA |
|   |   |   | GGTGGTTTGTTAAGCTTTATGTG |
|   |   |   | AAAGCCCTATGCTTAACATAGG |
|   |   |   | AACGGAATAAAGAACTGACAAA |
|   |   |   | CTAGAGTGCAGAAGAGGAAGGT |
|   |   |   | AGAATTCCCGGTGTAGCGGTGA |
|   |   |   | AATGCGTAGATATCTGGAGGAA |
|   |   |   | TACCAGTTGCGAAGGCGACCTT |
|   |   |   | CTGGGCTGACACTGACACTGAG |
|   |   |   | ATGCGAAAGCGTGGGGAGCAA |
|   |   |   | ACAGGATTAGATACCCTGGTAG |
|   |   |   | TCCACGCTGTAAACGATATCAA |
|   |   |   | CTAGCCGTTGGATTCTTAAAGA |
|   |   |   | ATTTTGTGGCGTAGCTAACGCG |
|   |   |   | ATAAGTTGATCGCCTGGGGAGT |
|   |   |   | ACGGTCGCAAGGCTAAAACTCA |
|   |   |   | AATGAATTGACGGGGGCCCGCA |
|   |   |   | CAAGCGGTGGAGCATGTGGTTT |
|   |   |   | AATTCGATGCAACGCGCAAAAC |
|   |   |   | CTTACCTACTCTTGACATCCAAA |
|   |   |   | GTACTTTCCAGAGATGGAAGGG |
|   |   |   | TGCCTTAGGGAACTTTGAGACA |
|   |   |   | GGTGCTGCATGGCTGTCGTCAG |
|   |   |   | CTCGTGTTGTGAAATGTTGGGT |
|   |   |   | TAAGTCCCGTAACGAGCGCAAC |
|   |   |   | CCTTGTCCTTAGTTGCCAACGC |
|   |   |   | ATAAGGCGGGAACTTTAAGGAG |
|   |   |   | ACTGCTGGTGATAAACCGGAGG |
|   |   |   | AAGGTGGGACGACGTCAAGT |
|   |   |   | CATCATGCCCTTAAGAGTAGG |
|   |   |   | GCAACACACGTGCTACAATGGC |
|   |   |   | AAAAACAAAGGGTCGCAAAATG |
|   |   |   | GTAACATGAAGCTAATCCCAAA |
|   |   |   | AAAATTGTCTTAGTTCGGATTGG |
|   |   |   | AGTCTGAAACTCGACTCCATAA |
|   |   |   | AGTCGGAATCGCTAGTAATCGT |
|   |   |   | GAATCAGAATGTCACGGTGAAT |
|   |   |   | ACGTTCTCGGGCCTTGTACACA |
|   |   |   | CCGCCCGTCACACCATGGAAGT |
|   |   |   | GAAATGCACCAGAAGTGGCAAG |
|   |   |   | TTTAACCAAAAAACAGGAGAAC |
|   |   |   | AGTCACTACGGTGTGGTTCATG |
|   |   |   | ACTGGGGTGAAGTCGTAACAAG |
|   |   |   | GTAGCTGTAGGGGAACCTGTGG |
|   |   |   | CTGGATCACCTCCTTAA |
|   |   |   | (SEQ ID NO: 2) |
| Buchnera aphidicola str. APS (Acyrthosiphonpisum) | Aphids (Aphidoidea) | bacteriocytes | AGAGTTTGATCATGGCTCAGAT |
|   |   |   | TGAACGCTGGCGGCAAGCCTAA |
|   |   |   | CACATGCAAGTCGAGCGGCAG |
|   |   |   | CGAGAAGAGAGCTTGCTCTCTT |
|   |   |   | TGTCGGCAAGCGGCAAACGGG |
|   |   |   | TGAGTAATATCTGGGGATCTAC |
|   |   |   | CCAAAAGAGGGGGATAACTACT |
|   |   |   | AGAAATGGTAGCTAATACCGCA |
|   |   |   | TAATGTTGAAAAACCAAAGTGG |
|   |   |   | GGGACCTTTTGGCCTCATGCTT |
|   |   |   | TTGGATGAACCCAGACGAGATT |

TABLE 1-continued

Examples of Target Bacteria and Host Insects

| | | | |
|---|---|---|---|
| | | | AGCTTGTTGGTAGAGTAATAGC |
| | | | CTACCAAGGCAACGATCTCTAG |
| | | | CTGGTCTGAGAGGATAACCAGC |
| | | | CACACTGGAACTGAGACACGGT |
| | | | CCAGACTCCTACGGGAGGCAG |
| | | | CAGTGGGGAATATTGCACAATG |
| | | | GGCGAAAGCCTGATGCAGCTAT |
| | | | GCCGCGTGTATGAAGAAGGCCT |
| | | | TAGGGTTGTAAAGTACTTTCAG |
| | | | CGGGGAGGAAAAAAATAAAACT |
| | | | AATAATTTTATTTCGTGACGTTA |
| | | | CCCGCAGAAGAAGCACCGGCT |
| | | | AACTCCGTGCCAGCAGCCGCG |
| | | | GTAATACGGAGGGTGCAAGCGT |
| | | | TAATCAGAATTACTGGGCGTAA |
| | | | AGAGCGCGTAGGTGGTTTTTTA |
| | | | AGTCAGGTGTGAAATCCCTAGG |
| | | | CTCAACCTAGGAACTGCATTTG |
| | | | AAACTGGAAAACTAGAGTTTCG |
| | | | TAGAGGGAGGTAGAATTCTAGG |
| | | | TGTAGCGGTGAAATGCGTAGAT |
| | | | ATCTGGAGGAATACCCGTGGCG |
| | | | AAAGCGGCCTCCTAAACGAAAA |
| | | | CTGACACTGAGGCGCGAAAGC |
| | | | GTGGGGAGCAAACAGGATTAGA |
| | | | TACCCTGGTAGTCCATGCCGTA |
| | | | AACGATGTCGACTTGGAGGTTG |
| | | | TTTCCAAGAGAAGTGACTTCCG |
| | | | AAGCTAACGCATTAAGTCGACC |
| | | | GCCTGGGGAGTACGGCCGCAA |
| | | | GGCTAAAACTCAAATGAATTGA |
| | | | CGGGGGCCCGCACAAGCGGTG |
| | | | GAGCATGTGGTTTAATTCGATG |
| | | | CAACGCGAAAAACCTTACCTGG |
| | | | TCTTGACATCCACAGAATTCTTT |
| | | | AGAAATAAAGAAGTGCCTTCGG |
| | | | GAGCTGTGAGACAGGTGCTGCA |
| | | | TGGCTGTCGTCAGCTCGTGTTG |
| | | | TGAAATGTTGGGTTAAGTCCCG |
| | | | CAACGAGCGCAACCCTTATCCC |
| | | | CTGTTGCCAGCGGTTCGGCCG |
| | | | GGAACTCAGAGGAGACTGCCG |
| | | | GTTATAAACCGGAGGAAGGTGG |
| | | | GGACGACGTCAAGTCATCATGG |
| | | | CCCTTACGACCAGGGCTACACA |
| | | | CGTGCTACAATGGTTTATACAAA |
| | | | GAGAAGCAAATCTGCAAAGACA |
| | | | AGCAAACCTCATAAAGTAAATC |
| | | | GTAGTCCGGACTGGAGTCTGCA |
| | | | ACTCGACTCCACGAAGTCGGAA |
| | | | TCGCTAGTAATCGTGGATCAGA |
| | | | ATGCCACGGTGAATACGTTCCC |
| | | | GGGCCTTGTACACACCGCCCGT |
| | | | CACACCATGGGAGTGGGTTGCA |
| | | | AAAGAAGCAGGTATCCTAACCC |
| | | | TTTAAAAGGAAGGCGCTTACCA |
| | | | CTTTGTGATTCATGACTGGGGT |
| | | | GAAGTCGTAACAAGGTAACCGT |
| | | | AGGGGAACCTGCGGTTGGATCA |
| | | | CCTCCTT |
| | | | (SEQ ID NO: 3) |
| *Buchnera aphidicola* str. Sg (*Schizaphis graminum*) | Aphids (Aphidoidea) | bacteriocytes | AAACTGAAGAGTTTGATCATGG |
| | | | CTCAGATTGAACGCTGGCGGCA |
| | | | AGCCTAACACATGCAAGTCGAG |
| | | | CGGCAGCGAAAAGAAAGCTTGC |
| | | | TTTCTTGTCGGCGAGCGGCAAA |
| | | | CGGGTGAGTAATATCTGGGGAT |
| | | | CTGCCCAAAAGAGGGGGATAAC |
| | | | TACTAGAAATGGTAGCTAATACC |
| | | | GCATAAAGTTGAAAAACCAAAG |
| | | | TGGGGGACCTTTTTTAAAGGCC |
| | | | TCATGCTTTTGGATGAACCCAG |
| | | | ACGAGATTAGCTTGTTGGTAAG |
| | | | GTAAAAGCTTACCAAGGCAACG |
| | | | ATCTCTAGCTGGTCTGAGAGGA |
| | | | TAACCAGCCACACTGGAACTGA |
| | | | GACACGGTCCAGACTCCTACGG |

TABLE 1-continued

Examples of Target Bacteria and Host Insects

| | | |
|---|---|---|
| | | GAGGCAGCAGTGGGGAATATTG |
| | | CACAATGGGCGAAAGCCTGATG |
| | | CAGCTATGCCGCGTGTATGAAG |
| | | AAGGCCTTAGGGTTGTAAAGTA |
| | | CTTTCAGCGGGGAGGAAAAAAT |
| | | TAAAACTAATAATTTTATTTTGTG |
| | | ACGTTACCCGCAGAAGAAGCAC |
| | | CGGCTAACTCCGTGCCAGCAGC |
| | | CGCGGTAATACGGAGGGTGCG |
| | | AGCGTTAATCAGAATTACTGGG |
| | | CGTAAAGAGCACGTAGGTGGTT |
| | | TTTTAAGTCAGATGTGAAATCCC |
| | | TAGGCTTAACCTAGGAACTGCA |
| | | TTTGAAACTGAAATGCTAGAGTA |
| | | TCGTAGAGGGAGGTAGAATTCT |
| | | AGGTGTAGCGGTGAAATGCGTA |
| | | GATATCTGGAGGAATACCCGTG |
| | | GCGAAAGCGGCCTCCTAAACGA |
| | | ATACTGACACTGAGGTGCGAAA |
| | | GCGTGGGGAGCAAACAGGATTA |
| | | GATACCCTGGTAGTCCATGCCG |
| | | TAAACGATGTCGACTTGGAGGT |
| | | TGTTTCCAAGAGAAGTGACTTC |
| | | CGAAGCTAACGCGTTAAGTCGA |
| | | CCGCCTGGGGAGTACGGCCGC |
| | | AAGGCTAAAACTCAAATGAATTG |
| | | ACGGGGGCCCGCACAAGCGGT |
| | | GGAGCATGTGGTTTAATTCGAT |
| | | GCAACGCGAAAAACCTTACCTG |
| | | GTCTTGACATCCACAGAATTTTT |
| | | TAGAAATAAAAAAGTGCCTTCG |
| | | GGAACTGTGAGACAGGTGCTGC |
| | | ATGGCTGTCGTCAGCTCGTGTT |
| | | GTGAAATGTTGGGTTAAGTCCC |
| | | GCAACGAGCGCAACCCTTATCC |
| | | CCTGTTGCCAGCGGTTCGGCC |
| | | GGGAACTCAGAGGAGACTGCC |
| | | GGTTATAAACCGGAGGAAGGTG |
| | | GGGACGACGTCAAGTCATCATG |
| | | GCCCTTACGACCAGGGCTACAC |
| | | ACGTGCTACAATGGTTTATACAA |
| | | AGAGAAGCAAATCTGTAAAGAC |
| | | AAGCAAACCTCATAAAGTAAATC |
| | | GTAGTCCGGACTGGAGTCTGCA |
| | | ACTCGACTCCACGAAGTCGGAA |
| | | TCGCTAGTAATCGTGGATCAGA |
| | | ATGCCACGGTGAATACGTTCCC |
| | | GGGCCTTGTACACACCGCCCGT |
| | | CACACCATGGGAGTGGGTTGCA |
| | | AAAGAAGCAGATTTCCTAACCA |
| | | CGAAAGTGGAAGGCGTCTACCA |
| | | CTTTGTGATTCATGACTGGGGT |
| | | GAAGTCGTAACAAGGTAACCGT |
| | | AGGGGAACCTGCGGTTGGATCA |
| | | CCTCCTTA |
| | | (SEQ ID NO: 4) |
| *Buchnera aphidicola* str. Bp (*Baizongia pistaciae*) | Aphids (Aphidoidea) | bacteriocytes ACTTAAAATTGAAGAGTTTGATC |
| | | ATGGCTCAGATTGAACGCTGGC |
| | | GGCAAGCTTAACACATGCAAGT |
| | | CGAGCGGCATCGAAGAAAAGTT |
| | | TACTTTTCTGGCGGCGAGCGGC |
| | | AAACGGGTGAGTAACATCTGGG |
| | | GATCTACCTAAAAGAGGGGGAC |
| | | AACCATTGGAAACGATGGCTAA |
| | | TACCGCATAATGTTTTTAAATAA |
| | | ACCAAAGTAGGGGACTAAAATT |
| | | TTTAGCCTTATGCTTTTAGATGA |
| | | ACCCAGACGAGATTAGCTTGAT |
| | | GGTAAGGTAATGGCTTACCAAG |
| | | GCGACGATCTCTAGCTGGTCTG |
| | | AGAGGATAACCAGCCACACTGG |
| | | AACTGAGATACGGTCCAGACTC |
| | | CTACGGGAGGCAGCAGTGGGG |
| | | AATATTGCACAATGGGCTAAAG |
| | | CCTGATGCAGCTATGCCGCGTG |
| | | TATGAAGAAGGCCTTAGGGTTG |
| | | TAAAGTACTTTCAGCGGGGAGG |

TABLE 1-continued

Examples of Target Bacteria and Host Insects

```
AAAGAATTATGTCTAATATACAT
ATTTTGTGACGTTACCCGAAGA
AGAAGCACCGGCTAACTCCGTG
CCAGCAGCCGCGGTAATACGG
AGGGTGCGAGCGTTAATCAGAA
TTACTGGGCGTAAAGAGCACGT
AGGCGGTTTATTAAGTCAGATG
TGAAATCCCTAGGCTTAACTTAG
GAACTGCATTTGAAACTAATAGA
CTAGAGTCTCATAGAGGGAGGT
AGAATTCTAGGTGTAGCGGTGA
AATGCGTAGATATCTAGAGGAA
TACCCGTGGCGAAAGCGACCTC
CTAAATGAAAACTGACGCTGAG
GTGCGAAAGCGTGGGGAGCAA
ACAGGATTAGATACCCTGGTAG
TCCATGCTGTAAACGATGTCGA
CTTGGAGGTTGTTTCCTAGAGA
AGTGGCTTCCGAAGCTAACGCA
TTAAGTCGACCGCCTGGGGAGT
ACGGTCGCAAGGCTAAAACTCA
AATGAATTGACGGGGGCCCGCA
CAAGCGGTGGAGCATGTGGTTT
AATTCGATGCAACGCGAAGAAC
CTTACCTGGTCTTGACATCCATA
GAATTTTTTAGAGATAAAAGAGT
GCCTTAGGGAACTATGAGACAG
GTGCTGCATGGCTGTCGTCAGC
TCGTGTTGTGAAATGTTGGGTT
AAGTCCCGCAACGAGCGCAACC
CCTATCCTTTGTTGCCATCAGGT
TATGCTGGGAACTCAGAGGAGA
CTGCCGGTTATAAACCGGAGGA
AGGTGGGGATGACGTCAAGTCA
TCATGGCCCTTACGACCAGGGC
TACACACGTGCTACAATGGCAT
ATACAAAGAGATGCAACTCTGC
GAAGATAAGCAAACCTCATAAA
GTATGTCGTAGTCCGGACTGGA
GTCTGCAACTCGACTCCACGAA
GTAGGAATCGCTAGTAATCGTG
GATCAGAATGCCACGGTGAATA
CGTTCCCGGGCCTTGTACACAC
CGCCCGTCACACCATGGGAGT
GGGTTGCAAAAGAAGCAGGTAG
CTTAACCAGATTATTTTATTGGA
GGGCGCTTACCACTTTGTGATT
CATGACTGGGGTGAAGTCGTAA
CAAGGTAACCGTAGGGGAACCT
GCGGTTGGATCACCTCCTTA
(SEQ ID NO: 5)
```

| | | | |
|---|---|---|---|
| *Buchnera aphidicola* BCc | Aphids (*Aphidoidea*) | bacteriocytes | ATGAGATCATTAATATATAAAAA TCATGTTCCAATTAAAAAATTAG GACAAAATTTTTTACAGAATAAA GAAATTATTAATCAGATAATTAA TTTAATAAATATTAATAAAAATGA TAATATTATTGAAATAGGATCAG GATTAGGAGCGTTAACTTTTCCT ATTTGTAGAATCATTAAAAAAAT GATAGTATTAGAAATTGATGAAG ATCTTGTGTTTTTTTAACTCAAA GTTTATTTATTAAAAAATTACAAA TTATAATTGCTGATATTATAAAAT TTGATTTTTGTTGTTTTTTTCTT TACAGAAATATAAAAAATATAGG TTTATTGGTAATTTACCATATAAT ATTGCTACTATATTTTTTTAAAA ACAATTAAATTTCTTTATAATATA ATTGATATGCATTTTATGTTTCA AAAAGAAGTAGCAAAGAGATTA TTAGCTACTCCTGGTACTAAAGA ATATGGTAGATTAAGTATTATTG CACAATATTTTTATAAGATAGAA ACTGTTATTAATGTTAATAAATTT AATTTTTTTCCTACTCCTAAAGT AGATTCTACTTTTTTACGATTTA CTCCTAAATATTTTAATAGTAAA |

TABLE 1-continued

Examples of Target Bacteria and Host Insects

| | | | |
|---|---|---|---|
| | | | TATAAAATAGATAAACATTTTTCT<br>GTTTTAGAATTAATTACTAGATT<br>TTCTTTTCAACATAGAAGAAAAT<br>TTTTAAATAATAATTTAATATCTT<br>TATTTTCTACAAAAGAATTAATTT<br>CTTTAGATATTGATCCATATTCA<br>AGAGCAGAAAATGTTTCTTTAAT<br>TCAATATTGTAAATTAATGAAAT<br>ATTATTTGAAAAGAAAAATTTTAT<br>GTTTAGATTAA<br>(SEQ ID NO: 6) |
| Buchnera aphidicola<br>(Cinara tujafilina) | Aphids<br>(Aphidoidea) | bacteriocytes | TTATCTTATTTCACATATACGTA<br>ATATTGCGCTGCGTGCACGAGG<br>ATTTTTTTGAATTTCAGATATATT<br>TGGTTTAATACGTTTAATAAAAC<br>GTATTTTTTTTTTATTTTTCTTA<br>TTTGCAATTCAGTAATAGGAAGT<br>TTTTTAGGTATATTTGGATAATT<br>ACTGTAATTCTTAATAAAGTTTTT<br>TACAATCCTATCTTCAATAGAAT<br>GAAAACTAATAATAGCAATTTTT<br>GATCCGGAATGTAATATGTTAAT<br>AATAATTTTTAATATTTTATGTAA<br>TTCATTTATTTCTTGGTTAATATA<br>TATTCGAAAAGCTTGAAATGTTC<br>TCGTAGCTGGATGTTTAAATTTG<br>TCATATTTTGGGATTGATTTTTTT<br>ATGATTTGAACTAACTCTAACGT<br>GCTTGTTATGGTTTTTTTTTTAT<br>TTGTAATATGATGGCTCGGGAT<br>ATTTTTTTTGCGTATTTTTCTTCG<br>CCAAAATTTTTTATTACCTGTTC<br>TATTGTTTTTTGGTTTGTTTTTTT<br>TAACCATTGACTAACTGATATTC<br>CAGATTTAGGGTTCATACGCAT<br>ATCTAAAGGTCCATCATTCATAA<br>ATGAAAATCCTCGGATACTAGA<br>ATTTAACTGTATTGAAGAAATAC<br>CTAAATCTAATAATATTCCATCT<br>ATTTTATCTCTATTTTTTCTTTT<br>TTTAATATTTTTTCAATATTAGAA<br>AATTTACCTAAAAATATTTTAAAT<br>CGCGAATCTTTTATTTTTTTCC<br>GATTTTTATAGATTGTGGGTCTT<br>GATCAATACTATATAACTTTCCA<br>TTAACCCCTAATTCTTGAAGAAT<br>TGCTTTTGAATGACCACCACCT<br>CCAAATGTACAATCAACATATGT<br>ACCGTCTTTTTTTATTTTAAGTA<br>TTGTATGATTTCTTTTGTTAAAA<br>CAGGTTTATGAATCAT<br>(SEQ ID NO: 7) |
| Buchnera aphidicola str.<br>G002 (Myzus persicae) | Aphids<br>(Aphidoidea) | bacteriocytes | ATGAAAAGTATAAAAACTTTTAA<br>AAAACACTTTCCTGTGAAAAAAT<br>ATGGACAAAATTTTCTTATTAAT<br>AAAGAGATCATAAAAAAATATTGT<br>TAAAAAAATTAATCCAAATATAG<br>AACAAACATTAGTAGAAATCGG<br>ACCAGGATTAGCTGCATTAACT<br>GAGCCCATATCTCAGTTATTAAA<br>AGAGTTAATAGTTATTGAAATAG<br>ACTGTAATCTATTATATTTTTAA<br>AAAAACAACCATTTTATTCAAAA<br>TTAATAGTTTTTTGTCAAGATGC<br>TTTAAACTTTAATTATACAAATTT<br>ATTTTATAAAAAAATAAATTAAT<br>TCGTATTTTTGGTAATTTACCAT<br>ATAATATCTCTACATCTTTAATTA<br>TTTTTTTATTTCAACACATTAGA<br>GTAATTCAAGATATGAATTTTAT<br>GCTTCAAAAAGAAGTTGCTGCA<br>AGATTAATTGCATTACCTGGAAA<br>TAAATATTACGGTCGTTTGAGCA<br>TTATATCTCAATATTATTGTGATA<br>TCAAAATTTTATTAAATGTTGCT<br>CCTGAAGATTTTTGGCCTATTCC |

TABLE 1-continued

Examples of Target Bacteria and Host Insects

| | | | |
|---|---|---|---|
| | | | GAGAGTTCATTCTATATTTGTAA<br>ATTTAACACCTCATCATAATTCT<br>CCTTATTTTGTTTATGATATTAAT<br>ATTTTAAGCCTTATTACAAATAA<br>GGCTTTCCAAAATAGAAGAAAA<br>ATATTACGTCATAGTTTAAAAAA<br>TTTATTTTCTGAAACAACTTTATT<br>AAATTTAGATATTAATCCCAGAT<br>TAAGAGCTGAAAATATTTCTGTT<br>TTTCAGTATTGTCAATTAGCTAA<br>TTATTTGTATAAAAAAATTATAC<br>TAAAAAAAATTAA<br>(SEQ ID NO: 8) |
| *Buchnera aphidicola* str. Ak (*Acyrthosiphon kondoi*) | Aphids (Aphidoidea) | bacteriocytes | ATTATAAAAAATTTTAAAAAACAT<br>TTTCCTTTAAAAAGGTATGGACA<br>AAATTTTCTTGTCAATACAAAAA<br>CTATTCAAAAGATAATTAATATA<br>ATTAATCCAAACACCAAACAAAC<br>ATTAGTGGAAATTGGACCTGGA<br>TTAGCTGCATTAACAAAACCAAT<br>TTGTCAATTATTAGAAGAATTAA<br>TTGTTATTGAAATAGATCCTAAT<br>TTATTGTTTTTATTAAAAAAACGT<br>TCATTTTATTCAAAATTAACAGTT<br>TTTTATCAAGACGCTTTAAATTT<br>CAATTATACAGATTTGTTTTATA<br>AGAAAAATCAATTAATTCGTGTT<br>TTTGGAAACTTGCCATATAATAT<br>TTCTACATCTTTAATTATTTCTTT<br>ATTCAATCATATTAAAGTTATTC<br>AAGATATGAATTTTATGTTACAG<br>AAAGAGGTTGCTGAAAGATTAA<br>TTTCTATTCCTGGAAATAAATCT<br>TATGGCCGTTTAAGCATTATTTC<br>TCAGTATTATTGTAAAATTAAAA<br>TATTATTAAATGTTGTACCTGAA<br>GATTTTCGACCTATACCGAAAGT<br>GCATTCTGTTTTTATCAATTTAA<br>CTCCTCATACCAATTCTCCATAT<br>TTTGTTTATGATACAAATATCCT<br>CAGTTCTATCACAAGAAATGCTT<br>TTCAAAATAGAAGGAAAATTTTG<br>CGTCATAGTTTAAAAAATTTATT<br>TTCTGAAAAGAACTAATTCAAT<br>TAGAAATTAATCCAAATTTACGA<br>GCTGAAAATATTTCTATCTTTCA<br>GTATTGTCAATTAGCTGATTATT<br>TATATAAAAAATTAAATAATCTTG<br>TAAAAATCAATTAA<br>(SEQ ID NO: 9) |
| *Buchnera aphidicola* str. Ua (*Uroleucon ambrosiae*) | Aphids (Aphidoidea) | bacteriocytes | ATGATACTAAATAAATATAAAAA<br>ATTTATTCCTTTAAAAAGATACG<br>GACAAAATTTTCTTGTAAATAGA<br>GAAATAATCAAAAATATTATCAA<br>AATAATTAATCCTAAAAAAACGC<br>AAACATTATTAGAAATTGGACCG<br>GGTTTAGGTGCGTTAACAAAAC<br>CTATTTGTGAATTTTTAAATGAA<br>CTTATCGTCATTGAAATAGATCC<br>TAATATATTATCTTTTTAAAGAA<br>ATGTATATTTTTTGATAAATTAAA<br>AATATATTGTCATAATGCTTTAG<br>ATTTTAATTATAAAAATATATTCT<br>ATAAAAAAAGTCAATTAATTCGT<br>ATTTTTGGAAATTTACCATATAA<br>TATTTCTACATCTTTAATAATATA<br>TTTATTTCGGAATATTGATATTAT<br>TCAAGATATGAATTTTATGTTAC<br>AACAAGAAGTGGCTAAAAGATT<br>AGTTGCTATTCCTGGTGAAAAA<br>CTTTATGGTCGTTTAAGTATTAT<br>ATCTCAATATTATTGTAATATTAA<br>AATATTATTACATATTCGACCTG<br>AAAATTTTCAACCTATTCCTAAA<br>GTTAATTCAATGTTTGTAAATTT<br>AACTCCGCATATTCATTCTCCTT |

TABLE 1-continued

Examples of Target Bacteria and Host Insects

| | | | |
|---|---|---|---|
| | | | ATTTTGTTTATGATATTAATTTAT
TAACTAGTATTACAAAACATGCT
TTTCAACATAGAAGAAAAATATT
GCGTCATAGTTTAAGAAATTTTT
TTTCTGAGCAAGATTTAATTCAT
TTAGAAATTAATCCAAATTTAAG
AGCTGAAAATGTTTCTATTATTC
AATATTGTCAATTGGCTAATAAT
TTATATAAAAAACATAAACAGTT
TATTAATAATTAA
(SEQ ID NO: 10) |
| *Buchnera aphidicola*
(*Aphis glycines*) | Aphids
(*Aphidoidea*) | bacteriocytes | ATGAAAAAGCATATTCCTATAAA
AAAATTTAGTCAAAATTTTCTTG
TAGATTTGAGTGTGATTAAAAAA
ATAATTAAATTTATTAATCCGCA
GTTAAATGAAATATTGGTTGAAA
TTGGACCGGGATTAGCTGCTAT
CACTCGACCTATTTGTGATTTGA
TAGATCATTTAATTGTGATTGAA
ATTGATAAAATTTTATTAGATAG
ATTAAAACAGTTCTCATTTTATT
CAAAATTAACAGTATATCATCAA
GATGCTTTAGCATTTGATTACAT
AAAGTTATTTAATAAAAAAAATA
AATTAGTTCGAATTTTTGGTAAT
TTACCATATCATGTTTCTACGTC
TTTAATATTGCATTTATTTAAAAG
AATTAATATTATTAAAGATATGA
ATTTTATGCTACAAAAAGAAGTT
GCTGAACGTTTAATTGCAACTC
CAGGTAGTAAATTATATGGTCGT
TTAAGTATTATTTCTCAATATTAT
TGTAATATAAAAGTTTTATTGCA
TGTGTCTTCAAAATGTTTTAAAC
CAGTTCCTAAAGTAGAATCAATT
TTTCTTAATTTGACACCTTATAC
TGATTATTTCCCTTATTTTACTTA
TAATGTAAACGTTCTTAGTTATA
TTACAAATTTAGCTTTTCAAAAA
AGAAGAAAAATATTACGTCATAG
TTTAGGTAAAATATTTTCTGAAA
AAGTTTTTATAAAATTAAATATTA
ATCCCAAATTAAGACCTGAGAAT
ATTTCTATATTACAATATTGTCA
GTTATCTAATTATATGATAGAAA
ATAATATTCATCAGGAACATGTT
TGTATTTAA
(SEQ ID NO: 11) |
| *Annandia pinicola* | (*Phylloxeroidea*) | bacteriocytes | AGATTGAACGCTGGCGGCATGC
CTTACACATGCAAGTCGAACGG
TAACAGGTCTTCGGACGCTGAC
GAGTGGCGAACGGGTGAGTAAT
ACATCGGAACGTGCCCAGTCGT
GGGGGATAACTACTCGAAAGAG
TAGCTAATACCGCATACGATCT
GAGGATGAAAGCGGGGGACCT
TCGGGCCTCGCGCGATTGGAG
CGGCCGATGGCAGATTAGGTAG
TTGGTGGGATAAAAGCTTACCA
AGCCGACGATCTGTAGCTGGTC
TGAGAGGACGACCAGCCACACT
GGAACTGAGATACGGTCCAGAC
TCTTACGGGAGGCAGCAGTGG
GGAATATTGCACAATGGGCGCA
AGCCTGATGCAGCTATGTCGCG
TGTATGAAGAAGACCTTAGGGT
TGTAAAGTACTTTCGATAGCATA
AGAAGATAATGAGACTAATAATT
TTATTGTCTGACGTTAGCTATAG
AAGAAGCACCGGCTAACTCCGT
GCCAGCAGCCGCGGTAATACG
GGGGGTGCTAGCGTTAATCGGA
ATTACTGGGCGTAAAGAGCATG
TAGGTGGTTTATTAAGTCAGATG
TGAAATCCCTGGACTTAATCTAG
GAACTGCATTTGAAACTAATAG |

TABLE 1-continued

Examples of Target Bacteria and Host Insects

|  |  |  |  |
|---|---|---|---|
|  |  |  | GCTAGAGTTTCGTAGAGGGAGG |
|  |  |  | TAGAATTCTAGGTGTAGCGGTG |
|  |  |  | AAATGCATAGATATCTAGAGGA |
|  |  |  | ATATCAGTGGCGAAGGCGACCT |
|  |  |  | TCTGGACGATAACTGACGCTAA |
|  |  |  | AATGCGAAAGCATGGGTAGCAA |
|  |  |  | ACAGGATTAGATACCCTGGTAG |
|  |  |  | TCCATGCTGTAAACGATGTCGA |
|  |  |  | CTAAGAGGTTGGAGGTATAACT |
|  |  |  | TTTAATCTCTGTAGCTAACGCGT |
|  |  |  | TAAGTCGACCGCCTGGGGAGTA |
|  |  |  | CGGTCGCAAGGCTAAAACTCAA |
|  |  |  | ATGAATTGACGGGGGCCTGCAC |
|  |  |  | AAGCGGTGGAGCATGTGGTTTA |
|  |  |  | ATTCGATGCAACGCGTAAAACC |
|  |  |  | TTACCTGGTCTTGACATCCACA |
|  |  |  | GAATTTTACAGAAATGTAGAAGT |
|  |  |  | GCAATTTGAACTGTGAGACAGG |
|  |  |  | TGCTGCATGGCTGTCGTCAGCT |
|  |  |  | CGTGTTGTGAAATGTTGGGTTA |
|  |  |  | AGTCCCGCAACGAGCGCAACC |
|  |  |  | CTTGTCCTTTGTTACCATAAGAT |
|  |  |  | TTAAGGAACTCAAAGGAGACTG |
|  |  |  | CCGGTGATAAACTGGAGGAAGG |
|  |  |  | CGGGGACGACGTCAAGTCATCA |
|  |  |  | TGGCCCTTATGACCAGGGCTAC |
|  |  |  | ACACGTGCTACAATGGCATATA |
|  |  |  | CAAAGAGATGCAATATTGCGAA |
|  |  |  | ATAAAGCCAATCTTATAAAATAT |
|  |  |  | GTCCTAGTTCGGACTGGAGTCT |
|  |  |  | GCAACTCGACTCCACGAAGTCG |
|  |  |  | GAATCGCTAGTAATCGTGGATC |
|  |  |  | AGCATGCCACGGTGAATATGTT |
|  |  |  | TCCAGGCCTTGTACACACCGCC |
|  |  |  | CGTCACACCATGGAAGTGGATT |
|  |  |  | GCAAAAGAAGTAAGAAAATTAA |
|  |  |  | CCTTCTTAACAAGGAAATAACTT |
|  |  |  | ACCACTTTGTGACTCATAACTG |
|  |  |  | GGGTGA |
|  |  |  | (SEQ ID NO: 12) |
| *Moranella endobia* | (*Coccoidea*) | bacteriocytes | TCTTTTTGGTAAGGAGGTGATC |
|  |  |  | CAACCGCAGGTTCCCCTACGGT |
|  |  |  | TACCTTGTTACGACTTCACCCCA |
|  |  |  | GTCATGAATCACAAAGTGGTAA |
|  |  |  | GCGCCCTCCTAAAAGGTTAGGC |
|  |  |  | TACCTACTTCTTTTGCAACCCAC |
|  |  |  | TTCCATGGTGTGACGGGCGGTG |
|  |  |  | TGTACAAGGCCCGGGAACGTAT |
|  |  |  | TCACCGTGGCATTCTGATCCAC |
|  |  |  | GATTACTAGCGATTCCTACTTCA |
|  |  |  | TGGAGTCGAGTTGCAGACTCCA |
|  |  |  | ATCCGGACTACGACGCACTTTA |
|  |  |  | TGAGGTCCGCTAACTCTCGCGA |
|  |  |  | GCTTGCTTCTCTTTGTATGCGC |
|  |  |  | CATTGTAGCACGTGTGTAGCCC |
|  |  |  | TACTCGTAAGGGCCATGATGAC |
|  |  |  | TTGACGTCATCCCCACCTTCCT |
|  |  |  | CCGGTTTATCACCGGCAGTCTC |
|  |  |  | CTTTGAGTTCCCGACCGAATCG |
|  |  |  | CTGGCAAAAAGGATAAGGGTT |
|  |  |  | GCGCTCGTTGCGGGACTTAACC |
|  |  |  | CAACATTTCACAACACGAGCTG |
|  |  |  | ACGACAGCCATGCAGCACCTGT |
|  |  |  | CTCAGAGTTCCCGAAGGTACCA |
|  |  |  | AAACATCTCTGCTAAGTTCTCTG |
|  |  |  | GATGTCAAGAGTAGGTAAGGTT |
|  |  |  | CTTCGCGTTGCATCGAATTAAA |
|  |  |  | CCACATGCTCCACCGCTTGTGC |
|  |  |  | GGGCCCCCGTCAATTCATTTGA |
|  |  |  | GTTTTAACCTTGCGGCCGTACT |
|  |  |  | CCCCAGGCGGTCGATTTAACGC |
|  |  |  | GTTAACTACGAAAGCCACAGTT |
|  |  |  | CAAGACCACAGCTTTCAAATCG |
|  |  |  | ACATAGTTTACGGCGTGGACTA |
|  |  |  | CCAGGGTATCTAATCCTGTTTG |
|  |  |  | CTCCCCACGCTTTCGTACCTGA |
|  |  |  | GCGTCAGTATTCGTCCAGGGGG |

TABLE 1-continued

Examples of Target Bacteria and Host Insects

| | | | |
|---|---|---|---|
| | | | CCGCCTTCGCCACTGGTATTCC
TCCAGATATCTACACATTTCACC
GCTACACCTGGAATTCTACCCC
CCTCTACGAGACTCTAGCCTAT
CAGTTTCAAATGCAGTTCCTAG
GTTAAGCCCAGGGATTTCACAT
CTGACTTAATAAACCGCCTACG
TACTCTTTACGCCCAGTAATTCC
GATTAACGCTTGCACCCTCCGT
ATTACCGCGGCTGCTGGCACG
GAGTTAGCCGGTGCTTCTTCTG
TAGGTAACGTCAATCAATAACC
GTATTAAGGATATTGCCTTCCTC
CCTACTGAAAGTGCTTTACAAC
CCGAAGGCCTTCTTCACACACG
CGGCATGGCTGCATCAGGGTTT
CCCCCATTGTGCAATATTCCCC
ACTGCTGCCTCCCGTAGGAGTC
TGGACCGTGTCTCAGTTCCAGT
GTGGCTGGTCATCCTCTCAGAC
CAGCTAGGGATCGTCGCCTAGG
TAAGCTATTACCTCACCTACTAG
CTAATCCCATCTGGGTTCATCT
GAAGGTGTGAGGCCAAAAGGTC
CCCCACTTTGGTCTTACGACATT
ATGCGGTATTAGCTACCGTTTC
CAGCAGTTATCCCCCTCCATCA
GGCAGATCCCCAGACTTTACTC
ACCCGTTCGCTGCTCGCCGGCA
AAAAAGTAAACTTTTTTCCGTTG
CCGCTCAACTTGCATGTGTTAG
GCCTGCCGCCAGCGTTCAATCT
GAGCCATGATCAAACTCTTCAAT
TAAA
(SEQ ID NO: 13) |
| *Ishikawaella capsulata* Mpkobe | (*Heteroptera*) | bacteriocytes | AAATTGAAGAGTTTGATCATGG
CTCAGATTGAACGCTAGCGGCA
AGCTTAACACATGCAAGTCGAA
CGGTAACAGAAAAAAGCTTGCT
TTTTTGCTGACGAGTGGCGGAC
GGGTGAGTAATGTCTGGGGATC
TACCTAATGGCGGGGGATAACT
ACTGGAAACGGTAGCTAATACC
GCATAATGTTGTAAAACCAAAGT
GGGGGACCTTATGGCCTCACAC
CATTAGATGAACCTAGATGGGA
TTAGCTTGTAGGTGGGGTAAAG
GCTCACCTAGGCAACGATCCCT
AGCTGGTCTGAGAGGATGACCA
GCCACACTGGAACTGAGATACG
GTCCAGACTCCTACGGGAGGCA
GCAGTGGGGAATCTTGCACAAT
GGGCGCAAGCCTGATGCAGCT
ATGTCGCGTGTATGAAGAAGGC
CTTAGGGTTGTAAAGTACTTTCA
TCGGGGAAGAAGGATATGAGCC
TAATATTCTCATATATTGACGTT
ACCTGCAGAAGAAGCACCGGCT
AACTCCGTGCCAGCAGCCGCG
GTAACACGGAGGGTGCGAGCG
TTAATCGGAATTACTGGGCGTA
AAGAGCACGTAGGTGGTTTATT
AAGTCATATGTGAAATCCCTGG
GCTTAACCTAGGAACTGCATGT
GAAACTGATAAACTAGAGTTTC
GTAGAGGGAGGTGGAATTCCAG
GTGTAGCGGTGAAATGCGTAGA
TATCTGGAGGAATATCAGAGGC
GAAGGCGACCTTCTGGACGAAA
ACTGACACTCAGGTGCGAAAGC
GTGGGAGCAAACAGGATTAGA
TACCCTGGTAGTCCACGCTGTA
AACAATGTCGACTAAAAAACTGT
GAGCTTGACTTGTGGTTTTTGTA
GCTAACGCATTAAGTCGACCGC
CTGGGGAGTACGGCCGCAAGG
TTAAAACTCAAATGAATTGACGG |

TABLE 1-continued

Examples of Target Bacteria and Host Insects

| | | | |
|---|---|---|---|
| | | | GGGTCCGCACAAGCGGTGGAG |
| | | | CATGTGGTTTAATTCGATGCAAC |
| | | | GCGAAAAACCTTACCTGGTCTT |
| | | | GACATCCAGCGAATTATATAGA |
| | | | AATATATAAGTGCCTTTCGGGG |
| | | | AACTCTGAGACGCTGCATGGCT |
| | | | GTCGTCAGCTCGTGTTGTGAAA |
| | | | TGTTGGGTTAAGTCCCGCAACG |
| | | | AGCGCCCTTATCCTCTGTTGCC |
| | | | AGCGGCATGGCCGGGAACTCA |
| | | | GAGGAGACTGCCAGTATTAAAC |
| | | | TGGAGGAAGGTGGGGATGACG |
| | | | TCAAGTCATCATGGCCCTTATG |
| | | | ACCAGGGCTACACACGTGCTAC |
| | | | AATGGTGTATACAAAGAGAAGC |
| | | | AATCTCGCAAGAGTAAGCAAAA |
| | | | CTCAAAAAGTACATCGTAGTTC |
| | | | GGATTAGAGTCTGCAACTCGAC |
| | | | TCTATGAAGTAGGAATCGCTAG |
| | | | TAATCGTGGATCAGAATGCCAC |
| | | | GGTGAATACGTTCTCTGGCCTT |
| | | | GTACACACCGCCCGTCACACCA |
| | | | TGGGAGTAAGTTGCAAAAGAAG |
| | | | TAGGTAGCTTAACCTTTATAGGA |
| | | | GGGCGCTTACCACTTTGTGATT |
| | | | TATGACTGGGGTGAAGTCGTAA |
| | | | CAAGGTAACTGTAGGGGAACCT |
| | | | GTGGTTGGATTACCTCCTTA |
| | | | (SEQ ID NO: 14) |
| *Baumannia cicadellinicola* | sharpshooter leafhoppers (*Cicadellinae*) | bacteriocytes | TTCAATTGAAGAGTTTGATCATG |
| | | | GCTCAGATTGAACGCTGGCGGT |
| | | | AAGCTTAACACATGCAAGTCGA |
| | | | GCGGCATCGGAAAGTAAATTAA |
| | | | TTACTTTGCCGGCAAGCGGCGA |
| | | | ACGGGTGAGTAATATCTGGGGA |
| | | | TCTACCTTATGGAGAGGGATAA |
| | | | CTATTGGAAACGATAGCTAACA |
| | | | CCGCATAATGTCGTCAGACCAA |
| | | | AATGGGGACCTAATTTAGGCC |
| | | | TCATGCCATAAGATGAACCCAG |
| | | | ATGAGATTAGCTAGTAGGTGAG |
| | | | ATAATAGCTCACCTAGGCAACG |
| | | | ATCTCTAGTTGGTCTGAGAGGA |
| | | | TGACCAGCCACACTGGAACTGA |
| | | | GACACGGTCCAGACTCCTACGG |
| | | | GAGGCAGCAGTGGGGAATCTT |
| | | | GCACAATGGGGGAAACCCTGAT |
| | | | GCAGCTATACCGCGTGTGTGAA |
| | | | GAAGGCCTTCGGGTTGTAAAGC |
| | | | ACTTTCAGCGGGGAAGAAAATG |
| | | | AAGTTACTAATAATAATTGTCAA |
| | | | TTGACGTTACCCGCAAAAGAAG |
| | | | CACCGGCTAACTCCGTGCCAGC |
| | | | AGCCGCGGTAAGACGGAGGGT |
| | | | GCAAGCGTTAATCGGAATTACT |
| | | | GGGCGTAAAGCGTATGTAGGC |
| | | | GGTTTATTTAGTCAGGTGTGAAA |
| | | | GCCCTAGGCTTAACCTAGGAAT |
| | | | TGCATTTGAAACTGGTAAGCTA |
| | | | GAGTCTCGTAGAGGGGGGAG |
| | | | AATTCCAGGTGTAGCGGTGAAA |
| | | | TGCGTAGAGATCTGGAAGAATA |
| | | | CCAGTGGCGAAGGCGCCCCCC |
| | | | TGGACGAAAACTGACGCTCAAG |
| | | | TACGAAAGCGTGGGGAGCAAAC |
| | | | AGGATTAGATACCCTGGTAGTC |
| | | | CACGCTGTAAACGATGTCGATT |
| | | | TGAAGGTTGTAGCCTTGAGCTA |
| | | | TAGCTTTCGAAGCTAACGCATTA |
| | | | AATCGACCGCCTGGGGAGTAC |
| | | | GACCGCAAGGTTAAAACTCAAA |
| | | | TGAATTGACGGGGGCCCGCAC |
| | | | AAGCGGTGGAGCATGTGGTTTA |
| | | | ATTCGATACAACGCGAAAAACC |
| | | | TTACCTACTCTTGACATCCAGAG |
| | | | TATAAAGCAGAAAAGCTTTAGTG |
| | | | CCTTCGGGAACTCTGAGACAGG |

TABLE 1-continued

Examples of Target Bacteria and Host Insects

| | | | |
|---|---|---|---|
| | | | TGCTGCATGGCTGTCGTCAGCT |
| | | | CGTGTTGTGAAATGTTGGGTTA |
| | | | AGTCCCGCAACGAGCGCAACC |
| | | | CTTATCCTTTGTTGCCAACGATT |
| | | | AAGTCGGGAACTCAAAGGAGAC |
| | | | TGCCGGTGATAAACCGGAGGAA |
| | | | GGTGAGGATAACGTCAAGTCAT |
| | | | CATGGCCCTTACGAGTAGGGCT |
| | | | ACACACGTGCTACAATGGTGCA |
| | | | TACAAAGAGAAGCAATCTCGTA |
| | | | AGAGTTAGCAAACCTCATAAAG |
| | | | TGCATCGTAGTCCGGATTAGAG |
| | | | TCTGCAACTCGACTCTATGAAG |
| | | | TCGGAATCGCTAGTAATCGTGG |
| | | | ATCAGAATGCCACGGTGAATAC |
| | | | GTTCCCGGGCCTTGTACACACC |
| | | | GCCCGTCACACCATGGGAGTGT |
| | | | ATTGCAAAAGAAGTTAGTAGCTT |
| | | | AACTCATAATACGAGAGGGCGC |
| | | | TTACCACTTTGTGATTCATAACT |
| | | | GGGGTGAAGTCGTAACAAGGTA |
| | | | ACCGTAGGGGAACCTGCGGTT |
| | | | GGATCACCTCCTTACACTAAA |
| | | | (SEQ ID NO: 15) |
| Sodalis like | Rhopalus sapporensis | wider tissue tropism | ATTGAACGCTGGCGGCAGGCCT |
| | | | AACACATGCAAGTCGAGCGGCA |
| | | | GCGGGAAGAAGCTTGCTTCTTT |
| | | | GCCGGCGAGCGGCGGACGGGT |
| | | | GAGTAATGTCTGGGGATCTGCC |
| | | | CGATGGAGGGGGATAACTACTG |
| | | | GAAACGGTAGCTAATACCGCAT |
| | | | AACGTCGCAAGACCAAAGTGGG |
| | | | GGACCTTCGGGCCTCACACCAT |
| | | | CGGATGAACCCAGGTGGGATTA |
| | | | GCTAGTAGGTGGGGTAATGGCT |
| | | | CACCTAGGCGACGATCCCTAGC |
| | | | TGGTCTGAGAGGATGACCAGTC |
| | | | ACACTGGAACTGAGACACGGTC |
| | | | CAGACTCCTACGGGAGGCAGC |
| | | | AGTGGGGAATATTGCACAATGG |
| | | | GGGAAACCCTGATGCAGCCATG |
| | | | CCGCGTGTGTGAAGAAGGCCTT |
| | | | CGGGTTGTAAAGCACTTTCAGC |
| | | | GGGGAGGAAGGCGATGGCGTT |
| | | | AATAGCGCTATCGATTGACGTT |
| | | | ACCCGCAGAAGAAGCACCGGC |
| | | | TAACTCCGTGCCAGCAGCCGCG |
| | | | GTAATACGGAGGGTGCGAGCG |
| | | | TTAATCGGAATTACTGGGCGTA |
| | | | AAGCGTACGCAGGCGGTCTGTT |
| | | | AAGTCAGATGTGAAATCCCCGG |
| | | | GCTCAACCTGGGAACTGCATTT |
| | | | GAAACTGGCAGGCTAGAGTCTC |
| | | | GTAGAGGGGGTAGAATTCCAG |
| | | | GTGTAGCGGTGAAATGCGTAGA |
| | | | GATCTGGAGGAATACCGGTGGC |
| | | | GAAGGCGGCCCCCTGGACGAA |
| | | | GACTGACGCTCAGGTACGAAAG |
| | | | CGTGGGGAGCAAACAGGATTAG |
| | | | ATACCCTGGTAGTCCACGCTGT |
| | | | AAACGATGTCGATTTGAAGGTT |
| | | | GTGGCCTTGAGCCGTGGCTTTC |
| | | | GGAGCTAACGTGTTAAATCGAC |
| | | | CGCCTGGGGAGTACGGCCGCA |
| | | | AGGTTAAAACTCAAATGAATTGA |
| | | | CGGGGGCCCGCACAAGCGGTG |
| | | | GAGCATGTGGTTTAATTCGATG |
| | | | CAACGCGAAGAACCTTACCTAC |
| | | | TCTTGACATCCAGAGAACTTGG |
| | | | CAGAGATGCTTTGGTGCCTTCG |
| | | | GGAACTCTGAGACAGGTGCTGC |
| | | | ATGGCTGTCGTCAGCTCGTGTT |
| | | | GTGAAATGTTGGGTTAAGTCCC |
| | | | GCAACGAGCGCAACCCTTATCC |
| | | | TTTATTGCCAGCGATTCGGTCG |
| | | | GGAACTCAAAGGAGACTGCCG |
| | | | GTGATAAACCGGAGGAAGGTG |

TABLE 1-continued

Examples of Target Bacteria and Host Insects

| | | |
|---|---|---|
| | | GGGATGACGTCAAGTCATCATG<br>GCCCTTACGAGTAGGGCTACAC<br>ACGTGCTACAATGGCGCATACA<br>AAGAGAAGCGATCTCGCGAGAG<br>TCAGCGGACCTCATAAAGTGCG<br>TCGTAGTCCGGATTGGAGTCTG<br>CAACTCGACTCCATGAAGTCGG<br>AATCGCTAGTAATCGTGGATCA<br>GAATGCCACGGTGAATACGTTC<br>CCGGGCCTTGTACACACCGCCC<br>GTCACACCATGGGAGTGGGTTG<br>CAAAAGAAGTAGGTAGCTTAAC<br>CTTCGGGAGGGCGCTTACCACT<br>TTGTGATTCATGACTGGGGTG<br>(SEQ ID NO: 16) |
| *Hartigia pinicola* | The pine bark adelgid | bacteriocytes AGATTTAACGCTGGCGGCAGGC<br>CTAACACATGCAAGTCGAGCGG<br>TACCAGAAGAAGCTTGCTTCTT<br>GCTGACGAGCGGCGGACGGGT<br>GAGTAATGTATGGGGATCTGCC<br>CGACAGAGGGGGATAACTATTG<br>GAAACGGTAGCTAATACCGCAT<br>AATCTCTGAGGAGCAAAGCAGG<br>GGAACTTCGGTCCTTGCGCTAT<br>CGGATGAACCCATATGGGATTA<br>GCTAGTAGGTGAGGTAATGGCT<br>CCCCTAGGCAACGATCCCTAGC<br>TGGTCTGAGAGGATGATCAGCC<br>ACACTGGGACTGAGACACGGC<br>CCAGACTCCTACGGGAGGCAG<br>CAGTGGGGAATATTGCACAATG<br>GGCGAAAGCCTGATGCAGCCAT<br>GCCGCGTGTATGAAGAAGGCTT<br>TAGGGTTGTAAAGTACTTTCAGT<br>CGAGAGGAAAACATTGATGCTA<br>ATATCATCAATTATTGACGTTTC<br>CGACAGAAGAAGCACCGGCTAA<br>CTCCGTGCCAGCAGCCGCGGT<br>AATACGGAGGGTGCAAGCGTTA<br>ATCGGAATTACTGGGCGTAAAG<br>CGCACGCAGGCGGTTAATTAAG<br>TTAGATGTGAAAGCCCCGGGCT<br>TAACCCAGGAATAGCATATAAAA<br>CTGGTCAACTAGAGTATTGTAG<br>AGGGGGGTAGAATTCCATGTGT<br>AGCGGTGAAATGCGTAGAGATG<br>TGGAGGAATACCAGTGGCGAAG<br>GCGGCCCCCTGGACAAAAACTG<br>ACGCTCAAATGCGAAAGCGTGG<br>GGAGCAAACAGGATTAGATACC<br>CTGGTAGTCCATGCTGTAAACG<br>ATGTCGATTTGGAGGTTGTTCC<br>CTTGAGGAGTAGCTTCCGTAGC<br>TAACGCGTTAAATCGACCGCCT<br>GGGGGAGTACGACTGCAAGGT<br>TAAAACTCAAATGAATTGACGG<br>GGGCCCGCACAAGCGGTGGAG<br>CATGTGGTTTAATTCGATGCAAC<br>GCGAAAAACCTTACCTACTCTT<br>GACATCCAGATAATTTAGCAGA<br>AATGCTTTAGTACCTTCGGGAA<br>ATCTGAGACAGGTGCTGCATGG<br>CTGTCGTCAGCTCGTGTTGTGA<br>AATGTTGGGTTAAGTCCCGCAA<br>CGAGCGCAACCCTTATCCTTTG<br>TTGCCAGCGATTAGGTCGGGAA<br>CTCAAAGGAGACTGCCGGTGAT<br>AAACCGGAGGAAGGTGGGGAT<br>GACGTCAAGTCATCATGGCCCT<br>TACGAGTAGGGCTACACACGTG<br>CTACAATGGCATATACAAAGGG<br>AAGCAACCTCGCGAGAGCAAGC<br>GAAACTCATAAATTATGTCGTAG<br>TTCAGATTGGAGTCTGCAACTC<br>GACTCCATGAAGTCGGAATCGC<br>TAGTAATCGTAGATCAGAATGCT<br>ACGGTGAATACGTTCCCGGGCC |

TABLE 1-continued

Examples of Target Bacteria and Host Insects

| | | | TTGTACACACCGCCCGTCACAC<br>CATGGGAGTGGGTTGCAAAAGA<br>AGTAGGTAACTTAACCTTATGGA<br>AAGCGCTTACCACTTTGTGATTC<br>ATAACTGGGGTG<br>(SEQ ID NO: 17) |
|---|---|---|---|
| *Wigglesworthia glossinidia* | tsetse fly (Diptera: Glossinidae) | bacteriocytes | |
| Beta proteobacteria | | | |
| *Tremblaya phenacola* | *Phenacoccus avenae* (TPPAVE). | bacteriomes | AGGTAATCCAGCCACACCTTCC<br>AGTACGGCTACCTTGTTACGAC<br>TTCACCCCAGTCACAACCCTTA<br>CCTTCGGAACTGCCCTCCTCAC<br>AACTCAAACCACCAAACACTTTT<br>AAATCAGGTTGAGAGAGGTTAG<br>GCCTGTTACTTCTGGCAAGAAT<br>TATTTCCATGGTGTGACGGGCG<br>GTGTGTACAAGACCCGAGAACA<br>TATTCACCGTGGCATGCTGATC<br>CACGATTACTAGCAATTCCAACT<br>TCATGCACTCGAGTTTCAGAGT<br>ACAATCCGAACTGAGGCCGGCT<br>TTGTGAGATTAGCTCCCTTTTGC<br>AAGTTGGCAACTCTTTGGTCCG<br>GCCATTGTATGATGTGTGAAGC<br>CCCACCCATAAAGGCCATGAGG<br>ACTTGACGTCATCCCCACCTTC<br>CTCCAACTTATCGCTGGCAGTC<br>TCTTTAAGGTAACTGACTAATCC<br>AGTAGCAATTAAAGACAGGGGT<br>TGCGCTCGTTACAGGACTTAAC<br>CCAACATCTCACGACACGAGCT<br>GACGACAGCCATGCAGCACCTG<br>TGCACTAATTCTCTTTCAAGCAC<br>TCCCGCTTCTCAACAGGATCTT<br>AGCCATATCAAAGGTAGGTAAG<br>GTTTTTCGCGTTGCATCGAATTA<br>ATCCACATCATCCACTGCTTGT<br>GCGGGTCCCCGTCAATTCCTTT<br>GAGTTTTAACCTTGCGGCCGTA<br>CTCCCCAGGCGGTCGACTTGTG<br>CGTTAGCTGCACCACTGAAAAG<br>GAAAACTGCCCAATGGTTAGTC<br>AACATCGTTTAGGGCATGGACT<br>ACCAGGGTATCTAATCCTGTTT<br>GCTCCCCATGCTTTAGTGTCTG<br>AGCGTCAGTAACGAACCAGGAG<br>GCTGCCTACGCTTTCGGTATTC<br>CTCCACATCTCTACACATTTCAC<br>TGCTACATGCGGAATTCTACCT<br>CCCCCTCTCGTACTCCAGCCTG<br>CCAGTAACTGCCGCATTCTGAG<br>GTTAAGCCTCAGCCTTTCACAG<br>CAATCTTAACAGGCAGCCTGCA<br>CACCCTTTACGCCCAATAAATCT<br>GATTAACGCTCGCACCCTACGT<br>ATTACCGCGGCTGCTGGCACGT<br>AGTTTGCCGGTGCTTATTCTTTC<br>GGTACAGTCACACCACCAAATT<br>GTTAGTTGGGTGGCTTTCTTTC<br>CGAACAAAGTGCTTTACAACC<br>CAAAGGCCTTCTTCACACACGC<br>GGCATTGCTGGATCAGGCTTCC<br>GCCCATTGTCCAAGATTCCTCA<br>CTGCTGCCTTCCTCAGAAGTCT<br>GGGCCGTGTCTCAGTCCCAGTG<br>TGGCTGGCCGTCCTCTCAGACC<br>AGCTACCGATCATTGCCTTGGG<br>AAGCATTACCTTTCCAACAAG<br>CTAATCAGACATCAGCCAATCT<br>CAGAGCGCAAGGCAATTGGTCC<br>CCTGCTTTCATTCTGCTTGGTAG<br>AGAACTTTATGCGGTATTAATTA<br>GGCTTTCACCTAGCTGTCCCCC |

TABLE 1-continued

Examples of Target Bacteria and Host Insects

|  |  |  |
|---|---|---|
|  |  | ACTCTGAGGCATGTTCTGATGC<br>ATTACTCACCCGTTTGCCACTTG<br>CCACCAAGCCTAAGCCCGTGTT<br>GCCGTTCGACTTGCATGTGTAA<br>GGCATGCCGCTAGCGTTCAATC<br>TGAGCCAGGATCAAACTCT<br>(SEQ ID NO: 18) |
| *Tremblaya princeps* | citrus mealybug bacteriomes<br>*Planococcus citri* | AGAGTTTGATCCTGGCTCAGAT<br>TGAACGCTAGCGGCATGCATTA<br>CACATGCAAGTCGTACGGCAGC<br>ACGGGCTTAGGCCTGGTGGCG<br>AGTGGCGAACGGGTGAGTAAC<br>GCCTCGGAACGTGCCTTGTAGT<br>GGGGGATAGCCTGGCGAAAGC<br>CAGATTAATACCGCATGAAGCC<br>GCACAGCATGCGCGGTGAAAGT<br>GGGGGATTCTAGCCTCACGCTA<br>CTGGATCGGCCGGGGTCTGATT<br>AGCTAGTTGGCGGGGTAATGGC<br>CCACCAAGGCTTAGATCAGTAG<br>CTGGTCTGAGAGGACGATCAGC<br>CACACTGGGACTGAGACACGG<br>CCCAGACTCCTACGGGAGGCA<br>GCAGTGGGGAATCTTGGACAAT<br>GGGCGCAAGCCTGATCCAGCA<br>ATGCCGCGTGTGTGAAGAAGGC<br>CTTCGGGTCGTAAAGCACTTTT<br>GTTCGGGATGAAGGGGGGCGT<br>GCAAACACCATGCCCTCTTGAC<br>GATACCGAAAGAATAAGCACCG<br>GCTAACTACGTGCCAGCAGCCG<br>CGGTAATACGTAGGGTGCGAGC<br>GTTAATCGGAATCACTGGGCGT<br>AAAGGGTGCGCGGGTGGTTTG<br>CCAAGACCCCTGTAAAATCCTA<br>CGGCCCAACCGTAGTGCTGCG<br>GAGGTTACTGGTAAGCTTGAGT<br>ATGGCAGAGGGGGGTAGAATTC<br>CAGGTGTAGCGGTGAAATGCGT<br>AGATATCTGGAGGAATACCGAA<br>GGCGAAGGCAACCCCCTGGGC<br>CATCACTGACACTGAGGCACGA<br>AAGCGTGGGGAGCAAACAGGA<br>TTAGATACCCTGGTAGTCCACG<br>CCCTAAACCATGTCGACTAGTT<br>GTCGGGGGAGCCCTTTTTCCT<br>CGGTGACGAAGCTAACGCATGA<br>AGTCGACCGCCTGGGGAGTAC<br>GACCGCAAGGTTAAAACTCAAA<br>GGAATTGACGGGGACCCGCAC<br>AAGCGGTGGATGATGTGGATTA<br>ATTCGATGCAACGCGAAAAACC<br>TTACCTACCCTTGACATGGCGG<br>AGATTCTGCCGAGAGGCGGAA<br>GTGCTCGAAAGAGAATCCGTGC<br>ACAGGTGCTGCATGGCTGTCGT<br>CAGCTCGTGTCGTGAGATGTTG<br>GGTTAAGTCCCATAACGAGCGC<br>AACCCCCGTCTTTAGTTGCTAC<br>CACTGGGGCACTCTATAGAGAC<br>TGCCGGTGATAAACCGGAGGAA<br>GGTGGGGACGACGTCAAGTCAT<br>CATGGCCTTTATGGGTAGGGCT<br>TCACACGTCATACAATGGCTGG<br>AGCAAAGGGTCGCCAACTCGAG<br>AGAGGGAGCTAATCCCACAAAC<br>CCAGCCCCAGTTCGGATTGCAC<br>TCTGCAACTCGAGTGCATGAAG<br>TCGGAATCGCTAGTAATCGTGG<br>ATCAGCATGCCACGGTGAATAC<br>GTTCTCGGGTCTTGTACACACC<br>GCCCGTCACACCATGGGAGTAA<br>GCCGCATCAGAAGCAGCCTCCC<br>TAACCCTATGCTGGGAAGGAGG<br>CTGCGAAGGTGGGGTCTATGAC |

TABLE 1-continued

Examples of Target Bacteria and Host Insects

| | | |
|---|---|---|
| | | TGGGGTGAAGTCGTAACAAGGT<br>AGCCGTACCGGAAGGTGCGGC<br>TGGATTACCT<br>(SEQ ID NO: 19) |
| *Vidania* | bacteriomes | |
| *Nasuia deltocephalinicola* | pestiferous insect bacteriomes host, *Macrosteles quadripunctulatus* (Hemiptera: Cicadellidae) | AGTTTAATCCTGGCTCAGATTTA<br>ACGCTTGCGACATGCCTAACAC<br>ATGCAAGTTGAACGTTGAAAATA<br>TTTCAAAGTAGCGTATAGGTGA<br>GTATAACATTTAAACATACCTTA<br>AAGTTCGGAATACCCCGATGAA<br>AATCGGTATAATACCGTATAAAA<br>GTATTTAAGAATTAAAGCGGGG<br>AAAACCTCGTGCTATAAGATTGT<br>TAAATGCCTGATTAGTTTGTTGG<br>TTTTTAAGGTAAAAGCTTACCAA<br>GACTTTGATCAGTAGCTATTCTG<br>TGAGGATGTATAGCCACATTGG<br>GATTGAAATAATGCCCAAACCT<br>CTACGGAGGGCAGCAGTGGGG<br>AATATTGGACAATGAGCGAAAG<br>CTTGATCCAGCAATGTCGCGTG<br>TGCGATTAAGGGAAACTGTAAA<br>GCACTTTTTTTAAGAATAAGAA<br>ATTTTAATTAATAATTAAAATTTT<br>TGAATGTATTAAAAGAATAAGTA<br>CCGACTAATCACGTGCCAGCAG<br>TCGCGGTAATACGTGGGGTGC<br>GAGCGTTAATCGGATTTATTGG<br>GCGTAAAGTGTATTCAGGCTGC<br>TTAAAAAGATTTATATTAAATATT<br>TAAATTAAATTTAAAAAATGTATA<br>AATTACTATTAAGCTAGAGTTTA<br>GTATAAGAAAAAAGAATTTTATG<br>TGTAGCAGTGAAATGCGTTGAT<br>ATATAAAGGAACGCCGAAAGCG<br>AAAGCATTTTTCTGTAATAGAAC<br>TGACGCTTATATACGAAAGCGT<br>GGGTAGCAAACAGGATTAGATA<br>CCCTGGTAGTCCACGCCCTAAA<br>CTATGTCAATTAACTATTAGAAT<br>TTTTTTTAGTGGTGTAGCTAACG<br>CGTTAAATTGACCGCCTGGGTA<br>TTACGATCGCAAGATTAAAACTC<br>AAAGGAATTGACGGGGACCAGC<br>ACAAGCGGTGGATGATGTGGAT<br>TAATTCGATGATACGCGAAAAA<br>CCTTACCTGCCCTTGACATGGT<br>TAGAATTTTATTGAAAAATAAAA<br>GTGCTTGGAAAAGAGCTAACAC<br>ACAGGTGCTGCATGGCTGTCGT<br>CAGCTCGTGTCGTGAGATGTTG<br>GGTTAAGTCCCGCAACGAGCGC<br>AACCCCTACTCTTAGTTGCTAAT<br>TAAAGAACTTTAAGAGAACAGCT<br>AACAATAAGTTTAGAGGAAGGA<br>GGGGATGACTTCAAGTCCTCAT<br>GGCCCTTATGGGCAGGGCTTCA<br>CACGTCATACAATGGTTAATACA<br>AAAAGTTGCAATATCGTAAGATT<br>GAGCTAATCTTTAAAATTAATCT<br>TAGTTCGGATTGTACTCTGCAA<br>CTCGAGTACATGAAGTTGGAAT<br>CGCTAGTAATCGCGGATCAGCA<br>TGCCGCGGTGAATAGTTTAACT<br>GGTCTTGTACACACCGCCCGTC<br>ACACCATGGAAATAAATCTTGTT<br>TTAAATGAAGTAATATATTTTATC<br>AAAACAGGTTTTGTAACCGGGG<br>TGAAGTCGTAACA<br>(SEQ ID NO: 20) |

TABLE 1-continued

| Examples of Target Bacteria and Host Insects | | | |
|---|---|---|---|
| *Zinderia insecticola* CARI | spittlebug *Clastoptera arizonana* | bacteriocytes | ATATAAATAAGAGTTTGATCCTG GCTCAGATTGAACGCTAGCGGT ATGCTTTACACATGCAAGTCGA ACGACAATATTAAAGCTTGCTTT AATATAAAGTGGCGAACGGGTG AGTAATATATCAAAACGTACCTT AAAGTGGGGGATAACTAATTGA AAAATTAGATAATACCGCATATT AATCTTAGGATGAAAATAGGAAT AATATCTTATGCTTTTAGATCGG TTGATATCTGATTAGCTAGTTGG TAGGGTAAATGCTTACCAAGGC AATGATCAGTAGCTGGTTTTAG CGAATGATCAGCCACACTGGAA CTGAGACACGGTCCAGACTTCT ACGGAAGGCAGCAGTGGGGAA TATTGGACAATGGGAGAAATCC TGATCCAGCAATACCGCGTGAG TGATGAAGGCCTTAGGGTCGTA AAACTCTTTTGTTAGGAAAGAAA TAATTTTAAATAATATTTAAAATT GATGACGGTACCTAAAGAATAA GCACCGGCTAACTACGTGCCAG CAGCCGCGGTAATACGTAGGGT GCAAGCGTTAATCGGAATTATT GGGCGTAAAGAGTGCGTAGGC TGTTATATAAGATAGATGTGAAA TACTTAAGCTTAACTTAAGAACT GCATTTATTACTGTTTAACTAGA GTTTATTAGAGAGAAGTGGAATT TTATGTGTAGCAGTGAAATGCG TAGATATATAAAGGAATATCGAT GGCGAAGGCAGCTTCTTGGAAT AATACTGACGCTGAGGCACGAA AGCGTGGGGAGCAAACAGGATT AGATACCCTGGTAGTCCACGCC CTAAACTATGTCTACTAGTTATT AAATTAAAAATAAAATTTAGTAA CGTAGCTAACGCATTAAGTAGA CCGCCTGGGGAGTACGATCGC AAGATTAAAACTCAAAGGAATTG ACGGGGACCCGCACAAGCGGT GGATGATGTGGATTAATTCGAT GCAACACGAAAAACCTTACCTA CTCTTGACATGTTTGGAATTTTA AAGAAATTTAAAAGTGCTTGAAA AAGAACCAAAACACAGGTGCTG CATGGCTGTCGTCAGCTCGTGT CGTGAGATGTTGGGTTAAGTCC CGCAACGAGCGCAACCCTTGTT ATTATTTGCTAATAAAAAGAACT TTAATAAGACTGCCAATGACAAA TTGGAGGAAGGTGGGGATGAC GTCAAGTCCTCATGGCCCTTAT GAGTAGGGCTTCACACGTCATA CAATGATATATACAATGGGTAG CAAATTTGTGAAAATGAGCCAAT CCTTAAAGTATATCTTAGTTCGG ATTGTAGTCTGCAACTCGACTA CATGAAGTTGGAATCGCTAGTA ATCGCGGATCAGCATGCCGCG GTGAATACGTTCTCGGGTCTTG TACACACCGCCCGTCACACCAT GGAAGTGATTTTTACCAGAAATT ATTTGTTTAACCTTTATTGGAAA AAAATAATTAAGGTAGAATTCAT GACTGGGGTGAAGTCGTAACAA GGTAGCAGTATCGGAAGGTGC GGCTGGATTACATTTTAAAT (SEQ ID NO: 21) |
| *Profftella armatura* | *Diaphorina citri*, the Asian *citrus* *psyllid* | bacteriomes | |

TABLE 1-continued

Examples of Target Bacteria and Host Insects

Alpha proteobacteria

| | | | |
|---|---|---|---|
| Hodgkinia | Cicada<br>*Diceroprocta<br>semicincta* | bacteriome | AATGCTGGCGGCAGGCCTAACA<br>CATGCAAGTCGAGCGGACAACG<br>TTCAAACGTTGTTAGCGGCGAA<br>CGGGTGAGTAATACGTGAGAAT<br>CTACCCATCCCAACGTGATAAC<br>ATAGTCAACACCATGTCAATAAC<br>GTATGATTCCTGCAACAGGTAA<br>AGATTTTATCGGGGATGGATGA<br>GCTCACGCTAGATTAGCTAGTT<br>GGTGAGATAAAAGCCCACCAAG<br>GCCAAGATCTATAGCTGGTCTG<br>GAAGGATGGACAGCCACATTGG<br>GACTGAGACAAGGCCCAACCCT<br>CTAAGGAGGGCAGCAGTGAGG<br>AATATTGGACAATGGGCGTAAG<br>CCTGATCCAGCCATGCCGCATG<br>AGTGATTGAAGGTCCAACGGAC<br>TGTAAAACTCTTTTCTCCAGAGA<br>TCATAAATGATAGTATCTGGTGA<br>TATAAGCTCCGGCCAACTTCGT<br>GCCAGCAGCCGCGGTAATACG<br>AGGGGAGCGAGTATTGTTCGGT<br>TTTATTGGGCGTAAAGGGTGTC<br>CAGGTTGCTAAGTAAGTTAACA<br>ACAAAATCTTGAGATTCAACCTC<br>ATAACGTTCGGTTAATACTACTA<br>AGCTCGAGCTTGGATAGAGACA<br>AACGGAATTCCGAGTGTAGAGG<br>TGAAATTCGTTGATACTTGGAG<br>GAACACCAGAGGCGAAGGCGG<br>TTTGTCATACCAAGCTGACACT<br>GAAGACACGAAAGCATGGGGA<br>GCAAACAGGATTAGATACCCTG<br>GTAGTCCATGCCCTAAACGTTG<br>AGTGCTAACAGTTCGATCAAGC<br>CACATGCTATGATCCAGGATTG<br>TACAGCTAACGCGTTAAGCACT<br>CCGCCTGGGTATTACGACCGCA<br>AGGTTAAAACTCAAAGGAATTG<br>ACGGAGACCCGCACAAGCGGT<br>GGAGCATGTGGTTTAATTCGAA<br>GCTACACGAAGAACCTTACCAG<br>CCCTTGACATACCATGGCCAAC<br>CATCCTGGAAACAGGATGTTGT<br>TCAAGTTAAACCCTTGAAATGCC<br>AGGAACAGGTGCTGCATGGCTG<br>TTGTCAGTTCGTGTCGTGAGAT<br>GTATGGTTAAGTCCCAAAACGA<br>ACACAACCCTCACCCATAGTTG<br>CCATAAACACAATTGGGTTCTCT<br>ATGGGTACTGCTAACGTAAGTT<br>AGAGGAAGGTGAGGACCACAA<br>CAAGTCATCATGGCCCTTATGG<br>GCTGGGCCACACACATGCTACA<br>ATGGTGGTTACAAAGAGCCGCA<br>ACGTTGTGAGACCGAGCAAATC<br>TCCAAAGACCATCTCAGTCCGG<br>ATTGTACTCTGCAACCCGAGTA<br>CATGAAGTAGGAATCGCTAGTA<br>ATCGTGGATCAGCATGCCACGG<br>TGAATACGTTCTCGGGTCTTGT<br>ACACGCCGCCCGTCACACCATG<br>GGAGCTTCGCTCCGATCGAAGT<br>CAAGTTACCCTTGACCACATCTT<br>GGCAAGTGACCGA<br>(SEQ ID NO: 22) |
| *Wolbachia* sp. wPip | Mosquito<br>*Culex<br>quinquefasciatus* | bacteriome | AAATTTGAGAGTTTGATCCTGG<br>CTCAGAATGAACGCTGGCGGCA<br>GGCCTAACACATGCAAGTCGAA<br>CGGAGTTATATTGTAGCTTGCTA<br>TGGTATAACTTAGTGGCAGACG<br>GGTGAGTAATGTATAGGAATCT<br>ACCTAGTAGTACGGAATAATTGT<br>TGGAAACGACAACTAATACCGT<br>ATACGCCCTACGGGGAAAAAT |

TABLE 1-continued

Examples of Target Bacteria and Host Insects

```
TTATTGCTATTAGATGAGCCTAT
ATTAGATTAGCTAGTTGGTGGG
GTAATAGCCTACCAAGGTAATG
ATCTATAGCTGATCTGAGAGGA
TGATCAGCCACACTGGAACTGA
GATACGGTCCAGACTCCTACGG
GAGGCAGCAGTGGGGAATATTG
GACAATGGGCGAAAGCCTGATC
CAGCCATGCCGCATGAGTGAAG
AAGGCCTTTGGGTTGTAAAGCT
CTTTTAGTGAGGAAGATAATGA
CGGTACTCACAGAAGAAGTCCT
GGCTAACTCCGTGCCAGCAGCC
GCGGTAATACGGAGAGGGCTA
GCGTTATTCGGAATTATTGGGC
GTAAAGGGCGCGTAGGCTGGTT
AATAAGTTAAAAGTGAAATCCCG
AGGCTTAACCTTGGAATTGCTTT
TAAAACTATTAATCTAGAGATTG
AAAGAGGATAGAGGAATTCCTG
ATGTAGAGGTAAAATTCGTAAAT
ATTAGGAGGAACACCAGTGGCG
AAGGCGTCTATCTGGTTCAAAT
CTGACGCTGAAGCGCGAAGGC
GTGGGGAGCAAACAGGATTAGA
TACCCTGGTAGTCCACGCTGTA
AACGATGAATGTTAAATATGGG
GAGTTTACTTTCTGTATTACAGC
TAACGCGTTAAACATTCCGCCT
GGGGACTACGGTCGCAAGATTA
AAACTCAAAGGAATTGACGGGG
ACCCGCACAAGCGGTGGAGCA
TGTGGTTTAATTCGATGCAACG
CGAAAAACCTTACCACTTCTTGA
CATGAAAATCATACCTATTCGAA
GGGATAGGGTCGGTTCGGCCG
GATTTTACACAAGTGTTGCATG
GCTGTCGTCAGCTCGTGTCGTG
AGATGTTGGGTTAAGTCCCGCA
ACGAGCGCAACCCTCATCCTTA
GTTGCCATCAGGTAATGCTGAG
TACTTTAAGGAAACTGCCAGTG
ATAAGCTGGAGGAAGGTGGGG
ATGATGTCAAGTCATCATGGCC
TTTATGGAGTGGGCTACACACG
TGCTACAATGGTGTCTACAATG
GGCTGCAAGGTGCGCAAGCCT
AAGCTAATCCCTAAAAGACATCT
CAGTTCGGATTGTACTCTGCAA
CTCGAGTACATGAAGTTGGAAT
CGCTAGTAATCGTGGATCAGCA
TGCCACGGTGAATACGTTCTCG
GGTCTTGTACACACTGCCCGTC
ACGCCATGGGAATTGGTTTCAC
TCGAAGCTAATGGCCTAACCGC
AAGGAAGGAGTTATTTAAAGTG
GGATCAGTGACTGGGGTGAAGT
CGTAACAAGGTAGCAGTAGGGG
AATCTGCAGCTGGATTACCTCC
TTA
(SEQ ID NO: 23)
```

Bacteroidetes

| | | | |
|---|---|---|---|
| *Uzinura diaspidicola* | armoured scale insects | bacteriocytes | AAAGGAGATATTCCAACCACAC CTTCCGGTACGGTTACCTTGTT ACGACTTAGCCCTAGTCATCAA GTTTACCTTAGGCAGACCACTG AAGGATTACTGACTTCAGGTAC CCCCGACTCCCATGGCTTGACG GGCGGTGTGTACAAGGTTCGAG AACATATTCACCGCGCCATTGC TGATGCGCGATTACTAGCGATT CCTGCTTCATAGAGTCGAATTG CAGACTCCAATCCGAACTGAGA CTGGTTTTAGAGATTAGCTCCT GATCACCCAGTGGCTGCCCTTT GTAACCAGCCATTGTAGCACGT |

TABLE 1-continued

Examples of Target Bacteria and Host Insects

GTGTAGCCCAAGGCATAGAGGC
CATGATGATTTGACATCATCCCC
ACCTTCCTCACAGTTTACACCG
GCAGTTTTGTTAGAGTCCCCGG
CTTTACCCGATGGCAACTAACA
ATAGGGGTTGCGCTCGTTATAG
GACTTAACCAAACACTTCACAG
CACGAACTGAAGACAACCATGC
AGCACCTTGTAATACGTCGTATA
GACTAAGCTGTTTCCAGCTTATT
CGTAATACATTTAAGCCTTGGTA
AGGTTCCTCGCGTATCATCGAA
TTAAACCACATGCTCCACCGCT
TGTGCGAACCCCCGTCAATTCC
TTTGAGTTTCAATCTTGCGACTG
TACTTCCCAGGTGGATCACTTAT
CGCTTTCGCTAAGCCACTGAAT
ATCGTTTTTCCAATAGCTAGTGA
TCATCGTTTAGGGCGTGGACTA
CCAGGGTATCTAATCCTGTTTG
CTCCCCACGCTTTCGTGCACTG
AGCGTCAGTAAAGATTTAGCAA
CCTGCCTTCGCTATCGGTGTTC
TGTATGATATCTATGCATTTCAC
CGCTACACCATACATTCCAGAT
GCTCCAATCTTACTCAAGTTTAC
CAGTATCAATAGCAATTTTACAG
TTAAGCTGTAAGCTTTCACTACT
GACTTAATAAACAGCCTACACA
CCCTTTAAACCCAATAAATCCGA
ATAACGTTGTGTCATCCGTATT
GCCGCGGCTGCTGGCACGGAA
TTAGCCGACACTTATTCGTATAG
TACCTTCAATCTCCTATCACGTA
AGATATTTTATTTCTATACAAAA
GCAGTTTACAACCTAAAAGACC
TTCATCCTGCACGCGACGTAGC
TGGTTCAGAGTTTCCTCCATTGA
CCAATATTCCTCACTGCTGCCT
CCCGTAGGAGTCTGGTCCGTGT
CTCAGTACCAGTGTGGAGGTAC
ACCCTCTTAGGCCCCCTACTGA
TCATAGTCTTGGTAGAGCCATTA
CCTCACCAACTAACTAATCAAAC
GCAGGCTCATCTTTTGCCACCT
AAGTTTTAATAAAGGCTCCATGC
AGAAACTTTATATTATGGGGGAT
TAATCAGAATTTCTTCTGGCTAT
ACCCCAGCAAAAGGTAGATTGC
ATACGTGTTACTCACCCATTCG
CCGGTCGCCGACAAATTAAAAA
TTTTTCGATGCCCCTCGACTTG
CATGTGTTAAGCTCGCCGCTAG
CGTTAATTCTGAGCCAGGATCA
AACTCTTCGTTGTAG
(SEQ ID NO: 24)

| | | | |
|---|---|---|---|
| *Sulcia muelleri* | Blue-Green Sharpshooter and several other leafhopper species | bacteriocytes | CTCAGGATAAACGCTAGCGGAG GGCTTAACACATGCAAGTCGAG GGGCAGCAAAATAATTATTTTT GGCGACCGGCAAACGGGTGAG TAATACATACGTAACTTTCCTTA TGCTGAGGAATAGCCTGAGGAA ACTTGGATTAATACCTCATAATA CAATTTTTTAGAAAGAAAAATTG TTAAAGTTTTATTATGGCATAAG ATAGGCGTATGTCCAATTAGTTA GTTGGTAAGGTAATGGCTTACC AAGACGATGATTGGTAGGGGGC CTGAGAGGGGCGTTCCCCCAC ATTGGTACTGAGACACGGACCA AACTTCTACGGAAGGCTGCAGT GAGGAATATTGGTCAATGGAGG AAACTCTGAACCAGCCACTCCG CGTGCAGGATGAAAGAAAGCCT TATTGGTTGTAAACTGCTTTTGT ATATGAATAAAAAATTCTAATTAT AGAAATAATTGAAGGTAATATAC |

TABLE 1-continued

Examples of Target Bacteria and Host Insects

| | | | |
|---|---|---|---|
| | | | GAATAAGTATCGACTAACTCTGT |
| | | | GCCAGCAGTCGCGGTAAGACA |
| | | | GAGGATACAAGCGTTATCCGGA |
| | | | TTTATTGGGTTTAAAGGGTGCG |
| | | | TAGGCGGTTTTTAAAGTCAGTA |
| | | | GTGAAATCTTAAAGCTTAACTTT |
| | | | AAAAGTGCTATTGATACTGAAAA |
| | | | ACTAGAGTAAGGTTGGAGTAAC |
| | | | TGGAATGTGTGGTGTAGCGGTG |
| | | | AAATGCATAGATATCACACAGAA |
| | | | CACCGATAGCGAAAGCAAGTTA |
| | | | CTAACCCTATACTGACGCTGAG |
| | | | TCACGAAAGCATGGGAGCAAA |
| | | | CAGGATTAGATACCCTGGTAGT |
| | | | CCATGCCGTAAACGATGATCAC |
| | | | TAACTATTGGGTTTTATACGTTG |
| | | | TAATTCAGTGGTGAAGCGAAAG |
| | | | TGTTAAGTGATCCACCTGAGGA |
| | | | GTACGACCGCAAGGTTGAAACT |
| | | | CAAAGGAATTGACGGGGGCCC |
| | | | GCACAATCGGTGGAGCATGTGG |
| | | | TTTAATTCGATGATACACGAGGA |
| | | | ACCTTACCAAGACTTAAATGTAC |
| | | | TACGAATAAATTGGAAACAATTT |
| | | | AGTCAAGCGACGGAGTACAAGG |
| | | | TGCTGCATGGTTGTCGTCAGCT |
| | | | CGTGCCGTGAGGTGTAAGGTTA |
| | | | AGTCCTTTAAACGAGCGCAACC |
| | | | CTTATTATTAGTTGCCATCGAGT |
| | | | AATGTCAGGGGACTCTAATAAG |
| | | | ACTGCCGGCGCAAGCCGAGAG |
| | | | GAAGGTGGGGATGACGTCAAAT |
| | | | CATCACGGCCCTTACGTCTTGG |
| | | | GCCACACACGTGCTACAATGAT |
| | | | CGGTACAAAAGGGAGCGACTG |
| | | | GGTGACCAGGAGCAAATCCAGA |
| | | | AAGCCGATCTAAGTTCGGATTG |
| | | | GAGTCTGAAACTCGACTCCATG |
| | | | AAGCTGGAATCGCTAGTAATCG |
| | | | TGCATCAGCCATGGCACGGTGA |
| | | | ATATGTTCCCGGGCCTTGTACA |
| | | | CACCGCCCGTCAAGCCATGGAA |
| | | | GTTGGAAGTACCTAAAGTTGGT |
| | | | TCGCTACCTAAGGTAAGTCTAAT |
| | | | AACTGGGGCTAAGTCGTAACAA |
| | | | GGTA |
| | | | (SEQ ID NO: 25) |

Yeast like

| | | | |
|---|---|---|---|
| *Symbiotaphrina buchneri* voucher JCM9740 | Anobiid beetles *Stegobium paniceum* | mycetome between the foregut and midgut | AGATTAAGCCATGCAAGTCTAA |
| | | | GTATAAGNAATCTATACNGTGAA |
| | | | ACTGCGAATGGCTCATTAAATC |
| | | | AGTTATCGTTTATTTGATAGTAC |
| | | | CTTACTACATGGATAACCGTGG |
| | | | TAATTCTAGAGCTAATACATGCT |
| | | | AAAAACCCCGACTTCGGAAGGG |
| | | | GTGTATTTATTAGATAAAAAACC |
| | | | AATGCCCTTCGGGGCTCCTTGG |
| | | | TGATTCATGATAACTTAACGAAT |
| | | | CGCATGGCCTTGCGCCGGCGA |
| | | | TGGTTCATTCAAATTTCTGCCCT |
| | | | ATCAACTTTCGATGGTAGGATA |
| | | | GTGGCCTACCATGGTTTTAACG |
| | | | GGTAACGGGGAATTAGGGTTCG |
| | | | ATTCCGGAGAGGGAGCCTGAG |
| | | | AAACGGCTACCACATCCAAGGA |
| | | | AGGCAGCAGGCGCGCAAATTAC |
| | | | CCAATCCCGACACGGGGAGGT |
| | | | AGTGACAATAAATACTGATACAG |
| | | | GGCTCTTTTGGGTCTTGTAATTG |
| | | | GAATGAGTACAATTTAAATCCCT |
| | | | TAACGAGGAACAATTGGAGGGC |
| | | | AAGTCTGGTGCCAGCAGCCGC |
| | | | GGTAATTCCAGCTCCAATAGCG |
| | | | TATATTAAAGTTGTTGCAGTTAA |
| | | | AAAGCTCGTAGTTGAACCTTGG |
| | | | GCCTGGCTGGCCGGTCCGCCT |

TABLE 1-continued

Examples of Target Bacteria and Host Insects

| | | | |
|---|---|---|---|
| | | | AACCGCGTGTACTGGTCCGGCC<br>GGGCCTTTCCTTCTGGGGAGCC<br>GCATGCCCTTCACTGGGTGTGT<br>CGGGGAACCAGGACTTTTACTT<br>TGAAAAAATTAGAGTGTTCAAAG<br>CAGGCCTATGCTCGAATACATT<br>AGCATGGAATAATAGAATAGGA<br>CGTGCGGTTCTATTTTGTTGGTT<br>TCTAGGACCGCCGTAATGATTA<br>ATAGGGATAGTCGGGGGCATCA<br>GTATTCAATTGTCAGAGGTGAA<br>ATTCTTGGATTTATTGAAGACTA<br>ACTACTGCGAAAGCATTTGCCA<br>AGGATGTTTTCATTAATCAGTGA<br>ACGAAAGTTAGGGGATCGAAGA<br>CGATCAGATACCGTCGTAGTCT<br>TAACCATAAACTATGCCGACTA<br>GGGATCGGGCGATGTTATTATT<br>TTGACTCGCTCGGCACCTTACG<br>AGAAATCAAAGTCTTTGGGTTCT<br>GGGGGGAGTATGGTCGCAAGG<br>CTGAAACTTAAAGAAATTGACG<br>GAAGGGCACCACCAGGAGTGG<br>AGCCTGCGGCTTAATTTGACTC<br>AACACGGGGAAACTCACCAGGT<br>CCAGACACATTAAGGATTGACA<br>GATTGAGAGCTCTTTCTTGATTA<br>TGTGGGTGGTGGTGCATGGCC<br>GTTCTTAGTTGGTGGAGTGATTT<br>GTCTGCTTAATTGCGATAACGA<br>ACGAGACCTTAACCTGCTAAAT<br>AGCCCGGTCCGCTTTGGCGGG<br>CCGCTGGCTTCTTAGAGGGACT<br>ATCGGCTCAAGCCGATGGAAGT<br>TTGAGGCAATAACAGGTCTGTG<br>ATGCCCTTAGATGTTCTGGGCC<br>GCACGCGCGCTACACTGACAGA<br>GCCAACGAGTAAATCACCTTGG<br>CCGGAAGGTCTGGGTAATCTTG<br>TTAAACTCTGTCGTGCTGGGGA<br>TAGAGCATTGCAATTATTGCTCT<br>TCAACGAGGAATTCCTAGTAAG<br>CGCAAGTCATCAGCTTGCGCTG<br>ATTACGTCCCTGCCCTTTGTACA<br>CACCGCCCGTCGCTACTACCGA<br>TTGAATGGCTCAGTGAGGCCTT<br>CGGACTGGCACAGGGACGTTG<br>GCAACGACGACCCAGTGCCGG<br>AAAGTTGGTCAAACTTGGTCATT<br>TAGAGGAAGTAAAAGTCGTAAC<br>AAGGTTTCCGTAGGTGAACCTG<br>CGGAAGGATCATTA<br>(SEQ ID NO: 26) |
| Symbiotaphrina kochii<br>voucher CBS 589.63 | Anobiid beetles<br>Lasioderma<br>serricorne | mycetome | TACCTGGTTGATTCTGCCAGTA<br>GTCATATGCTTGTCTCAAAGATT<br>AAGCCATGCAAGTCTAAGTATA<br>AGCAATCTATACGGTGAAACTG<br>CGAATGGCTCATTAAATCAGTTA<br>TCGTTTATTTGATAGTACCTTAC<br>TACATGGATAACCGTGGTAATT<br>CTAGAGCTAATACATGCTAAAAA<br>CCTCGACTTCGGAAGGGGTGTA<br>TTTATTAGATAAAAAACCAATGC<br>CCTTCGGGGCTCCTTGGTGATT<br>CATGATAACTTAACGAATCGCAT<br>GGCCTTGCGCCGGCGATGGTT<br>CATTCAAATTTCTGCCCTATCAA<br>CTTTCGATGGTAGGATAGTGGC<br>CTACCATGGTTTCAACGGGTAA<br>CGGGGAATTAGGGTTCGATTCC<br>GGAGAGGGAGCCTGAGAAACG<br>GCTACCACATCCAAGGAAGGCA<br>GCAGGCGCGCAAATTACCCAAT<br>CCCGACACGGGGAGGTAGTGA<br>CAATAAATACTGATACAGGGCT<br>CTTTTGGGTCTTGTAATTGGAAT<br>GAGTACAATTTAAATCCCTTAAC |

TABLE 1-continued

Examples of Target Bacteria and Host Insects

|  |  |  | GAGGAACAATTGGAGGGCAAGT<br>CTGGTGCCAGCAGCCGCGGTA<br>ATTCCAGCTCCAATAGCGTATAT<br>TAAAGTTGTTGCAGTTAAAAAGC<br>TCGTAGTTGAACCTTGGGCCTG<br>GCTGGCCGGTCCGCCTAACCG<br>CGTGTACTGGTCCGGCCGGGC<br>CTTTCCTTCTGGGGAGCCGCAT<br>GCCCTTCACTGGGTGTGTCGGG<br>GAACCAGGACTTTTACTTTGAAA<br>AAATTAGAGTGTTCAAAGCAGG<br>CCTATGCTCGAATACATTAGCAT<br>GGAATAATAGAATAGGACGTGT<br>GGTTCTATTTTGTTGGTTTCTAG<br>GACCGCCGTAATGATTAATAGG<br>GATAGTCGGGGGCATCAGTATT<br>CAATTGTCAGAGGTGAAATTCTT<br>GGATTTATTGAAGACTAACTACT<br>GCGAAAGCATTTGCCAAGGATG<br>TTTTCATTAATCAGTGAACGAAA<br>GTTAGGGGATCGAAGACGATCA<br>GATACCGTCGTAGTCTTAACCA<br>TAAACTATGCCGACTAGGGATC<br>GGGCGATGTTATTATTTTGACTC<br>GCTCGGCACCTTACGAGAAATC<br>AAAGTCTTTGGGTTCTGGGGGG<br>AGTATGGTCGCAAGGCTGAAAC<br>TTAAAGAAATTGACGGAAGGGC<br>ACCACCAGGAGTGGAGCCTGC<br>GGCTTAATTTGACTCAACACGG<br>GGAAACTCACCAGGTCCAGACA<br>CATTAAGGATTGACAGATTGAG<br>AGCTCTTTCTTGATTATGTGGGT<br>GGTGGTGCATGGCCGTTCTTAG<br>TTGGTGGAGTGATTTGTCTGCT<br>TAATTGCGATAACGAACGAGAC<br>CTTAACCTGCTAAATAGCCCGG<br>TCCGCTTTGGCGGGCCGCTGG<br>CTTCTTAGAGGGACTATCGGCT<br>CAAGCCGATGGAAGTTTGAGGC<br>AATAACAGGTCTGTGATGCCCT<br>TAGATGTTCTGGGCCGCACGCG<br>CGCTACACTGACAGAGCCAACG<br>AGTACATCACCTTGGCCGGAAG<br>GTCTGGGTAATCTTGTTAAACTC<br>TGTCGTGCTGGGGATAGAGCAT<br>TGCAATTATTGCTCTTCAACGAG<br>GAATTCCTAGTAAGCGCAAGTC<br>ATCAGCTTGCGCTGATTACGTC<br>CCTGCCCTTTGTACACACCGCC<br>CGTCGCTACTACCGATTGAATG<br>GCTCAGTGAGGCCTTCGGACTG<br>GCACAGGGACGTTGGCAACGA<br>CGACCCAGTGCCGGAAAGTTCG<br>TCAAACTTGGTCATTTAGAGGAA<br>GNNNAAGTCGTAACAAGGTTTC<br>CGTAGGTGAACCTGCGGAAGG<br>ATCATTA<br>(SEQ ID NO: 27) |
| --- | --- | --- | --- |
| Primary extracelullar<br>symbiont | Host | location | 16 rRNA |
| fenitrothion-degrading<br>bacteria |  |  |  |
| Burkholderia sp. SFA1 | Riptortus<br>pedestris | Gut | AGTTTGATCCTGGCTCAGATTG<br>AACGCTGGCGGCATGCCTTACA<br>CATGCAAGTCGAACGGCAGCAC<br>GGGGGCAACCCTGGTGGCGAG<br>TGGCGAACGGGTGAGTAATACA<br>TCGGAACGTGTCCTGTAGTGGG<br>GGATAGCCCGGCGAAAGCCGG<br>ATTAATACCGCATACGACCTAA<br>GGGAGAAAGCGGGGGATCTTC<br>GGACCTCGCGCTATAGGGGCG<br>GCCGATGGCAGATTAGCTAGTT<br>GGTGGGGTAAAGGCCTACCAA |

TABLE 1-continued

Examples of Target Bacteria and Host Insects

| | | | |
|---|---|---|---|
| | | | GGCGACGATCTGTAGCTGGTCT<br>GAGAGGACGACCAGCCACACT<br>GGGACTGAGACACGGCCCAGA<br>CTCCTACGGGAGGCAGCAGTG<br>GGGAATTTTGGACAATGGGGGC<br>AACCCTGATCCAGCAATGCCGC<br>GTGTGTGAAGAAGGCTTCGGGT<br>TGTAAAGCACTTTTGTCCGGAA<br>AGAAAACTTCGTCCCTAATATG<br>GATGGAGGATGACGGTACCGG<br>AAGAATAAGCACCGGCTAACTA<br>CGTGCCAGCAGCCGCGGTAATA<br>CGTAGGGTGCGAGCGTTAATCG<br>GAATTACTGGGCGTAAAGCGTG<br>CGCAGGCGGTCTGTTAAGACCG<br>ATGTGAAATCCCCGGGCTTAAC<br>CTGGGAACTGCATTGGTGACTG<br>GCAGGCTTTGAGTGTGGCAGAG<br>GGGGGTAGAATTCCACGTGTAG<br>CAGTGAAATGCGTAGAGATGTG<br>GAGGAATACCGATGGCGAAGG<br>CAGCCCCCTGGGCCAACTACTG<br>ACGCTCATGCACGAAAGCGTGG<br>GGAGCAAACAGGATTAGATACC<br>CTGGTAGTCCACGCCCTAAACG<br>ATGTCAACTAGTTGTTGGGGAT<br>TCATTTCCTTAGTAACGTAGCTA<br>ACGCGTGAAGTTGACCGCCTGG<br>GGAGTACGGTCGCAAGATTAAA<br>ACTCAAAGGAATTGACGGGGAC<br>CCGCACAAGCGGTGGATGATGT<br>GGATTAATTCGATGCAACGCGA<br>AAAACCTTACCTACCCTTGACAT<br>GGTCGGAACCCTGCTGAAAGGT<br>GGGGGTGCTCGAAAGAGAACC<br>GGCGCACAGGTGCTGCATGGC<br>TGTCGTCAGCTCGTGTCGTGAG<br>ATGTTGGGTTAAGTCCCGCAAC<br>GAGCGCAACCCTTGTCCTTAGT<br>TGCTACGCAAGAGCACTCTAAG<br>GAGACTGCCGGTGACAAACCG<br>GAGGAAGGTGGGGATGACGTC<br>AAGTCCTCATGGCCCTTATGGG<br>TAGGGCTTCACACGTCATACAA<br>TGGTCGGAACAGAGGGTTGCCA<br>AGCCGCGAGGTGGAGCCAATC<br>CCAGAAAACCGATCGTAGTCCG<br>GATCGCAGTCTGCAACTCGACT<br>GCGTGAAGCTGGAATCGCTAGT<br>AATCGCGGATCAGCATGCCGCG<br>GTGAATACGTTCCCGGGTCTTG<br>TACACACCGCCCGTCACACCAT<br>GGGAGTGGGTTTCACCAGAAGT<br>AGGTAGCCTAACCGCAAGGAG<br>GGCGCTTACCACGGTGGGATTC<br>ATGACTGGGGTGAAGTCGTAAC<br>AAGGTAGC<br>(SEQ ID NO: 28) |
| Burkholderia sp. KM-A | Riptortus pedestris | Gut | GCAACCCTGGTGGCGAGTGGC<br>GAACGGGTGAGTAATACATCGG<br>AACGTGTCCTGTAGTGGGGGAT<br>AGCCCGGCGAAAGCCGGATTAA<br>TACCGCATACGATCTACGGAAG<br>AAAGCGGGGATCCTTCGGGA<br>CCTCGCGCTATAGGGGCGGCC<br>GATGGCAGATTAGCTAGTTGGT<br>GGGGTAAAGGCCTACCAAGGC<br>GACGATCTGTAGCTGGTCTGAG<br>AGGACGACCAGCCACACTGGG<br>ACTGAGACACGGCCCAGACTCC<br>TACGGGAGGCAGCAGTGGGGA<br>ATTTTGGACAATGGGGGCAACC<br>CTGATCCAGCAATGCCGCGTGT<br>GTGAAGAAGGCCTTCGGGTTGT<br>AAAGCACTTTTGTCCGGAAAGA<br>AAACGTCTTGGTTAATACCTGA<br>GGCGGATGACGGTACCGGAAG |

US 11,690,387 B2

TABLE 1-continued

Examples of Target Bacteria and Host Insects

| | | | |
|---|---|---|---|
| | | | AATAAGCACCGGCTAACTACGT |
| | | | GCCAGCAGCCGCGGTAATACGT |
| | | | AGGGTGCGAGCGTTAATCGGAA |
| | | | TTACTGGGCGTAAAGCGTGCGC |
| | | | AGGCGGTCTGTTAAGACCGATG |
| | | | TGAAATCCCCGGGCTTAACCTG |
| | | | GGAACTGCATTGGTGACTGGCA |
| | | | GGCTTTGAGTGTGGCAGAGGG |
| | | | GGGTAGAATTCCACGTGTAGCA |
| | | | GTGAAATGCGTAGAGATGTGGA |
| | | | GGAATACCGATGGCGAAGGCA |
| | | | GCCCCCTGGGCCAACACTGAC |
| | | | GCTCATGCACGAAAGCGTGGG |
| | | | GAGCAAACAGGATTAGATACCC |
| | | | TGGTAGTCCACGCCCTAAACGA |
| | | | TGTCAACTAGTTGTTGGGGATT |
| | | | CATTTCCTTAGTAACGTAGCTAA |
| | | | CGCGTGAAGTTGACCGCCTGG |
| | | | GGAGTACGGTCGCAAGATTAAA |
| | | | ACTCAAAGGAATTGACGGGGAC |
| | | | CCGCACAAGCGGTGGATGATGT |
| | | | GGATTAATTCGATGCAACGCGA |
| | | | AAAACCTTACCTACCCTTGACAT |
| | | | GGTCGGAAGTCTGCTGAGAGGT |
| | | | GGACGTGCTCGAAAGAGAACC |
| | | | GGCGCACAGGTGCTGCATGGC |
| | | | TGTCGTCAGCTCGTGTCGTGAG |
| | | | ATGTTGGGTTAAGTCCCGCAAC |
| | | | GAGCGCAACCCTTGTCCTTAGT |
| | | | TGCTACGCAAGAGCACTCTAAG |
| | | | GAGACTGCCGGTGACAAACCG |
| | | | GAGGAAGGTGGGGATGACGTC |
| | | | AAGTCCTCATGGCCCTTATGGG |
| | | | TAGGGCTTCACACGTCATACAA |
| | | | TGGTCGGAACAGAGGGTTGCCA |
| | | | AGCCGCGAGGTGGAGCCAATC |
| | | | CCAGAAAACCGATCGTAGTCCG |
| | | | GATCGCAGTCTGCAACTCGACT |
| | | | GCGTGAAGCTGGAATCGCTAGT |
| | | | AATCGCGGATCAGCATGCCGCG |
| | | | GTGAATACGTTCCCGGGTCTTG |
| | | | TACACACCGCCCGTCACACCAT |
| | | | GGGAGTGGGTTTCACCAGAAGT |
| | | | AGGTAGCCTAACCGCAAGGAG |
| | | | GGCGCTTACCACGGTGGGATTC |
| | | | ATGACTGGGGTGAAGT |
| | | | (SEQ ID NO: 29) |
| Burkholderia sp. KM-G | Riptortus pedestris | Gut | GCAACCCTGGTGGCGAGTGGC |
| | | | GAACGGGTGAGTAATACATCGG |
| | | | AACGTGTCCTGTAGTGGGGGAT |
| | | | AGCCCGGCGAAAGCCGGATTAA |
| | | | TACCGCATACGACCTAAGGGAG |
| | | | AAAGCGGGGATCTTCGGACCT |
| | | | CGCGCTATAGGGGCGGCCGAT |
| | | | GGCAGATTAGCTAGTTGGTGGG |
| | | | GTAAAGGCCTACCAAGGCGACG |
| | | | ATCTGTAGCTGGTCTGAGAGGA |
| | | | CGACCAGCCACACTGGGACTGA |
| | | | GACACGGCCCAGACTCCTACG |
| | | | GGAGGCAGCAGTGGGGAATTTT |
| | | | GGACAATGGGGGCAACCCTGAT |
| | | | CCAGCAATGCCGCGTGTGTGAA |
| | | | GAAGGCCTTCGGGTTGTAAAGC |
| | | | ACTTTTGTCCGGAAAGAAAACTT |
| | | | CGAGGTTAATACCCTTGGAGGA |
| | | | TGACGGTACCGGAAGAATAAGC |
| | | | ACCGGCTAACTACGTGCCAGCA |
| | | | GCCGCGGTAATACGTAGGGTG |
| | | | CGAGCGTTAATCGGAATTACTG |
| | | | GGCGTAAAGCGTGCGCAGGCG |
| | | | GTCTGTTAAGACCGATGTGAAA |
| | | | TCCCCGGGCTTAACCTGGGAAC |
| | | | TGCATTGGTGACTGGCAGGCTT |
| | | | TGAGTGTGGCAGAGGGGGGTA |
| | | | GAATTCCACGTGTAGCAGTGAA |
| | | | ATGCGTAGAGATGTGGAGGAAT |
| | | | ACCGATGGCGAAGGCAGCCCC |

TABLE 1-continued

Examples of Target Bacteria and Host Insects

| | | | |
|---|---|---|---|
| | | | CTGGGCCAACACTGACGCTCAT |
| | | | GCACGAAAGCGTGGGGAGCAA |
| | | | ACAGGATTAGATACCCTGGTAG |
| | | | TCCACGCCCTAAACGATGTCAA |
| | | | CTAGTTGTTGGGGATTCATTTCC |
| | | | TTAGTAACGTAGCTAACGCGTG |
| | | | AAGTTGACCGCCTGGGGAGTAC |
| | | | GGTCGCAAGATTAAAACTCAAA |
| | | | GGAATTGACGGGGACCCGCAC |
| | | | AAGCGGTGGATGATGTGGATTA |
| | | | ATTCGATGCAACGCGAAAAACC |
| | | | TTACCTACCCTTGACATGGTCG |
| | | | GAAGTCTGCTGAGAGGTGGAC |
| | | | GTGCTCGAAAGAGAACCGGCG |
| | | | CACAGGTGCTGCATGGCTGTCG |
| | | | TCAGCTCGTGTCGTGAGATGTT |
| | | | GGGTTAAGTCCCGCAACGAGC |
| | | | GCAACCCTTGTCCTTAGTTGCT |
| | | | ACGCAAGAGCACTCTAAGGAGA |
| | | | CTGCCGGTGACAAACCGGAGG |
| | | | AAGGTGGGGATGACGTCAAGTC |
| | | | CTCATGGCCCTTATGGGTAGGG |
| | | | CTTCACACGTCATACAATGGTC |
| | | | GGAACAGAGGGTTGCCAAGCC |
| | | | GCGAGGTGGAGCCAATCCCAG |
| | | | AAAACCGATCGTAGTCCGGATC |
| | | | GCAGTCTGCAACTCGACTGCGT |
| | | | GAAGCTGGAATCGCTAGTAATC |
| | | | GCGGATCAGCATGCCGCGGTG |
| | | | AATACGTTCCCGGGTCTTGTAC |
| | | | ACACCGCCCGTCACACCATGGG |
| | | | AGTGGGTTTCACCAGAAGTAGG |
| | | | TAGCCTAACCTGCAAAGGAGGG |
| | | | CGCTTACCACG |
| | | | (SEQ ID NO: 30) |
| Bees | | | |
| *Snodgrassella alvi* | Honeybee (*Apis mellifera*) and *Bombus spp.* | Ileum | GAGAGTTTGATCCTGGCTCAGA |
| | | | TTGAACGCTGGCGGCATGCCTT |
| | | | ACACATGCAAGTCGAACGGCAG |
| | | | CACGGAGAGCTTGCTCTCTGGT |
| | | | GGCGAGTGGCGAACGGGTGAG |
| | | | TAATGCATCGGAACGTACCGAG |
| | | | TAATGGGGGATAACTGTCCGAA |
| | | | AGGATGGCTAATACCGCATACG |
| | | | CCCTGAGGGGAAAGCGGGGG |
| | | | ATCGAAAGACCTCGCGTTATTT |
| | | | GAGCGGCCGATGTTGGATTAGC |
| | | | TAGTTGGTGGGGTAAAGGCCTA |
| | | | CCAAGGCGACGATCCATAGCG |
| | | | GGTCTGAGAGGATGATCCGCCA |
| | | | CATTGGGACTGAGACACGGCCC |
| | | | AAACTCCTACGGGAGGCAGCAG |
| | | | TGGGGAATTTTGGACAATGGGG |
| | | | GGAACCCTGATCCAGCCATGCC |
| | | | GCGTGTCTGAAGAAGGCCTTCG |
| | | | GGTTGTAAAGGACTTTTGTTAG |
| | | | GGAAGAAAAGCCGGGTGTTAAT |
| | | | ACCATCTGGTGCTGACGGTACC |
| | | | TAAAGAATAAGCACCGGCTAAC |
| | | | TACGTGCCAGCAGCCGCGGTAA |
| | | | TACGTAGGGTGCGAGCGTTAAT |
| | | | CGGAATTACTGGGCGTAAAGCG |
| | | | AGCGCAGACGGTTAATTAAGTC |
| | | | AGATGTGAAATCCCCGAGCTCA |
| | | | ACTTGGGACGTGCATTTGAAAC |
| | | | TGGTTAACTAGAGTGTGTCAGA |
| | | | GGGAGGTAGAATTCCACGTGTA |
| | | | GCAGTGAAATGCGTAGAGATGT |
| | | | GGAGGAATACCGATGGCGAAG |
| | | | GCAGCCTCCTGGGATAACACTG |
| | | | ACGTTCATGCTCGAAAGCGTGG |
| | | | GTAGCAAACAGGATTAGATACC |
| | | | CTGGTAGTCCACGCCCTAAACG |
| | | | ATGACAATTAGCTGTTGGGACA |
| | | | CTAGATGTCTTAGTAGCGAAGC |
| | | | TAACGCGTGAAATTGTCCGCCT |

TABLE 1-continued

Examples of Target Bacteria and Host Insects

| | | | |
|---|---|---|---|
| | | | GGGGAGTACGGTCGCAAGATTA
AAACTCAAAGGAATTGACGGGG
ACCCGCACAAGCGGTGGATGAT
GTGGATTAATTCGATGCAACGC
GAAGAACCTTACCTGGTCTTGA
CATGTACGGAATCTCTTAGAGA
TAGGAGAGTGCCTTCGGGAACC
GTAACACAGGTGCTGCATGGCT
GTCGTCAGCTCGTGTCGTGAGA
TGTTGGGTTAAGTCCCGCAACG
AGCGCAACCCTTGTCATTAGTT
GCCATCATTAAGTTGGGCACTC
TAATGAGACTGCCGGTGACAAA
CCGGAGGAAGGTGGGGATGAC
GTCAAGTCCTCATGGCCCTTAT
GACCAGGGCTTCACACGTCATA
CAATGGTCGGTACAGAGGGTAG
CGAAGCCGCGAGGTGAAGCCA
ATCTCAGAAAGCCGATCGTAGT
CCGGATTGCACTCTGCAACTCG
AGTGCATGAAGTCGGAATCGCT
AGTAATCGCAGGTCAGCATACT
GCGGTGAATACGTTCCCGGGTC
TTGTACACACCGCCCGTCACAC
CATGGGAGTGGGGGATACCAG
AATTGGGTAGACTAACCGCAAG
GAGGTCGCTTAACACGGTATGC
TTCATGACTGGGGTGAAGTCGT
AACAAGGTAGCCGTAG
(SEQ ID NO: 33) |
| *Gilliamella apicola* | honeybee (*Apis mellifera*) and *Bombus spp.* | Ileum | TTAAATTGAAGAGTTTGATCATG
GCTCAGATTGAACGCTGGCGGC
AGGCTTAACACATGCAAGTCGA
ACGGTAACATGAGTGCTTGCAC
TTGATGACGAGTGGCGGACGG
GTGAGTAAAGTATGGGGATCTG
CCGAATGGAGGGGGACAACAG
TTGGAAACGACTGCTAATACCG
CATAAAGTTGAGAGACCAAAGC
ATGGGACCTTCGGGCCATGCG
CCATTTGATGAACCCATATGGG
ATTAGCTAGTTGGTAGGGTAAT
GGCTTACCAAGGCGACGATCTC
TAGCTGGTCTGAGAGGATGACC
AGCCACACTGGAACTGAGACAC
GGTCCAGACTCCTACGGGAGG
CAGCAGTGGGGAATATTGCACA
ATGGGGGAAACCCTGATGCAGC
CATGCCGCGTGTATGAAGAAGG
CCTTCGGGTTGTAAAGTACTTTC
GGTGATGAGGAAGGTGGTGTAT
CTAATAGGTGCATCAATTGACG
TTAATTACAGAAGAAGCACCGG
CTAACTCCGTGCCAGCAGCCGC
GGTAATACGGAGGGTGCGAGC
GTTAATCGGAATGACTGGGCGT
AAAGGGCATGTAGGCGGATAAT
TAAGTTAGGTGTGAAAGCCCTG
GGCTCAACCTAGGAATTGCACT
TAAAACTGGTTAACTAGAGTATT
GTAGAGGAAGGTAGAATTCCAC
GTGTAGCGGTGAAATGCGTAGA
GATGTGGAGGAATACCGGTGG
CGAAGGCGGCCTTCTGGACAG
ATACTGACGCTGAGATGCGAAA
GCGTGGGGAGCAAACAGGATTA
GATACCCTGGTAGTCCACGCTG
TAAACGATGTCGATTTGGAGTTT
GTTGCCTAGAGTGATGGGCTCC
GAAGCTAACGCGATAAATCGAC
CGCCTGGGGAGTACGGCCGCA
AGGTTAAAACTCAAATGAATTGA
CGGGGGCCCGCACAAGCGGTG
GAGCATGTGGTTTAATTCGATG
CAACGCGAAGAACCTTACCTGG
TCTTGACATCCACAGAATCTTGC
AGAGATGCGGGAGTGCCTTCG |

TABLE 1-continued

Examples of Target Bacteria and Host Insects

| | | | |
|---|---|---|---|
| | | | GGAACTGTGAGACAGGTGCTGC<br>ATGGCTGTCGTCAGCTCGTGTT<br>GTGAAATGTTGGGTTAAGTCCC<br>GCAACGAGCGCAACCCTTATCC<br>TTTGTTGCCATCGGTTAGGCCG<br>GGAACTCAAAGGAGACTGCCGT<br>TGATAAAGCGGAGGAAGGTGG<br>GGACGACGTCAAGTCATCATGG<br>CCCTTACGACCAGGGCTACACA<br>CGTGCTACAATGGCGTATACAA<br>AGGGAGGCGACCTCGCGAGAG<br>CAAGCGGACCTCATAAAGTACG<br>TCTAAGTCCGGATTGGAGTCTG<br>CAACTCGACTCCATGAAGTCGG<br>AATCGCTAGTAATCGTGAATCA<br>GAATGTCACGGTGAATACGTTC<br>CCGGGCCTTGTACACACCGCCC<br>GTCACACCATGGGAGTGGGTTG<br>CACCAGAAGTAGATAGCTTAAC<br>CTTCGGGAGGGCGTTTACCACG<br>GTGTGGTCCATGACTGGGGTGA<br>AGTCGTAACAAGGTAACCGTAG<br>GGGAACCTGCGGTTGGATCACC<br>TCCTTAC<br>(SEQ ID NO: 34) |
| Bartonella apis | honeybee (Apis mellifera) | Gut | AAGCCAAAATCAAATTTTCAACT<br>TGAGAGTTTGATCCTGGCTCAG<br>AACGAACGCTGGCGGCAGGCT<br>TAACACATGCAAGTCGAACGCA<br>CTTTTCGGAGTGAGTGGCAGAC<br>GGGTGAGTAACGCGTGGGAAT<br>CTACCTATTTCTACGGAATAACG<br>CAGAGAAATTTGTGCTAATACC<br>GTATACGTCCTTCGGGAGAAAG<br>ATTTATCGGAGATAGATGAGCC<br>CGCGTTGGATTAGCTAGTTGGT<br>GAGGTAATGGCCCACCAAGGC<br>GACGATCCATAGCTGGTCTGAG<br>AGGATGACCAGCCACATTGGGA<br>CTGAGACACGGCCCAGACTCCT<br>ACGGGAGGCAGCAGTGGGGAA<br>TATTGGACAATGGGCGCAAGCC<br>TGATCCAGCCATGCCGCGTGAG<br>TGATGAAGGCCCTAGGGTTGTA<br>AAGCTCTTTCACCGGTGAAGAT<br>AATGACGGTAACCGGAGAAGAA<br>GCCCCGGCTAACTTCGTGCCAG<br>CAGCCGCGGTAATACGAAGGG<br>GGCTAGCGTTGTTCGGATTTAC<br>TGGGCGTAAAGCGCACGTAGG<br>CGGATATTTAAGTCAGGGGTGA<br>AATCCCGGGGCTCAACCCCGG<br>AACTGCCTTTGATACTGGATATC<br>TTGAGTATGGAAGAGGTAAGTG<br>GAATTCCGAGTGTAGAGGTGAA<br>ATTCGTAGATATTCGGAGGAAC<br>ACCAGTGGCGAAGGCGGCTTA<br>CTGGTCCATTACTGACGCTGAG<br>GTGCGAAAGCGTGGGGAGCAA<br>ACAGGATTAGATACCCTGGTAG<br>TCCACGCTGTAAACGATGAATG<br>TTAGCCGTTGGACAGTTTACTG<br>TTCGGTGGCGCAGCTAACGCAT<br>TAAACATTCCGCCTGGGGAGTA<br>CGGTCGCAAGATTAAAACTCAA<br>AGGAATTGACGGGGGCCCGCA<br>CAAGCGGTGGAGCATGTGGTTT<br>AATTCGAAGCAACGCGCAGAAC<br>CTTACCAGCCCTTGACATCCCG<br>ATCGCGGATGGTGGAGACACC<br>GTCTTTCAGTTCGGCTGGATCG<br>GTGACAGGTGCTGCATGGCTGT<br>CGTCAGCTCGTGTCGTGAGATG<br>TTGGGTTAAGTCCCGCAACGAG<br>CGCAACCCTCGCCCTTAGTTGC<br>CATCATTTAGTTGGGCACTCTAA<br>GGGGACTGCCGGTGATAAGCC |

TABLE 1-continued

Examples of Target Bacteria and Host Insects

| | | | |
|---|---|---|---|
| | | | GAGAGGAAGGTGGGGATGACG<br>TCAAGTCCTCATGGCCCTTACG<br>GGCTGGGCTACACACGTGCTAC<br>AATGGTGGTGACAGTGGGCAG<br>CGAGACCGCGAGGTCGAGCTA<br>ATCTCCAAAAGCCATCTCAGTTC<br>GGATTGCACTCTGCAACTCGAG<br>TGCATGAAGTTGGAATCGCTAG<br>TAATCGTGGATCAGCATGCCAC<br>GGTGAATACGTTCCCGGGCCTT<br>GTACACACCGCCCGTCACACCA<br>TGGGAGTTGGTTTTACCCGAAG<br>GTGCTGTGCTAACCGCAAGGAG<br>GCAGGCAACCACGGTAGGGTC<br>AGCGACTGGGGTGAAGTCGTAA<br>CAAGGTAGCCGTAGGGGAACCT<br>GCGGCTGGATCACCTCCTTTCT<br>AAGGAAGATGAAGAATTGGAA<br>(SEQ ID NO: 35) |
| *Parasaccharibacter apium* | honeybee (*Apis mellifera*) | Gut | CTACCATGCAAGTCGCACGAAA<br>CCTTTCGGGGTTAGTGGCGGAC<br>GGGTGAGTAACGCGTTAGGAAC<br>CTATCTGGAGGTGGGGGATAAC<br>ATCGGGAAACTGGTGCTAATAC<br>CGCATGATGCCTGAGGGCCAAA<br>GGAGAGATCCGCCATTGGAGG<br>GGCCTGCGTTCGATTAGCTAGT<br>TGGTTGGGTAAAGGCTGACCAA<br>GGCGATGATCGATAGCTGGTTT<br>GAGAGGATGATCAGCCACACTG<br>GGACTGAGACACGGCCCAGAC<br>TCCTACGGGAGGCAGCAGTGG<br>GGAATATTGGACAATGGGGGCA<br>ACCCTGATCCAGCAATGCCGCG<br>TGTGTGAAGAAGGTCTTCGGAT<br>TGTAAAGCACTTTCACTAGGGA<br>AGATGATGACGGTACCTAGAGA<br>AGAAGCCCCGGCTAACTTCGTG<br>CCAGCAGCCGCGGTAATACGAA<br>GGGGGCTAGCGTTGCTCGGAA<br>TGACTGGGCGTAAAGGGCGCG<br>TAGGCTGTTTGTACAGTCAGAT<br>GTGAAATCCCCGGGCTTAACCT<br>GGGAACTGCATTTGATACGTGC<br>AGACTAGAGTCCGAGAGAGGGT<br>TGTGGAATTCCCAGTGTAGAGG<br>TGAAATTCGTAGATATTGGGAA<br>GAACACCGGTTGCGAAGGCGG<br>CAACCTGGCTNNNNNNNNNNNN<br>NNNNNNNNNNNNNNNNNNNNNN<br>NNNNNNNNNNNNNNNNNNNNNN<br>NNNNNNNNNNNNNNNNNNNNNN<br>NNNNNNNNNNNNNNNNNNNNNN<br>NNNNNNNNNNNNNNNNNNNGAG<br>CTAACGCGTTAAGCACACCGCC<br>TGGGGAGTACGGCCGCAAGGT<br>TGAAACTCAAAGGAATTGACGG<br>GGGCCCGCACAAGCGGTGGAG<br>CATGTGGTTTAATTCGAAGCAA<br>CGCGCAGAACCTTACCAGGGCT<br>TGCATGGGGAGGCTGTATTCAG<br>AGATGGATATTTCTTCGGACCT<br>CCCGCACAGGTGCTGCATGGCT<br>GTCGTCAGCTCGTGTCGTGAGA<br>TGTTGGGTTAAGTCCCGCAACG<br>AGCGCAACCCTTGTCTTTAGTT<br>GCCATCACGTCTGGGTGGGCA<br>CTCTAGAGAGACTGCCGGTGAC<br>AAGCCGGAGGAAGGTGGGGAT<br>GACGTCAAGTCCTCATGGCCCT<br>TATGTCCTGGGCTACACACGTG<br>CTACAATGGCGGTGACAGAGG<br>GATGCTACATGGTGACATGGTG<br>CTGATCTCAAAAAACCGTCTCA<br>GTTCGGATTGTACTCTGCAACT<br>CGAGTGCATGAAGGTGGAATCG<br>CTAGTAATCGCGGATCAGCATG |

TABLE 1-continued

Examples of Target Bacteria and Host Insects

| | | | |
|---|---|---|---|
| | | | CCGCGGTGAATACGTTCCCGG<br>GCCTTGTACACACCGCCCGTCA<br>CACCATGGGAGTTGGTTTGACC<br>TTAAGCCGGTGAGCGAACCGCA<br>AGGAACGCAGCCGACCACCGG<br>TTCGGGTTCAGCGACTGGGGG<br>A<br>(SEQ ID NO: 36) |
| Lactobacillus kunkeei | honeybee (Apis mellifera) | Gut | TTCCTTAGAAAGGAGGTGATCC<br>AGCCGCAGGTTCTCCTACGGCT<br>ACCTTGTTACGACTTCACCCTAA<br>TCATCTGTCCCACCTTAGACGA<br>CTAGCTCCTAAAAGGTTACCCC<br>ATCGTCTTTGGGTGTTACAAACT<br>CTCATGGTGTGACGGGCGGTGT<br>GTACAAGGCCCGGGAACGTATT<br>CACCGTGGCATGCTGATCCACG<br>ATTACTAGTGATTCCAACTTCAT<br>GCAGGCGAGTTGCAGCCTGCA<br>ATCCGAACTGAGAATGGCTTTA<br>AGAGATTAGCTTGACCTCGCGG<br>TTTCGCGACTCGTTGTACCATC<br>CATTGTAGCACGTGTGTAGCCC<br>AGCTCATAAGGGGCATGATGAT<br>TTGACGTCGTCCCCACCTTCCT<br>CCGGTTTATCACCGGCAGTCTC<br>ACTAGAGTGCCCAACTAAATGC<br>TGGCAACTAATAATAAGGGTTG<br>CGCTCGTTGCGGGACTTAACCC<br>AACATCTCACGACACGAGCTGA<br>CGACAACCATGCACCACCTGTC<br>ATTCTGTCCCCGAAGGGAACGC<br>CCAATCTCTTGGGTTGGCAGAA<br>GATGTCAAGAGCTGGTAAGGTT<br>CTTCGCGTAGCATCGAATTAAA<br>CCACATGCTCCACCACTTGTGC<br>GGGCCCCCGTCAATTCCTTTGA<br>GTTTCAACCTTGCGGTCGTACT<br>CCCCAGGCGGAATACTTAATGC<br>GTTAGCTGCGGCACTGAAGGG<br>CGGAAACCCTCCAACACCTAGT<br>ATTCATCGTTTACGGCATGGAC<br>TACCAGGGTATCTAATCCTGTTC<br>GCTACCCATGCTTTCGAGCCTC<br>AGCGTCAGTAACAGACCAGAAA<br>GCCGCCTTCGCCACTGGTGTTC<br>TTCCATATATCTACGCATTTCAC<br>CGCTACACATGGAGTTCCACTT<br>TCCTCTTCTGTACTCAAGTTTTG<br>TAGTTTCCACTGCACTTCCTCAG<br>TTGAGCTGAGGGCTTTCACAGC<br>AGACTTACAAAACCGCCTGCGC<br>TCGCTTTACGCCCAATAAATCC<br>GGACAACGCTTGCCACCTACGT<br>ATTACCGCGGCTGCTGGCACGT<br>AGTTAGCCGTGGCTTTCTGGTT<br>AAATACCGTCAAAGTGTTAACA<br>GTTACTCTAACACTTGTTCTTCT<br>TTAACAACAGAGTTTTACGATCC<br>GAAAACCTTCATCACTCACGCG<br>GCGTTGCTCCATCAGACTTTCG<br>TCCATTGTGGAAGATTCCCTACT<br>GCTGCCTCCCGTAGGAGTCTGG<br>GCCGTGTCTCAGTCCCAATGTG<br>GCCGATTACCCTCTCAGGTCGG<br>CTACGTATCATCGTCTTGGTGG<br>GCTTTTATCTCACCAACTAACTA<br>ATACGGCGCGGGTCCATCCCAA<br>AGTGATAGCAAAGCCATCTTTC<br>AAGTTGGAACCATGCGGTTCCA<br>ACTAATTATGCGGTATTAGCACT<br>TGTTTCCAAATGTTATCCCCCGC<br>TTCGGGGCAGGTTACCCACGTG<br>TTACTCACCAGTTCGCCACTCG<br>CTCCGAATCCAAAAATCATTTAT<br>GCAAGCATAAAATCAATTTGGG<br>AGAACTCGTTCGACTTGCATGT |

TABLE 1-continued

Examples of Target Bacteria and Host Insects

| | | | |
|---|---|---|---|
| | | | ATTAGGCACGCCGCCAGCGTTC<br>GTCCTGAGCCAGGATCAAACTC<br>TCATCTTAA<br>(SEQ ID NO: 37) |
| Lactobacillus Firm-4 | honeybee (Apis mellifera) | Gut | ACGAACGCTGGCGGCGTGCCT<br>AATACATGCAAGTCGAGCGCGG<br>GAAGTCAGGGAAGCCTTCGGGT<br>GGAACTGGTGGAACGAGCGGC<br>GGATGGGTGAGTAACACGTAGG<br>TAACCTGCCCTAAAGCGGGGGA<br>TACCATCTGGAAACAGGTGCTA<br>ATACCGCATAAACCCAGCAGTC<br>ACATGAGTGCTGGTTGAAAGAC<br>GGCTTCGGCTGTCACTTTAGGA<br>TGGACCTGCGGCGTATTAGCTA<br>GTTGGTGGAGTAACGGTTCACC<br>AAGGCAATGATACGTAGCCGAC<br>CTGAGAGGGTAATCGGCCACAT<br>TGGGACTGAGACACGGCCCAAA<br>CTCCTACGGGAGGCAGCAGTA<br>GGGAATCTTCCACAATGGACGC<br>AAGTCTGATGGAGCAACGCCGC<br>GTGGATGAAGAAGGTCTTCGGA<br>TCGTAAAATCCTGTTGTTGAAGA<br>AGAACGGTTGTGAGAGTAACTG<br>CTCATAACGTGACGGTAATCAA<br>CCAGAAAGTCACGGCTAACTAC<br>GTGCCAGCAGCCGCGGTAATAC<br>GTAGGTGGCAAGCGTTGTCCG<br>GATTTATTGGGCGTAAAGGGAG<br>CGCAGGCGGTCTTTTAAGTCTG<br>AATGTGAAAGCCCTCAGCTTAA<br>CTGAGGAAGAGCATCGGAAACT<br>GAGAGACTTGAGTGCAGAAGAG<br>GAGAGTGGAACTCCATGTGTAG<br>CGGTGAAATGCGTAGATATATG<br>GAAGAACACCAGTGGCGAAGG<br>CGGCTCTCTGGTCTGTTACTGA<br>CGCTGAGGCTCGAAAGCATGG<br>GTAGCGAACAGGATTAGATACC<br>CTGGTAGTCCATGCCGTAAACG<br>ATGAGTGCTAAGTGTTGGGAGG<br>TTTCCGCCTCTCAGTGCTGCAG<br>CTAACGCATTAAGCACTCCGCC<br>TGGGGAGTACGACCGCAAGGTT<br>GAAACTCAAAGGAATTGACGGG<br>GGCCCGCACAAGCGGTGGAGC<br>ATGTGGTTTAATTCGAAGCAAC<br>GCGAAGAACCTTACCAGGTCTT<br>GACATCTCCTGCAAGCCTAAGA<br>GATTAGGGGTTCCCTTCGGGGA<br>CAGGAAGACAGGTGGTGCATG<br>GTTGTCGTCAGCTCGTGTCGTG<br>AGATGTTGGGTTAAGTCCCGCA<br>ACGAGCGCAACCCTTGTTACTA<br>GTTGCCAGCATTAAGTTGGGCA<br>CTCTAGTGAGACTGCCGGTGAC<br>AAACCGGAGGAAGGTGGGGAC<br>GACGTCAAATCATCATGCCCCT<br>TATGACCTGGGCTACACACGTG<br>CTACAATGGATGGTACAATGAG<br>AAGCGAACTCGCGAGGGGAAG<br>CTGATCTCTGAAAACCATTCTCA<br>GTTCGGATTGCAGGCTGCAACT<br>CGCCTGCATGAAGCTGGAATCG<br>CTAGTAATCGCGGATCAGCATG<br>CCGCGGTGAATACGTTCCCGG<br>GCCTTGTACACACCGCCC<br>(SEQ ID NO: 38) |

Silk worm

| | | | |
|---|---|---|---|
| Enterococcus | Bombyx mori | Gut | AGGTGATCCAGCCGCACCTTCC<br>GATACGGCTACCTTGTTACGAC<br>TTCACCCCAATCATCTATCCCAC<br>CTTAGGCGGCTGGCTCCAAAAA<br>GGTTACCTCACCGACTTCGGGT |

TABLE 1-continued

Examples of Target Bacteria and Host Insects

|  |  |  |  |
|---|---|---|---|
|  |  |  | GTTACAAACTCTCGTGGTGTGA |
|  |  |  | CGGGCGGTGTGTACAAGGCCC |
|  |  |  | GGGAACGTATTCACCGCGGCGT |
|  |  |  | GCTGATCCGCGATTACTAGCGA |
|  |  |  | TTCCGGCTTCATGCAGGCGAGT |
|  |  |  | TGCAGCCTGCAATCCGAACTGA |
|  |  |  | GAGAAGCTTTAAGAGATTTGCA |
|  |  |  | TGACCTCGCGGTCTAGCGACTC |
|  |  |  | GTTGTACTTCCCATTGTAGCAC |
|  |  |  | GTGTGTAGCCCAGGTCATAAGG |
|  |  |  | GGCATGATGATTTGACGTCATC |
|  |  |  | CCCACCTTCCTCCGGTTTGTCA |
|  |  |  | CCGGCAGTCTCGCTAGAGTGCC |
|  |  |  | CAACTAAATGATGGCAACTAAC |
|  |  |  | AATAAGGGTTGCGCTCGTTGCG |
|  |  |  | GGACTTAACCCAACATCTCACG |
|  |  |  | ACACGAGCTGACGACAACCATG |
|  |  |  | CACCACCTGTCACTTTGTCCCC |
|  |  |  | GAAGGGAAAGCTCTATCTCTAG |
|  |  |  | AGTGGTCAAAGGATGTCAAGAC |
|  |  |  | CTGGTAAGGTTCTTCGCGTTGC |
|  |  |  | TTCGAATTAAACCACATGCTCCA |
|  |  |  | CCGCTTGTGCGGGCCCCCGTC |
|  |  |  | AATTCCTTTGAGTTTCAACCTTG |
|  |  |  | CGGTCGTACTCCCCAGGCGGA |
|  |  |  | GTGCTTAATGCGTTTGCTGCAG |
|  |  |  | CACTGAAGGGCGGAAACCCTCC |
|  |  |  | AACACTTAGCACTCATCGTTTAC |
|  |  |  | GGCGTGGACTACCAGGGTATCT |
|  |  |  | AATCCTGTTTGCTCCCCACGCT |
|  |  |  | TTCGAGCCTCAGCGTCAGTTAC |
|  |  |  | AGACCAGAGAGCCGCCTTCGC |
|  |  |  | CACTGGTGTTCCTCCATATATCT |
|  |  |  | ACGCATTTCACCGCTACACATG |
|  |  |  | GAATTCCACTCTCCTCTTCTGCA |
|  |  |  | CTCAAGTCTCCCAGTTTCCAAT |
|  |  |  | GACCCTCCCCGGTTGAGCCGG |
|  |  |  | GGGCTTTCACATCAGACTTAAG |
|  |  |  | AAACCGCCTGCGCTCGCTTTAC |
|  |  |  | GCCCAATAAATCCGGACAACGC |
|  |  |  | TTGCCACCTACGTATTACCGCG |
|  |  |  | GCTGCTGGCACGTAGTTAGCCG |
|  |  |  | TGGCTTTCTGGTTAGATACCGT |
|  |  |  | CAGGGGACGTTCAGTTACTAAC |
|  |  |  | GTCCTTGTTCTTCTCTAACAACA |
|  |  |  | GAGTTTTACGATCCGAAAACCTT |
|  |  |  | CTTCACTCACGCGGCGTTGCTC |
|  |  |  | GGTCAGACTTTCGTCCATTGCC |
|  |  |  | GAAGATTCCCTACTGCTGCCTC |
|  |  |  | CCGTAGGAGTCTGGGCCGTGT |
|  |  |  | CTCAGTCCCAGTGTGGCCGATC |
|  |  |  | ACCCTCTCAGGTCGGCTATGCA |
|  |  |  | TCGTGGCCTTGGTGAGCCGTTA |
|  |  |  | CCTCACCAACTAGCTAATGCAC |
|  |  |  | CGCGGGTCCATCCATCAGCGAC |
|  |  |  | ACCCGAAAGCGCCTTTCACTCT |
|  |  |  | TATGCCATGCGGCATAAACTGT |
|  |  |  | TATGCGGTATTAGCACCTGTTTC |
|  |  |  | CAAGTGTTATCCCCCTCTGATG |
|  |  |  | GGTAGGTTACCCACGTGTTACT |
|  |  |  | CACCCGTCCGCCACTCCTCTTT |
|  |  |  | CCAATTGAGTGCAAGCACTCGG |
|  |  |  | GAGGAAAGAAGCGTTCGACTTG |
|  |  |  | CATGTATTAGGCACGCCGCCAG |
|  |  |  | CGTTCGTCCTGAGCCAGGATCA |
|  |  |  | AACTCT |
|  |  |  | (SEQ ID NO: 39) |
| Delftia | Bombyx mori | Gut | CAGAAAGGAGGTGATCCAGCC |
|  |  |  | GCACCTTCCGATACGGCTACCT |
|  |  |  | TGTTACGACTTCACCCCAGTCA |
|  |  |  | CGAACCCCGCCGTGGTAAGCG |
|  |  |  | CCCTCCTTGCGGTTAGGCTACC |
|  |  |  | TACTTCTGGCGAGACCCGCTCC |
|  |  |  | CATGGTGTGACGGGCGGTGTG |
|  |  |  | TACAAGACCCGGGAACGTATTC |
|  |  |  | ACCGCGGCATGCTGATCCGCG |
|  |  |  | ATTACTAGCGATTCCGACTTCAC |

TABLE 1-continued

Examples of Target Bacteria and Host Insects

|  |  |  | GCAGTCGAGTTGCAGACTGCGA<br>TCCGGACTACGACTGGTTTTAT<br>GGGATTAGCTCCCCCTCGCGG<br>GTTGGCAACCCTCTGTACCAGC<br>CATTGTATGACGTGTGTAGCCC<br>CACCTATAAGGGCCATGAGGAC<br>TTGACGTCATCCCCACCTTCCT<br>CCGGTTTGTCACCGGCAGTCTC<br>ATTAGAGTGCTCAACTGAATGTA<br>GCAACTAATGACAAGGGTTGCG<br>CTCGTTGCGGGACTTAACCCAA<br>CATCTCACGACACGAGCTGACG<br>ACAGCCATGCAGCACCTGTGTG<br>CAGGTTCTCTTTCGAGCACGAA<br>TCCATCTCTGGAAACTTCCTGC<br>CATGTCAAAGGTGGGTAAGGTT<br>TTTCGCGTTGCATCGAATTAAAC<br>CACATCATCCACCGCTTGTGCG<br>GGTCCCCGTCAATTCCTTTGAG<br>TTTCAACCTTGCGGCCGTACTC<br>CCCAGGCGGTCAACTTCACGCG<br>TTAGCTTCGTTACTGAGAAAACT<br>AATTCCCAACAACCAGTTGACAT<br>CGTTTAGGGCGTGGACTACCAG<br>GGTATCTAATCCTGTTTGCTCCC<br>CACGCTTTCGTGCATGAGCGTC<br>AGTACAGGTCCAGGGGATTGCC<br>TTCGCCATCGGTGTTCCTCCGC<br>ATATCTACGCATTTCACTGCTAC<br>ACGCGGAATTCCATCCCCCTCT<br>ACCGTACTCTAGCCATGCAGTC<br>ACAAATGCAGTTCCCAGGTTGA<br>GCCCGGGGATTTCACATCTGTC<br>TTACATAACCGCCTGCGCACGC<br>TTTACGCCCAGTAATTCCGATTA<br>ACGCTCGCACCCTACGTATTAC<br>CGCGGCTGCTGGCACGTAGTTA<br>GCCGGTGCTTATTCTTACGGTA<br>CCGTCATGGGCCCCCTGTATTA<br>GAAGGAGCTTTTTCGTTCCGTA<br>CAAAAGCAGTTTACAACCCGAA<br>GGCCTTCATCCTGCACGCGGCA<br>TTGCTGGATCAGGCTTTCGCCC<br>ATTGTCCAAAATTCCCCACTGCT<br>GCCTCCCGTAGGAGTCTGGGC<br>CGTGTCTCAGTCCCAGTGTGGC<br>TGGTCGTCCTCTCAGACCAGCT<br>ACAGATCGTCGGCTTGGTAAGC<br>TTTTATCCCACCAACTACCTAAT<br>CTGCCATCGGCCGCTCCAATCG<br>CGCGAGGCCCGAAGGGCCCCC<br>GCTTTCATCCTCAGATCGTATG<br>CGGTATTAGCTACTCTTTCGAGT<br>AGTTATCCCCCACGACTGGGCA<br>CGTTCCGATGTATTACTCACCC<br>GTTCGCCACTCGTCAGCGTCCG<br>AAGACCTGTTACCGTTCGACTT<br>GCATGTGTAAGGCATGCCGCCA<br>GCGTTCAATCTGAGCCAGGATC<br>AAACTCTACAGTTCGATCT<br>(SEQ ID NO: 40) |
| Pelomonas | Bombyx mori | Gut | ATCCTGGCTCAGATTGAACGCT<br>GGCGGCATGCCTTACACATGCA<br>AGTCGAACGGTAACAGGTTAAG<br>CTGACGAGTGGCGAACGGGTG<br>AGTAATATATCGGAACGTGCCC<br>AGTCGTGGGGATAACTGCTCG<br>AAAGAGCAGCTAATACCGCATA<br>CGACCTGAGGGTGAAAGCGGG<br>GGATCGCAAGACCTCGCNNGAT<br>TGGAGCGGCCGATATCAGATTA<br>GGTAGTTGGTGGGGTAAAGGC<br>CCACCAAGCCAACGATCTGTAG<br>CTGGTCTGAGAGGACGACCAG<br>CCACACTGGGACTGAGACACG<br>GCCCAGACTCCTACGGGAGGC<br>AGCAGTGGGGAATTTTGGACAA |

TABLE 1-continued

Examples of Target Bacteria and Host Insects

```
TGGGCGCAAGCCTGATCCAGC
CATGCCGCGTGCGGGAAGAAG
GCCTTCGGGTTGTAAACCGCTT
TTGTCAGGGAAGAAAAGGTTCT
GGTTAATACCTGGGACTCATGA
CGGTACCTGAAGAATAAGCACC
GGCTAACTACGTGCCAGCAGCC
GCGGTAATACGTAGGGTGCAAG
CGTTAATCGGAATTACTGGGCG
TAAAGCGTGCGCAGGCGGTTAT
GCAAGACAGAGGTGAAATCCCC
GGGCTCAACCTGGGAACTGCCT
TTGTGACTGCATAGCTAGAGTA
CGGTAGAGGGGGATGGAATTC
CGCGTGTAGCAGTGAAATGCGT
AGATATGCGGAGGAACACCGAT
GGCGAAGGCAATCCCCTGGAC
CTGTACTGACGCTCATGCACGA
AAGCGTGGGGAGCAAACAGGA
TTAGATACCCTGGTAGTCCACG
CCCTAAACGATGTCAACTGGTT
GTTGGGAGGGTTTCTTCTCAGT
AACGTANNTAACGCGTGAAGTT
GACCGCCTGGGGAGTACGGCC
GCAAGGTTGAAACTCAAAGGAA
TTGACGGGGACCCGCACAAGC
GGTGGATGATGTGGTTTAATTC
GATGCAACGCGAAAAACCTTAC
CTACCCTTGACATGCCAGGAAT
CCTGAAGAGATTTGGGAGTGCT
CGAAAGAGAACCTGGACACAGG
TGCTGCATGGCCGTCGTCAGCT
CGTGTCGTGAGATGTTGGGTTA
AGTCCCGCAACGAGCGCAACC
CTTGTCATTAGTTGCTACGAAAG
GGCACTCTAATGAGACTGCCGG
TGACAAACCGGAGGAAGGTGG
GGATGACGTCAGGTCATCATGG
CCCTTATGGGTAGGGCTACACA
CGTCATACAATGGCCGGGACAG
AGGGCTGCCAACCCGCGAGGG
GGAGCTAATCCCAGAAACCCGG
TCGTAGTCCGGATCGTAGTCTG
CAACTCGACTGCGTGAAGTCGG
AATCGCTAGTAATCGCGGATCA
GCTTGCCGCGGTGAATACGTTC
CCGGGTCTTGTACACACCGCCC
GTCACACCATGGGAGCGGGTTC
TGCCAGAAGTAGTTAGCCTAAC
CGCAAGGAGGGCGATTACCAC
GGCAGGGTTCGTGACTGGGGT
GAAGTCGTAACAAGGTAGCCGT
ATCGGAAGGTGCGGCTGGATCA
C
(SEQ ID NO: 41)
```

Any number of bacterial species may be targeted by the compositions or methods described herein. For example, in some instances, the modulating agent may target a single bacterial species. In some instances, the modulating agent may target at least about any of 1, 2, 3, 4, 5, 6, 7, 8, 9, 10, 15, 20, 30, 40, 50, 60, 70, 80, 90, 100, 150, 200, 250, 500, or more distinct bacterial species. In some instances, the modulating agent may target any one of about 1 to about 5, about 5 to about 10, about 10 to about 20, about 20 to about 50, about 50 to about 100, about 100 to about 200, about 200 to about 500, about 10 to about 50, about 5 to about 20, or about 10 to about 100 distinct bacterial species. In some instances, the modulating agent may target at least about any of 1, 2, 3, 4, 5, 6, 7, 8, 9, 10, 15, 20, 30, 40, 50, 60, 70, 80, 90, 100, or more phyla, classes, orders, families, or genera of bacteria.

In some instances, the modulating agent may increase a population of one or more bacteria (e.g., symbiotic bacteria) by at least about any of 10%, 20%, 30%, 40%, 50%, 60%, 70%, 80%, 90% or more in the host in comparison to a host organism to which the modulating agent has not been administered. In some instances, the modulating agent may reduce the population of one or more bacteria (e.g., pathogenic or parasitic bacteria) by at least about any of 10%, 20%, 30%, 40%, 50%, 60%, 70%, 80%, 90%, or more in the host in comparison to a host organism to which the modulating agent has not been administered. In some instances, the modulating agent may eradicate the population of a bacterium (e.g., a pathogenic or parasitic bacteria) in the host. In some instances, the modulating agent may increase the level of one or more symbiotic bacteria by at least about any of 10%, 20%, 30%, 40%, 50%, 60%, 70%, 80%, 90% or more in the host and/or decreases the level of one or more pathogenic bacteria by at least about any of 10%, 20%, 30%, 40%, 50%, 60%, 70%, 80%, 90%, or more in the host in comparison to a host organism to which the modulating agent has not been administered.

In some instances, the modulating agent may alter the bacterial diversity and/or bacterial composition of the host. In some instances, the modulating agent may increase the bacterial diversity in the host relative to a starting diversity by at least about any of 10%, 20%, 30%, 40%, 50%, 60%, 70%, 80%, 90%, or more in comparison to a host organism to which the modulating agent has not been administered. In some instances, the modulating agent may decrease the bacterial diversity in the host relative to a starting diversity by at least about any of 10%, 20%, 30%, 40%, 50%, 60%, 70%, 80%, 90%, or more in comparison to a host organism to which the modulating agent has not been administered.

In some instances, the modulating agent may alter the function, activity, growth, and/or division of one or more bacterial cells. For example, the modulating agent may alter the expression of one or genes in the bacteria. In some instances, the modulating agent may alter the function of one or more proteins in the bacteria. In some instances, the modulating agent may alter the function of one or more cellular structures (e.g., the cell wall, the outer or inner membrane) in the bacteria. In some instances, the modulating agent may kill (e.g., lyse) the bacteria.

The target bacterium may reside in one or more parts of the insect. Further, the target bacteria may be intracellular or extracellular. In some instances, the bacteria reside in or on one or more parts of the host gut, including, e.g., the foregut, midgut, and/or hindgut. In some instances, the bacteria reside as an intracellular bacteria within a cell of the host insect. In some instances, the bacteria reside in a bacteriocyte of the host insect.

Changes to the populations of bacteria in the host may be determined by any methods known in the art, such as microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), and DNA sequencing. In some instances, a sample of the host treated with a modulating agent is sequenced (e.g., by metagenomics sequencing of 16S rRNA or rDNA) to determine the microbiome of the host after delivery or administration of the modulating agent. In some instances, a sample of a host that did not receive the modulating agent is also sequenced to provide a reference.

ii. Fungi

Exemplary fungi that may be targeted in accordance with the methods and compositions provided herein, include, but are not limited to *Amylostereum areolatum, Epichloe* spp, *Pichia pinus, Hansenula capsulate, Daldinia decipien, Ceratocytis* spp, *Ophiostoma* spp, and *Attamyces bromatificus*. Non-limiting examples of yeast and yeast-like symbionts found in insects include *Candida, Metschnikowia, Debaromyces, Scheffersomyces shehatae* and *Scheffersomyces stipites, Starmerella, Pichia, Trichosporon, Cryptococcus, Pseudozyma*, and yeast-like symbionts from the subphylum *Pezizomycotina* (e.g., *Symbiotaphrina bucneri* and *Symbiotaphrina kochii*). Non-limiting examples of yeast that may be targeted by the methods and compositions herein are listed in Table 2.

TABLE 2

| Insect Species | Order: Family | Yeast Location (Species) |
|---|---|---|
| *Stegobium paniceum* (=*Sitodrepa panicea*) | Coleoptera: Anobiidae | Mycetomes (*Saccharomyces*) Cecae (*Torulopsis buchnerii*) Mycetome between foregut and midgut Mycetomes (*Symbiotaphrina buchnerii*) Mycetomes and digestive tube (*Torulopsis buchnerii*) Gut cecae (*Symbiotaphrina buchnerii*) |
| *Lasioderma serricorne* | Coleoptera: Anobiidae | Mycetome between foregut and midgut (*Symbiotaphrina kochii*) |
| *Ernobius abietis* | Coleoptera: Anobiidae | Mycetomes (*Torulopsis karawaiewii*) (*Candida karawaiewii*) |
| *Ernobius mollis* | Coleoptera: Anobiidae | Mycetomes (*Torulopsis ernobii*) (*Candida ernobii*) |
| *Hemicoelus gibbicollis* | Coleoptera: Anobiidae | Larval mycetomes |
| *Xestobium plumbeum* | Coleoptera: Anobiidae | Mycetomes (*Torulopsis xestobii*) (*Candida xestobii*) |
| *Criocephalus rusticus* | Coleoptera: Cerambycidae | Mycetomes |
| *Phoracantha semipunctata* | Coleoptera: Cerambycidae | Alimentary canal (*Candida guilliermondii, C. tenuis*) Cecae around midgut (*Candida guilliermondii*) |
| *Harpium inquisitor* | Coleoptera: Cerambycidae | Mycetomes (*Candida rhagii*) |
| *Harpium mordax* H. *sycophanta* | Coleoptera: Cerambycidae | Cecae around midgut (*Candida tenuis*) |
| *Gaurotes virginea* | Coleoptera: Cerambycidae | Cecae around midgut (*Candida rhagii*) |
| *Leptura rubra* | Coleoptera: Cerambycidae | Cecae around midgut (*Candida tenuis*) Cecae around midgut (*Candida parapsilosis*) |
| *Leptura maculicornis* L. *cerambyciformis* | Coleoptera: Cerambycidae | Cecae around midgut (*Candida parapsilosis*) |
| *Leptura sanguinolenta* | Coleoptera: Cerambycidae | Cecae around midgut (*Candida* sp.) |
| *R hagium bifasciatum* | Coleoptera: Cerambycidae | Cecae around midgut (*Candida tenuis*) |
| *Rhagium inquisitor* | Coleoptera: Cerambycidae | Cecae around midgut (*Candida guilliermondii*) |
| *Rhagium mordax* | Coleoptera: Cerambycidae | Cecae around midgut (*Candida*) |
| *Carpophilus hemipterus* | Coleoptera: Nitidulidae | Intestinal tract (10 yeast species) |

TABLE 2-continued

| Insect Species | Order: Family | Yeast Location (Species) |
|---|---|---|
| *Odontotaenius disjunctus* | Coleoptera: Passalidae | Hindgut (*Enteroramus dimorphus*) |
| *Odontotaenius disjunctus* | Coleoptera: Passalidae | Gut (*Pichia stipitis*, *P. segobiensis*, *Candida shehatae*) |
| *Verres sternbergianus* | | (*C. ergatensis*) |
| *Scarabaeus semipunctatus* *Chironitis furcifer* | Coleoptera: Scarabaeidae | Digestive tract (10 yeast species) |
| Unknown species | Coleoptera: Scarabaeidae | Guts (*Trichosporon cutaneum*) |
| *Dendroctonus* and *Ips* spp. | Coleoptera: Scolytidae | Alimentary canal (13 yeast species) |
| *Dendroctonus frontalis* | Coleoptera: Scolytidae | Midgut (*Candida* sp.) |
| *Ips sexdentatus* | Coleoptera: Scolytidae | Digestive tract (*Pichia bovis*, *P. rhodanensis*) |
| | | *Hansenula holstii* (*Candida rhagii*) |
| | | Digestive tract |
| | | (*Candida pulcherina*) |
| *Ips typographus* | Coleoptera: Scolytidae | Alimentary canal |
| | | Alimentary tracts (*Hansenula capsulata*, *Candida parapsilosis*) |
| | | Guts and beetle homogenates (*Hansenula holstii*, *H. capsulata*, *Candida diddensii*, *C. mohschtana*, *C. nitratophila*, *Cryptococcus albidus*, *C. laurentii*) |
| *Trypodendron lineatum* | Coleoptera: Scolytidae | Not specified |
| *Xyloterinus politus* | Coleoptera: Scolytidae | Head, thorax, abdomen (*Candida*, *Pichia*, *Saccharomycopsis*) |
| *Periplaneta americana* | Dictyoptera: Blattidae | Hemocoel (*Candida* sp. nov.) |
| *Blatta orientalis* | Dictyoptera: Blattidae | Intestinal tract (*Kluyveromyces blattae*) |
| *Blatella germanica* | Dictyoptera: Blattellidae | Hemocoel |
| *Cryptocercus punctulatus* | Dictyoptera: Cryptocercidae | Hindgut (1 yeast species) |
| *Philophylla heraclei* | Diptera: Tephritidae | Hemocoel |
| *Aedes* (4 species) | Diptera: Culicidae | Internal microflora (9 yeast genera) |
| *Drosophila pseudoobscura* | Diptera: Drosophilidae | Alimentary canal (24 yeast species) |
| *Drosophila* (5 spp.) | Diptera: Drosophilidae | Crop (42 yeast species) |
| *Drosophila melanogaster* | Diptera: Drosophilidae | Crop (8 yeast species) |
| *Drosophila* (4 spp.) | Diptera: Drosophilidae | Crop (7 yeast species) |
| *Drosophila* (6 spp.) | Diptera: Drosophilidae | Larval gut (17 yeast species) |
| *Drosophila* (20 spp.) | Diptera: Drosophilidae | Crop (20 yeast species) |
| *Drosophila* (8 species groups) | Diptera: Drosophilidae | Crop (*Kloeckera*,*Candida*, *Kluyveromyces*) |
| *Drosophila serido* | Diptera: Drosophilidae | Crop (18 yeast species) |
| *Drosophila* (6 spp.) | Diptera: Drosophilidae | Intestinal epithelium (*Coccidiascus legeri*) |
| *Protaxymia melanoptera* | Diptera | Unknown (*Candida*, *Cryptococcus*, *Sporoblomyces*) |
| *Astegopteryx styraci* | Homoptera: Aphididae | Hemocoel and fat body |
| *Tuberaphis* sp. *Hamiltonaphis styraci* *Glyphinaphis bambusae* *Cerataphis* sp. | Homoptera: Aphididae | Tissue sections |
| *Hamiltonaphis styraci* | Homoptera: Aphididae | Abdominal hemocoel |
| *Cofana unimaculata* | Homoptera: Cicadellidae | Fat body |
| *Leofa unicolor* | Homoptera: Cicadellidae | Fat body |
| Lecaniines, etc. | Homoptera: Coccoidea d | Hemolymph, fatty tissue, etc. |
| *Lecanium* sp. | Homoptera: Coccidae | Hemolymph, adipose tissue |
| *Ceroplastes* (4 sp.) | Homoptera: Coccidae | Blood smears |
| *Laodelphax striatellus* | Homoptera: Delphacidae | Fat body |
| | | Eggs |
| | | Eggs (*Candida*) |
| *Nilaparvata lugens* | Homoptera: Delphacidae | Fat body |
| | | Eggs (2 unidentified yeast species) |
| | | Eggs, nymphs (*Candida*) |
| | | Eggs (7 unidentified yeast species) |
| | | Eggs (*Candida*) |
| *Nisia nervosa* *Nisia grandiceps* *Perkinsiella* spp. *Sardia rostrata* *Sogatella furcifera* | Homoptera: Delphacidae | Fat body |
| *Sogatodes orizicola* | Homoptera: Delphacidae | Fat body |
| *Amrasca devastans* | Homoptera: Jassidae | Eggs, mycetomes, hemolymph |

TABLE 2-continued

| Insect Species | Order: Family | Yeast Location (Species) |
| --- | --- | --- |
| *Tachardina lobata* | Homoptera: Kerriidae | Blood smears (*Torulopsis*) |
| *Laccifer* (=*Lakshadia*) sp. | Homoptera: Kerriidae | Blood smears (*Torula variabilis*) |
| *Comperia merceti* | Hymenoptera: Encyrtidae | Hemolymph, gut, poison gland |
| *Solenopsis invicta* | Hymenoptera: Formicidae | Hemolymph (*Myrmecomyces annellisae*) |
| *S. quinquecuspis* | | |
| *Solenopsis invicta* | Hymenoptera: Formicidae | Fourth instar larvae (*Candida parapsilosis, Yarrowia lipolytica*) Gut and hemolymph (*Candida parapsilosis, C. lipolytica, C. guillermondii, C. rugosa, Debaryomyces hansenii*) |
| *Apis mellifera* | Hymenoptera: Apidae | Digestive tracts (*Torulopsis* sp.) Intestinal tract (*Torulopsis apicola*) Digestive tracts (8 yeast species) Intestinal contents (12 yeast species) Intestinal contents (7 yeast species) Intestines (14 yeast species) Intestinal tract (*Pichia melissophila*) Intestinal tracts (7 yeast species) Alimentary canal (*Hansenula silvicola*) Crop and gut (13 yeast species) |
| *Apis mellifera* | Hymenoptera: Apidae | Midguts (9 yeast genera) |
| *Anthophora occidentalis* | Hymenoptera: Anthophoridae | |
| *Nomia melanderi* | Hymenoptera: Halictidae | |
| *Halictus rubicundus* | Hymenoptera: Halictidae | |
| *Megachile rotundata* | Hymenoptera: Megachilidae | |

Any number of fungal species may be targeted by the compositions or methods described herein. For example, in some instances, the modulating agent may target a single fungal species. In some instances, the modulating agent may target at least about any of 1, 2, 3, 4, 5, 6, 7, 8, 9, 10, 15, 20, 30, 40, 50, 60, 70, 80, 90, 100, 150, 200, 250, 500, or more distinct fungal species. In some instances, the modulating agent may target any one of about 1 to about 5, about 5 to about 10, about 10 to about 20, about 20 to about 50, about 50 to about 100, about 100 to about 200, about 200 to about 500, about 10 to about 50, about 5 to about 20, or about 10 to about 100 distinct fungal species. In some instances, the modulating agent may target at least about any of 1, 2, 3, 4, 5, 6, 7, 8, 9, 10, 15, 20, 30, 40, 50, 60, 70, 80, 90, 100, or more phyla, classes, orders, families, or genera of fungi.

In some instances, the modulating agent may increase a population of one or more fungi (e.g., symbiotic fungi) by at least about any of 10%, 20%, 30%, 40%, 50%, 60%, 70%, 80%, 90% or more in the host in comparison to a host organism to which the modulating agent has not been administered. In some instances, the modulating agent may reduce the population of one or more fungi (e.g., pathogenic or parasitic fungi) by at least about any of 10%, 20%, 30%, 40%, 50%, 60%, 70%, 80%, 90% or more in the host in comparison to a host organism to which the modulating agent has not been administered. In some instances, the modulating agent may eradicate the population of a fungi (e.g., a pathogenic or parasitic fungi) in the host. In some instances, the modulating agent may increase the level of one or more symbiotic fungi by at least about any of 10%, 20%, 30%, 40%, 50%, 60%, 70%, 80%, 90% or more in the host and/or may decrease the level of one or more pathogenic fungi by at least about any of 10%, 20%, 30%, 40%, 50%, 60%, 70%, 80%, 90% or more in the host in comparison to a host organism to which the modulating agent has not been administered.

In some instances, the modulating agent may alter the fungal diversity and/or fungal composition of the host. In some instances, the modulating agent may increase the fungal diversity in the host relative to a starting diversity by at least about any of 10%, 20%, 30%, 40%, 50%, 60%, 70%, 80%, 90%, or more in comparison to a host organism to which the modulating agent has not been administered. In some instances, the modulating agent may decrease the fungal diversity in the host relative to a starting diversity by at least about any of 10%, 20%, 30%, 40%, 50%, 60%, 70%, 80%, 90%, or more in comparison to a host organism to which the modulating agent has not been administered.

In some instances, the modulating agent may alter the function, activity, growth, and/or division of one or more fungi. For example, the modulating agent may alter the expression of one or more genes in the fungus. In some instances, the modulating agent may alter the function of one or more proteins in the fungus. In some instances, the modulating agent may alter the function of one or more cellular components in the fungus. In some instances, the modulating agent may kill the fungus.

Further, the target fungus may reside in one or more parts of the insect. In some instances, the fungus resides in or on one or more parts of the insect gut, including, e.g., the foregut, midgut, and/or hindgut. In some instances, the fungus lives extracellularly in the hemolymph, fat bodies or in specialized structures in the host.

Changes to the population of fungi in the host may be determined by any methods known in the art, such as microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), and DNA sequencing. In some instances, a sample of the host treated with a modulating agent is sequenced (e.g., by metagenomics sequencing) to determine the microbiome of the host after delivery or administration of the modulating agent. In some instances, a sample of a host that did not receive the modulating agent is also sequenced to provide a reference.

III. Modulating Agents

The modulating agent of the methods and compositions provided herein may include a phage, a polypeptide, a small molecule, an antibiotic, a secondary metabolite, a bacterium, a fungus, or any combination thereof.

i. Phage

The modulating agent described herein may include a phage (e.g., a lytic phage or a non-lytic phage). In some instances, an effective concentration of any phage described herein may altering a level, activity, or metabolism of one or more microorganisms (as described herein) resident in a host described herein, the alteration resulting in an increase in the host's fitness. In some instances, the modulating agent includes at least one phage selected from the order Tectiviridae, Myoviridae, Siphoviridae, Podoviridae, Caudovirales, Lipothrixviridae, Rudiviridae, or Ligamenvirales. In some instances, the composition includes at least one phage selected from the family Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, and Tectiviridae. Further non-limiting examples of phages useful in the methods and compositions are listed in Table 3.

cell resident in the host, the phage causes lysis in the target bacterial cell. In some instances, the lytic phage targets and kills a bacterium resident in a host insect to increase the fitness of the host. Alternatively or additionally, the phage of the modulating agent may be a non-lytic phage (also referred to as lysogenic or temperate phage). Thus, after delivery of the non-lytic phage to a bacterial cell resident in the host, the bacterial cell may remain viable and able to stably maintain expression of genes encoded in the phage genome. In some instances, a non-lytic phage is used to alter gene expression in a bacterium resident in a host insect to increase the fitness of the host. In some instances, the modulating agent includes a mixture of lytic and non-lytic phage.

The modulating agent described herein may include phage with either a narrow or broad bacterial target range. In some instances, the phage has a narrow bacterial target range. In some instances, the phage is a promiscuous phage with a large bacterial target range. For example, the promiscuous phage may target at least about any of 5, 10, 20, 30, 40, 50, or more bacterium resident in the host. A phage with a narrow bacterial target range may target a specific bacterial strain in the host without affecting another, e.g., non-targeted, bacterium in the host. For example, the phage

TABLE 3

Examples of Phage and Targeted Bacteria

| Phage and Accession # | Target bacteria | Target host |
|---|---|---|
| SA1(NC_027991), phiP68 (NC_004679) | Staphylococcus sp. | Apidae family |
| WO (AB036666.1) | Wolbachia sp. | Aedes aegypt; Drosophila melanogaster; Plasmodium sp; Teleogryllus taiwanemma; Bombyx mori |
| KL1 (NC_018278), BcepNazgul (NC_005091) PhiE125 (NC_003309) | Burkholderia sp. | Riptortus sp.; Pyrrhocoris apterus. |
| Fern (NC_028851), Xenia (NC_028837), HB10c2 (NC_028758) | Paenibacillus larvae | bumble bees: Bombus sp.; honey bees: A. mellifera |
| CP2 (NC_020205), XP10 (NC_004902), XP15 (NC_007024), phiL7 (NC_012742) | Xanthomonas sp. | Plebeina denoiti; Apidae family; Apis mellifera; Drosphilidae family; and Chloropidae family |
| PP1 (NC_019542), PM1 (NC_023865) | Pectobacterium carotovorum subsp. carotovorum | Apidae family |
| ΦRSA1 (NC_009382), ΦRSB1 (NC_011201), ΦRSL1 (NC_010811), RSM1 (NC_008574) | Ralstonia solanacearum | Bombyx mori |
| SF1(NC_028807) | Streptomyces scabies | Philantus sp.; Trachypus sp |
| ECML-4 (NC_025446), ECML-117 (NC_025441), ECML-134 (NC_025449) | Escherichia coli | Apidae family; Varroa destructor |
| SSP5(JX274646.1), SSP6 (NC_004831), SFP10 (NC_016073), F18SE (NC_028698) | Salmonella sp. | Drosphilidae family |
| γ (NC_001416), Bcp1 (NC_024137) | Bacillus sp. | Gypsy moth; Lymantria dispar; Varroa destructor |
| Phi1 (NC_009821) | Enterococcus sp. | Schistocerca gragaria |
| ΦKMV (NC_005045), ΦEL(AJ697969.1), ΦKZ (NC_004629) | Pseudomonas sp. | Lymantria dispar; Apidae family |
| A2 (NC_004112), phig1e (NC_004305) | Lactobacilli sp. | Apidae family; Drosophila family; Varroa destructor |
| KLPN1 (NC_028760) | Klebsiella sp | C. capitata |
| vB_AbaM_Acibel004 (NC_025462), vB_AbaP_Acibel007 (NC_025457) | Acinetobacter sp. | Schistocerca gragaria |

In some instances, a modulating agent includes a lytic phage. Thus, after delivery of the lytic phage to a bacterial may target no more than about any of 50, 40, 30, 20, 10, 8, 6, 4, 2, or 1 bacterium resident in the host.

The compositions described herein may include any number of phage, such as at least about any one of 1, 2, 3, 4, 5, 10, 15, 20, 30, 40, 50, 100, or more phage. In some instances, the composition includes phage from one or more (e.g., 2, 3, 4, 5, 6, 7, 8, 9, 10, or more phage) families, one or more orders (e.g., 2, 3, 4, 5, 6, 7, 8, 9, 10, or more phage), or one or more species (e.g., 1, 2, 3, 4, 5, 10, 15, 20, 30, 40, 50, 100, or more phage). Compositions including one or more phage are also referred herein as "phage cocktails." Phage cocktails are useful because they allow for targeting of a wider host range of bacteria. Furthermore, they allow for each bacterial strain (i.e. subspecies) to be targeted by multiple orthogonal phages, thereby preventing or significantly delaying the onset of resistance. In some instances, a cocktail includes multiple phages targeting one bacterial species. In some instances, a cocktail includes multiple phages targeting multiple bacterial species. In some instances, a one-phage "cocktail" includes a single promiscuous phage (i.e. a phage with a large host range) targeting many strains within a species.

Suitable concentrations of the phage in the modulating agent described herein depends on factors such as efficacy, survival rate, transmissibility of the phage, number of distinct phage, and/or lysin types in the compositions, formulation, and methods of application of the composition. In some instances, the phage is in a liquid or a solid formulation. In some instances, the concentration of each phage in any of the compositions described herein is at least about any of $10^2$, $10^3$, $10^4$, $10^5$, $10^6$, $10^7$, $10^8$, $10^9$, $10^{10}$ or more pfu/ml. In some instances, the concentration of each phage in any of the compositions described herein is no more than about any of $10^2$, $10^3$, $10^4$, $10^5$, $10^6$, $10^7$, $10^8$, $10^9$ pfu/ml. In some instances, the concentration of each phage in the composition is any of about $10^2$ to about $10^3$, about $10^3$ to about $10^4$, about $10^4$ to about $10^5$, about $10^5$ to about $10^6$, about $10^7$ to about $10^8$, about $10^8$ to about $10^9$, about $10^2$ to about $10^4$, about $10^4$ to about $10^6$, about $10^6$ to about $10^9$, or about $10^3$ to about $10^8$ pfu/ml. In some instances, wherein the composition includes at least two types of phages, the concentration of each type of the phages may be the same or different. For example, in some instances, the concentration of one phage in the cocktail is about $10^8$ pfu/ml and the concentration of a second phage in the cocktail is about $10^6$ pfu/ml.

A modulating agent including a phage as described herein can be contacted with the target host in an amount and for a time sufficient to: (a) reach a target level (e.g., a predetermined or threshold level) of phage concentration inside a target host; (b) reach a target level (e.g., a predetermined or threshold level) of phage concentration inside a target host gut; (c) reach a target level (e.g., a predetermined or threshold level) of phage concentration inside a target host bacteriocyte; (d) modulate the level, or an activity, of one or more microorganism (e.g., endosymbiont) in the target host; or/and (e) modulate fitness of the target host.

As illustrated by Example 7 and 9, phages can be used as a modulating agents by eliminating bacterial pathogens such as *Serratia marcescens, Erwinia catotovora*, and *Pseudomonas enzomophila* from insect hosts, such as crickets.

ii. Polypeptides

Numerous polypeptides (e.g., a bacteriocin, R-type bacteriocin, nodule C-rich peptide, antimicrobial peptide, lysin, or bacteriocyte regulatory peptide) may be used in the compositions and methods described herein. In some instances, an effective concentration of any peptide or polypeptide described herein may alter a level, activity, or metabolism of one or more microorganisms (as described herein) resident in a host, the alteration resulting in an increase in the host's fitness. Polypeptides included herein may include naturally occurring polypeptides or recombinantly produced variants. For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide.

A modulating agent comprising a polypeptide as described herein can be contacted with the target host in an amount and for a time sufficient to: (a) reach a target level (e.g., a predetermined or threshold level) of concentration inside a target host; (b) reach a target level (e.g., a predetermined or threshold level) of concentration inside a target host gut; (c) reach a target level (e.g., a predetermined or threshold level) of concentration inside a target host bacteriocyte; (d) modulate the level, or an activity, of one or more microorganism (e.g., endosymbiont) in the target host; or/and (e) modulate fitness of the target host.

(a) Bacteriocins

The modulating agent described herein may include a bacteriocin. In some instances, the bacteriocin is naturally produced by Gram-positive bacteria, such as *Pseudomonas, Streptomyces, Bacillus, Staphylococcus*, or lactic acid bacteria (LAB, such as *Lactococcus lactis*). In some instances, the bacteriocin is naturally produced by Gram-negative bacteria, such as *Hafnia alvei, Citrobacter freundii, Klebsiella oxytoca, Klebsiella pneumonia, Enterobacter cloacae, Serratia plymithicum, Xanthomonas campestris, Erwinia carotovora, Ralstonia solanacearum*, or *Escherichia coli*. Exemplary bacteriocins include, but are not limited to, Class I-IV LAB antibiotics (such as lantibiotics), colicins, microcins, and pyocins. Non-limiting examples of bacteriocins are listed in Table 4.

TABLE 4

Examples of Bacteriocins

| Class | Name | Producer | Targets | Sequence |
|---|---|---|---|---|
| Class I | nisin | Lactococcus lactis | Active on Gram-positive bacteria: Enterococcus- Lactobacillus- Lactococcus- Leuconostoc- Listeria- clostridium | ITSISLCTPGCKT GALMGCNMKTA TCHCSIHVSK (SEQ ID NO: 42) |

TABLE 4-continued

Examples of Bacteriocins

| Class | Name | Producer | Targets | Sequence |
|---|---|---|---|---|
| | epidermin | Staphylococcus epidermis | Gram-positive bacteria | IASKFICTPGCA KTGSFNSYCC (SEQ ID NO: 43) |
| Class II | | | | |
| Class II a | pediocin PA-1 | Pediococcus acidilactici | Pediococci- Lactobacilli- Leuconostoc- Brochothrix thermosphacta- propionibacteria- Bacilli- Enterococci- Staphylococci- Listeria clostridia- Listeria monocytogenes- Listeria innocua | KYYGNGVTCG KHSCSVDWGK ATTCIINNGAMA WATGGHQGNH KC (SEQ ID NO: 44) |
| Class II b | Enterocin P | Enterococcus faecium | Lactobacillus sakei- Enterococcus faecium | ATRSYGNGVYC NNSKCWVNWG EAKENIAGIVISG WASGLAGMGH (SEQ ID NO: 45) |
| Class II c | lactococcin G | Streptococcus lactis | Gram-positive bacteria | GTWDDIGQGIG RVAYWVGKAM GNMSDVNQAS RINRKKKH (SEQ ID NO: 46) |
| Class II d | Lactacin-F | Lactobacillus johnsonii | Lactobacilli- Enterococcus faecalis | NRWGDTVLSAA SGAGTGIKACK SFGPWGMAICG VGGAAIGGYFG YTHN (SEQ ID NO: 47) |
| Class III | | | | |
| Class III a | Enterocin AS-48 | Enterococcus faecalis | Broad spectrum: Gram positive and Gram negative bacteria. | MAKEFGIPAAVA GTVLNVVEAGG WVTTIVSILTAV GSGGLSLLAAA GRESIKAYLKKE IKKKGKRAVIAW (SEQ ID NO: 48) |
| Class III b | aureocin A70 | Staphylococcus aureus | Broad spectrum: Gram positive and Gram negative bacteria. | MSWLNFLKYIAK YGKKAVSAAWK YKGKVLEWLNV GPTLEWVWQKL KKIAGL (SEQ ID NO: 49) |
| Class IV | Garvicin A | Lactococcus garvieae | Broad spectrum: Gram positive and Gram negative bacteria. | IGGALGNALNGL GTWANMMNGG GFVNQWQVYA NKGKINQYRPY (SEQ ID NO: 50) |
| Un- classified | Colicin V | Escherichia coli | Active against Escherichia coli (also closely related bacteria)- Enterobacteriaceae | MRTLTLNELDS VSGGASGRDIA MAIGTLSGQFV AGGIGAAAGGV AGGAIYDYAST HKPNPAMSPSG LGGTIKQKPEGI PSEAWNYAAGR LCNWSPNNLSD VCL (SEQ ID NO: 51) |

In some instances, the bacteriocin is a colicin, a pyocin, or a microcin produced by Gram-negative bacteria. In some instances, the bacteriocin is a colicin. The colicin may be a group A colicin (e.g., uses the Tol system to penetrate the outer membrane of a target bacterium) or a group B colicin (e.g., uses the Ton system to penetrate the outer membrane of a target bacterium). In some instances, the bacteriocin is a microcin. The microcin may be a class I microcin (e.g., <5 kDa, has post-translational modifications) or a class II microcin (e.g., 5-10 kDa, with or without post-translational modifications). In some instances, the class II microcin is a class IIa microcin (e.g., requires more than one genes to synthesize and assemble functional peptides) or a class IIb microcin (e.g., linear peptides with or without post-translational modifications at C-terminus). In some instances, the bacteriocin is a pyocin. In some instances, the pyocin is an R-pyocin, F-pyocin, or S-pyocin.

In some instances, the bacteriocin is a class I, class II, class III, or class IV bacteriocin produced by Gram-positive bacteria. In some instances, the modulating agent includes a Class I bacteriocin (e.g., lanthionine-containing antibiotics (lantibiotics) produced by a Gram-positive bacteria). The class I bacteriocins or lantibiotic may be a low molecular weight peptide (e.g., less than about 5 kDa) and may possess post-translationally modified amino acid residues (e.g., lanthionine, β-methyllanthionine, or dehydrated amino acids).

In some instances, the bacteriocin is a Class II bacteriocin (e.g., non-lantibiotics produced by Gram-positive bacteria). Many are positively charged, non-lanthionine-containing peptides, which unlike lantibiotics, do not undergo extensive post-translational modification. The Class II bacteriocin may belong to one of the following subclasses: "pediocin-like" bacteriocins (e.g., pediocin PA-1 and carnobacteriocin X (Class IIa)); two-peptide bacteriocins (e.g., lactacin F and ABP-118 (Class IIb)); circular bacteriocins (e.g., carnocyclin A and enterocin AS-48 (Class IIc)); or unmodified, linear, non-pediocin-like bacteriocins (e.g., epidermicin NI01 and lactococcin A (Class IId)).

In some instances, the bacteriocin is a Class III bacteriocin (e.g., produced by Gram-positive bacteria). Class III bacteriocins may have a molecular weight greater than 10 kDa and may be heat unstable proteins. The Class III bacteriocins can be further subdivided into Group IIIA and Group IIIB bacteriocins. The Group IIIA bacteriocins include bacteriolytic enzymes which kill sensitive strains by lysis of the cell well, such as Enterolisin A. Group IIIB bacteriocins include non-lytic proteins, such as Caseicin 80, Helveticin J, and lactacin B.

In some instances, the bacteriocin is a Class IV bacteriocin (e.g., produced by Gram-positive bacteria). Class IV bacteriocins are a group of complex proteins, associated with other lipid or carbohydrate moieties, which appear to be required for activity. They are relatively hydrophobic and heat stable. Examples of Class IV bacteriocins leuconocin S, lactocin 27, and lactocin S.

In some instances, the bacteriocin is an R-type bacteriocin. R-type bacteriocins are contractile bacteriocidal protein complexes. Some R-type bacteriocins have a contractile phage-tail-like structure. The C-terminal region of the phage tail fiber protein determines target-binding specificity. They may attach to target cells through a receptor-binding protein, e.g., a tail fiber. Attachment is followed by sheath contraction and insertion of the core through the envelope of the target bacterium. The core penetration results in a rapid depolarization of the cell membrane potential and prompt cell death. Contact with a single R-type bacteriocin particle can result in cell death. An R-type bacteriocin, for example, may be thermolabile, mild acid resistant, trypsin resistant, sedimentable by centrifugation, resolvable by electron microscopy, or a combination thereof. Other R-type bacteriocins may be complex molecules including multiple proteins, polypeptides, or subunits, and may resemble a tail structure of bacteriophages of the myoviridae family. In naturally occurring R-type bacteriocins, the subunit structures may be encoded by a bacterial genome, such as that of *C. difficile* or *P. aeruginosa* and form R-type bacteriocins to serve as natural defenses against other bacteria. In some instances, the R-type bacteriocin is a pyocin. In some instances, the pyocin is an R-pyocin, F-pyocin, or S-pyocin.

In some instances, the bacteriocin is a functionally active variant of the bacteriocins described herein. In some instances, the variant of the bacteriocin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a bacteriocin described herein or a naturally occurring bacteriocin.

In some instances, the bacteriocin may be bioengineered, according to standard methods, to modulate their bioactivity, e.g., increase or decrease or regulate, or to specify their target microorganisms. In other instances, the bacteriocin is produced by the translational machinery (e.g. a ribosome, etc.) of a microbial cell. In some instances, the bacteriocin is chemically synthesized. Some bacteriocins can be derived from a polypeptide precursor. The polypeptide precursor can undergo cleavage (e.g., processing by a protease) to yield the polypeptide of the bacteriocin itself. As such, in some instances, the bacteriocin is produced from a precursor polypeptide. In some other instances, the bacteriocin includes a polypeptide that has undergone post-translational modifications, for example, cleavage, or the addition of one or more functional groups.

The bacteriocins described herein may be formulated in a composition for any of the uses described herein. The compositions disclosed herein may include any number or type (e.g., classes) of bacteriocins, such as at least about any one of 1 bacteriocin, 2, 3, 4, 5, 10, 15, 20, 30, 40, 50, 100, or more bacteriocins. Suitable concentrations of each bacteriocin in the compositions described herein depends on factors such as efficacy, stability of the bacteriocin, number of distinct bacteriocin types in the compositions, formulation, and methods of application of the composition. In some instances, each bacteriocin in a liquid composition is from about 0.01 ng/ml to about 100 mg/mL. In some instances, each bacteriocin in a solid composition is from about 0.01 ng/g to about 100 mg/g. In some instances, wherein the composition includes at least two types of bacteriocins, the concentration of each type of the bacteriocins may be the same or different. In some instances, the bacteriocin is provided in a composition including a bacterial cell that secretes the bacteriocin. In some instances, the bacteriocin is provided in a composition including a polypeptide (e.g., a polypeptide isolated from a bacterial cell).

Bacteriocins may neutralize (e.g., kill) at least one microorganism other than the individual bacterial cell in which the polypeptide is made, including cells clonally related to the bacterial cell and other microbial cells. As such, a bacterial cell may exert cytotoxic or growth-inhibiting effects on a plurality of microbial organisms by secreting bacteriocins. In some instances, the bacteriocin targets and kills one or more species of bacteria resident in the host via cytoplasmic membrane pore formation, cell wall interference (e.g., peptidoglycanase activity), or nuclease activity (e.g., DNase activity, 16S rRNase activity, or tRNase activity).

In some instances, the bacteriocin has a neutralizing activity. Neutralizing activity of bacteriocins may include, but is not limited to, arrest of microbial reproduction, or cytotoxicity. Some bacteriocins have cytotoxic activity, and thus can kill microbial organisms, for example bacteria, yeast, algae, and the like. Some bacteriocins can inhibit the reproduction of microbial organisms, for example bacteria, yeast, algae, and the like, for example by arresting the cell cycle.

In some instances, the bacteriocin has killing activity. The killing mechanism of bacteriocins is specific to each group of bacteriocins. In some instances, the bacteriocin has narrow-spectrum bioactivity. Bacteriocins are known for their very high potency against their target strains. Some bacteriocin activity is limited to strains that are closely related to the bacteriocin producer strain (narrow-spectrum bioactivity). In some instances, the bacteriocin has broad-spectrum bioactivity against a wide range of genera.

In some instances, bacteriocins interact with a receptor molecule or a docking molecule on the target bacterial cell membrane. For example, nisin is extremely potent against its target bacterial strains, showing antimicrobial activity even at a single-digit nanomolar concentration. The nisin molecule has been shown to bind to lipid II, which is the main transporter of peptidoglycan subunits from the cytoplasm to the cell wall In some instances, the bacteriocin has anti-fungal activity. A number of bacteriocins with anti-yeast or anti-fungal activity have been identified. For example, bacteriocins from *Bacillus* have been shown to have neutralizing activity against some yeast strains (see, for example, Adetunji and Olaoye, *Malaysian Journal of Microbiology* 9:130-13, 2013). In another example, an *Enterococcus faecalis* peptide has been shown to have neutralizing activity against *Candida* species (see, for example, Shekh and Roy, *BMC Microbiology* 12:132, 2012). In another example, bacteriocins from *Pseudomonas* have been shown to have neutralizing activity against fungi, such as *Curvularia lunata*, *Fusarium* species, *Helminthosporium* species, and *Biopolaris* species (see, for example, Shalani and Srivastava, *The Internet Journal of Microbiology* Volume 5 Number 2, 2008). In another example, botrycidin AJ1316 and alirin B1 from *B. subtilis* have been shown to have antifungal activities.

A modulating agent including a bacteriocin as described herein can be contacted with the target host in an amount and for a time sufficient to: (a) reach a target level (e.g., a predetermined or threshold level) of bacteriocin concentration inside a target host; (b) reach a target level (e.g., a predetermined or threshold level) of bacteriocin concentration inside a target host gut; (c) reach a target level (e.g., a predetermined or threshold level) of bacteriocin concentration inside a target host bacteriocyte; (d) modulate the level, or an activity, of one or more microorganism (e.g., endosymbiont) in the target host; or/and (e) modulate fitness of the target host.

(b) Lysins

The modulating agent described herein may include a lysin (e.g., also known as a murein hydrolase or peptidoglycan autolysin). Any lysin suitable for inhibiting a bacterium resident in the host may be used. In some instances, the lysin is one that can be naturally produced by a bacterial cell. In some instances, the lysin is one that can be naturally produced by a bacteriophage. In some instances, the lysin is obtained from a phage that inhibits a bacterium resident in the host. In some instances, the lysin is engineered based on a naturally occurring lysin. In some instances, the lysin is engineered to be secreted by a host bacterium, for example, by introducing a signal peptide to the lysin. In some instances, the lysin is used in combination with a phage holin. In some instances, a lysin is expressed by a recombinant bacterium host that is not sensitive to the lysin. In some instances, the lysin is used to inhibit a Gram-positive or Gram-negative bacterium resident in the host.

The lysin may be any class of lysin and may have one or more substrate specificities. For example, the lysin may be a glycosidase, an endopeptidase, a carboxypeptidase, or a combination thereof. In some instances, the lysin cleaves the β-1-4 glycosidic bond in the sugar moiety of the cell wall, the amide bond connecting the sugar and peptide moieties of the bacterial cell wall, and/or the peptide bonds between the peptide moieties of the cell wall. The lysin may belong to one or more specific lysin groups, depending on the cleavage site within the peptidoglycan. In some instances, the lysin is a N-acetyl-β-D-muramidase (e.g., lysozyme), lytic transglycosylase, N-acetyl-β-D-glucosaminidase, N-acetylmuramyl-L-alanine amidase, L,D-endopeptidase, D,D-endopeptidase, D,D-carboxypeptidase, L,D-carboxypeptidase, or L,D-transpeptidase. Non-limiting examples of lysins and their activities are listed in Table 5.

TABLE 5

Examples of Lysins

| Target Bacteria | Producer | Lysins | Activity | Sequence |
|---|---|---|---|---|
| S. pneumoniae | Cpl | Cpl-1 | Muramidase | MVKKNDLFVDVSSHNGY<br>DITGILEQMGTTNTIIKISES<br>TTYLNPCLSAQVEQSNPI<br>GFYHFARFGGDVAEAERE<br>AQFFLDNVPMQVKYLVLD<br>YEDDPSGDAQANTNACL<br>RFMQMIADAGYKPIYYSY<br>KPFTHDNVDYQQILAQFP<br>NSLWIAGYGLNDGTANFE<br>YFPSMDGIRWWQYSSNP<br>FDKNIVLLDDEEDDKPKTA<br>GTWKQDSKGWWFRRNN<br>GSFPYNKWEKIGGVWYY<br>FDSKGYCLTSEWLKDNEK<br>WYYLKDNGAMATGWVLV<br>GSEWYYMDDSGAMVTG |

TABLE 5-continued

Examples of Lysins

| Target Bacteria | Producer | Lysins | Activity | Sequence |
|---|---|---|---|---|
| | | | | WVKYKNNWYYMTNERGN MVSNEFIKSGKGWYFMNT NGELADNPSFTKEPDGLIT VA (SEQ ID NO: 52) |
| S. pneumoniae | Dp-1 | Pal | Amidase | MGVDIEKGVAWMQARKG RVSYSMDFRDGPDSYDC SSSMYYALRSAGASSAG WAVNTEYMHAWLIENGY ELISENAPWDAKRGDIFIW GRKGASAGAGGHTGMFI DSDNIIHCNYAYDGISVND HDERWYYAGQPYYYVYR LTNANAQPAEKKLGWQK DATGFWYARANGTYPKD EFEYIEENKSWFYFDDQG YMLAEKWLKHTDGNWYW FDRDGYMATSWKRIGES WYYFNRDGSMVTGWIKY YDNWYYCDATNGDMKSN AFIRYNDGWYLLLPDGRL ADKPQFTVEPDGLITAKV (SEQ ID NO: 53) |
| S. pyogenes | C1 | C1 | Amidase | N/A |
| B. anthracis | γ | PlyG | Amidase | MEIQKKLVDPSKYGTKCP YTMKPKYITVHNTYNDAP AENEVSYMISNNNEVSFHI AVDDKKAIQGIPLERNAW ACGDGNGSGNRQSISVEI CYSKSGGDRYYKAEDNA VDVVRQLMSMYNIPIENV RTHQSWSGKYCPHRMLA EGRWGAFIQKVKNGNVAT TSPTKQNIIQSGAFSPYET PDVMGALTSLKMTADFIL QSDGLTYFISKPTSDAQLK AMKEYLDRKGWWYEVK (SEQ ID NO: 54) |
| B. anthracis | Ames prophage | PlyPH | Amidase | N/A |
| E. faecalis and E. faecium | Phi1 | PlyV12 | Amidase | N/A |
| S. aureus | ΦMR11 | MV-L | Endopeptidase and amidase | MQAKLTKKEFIEWLKTSE GKQFNVDLWYGFQCFDY ANAGWKVLFGLLLKGLGA KDIPFANNFDGLATVYQN TPDFLAQPGDMVVFGSNY GAGYGHVAWVIEATLDYII VYEQNWLGGGWTDRIEQ PGWGWEKVTRRQHAYDF PMWFIRPNFKSETAPRSI QSPTQASKKETAKPQPKA VELKIIKDVVKGYDLPKRG GNPKGIVIHNDAGSKGAT AEAYRNGLVNAPLSRLEA GIAHSYVSGNTVWQALDE SQVGWHTANQLGNKYYY GIEVCQSMGADNATFLKN EQATFQECARLLKKWGLP ANRNTIRLHNEFTSTSCPH RSSVLHTGFDPVTRGLLP EDKQLQLKDYFIKQIRVYM DGKIPVATVSNESSASSN TVKPVASAWKRNKYGTYY MEENARFTNGNQPITVRKI GPFLSCPVAYQFQPGGY CDYTEVMLQDGHVWVGY TWEGQRYYLPIRTWNGS APPNQILGDLWGEIS (SEQ ID NO: 55) |

TABLE 5-continued

Examples of Lysins

| Target Bacteria | Producer | Lysins | Activity | Sequence |
|---|---|---|---|---|
| S. pyogenes | C1 | PlyC | Amidase | N/A |
| S. agalactiae | B30 | GBS lysin | Muramidase and endopeptidase | MVINIEQAIAWMASRKGK VTYSMDYRNGPSSYDCS SSVYFALRSAGASDNGW AVNTEYEHDWLIKNGYVLI AENTNWNAQRGDIFIWGK RGASAGAFGHTGMFVDP DNIIHCNYGYNSITVNNHD EIWGYNGQPYVYAYRYS GKQSNAKVDNKSVVSKFE KELDVNTPLSNSNMPYYE ATISEDYYVESKPDVNSTD KELLVAGTRVRVYEKVKG WARIGAPQSNQWVEDAY LIDATDM (SEQ ID NO: 56) |
| S. aureus | P68 | Lys16 | Endopeptidase | N/A |
| S. aureus | K | LysK | Amidase and endopeptidase | MAKTQAEINKRLDAYAKG TVDSPYRVKKATSYDPSF GVMEAGAIDADGYYHAQ CQDLITDYVLWLTDNKVR TWGNAKDQIKQSYGTGFK IHENKPSTVPKKGWIAVFT SGSYEQWGHIGIVYDGGN TSTFTILEQNWNGYANKK PTKRVDNYYGLTHFIEIPV KAGTTVKKETAKKSASKT PAPKKKATLKVSKNHINYT MDKRGKKPEGMVIHNDA GRSSGQQYENSLANAGY ARYANGIAHYYGSEGYVW EAIDAKNQIAWHTGDGTG ANSGNFRFAGIEVCQSMS ASDAQFLKNEQAVFQFTA EKFKEWGLTPNRKTVRLH MEFVPTACPHRSMVLHTG FNPVTQGRPSQAIMNKLK DYFIKQIKNYMDKGTSSST VVKDGKTSSASTPATRPV TGSWKKNQYGTWYKPEN ATFVNGNQPIVTRIGSPFL NAPVGGNLPAGATIVYDE VCIQAGHIWIGYNAYNGN RVYCPVRTCQGVPPNQIP GVAWGVFK (SEQ ID NO: 57) |
| L. monocytogenes | A118 | Ply118 | Amidase | MTSYYYSRSLANVNKLAD NTKAAARKLLDWSESNGI EVLIYETIRTKEQQAANVN SGASQTMRSYHLVGQAL DFVMAKGKTVDWGAYRS DKGKKFVAKAKSLGFEW GGDWSGFVDNPHLQFNY KGYGTDTFGKGASTSNSS KPSADTNTNSLGLVDYMN LNKLDSSFANRKKLATSY GIKNYSGTATQNTTLLAKL KAGKPHTPASKNTYYTEN PRKVKTLVQCDLYKSVDF TTKNQTGGTFPPGTVFTIS GMGKTKGGTPRLKTKSG YYLTANTKFVKKI (SEQ ID NO: 58) |
| L. monocytogenes | A511 | Ply511 | Amidase | MVKYTVENKIIAGLPKGKL KGANFVIAHETANSKSTID NEVSYMTRNWKNAFVTH FVGGGGRVVQVANVNYV SWGAGQYANSYSYAQVE LCRTSNATTFKKDYEVYC QLLVDLAKKAGIPITLDSG |

TABLE 5-continued

Examples of Lysins

| Target Bacteria | Producer | Lysins | Activity | Sequence |
|---|---|---|---|---|
| | | | | SKTSDKGIKSHKWVADKL<br>GGTTHQDPYAYLSSWGIS<br>KAQFASDLAKVSGGGNT<br>GTAPAKPSTPAPKPSTPS<br>TNLDKLGLVDYMNAKKMD<br>SSYSNRDKLAKQYGIANY<br>SGTASQNTTLLSKIKGGAP<br>KPSTPAPKPSTSTAKKIYF<br>PPNKGNWSVYPTNKAPV<br>KANAIGAINPTKFGGLTYTI<br>QKDRGNGVYEIQTDQFG<br>RVQVYGAPSTGAVIKK<br>(SEQ ID NO: 59) |
| *L. monocytogenes* | A500 | Ply500 | Endopeptidase | MALTEAWLIEKANRKLNA<br>GGMYKITSDKTRNVIKKM<br>AKEGIYLCVAQGYRSTAE<br>QNALYAQGRTKPGAIVTN<br>AKGGQSNHNYGVAVDLC<br>LYTNDGKDVIWESTTSRW<br>KKVVAAMKAEGFKWGGD<br>WKSFKDYPHFELCDAVSG<br>EKIPAATQNTNTNSNRYE<br>GKVIDSAPLLPKMDFKSSP<br>FRMYKVGTEFLVYDHNQY<br>WYKTYIDDKLYYMYKSFC<br>DVVAKKDAKGRIKVRIKSA<br>KDLRIPVWNNIKLNSGKIK<br>WYAPNVKLAWYNYRRGY<br>LELWYPNDGWYYTAEYFL<br>K<br>(SEQ ID NO: 60) |
| *S. pneumoniae* | ΦDp-1 | Pal, S | Endopeptidase and amidase | N/A |
| *S. agalactiae* | LambdaSa1 prophage | LambdaSa1 | Glycosidase | MVINIEQAIAWMASRKGK<br>VTYSMDYRNGPSSYDCS<br>SSVYFALRSAGASDNGW<br>AVNTEYEHDWLIKNGYVLI<br>AENTNWNAQRGDIFIWGK<br>RGASAGAFGHTGMFVDP<br>DNIIHCNYGYNSITVNNHD<br>EIWGYNGQPYVYAYRYAR<br>KQSNAKVDNQSVVSKFEK<br>ELDVNTPLSNSNMPYYEA<br>TISEDYYVESKPDVNSTDK<br>ELLVAGTRVRVYEKVKGW<br>ARIGAPQSNQWVEDAYLI<br>DATDM<br>(SEQ ID NO: 61) |
| *S. agalactiae* | LambdaSa2 prophage | LambdaSa2 | Glycosidase and endopeptidase | MEINTEIAIAWMSARQGKV<br>SYSMDYRDGPNSYDCSS<br>SVYYALRSAGASSAGWA<br>VNTEYMHDWLIKNGYELIA<br>ENVDWNAVRGDIAIWGM<br>RGHSSGAGGHVVMFIDPE<br>NIIHCNWANNGITVNNYN<br>QTAAASGWMYCYVYRLK<br>SGASTQGKSLDTLVKETL<br>AGNYGNGEARKAVLGNQ<br>YEAVMSVINGKTTTNQKT<br>VDQLVQEVIAGKHGNGEA<br>RKKSLGSQYDAVQKRVTE<br>LLKKQPSEPFKAQEVNKP<br>TETKTSQTELTGQATATK<br>EEGDLSFNGTILKKAVLDK<br>ILGNCKKHDILPSYALTILH<br>YEGLWGTSAVGKADNNW<br>GGMTWTGQGNRPSGVTV<br>TQGSARPSNEGGHYMHY<br>ASVDDFLTDWFYLLRAGG<br>SYKVSGAKTFSEAIKGMF<br>KVGGAVYDYAASGFDSYI<br>VGASSRLKAIEAENGSLD |

TABLE 5-continued

Examples of Lysins

| Target Bacteria | Producer | Lysins | Activity | Sequence |
|---|---|---|---|---|
| | | | | KFDKATDIGDGSKDKIDITI EGIEVTINGITYELTKKPV (SEQ ID NO: 62) |
| S. uberis | (AT00700407) prophage | Ply700 | Amidase | MTDSIQEMRKLQSIPVRY DMGDRYGNDADRDGRIE MDCSSAVSKALGISMTNN TETLQQALPAIGYGKIHDA VDGTFDMQAYDVIIWAPR DGSSSLGAFGHVLIATSPT TAIHCNYGSDGITENDYNY IWEINGRPREIVFRKGVTQ TQATVTSQFERELDVNAR LTVSDKPYYEATLSEDYY VEAGPRIDSQDKELIKAGT RVRVYEKLNGWSRINHPE SAQWVEDSYLVDATEM (SEQ ID NO: 63) |
| S. suis | SMP | LySMP | Glycosidase and endopeptidase | N/A |
| B. anthracis | Bcp1 | PlyB | Muramidase | N/A |
| S. aureus | Phi11 and Phi12 | Phi11 lysin | Amidase and endopeptidase | MQAKLTKNEFIEWLKTSE GKQFNVDLWYGFQCFDY ANAGWKVLFGLLLKGLGA KDIPFANNFDGLATVYQN TPDFLAQPGDMVVFGSNY GAGYGHVAWVIEATLDYII VYEQNWLGGGWTDGIEQ PGWGWEKVTRRQHAYDF PMWFIRPNFKSETAPRSV QSPTQAPKKETAKPQPKA VELKIIKDVVKGYDLPKRG SNPKGIVIHNDAGSKGATA EAYRNGLVNAPLSRLEAGI AHSYVSGNTVWQALDES QVGWHTANQIGNKYYYGI EVCQSMGADNATFLKNE QATFQECARLLKKWGLPA NRNTIRLHNEFTSTSCPH RSSVLHTGFDPVTRGLLP EDKRLQLKDYFIKQIRAYM DGKIPVATVSNESSASSN TVKPVASAWKRNKYGTYY MEESARFTNGNQPITVRK VGPFLSCPVGYQFQPGG YCDYTEVMLQDGHVWVG YTWEGQRYYLPIRTWNG SAPPNQILGDLWGEIS (SEQ ID NO: 64) |
| S. aureus | ΦH5 | LysH5 | Amidase and endopeptidase | MQAKLTKKEFIEWLKTSE GKQYNADGWYGFQCFDY ANAGWKALFGLLLKGVGA KDIPFANNFDGLATVYQN TPDFLAQPGDMVVFGSNY GAGYGHVAWVIEATLDYII VYEQNWLGGGWTDGVQ QPGSGWEKVTRRQHAYD FPMWFIRPNFKSETAPRS VQSPTQASKKETAKPQPK AVELKIIKDVVKGYDLPKR GSNPNFIVIHNDAGSKGAT AEAYRNGLVNAPLSRLEA GIAHSYVSGNTVWQALDE SQVGWHTANQIGNKYGY GIEVCQSMGADNATFLKN EQATFQECARLLKKWGLP ANRNTIRLHNEFTSTSCPH RSSVLHTGFDPVTRGLLP EDKRLQLKDYFIKQIRAYM DGKIPVATVSNDSSASSN TVKPVASAWKRNKYGTYY |

TABLE 5-continued

Examples of Lysins

| Target Bacteria | Producer | Lysins | Activity | Sequence |
|---|---|---|---|---|
| | | | | MEESARFTNGNQPITVRK VGPFLSCPVGYQFQPGG YCDYTEVMLQDGHVWVG YTWEGQRYYLPIRTWNG SAPPNQILGDLWGEIS (SEQ ID NO: 65) |
| S. warneri | ΦWMY | LysWMY | Amidase and endopeptidase | MKTKAQAKSWINSKIGKGI DWDGMYGYQCMDEAVD YIHHVTDGKVTMWGNAID APKNNFQGLCTVYTNTPE FRPAYGDVIVWSYGTFAT YGHIAIVVNPDPYGDLQYI TVLEQNWNGNGIYKTEFA TIRTHDYTGVSHFIRPKFA DEVKETAKTVNKLSVQKKI VTPKNSVERIKNYVKTSG YINGEHYELYNRGHKPKG VVIHNTAGTASATQEGQR LTNMTFQQLANGVAHVYI DKNTIYETLPEDRIAWHVA QQYGNTEFYGIEVCGSRN TDKEQFLANEQVAFQEAA RRLKSWGMRANRNTVRL HHTFSSTECPDMSMLLHT GYSMKNGKPTQDITNKCA DYFMKQINAYIDGKQPTST VVGSSSSNKLKAKNKDKS TGWNTNEYGTLWKKEHA TFTCGVRQGIVTRTTGPF TSCPQAGVLYYGQSVNY DTVCKQDGYVWISWTTS DGYDVWMPIRTWDRSTD KVSEIWGTIS (SEQ ID NO: 66) |
| Streptococci (GBS) | ΦNCTC 11261 | PlyGBS | Muramidase and endopeptidase | MATYQEYKSRSNGNAYDI DGSFGAQCWDGYADYCK YLGLPYANCTNTGYARDI WEQRHENGILNYFDEVEV MQAGDVAIFMVVDGVTPY SHVAIFDSDAGGYGWFL GQNQGGANGAYNIVKIPY SATYPTAFRPKVFKNAVT VTGNIGLNKGDYFIDVSAY QQADLTTTCQQAGTTKTII KVSESIAWLSDRHQQAN TSDPIGYYHFGRFGGDSA LAQREADLFLSNLPSKKV SYLVIDYEDSASADKQAN TNAVIAFMDKIASAGYKPI YYSYKPFTLNNIDYQKIIAK YPNSIWIAGYPDYEVRTEP LWEFFPSMDGVRWWQFT SVGVAGGLDKNIVLLADD SSKMDIPKVDKPQELTFY QKLATNTKLDNSNVPYYE ATLSTDYYVESKPNASSA DKEFIKAGTRVRVYEKVN GWSRINHPESAQWVEDS YLVNATDM (SEQ ID NO: 67) |
| C. perfringens | Φ3626 | Ply3626 | Amidase | N/A |
| C. difficile | ΦCD27 | CD27 lysin | Amidase | N/A |
| E. faecalis | Φ1 | PlyV12 | Amidase | N/A |
| A. naeslundii | ΦAv-1- | Av-1 lysin | Putative amidase/ muramidase | N/A |
| L. gasseri | ΦgaY | LysgaY | Muramidase | N/A |

TABLE 5-continued

Examples of Lysins

| Target Bacteria | Producer | Lysins | Activity | Sequence |
|---|---|---|---|---|
| S. aureus | ΦSA4 | LysSA4 | Amidase and endopeptidase | N/A |
| S. haemolyticus | ΦSH2 | SH2 | Amidase and endopeptidase | N/A |
| B. thuringiensis | ΦBtCS33 | PlyBt33 | Amidase | N/A |
| L. monocytogenes | ΦP40 | PlyP40 | Amidase | N/A |
| L. monocytogenes | ΦFWLLm3 | LysZ5 | Amidase | MVKYTVENKIIAGLPKGKL KGANFVIAHETANSKSTID NEVSYMTRNWQNAFVTH FVGGGGRVVQVANVNYV SWGAGQYANSYSYAQVE LCRTSNATTFKKDYEVYC QLLVDLAKKAGIPITLDSG SKTSDKGIKSHKWVADKL GGTTHQDPYAYLSSWGIS KAQFASDLAKVSGGGNT GTAPAKPSTPSTNLDKLG LVDYMNAKKMDSSYSNR AKLAKQYGIANYSGTASQ NTTLLSKIKGGAPKPSTPA PKPSTSTAKKIYFPPNKGN WSVYPTNKAPVKANAIGAI NPTKFGGLTYTIQKDRGN GVYEIQTDQFGRVQVYGA PSTGAVIKK (SEQ ID NO: 68) |
| B. cereus | ΦBPS13 | LysBPS13 | Amidase | MAKREKYIFDVEAEVGKA AKSIKSLEAELSKLQKLNK EIDATGGDRTEKEMLATL KAAKEVNAEYQKMQRILK DLSKYSGKVSRKEFNDSK VINNAKTSVQGGKVTDSF GQMLKNMERQINSVNKQ FDNHRKAMVDRGQQYTP HLKTNRKDSQGNSNPSM MGRNKSTTQDMEKAVDK FLNGQNEATTGLNQALYQ LKEISKLNRRSESLSRRAS ASGYMSFQQYSNFTGDR RTVQQTYGGLKTANRERV LELSGQATGISKELDRLNS KKGLTAREGEERKKLMRQ LEGIDAELTARKKLNSSLD ETTSNMEKFNQSLVDAQV SVKPERGTMRGMMYERA PAIALAIGGAITATIGKLYS EGGNHSKAMRPDEMYVG QQTGAVGANWRPNRTAT MRSGLGNHLGFTGQEMM EFQSNYLSANGYHGAED MKAATTGQATFARATGLG SDEVKDFFNTAYRSGGID GNQTKQFQNAFLGAMKQ SGAVGREKDQLKALNGIL SSMSQNRTVSNQDMMRT VGLQSAISSSGVASLQGT KGGALMEQLDNGIREGFN DPQMRVLFGQGTKYQGM GGRAALRKQMEKGISDPD NLNTLIDASKASAGQDPA EQAEVLATLASKMGVNMS SDQARGLIDLQPSGKLTK ENIDKVMKEGLKEGSIESA KRDKAYSESKASIDNSSE AATAKQATELNDMGSKLR QANAALGGLPAPLYTAIAA VVAFTAAVAGSALMFKGA SWLKGGMASKYGGKGGK GGKGGGTGGGGAGGA AATGAGAAAGAGGVGAA |

TABLE 5-continued

Examples of Lysins

| Target Bacteria | Producer | Lysins | Activity | Sequence |
|---|---|---|---|---|
| | | | | AAGEVGAGVAAGGAAAG<br>AAAGGSKLAGVGKGFMK<br>GAGKLMLPLGILMGASEIM<br>QAPEEAKGSAIGSAVGGI<br>GGGIAGGAATGAIAGSFL<br>GPIGTAVGGIAGGIAGGFA<br>GSSLGETIGGWFDSGPKE<br>DASAADKAKADASAAALA<br>AAAGTSGAVGSSALQSQ<br>MAQGITGAPNMSQVGSM<br>ASALGISSGAMASALGISS<br>GQENQIQTMTDKENTNTK<br>KANEAKKGDNLSYERENI<br>SMYERVLTRAEQILAQAR<br>AQNGIMGVGGGTAGAG<br>GGINGFTGGGKLQFLAAG<br>QKWSSSNLQQHDLGFTD<br>QNLTAEDLDKWIDSKAPQ<br>GSMMRGMGATFLKAGQE<br>YGLDPRYLIAHAAEESGW<br>GTSKIARDKGNFFGIGAFD<br>DSPYSSAYEFKDGTGSAA<br>ERGIMGGAKWISEKYYGK<br>GNTTLDKMKAAGYATNAS<br>WAPNIASIMAGAPTGSGS<br>GNVTATINVNVKGDEKVS<br>DKLKNSSDMKKAGKDIGS<br>LLGFYSREMTIA<br>(SEQ ID NO: 69) |
| S. aureus | ΦGH15 | LysGH15 | Amidase and endopeptidase | MAKTQAEINKRLDAYAKG<br>TVDSPYRIKKATSYDPSFG<br>VMEAGAIDADGYYHAQC<br>QDLITDYVLWLTDNKVRT<br>WGNAKDQIKQSYGTGFKI<br>HENKPSTVPKKGWIAVFT<br>SGSYQQWGHIGIVYDGG<br>NTSTFTILEQNWNGYANK<br>KPTKRVDNYYGLTHFIEIP<br>VKAGTTVKKETAKKSASK<br>TPAPKKKATLKVSKNHINY<br>TMDKRGKKPEGMVIHNDA<br>GRSSGQQYENSLANAGY<br>ARYANGIAHYYGSEGYVW<br>EAIDAKNQIAWHTGDGTG<br>ANSGNFRFAGIEVCQSMS<br>ASDAQFLKNEQAVFQFTA<br>EKFKEWGLTPNRKTVRLH<br>MEFVPTACPHRSMVLHTG<br>FNPVTQGRPSQAIMNKLK<br>DYFIKQIKNYMDKGTSSST<br>VVKDGKTSSASTPATRPV<br>TGSWKKNQYGTWYKPEN<br>ATFVNGNQPIVTRIGSPFL<br>NAPVGGNLPAGATIVYDE<br>VCIQAGHIWIGYNAYNGD<br>RVYCPVRTCQGVPPNHIP<br>GVAWGVFK<br>(SEQ ID NO: 70) |
| S. aureus | ΦvB SauS-PLA88 | HydH5 | Endopeptidase and glycosidase | N/A |
| E. faecalis | ΦF168/08 | Lys168 | Endopeptidase | N/A |
| E. faecalis | ΦF170/08 | Lys170 | Amidase | N/A |
| S. aureus | ΦP-27/HP | P-27/HP | Nonspecified | N/A |
| C. perfringens | ΦSM101 | Psm | Muramidase | N/A |
| C. sporogenes | Φ8074-B1 | 0574L | Amidase | MKIGIDMGHTLSGADYGV<br>VGLRPESVLTREVGTKVIY<br>KLQKLGHVVVNCTVDKAS<br>SVSESLYTRYYRANQANV |

TABLE 5-continued

Examples of Lysins

| Target Bacteria | Producer | Lysins | Activity | Sequence |
|---|---|---|---|---|
| | | | | DLFISIHFNATPGGTGTEV YTYAGRQLGEATRIRQEF KSLGLRDRGTKDGSGLAV IRNTKAKAMLVECCFCDN PNDMKLYNSESFSNAIVK GITGKLPNGESGNNNQG GNKVKAVVIYNEGADRRG AEYLADYLNCPTISNSRTF DYSCVEHVYAVGGKKEQ YTKYLKTLLSGANRYDTM QQILNFINGGK (SEQ ID NO: 71) |
| S. typhimurium | ΦSPN1S | SPN1S | Glycosidase | MDINQFRRASGINEQLAA RWFPHITTAMNEFGITKPD DQAMFIAQVGHESGGFTR LQENFNYSVNGLSGFIRA GRITPDQANALGRKTYEK SLPLERQRAIANLVYSKR MGNNGPGDGWNYRGRG LIQITGLNNYRDCGNGLKV DLVAQPELLAQDEYAARS AAWFFSSKGCMKYTGDL VRVTQIINGGQNGIDDRRT RYAAARKVLAL (SEQ ID NO: 72) |
| C. michiganensis | ΦCMP1 | CMP1 | Peptidase | N/A |
| C. michiganensis | ΦCN77 | CN77 | Peptidase | MGYWGYPNGQIPNDKMA LYRGCLLRADAAAQAYAL QDAYTRATGKPLVILEGY RDLTRQKYLRNLYLSGRG NIAAVPGLSNHGWGLACD FAAPLNSSGSEEHRWMR QNAPLFGFDWARGKADN EPWHWEYGNVPVSRWA SLDVTPIDRNDMADITEGQ MQRIAVILLDTEIQTPLGPR LVKHALGDALLLGQANAN SIAEVPDKTWDVLVDHPL AKNEDGTPLKVRLGDVAK YEPLEHQNTRDAIAKLGTL QFTDKQLATIGAGVKPIDE ASLVKKIVDGVRALFGRAA A (SEQ ID NO: 73) |
| A. baumannii | ΦAB2 | LysAB2 | Glycosidase | MILTKDGFSIIRNELFGGKL DQTQVDAINFIVAKATESG LTYPEAAYLLATIYHETGL PSGYRTMQPIKEAGSDSY LRSKKYYPYIGYGYVQLT WKENYERIGKLIGVDLIKN PEKALEPLIAIQIAIKGMLN GWFTGVGFRRKRPVSKY NKQQYVAARNIINGKDKA ELIAKYAIIFERALRSL (SEQ ID NO: 74) |
| B. cereus | ΦB4 | LysB4 | Endopeptidase | MAMALQTLIDKANRKLNV SGMRKDVADRTRAVITQM HAQGIYICVAQGFRSFAE QNALYAQGRTKPGSIVTN ARGGQSNHNYGVAVDLC LYTQDGSDVIWTVEGNFR KVIAAMKAQGFKWGGDW VSFKDYPHFELYDVVGGQ KPPADNGGAVDNGGGSG STGGSGGGSTGGGSTGG GYDSSWFTKETGTFVTNT SIKLRTAPFTSADVIATLPA GSPVNYNGFGIEYDGYV WIRQPRSNGYGYLATGES KGGKRQNYWGTFK (SEQ ID NO: 75) |

TABLE 5-continued

Examples of Lysins

| Target Bacteria | Producer | Lysins | Activity | Sequence |
|---|---|---|---|---|
| P. aeruginosa | ΦKMV | KMV45 | Nonspecified | N/A |
| C. tyrobutyricum | ΦCTP1 | Ctp1I | Glycosidase | MKKIADISNLNGNVDVKLL FNLGYIGIIAKASEGGTFV DKYYKQNYTNTKAQGKIT GAYHFANFSTIAKAQQEA NFFLNCIAGTTPDFVVLDL EQQCTGDITDACLAFLNIV AKKFKCVVYCNSSFIKEHL NSKICAYPLWIANYGVATP AFTLWTKYAMWQFTEKG QVSGISGYIDFSYITDEFIK YIKGEDEVENLVVYNDGA DQRAAEYLADRLACPTIN NARKFDYSNVKNVYAVG GNKEQYTSYLTTLIAGSTR YTTMQAVLDYIKNLK (SEQ ID NO: 76) |
| P. aeruginosa | ΦEL | EL188 | Transglycosylase | N/A |
| P. aeruginosa | ΦKZ | KZ144 | Transglycosylase | N/A |
| S. aureus | | Ply187 | Cell Wall Hydrolase | MALPKTGKPTAKQVVDW AINLIGSGVDVDGYYGRQ CWDLPNYIFNRYWNFKTP GNARDMAWYRYPEGFKV FRNTSDFVPKPGDIAVWT GGNYNWNTWGHTGIVVG PSTKSYFYSVDQNWNNS NSYVGSPAAKIKHSYFGV THFVRPAYKAEPKPTPPA QNNPAPKDPEPSKKPESN KPIYKVVTKILFTTAHIEHV KANRFVHYITKSDNHNNK PNKIVIKNTNTALSTIDVYR YRDELDKDEIPHFFVDRLN VWACRPIEDSINGYHDSV VLSITETRTALSDNFKMNE IECLSLAESILKANNKKMS ASNIIVDNKAWRTFKLHTG KDSLKSSSFTSKDYQKAV NELIKLFNDKDKLLNNKPK DVVERIRIRTIVKENTKFVP SELKPRNNIRDKQDSKIDR VINNYTLKQALNIQYKLNP KPQTSNGVSWYNASVNQI KSAMDTTKIFNNNVQVYQ FLKLNQYQGIPVDKLNKLL VGKGTLANQGHAFADGC KKYNINEIYLIAHRFLESAN GTSFFASGKTGVYNYFGI GAFDNNPNNAMAFARSH GWTSPTKAIIGGAEFVGK GYFNVGQNTLYRMRWNP QKPGTHQYATDISWAKVQ AQMISAMYKEIGLTGDYFI YDQYKK (SEQ ID NO: 77) |
| P. uorescens | ΦOBP | OBPgp279 | Glycosidase | N/A |
| L. monocytogenes | ΦP35 | PlyP35 | Amidase | MARKFTKAELVAKAEKKV GGLKPDVKKAVLSAVKEA YDRYGIGIIVSQGYRSIAE QNGLYAQGRTKPGNIVTN AKGGQSNHNFGVAVDFAI DLIDDGKIDSWQPSATIVN MMKRRGFKWGGDWKSF TDLPHFEACDWYRGERK YKVDTSEWKKKENINIVIK DVGYFQDKPQFLNSKSVR QWKHGTKVKLTKHNSHW YTGVVKDGNKSVRGYIYH SMAKVTSKNSDGSVNATI |

TABLE 5-continued

Examples of Lysins

| Target Bacteria | Producer | Lysins | Activity | Sequence |
|---|---|---|---|---|
| | | | | NAHAFCWDNKKLNGGDFI<br>NLKRGFKGITHPASDGFY<br>PLYFASRKKTFYIPRYMFD<br>IKK<br>(SEQ ID NO: 78) |
| L. fermentum | ΦPYB5 | Lyb5 | Muramidase | N/A |
| S. pneumoniae | ΦCP-7 | Cpl-7 | Muramidase | MVKKNDLFVDVASHQGY<br>DISGILEEAGTTNTIIKVSE<br>STSYLNPCLSAQVSQSNPI<br>GFYHFAWFGGNEEEAEA<br>EARYFLDNVPTQVKYLVL<br>DYEDHASASVQRNTTACL<br>RFMQIIAEAGYTPIYYSYK<br>PFTLDNVDYQQILAQFPN<br>SLWIAGYGLNDGTANFEY<br>FPSMDGIRWWQYSSNPF<br>DKNIVLLDDEKEDNINNEN<br>TLKSLTTVANEVIQGLWG<br>NGQERYDSLANAGYDPQ<br>AVQDKVNEILNAREIADLT<br>TVANEVIQGLWGNGQER<br>YDSLANAGYDPQAVQDK<br>VNEILNAREIADLTTVANE<br>VIQGLWGNGQERYDSLA<br>NAGYDPQAVQDKVNELLS<br>(SEQ ID NO: 79) |
| P. chlororaphis201 | Φ2-1 | 201φ92-1gp229 | Glycosidase | N/A |
| S. enterica | ΦPVP-SE1) | PVP-SE1gp146 | Glycosidase | N/A |
| Corynebacterium | ΦBFK20 | BKF20 | Amidase | N/A |
| E. faecalis | ΦEFAP-1 | EFAL-1 | Amidase | MKLKGILLSVVTTFGLLFG<br>ATNVQAYEVNNEFNLQP<br>WEGSQQLAYPNKIILHETA<br>NPRATGRNEATYMKNNW<br>FNAHTTAIVGDGGIVYKVA<br>PEGNVSWGAGNANPYAP<br>VQIELQHTNDPELFKANYK<br>AYVDYTRDMGKKFGIPMT<br>LDQGGSLWEKGVVSHQW<br>VTDFVWGDHTDPYGYLA<br>KMGISKAQLAHDLANGVS<br>GNTATPTPKPDKPKPTQP<br>SKPSNKKRFNYRVDGLEY<br>VNGMWQIYNEHLGKIDFN<br>WTENGIPVEVVDKVNPAT<br>GQPTKDQVLKVGDYFNF<br>QENSTGVVQEQTPYMGY<br>TLSHVQLPNEFIWLFTDSK<br>QALMYQ<br>(SEQ ID NO: 80) |
| Lactobacilli | lambdaSA2 | LysA, LysA2, and Lysga Y | Nonspecified | N/A |
| S. aureus | | SAL-1 | Nonspecified | N/A |

In some instances, the lysin is a functionally active variant of the lysins described herein. In some instances, the variant of the lysin has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a lysin described herein or a naturally occurring lysin.

In some instances, the lysin may be bioengineered to modulate its bioactivity, e.g., increase or decrease or regulate, or to specify a target microorganism. In some instances, the lysin is produced by the translational machinery (e.g. a ribosome, etc.) of a microbial cell. In some instances, the lysin is chemically synthesized. In some instances, the lysin is derived from a polypeptide precursor. The polypeptide precursor can undergo cleavage (for example, processing by a protease) to yield the polypeptide of the lysin itself. As such, in some instances, the lysin is produced from a precursor polypeptide. In some instances, the lysin includes a polypeptide that has undergone post-translational modifications, for example, cleavage, or the addition of one or more functional groups.

The lysins described herein may be formulated in a composition for any of the uses described herein. The compositions disclosed herein may include any number or type (e.g., classes) of lysins, such as at least about any one of 1 lysin, 2, 3, 4, 5, 10, 15, 20, or more lysins. A suitable concentration of each lysin in the composition depends on factors such as efficacy, stability of the lysin, number of distinct lysin, the formulation, and methods of application of the composition. In some instances, each lysin in a liquid composition is from about 0.1 ng/mL to about 100 mg/mL. In some instances, each lysin in a solid composition is from about 0.1 ng/g to about 100 mg/g. In some instances, wherein the composition includes at least two types of lysins, the concentration of each type of lysin may be the same or different.

A modulating agent including a lysin as described herein can be contacted with the target host in an amount and for a time sufficient to: (a) reach a target level (e.g., a predetermined or threshold level) of lysin concentration inside a target host; (b) reach a target level (e.g., a predetermined or threshold level) of lysin concentration inside a target host gut; (c) reach a target level (e.g., a predetermined or threshold level) of lysin concentration inside a target host bacteriocyte; (d) modulate the level, or an activity, of one or more microorganism (e.g., endosymbiont) in the target host; or/and (e) modulate fitness of the target host.

(c) Antimicrobial Peptides

The modulating agent described herein may include an antimicrobial peptide (AMP). Any AMP suitable for inhibiting a microorganism resident in the host may be used. AMPs are a diverse group of molecules, which are divided into subgroups on the basis of their amino acid composition and structure. The AMP may be derived or produced from any organism that naturally produces AMPs, including AMPs derived from plants (e.g., copsin), insects (e.g., drosocin, scorpion peptide (e.g., Uy192, UyCT3, D3, D10, Uy17, Uy192), mastoparan, poneratoxin, cecropin, moricin, melittin), frogs (e.g., magainin, dermaseptin, aurein), and mammals (e.g., cathelicidins, defensins and protegrins). For example, the AMP may be a scorpion peptide, such as Uy192 (5'-FLSTIWNGIKGLL-3'; SEQ ID NO: 221), UyCT3 (5'-LSAIWSGIKSLF-3; SEQ ID NO: 222), D3 (5'-LWGKLWEGVKSLI-3'; SEQ ID NO: 223), and D10 (5'-FPFLKLSLKIPKSAIKSAIKRL-3'; SEQ ID NO: 224), Uy17 (5'-ILSAIWSGIKGLL-3'; SEQ ID NO: 225), or a combination thereof. Other non-limiting examples of AMPs are listed in Table 6.

TABLE 6

Examples of Antimicrobial Peptides

| Type | Characteristic | Example AMP | Sequence |
| --- | --- | --- | --- |
| Anionic peptides | rich in glutamic and aspartic acid | dermcidin | SSLLEKGLDGAKKAVGGLGKL GKDAVEDLESVGKGAVHDVKD VLDSVL (SEQ ID NO: 81) |
| Linear cationic α-helical peptides | lack cysteine | cecropin A | KWKLFKKIEKVGQNIRDGIIKAG PAVAVVGQATQIAK (SEQ ID NO: 82) |
| | | andropin | MKYFSVLVVLTLILAIVDQSDAFI NLLDKVEDALHTGAQAGFKLIR PVERGATPKKSEKPEK (SEQ ID NO: 83) |
| | | moricin | MNILKFFFVFIVAMSLVSCSTAA PAKIPIKAIKTVGKAVGKGLRAI NIASTANDVFNFLKPKKRKH (SEQ ID NO: 84) |
| | | ceratotoxin | MANLKAVFLICIVAFIALQCVVA EPAAEDSVVVKRSIGSALKKAL PVAKKIGKIALPIAKAALPVAAG LVG (SEQ ID NO: 85) |
| Cationic peptide enriched for specific amino acid | rich in proline, arginine, phenylalanine, glycine, tryptophan | abaecin | MKVVIFIFALLATICAAFAYVPLP NVPQPGRRPFPTFGQGPFNP KIKWPQGY (SEQ ID NO: 86) |
| | | apidaecins | KNFALAILVVTFVVAVFGNTNLD PPTRPTRLRREAKPEAEPGNN RPVYIPQPRPPHPRLRREAEPE AEPGNNRPVYIPQPRPPHPRL RREAELEAEPGNNRPVYISQP RPPHPRLRREAEPEAEPGNNR PVYIPQPRPPHPRLRREAELEA EPGNNRPVYISQPRPPHPRLR REAEPEAEPGNNRPVYIPQPR PPHPRLRREAEPEAEPGNNRP VYIPQPRPPHPRLRREAEPEAE PGNNRPVYIPQPRPPHPRLRR EAKPEAKPGNNRPVYIPQPRP PHPRI (SEQ ID NO: 87) |

TABLE 6-continued

Examples of Antimicrobial Peptides

| Type | Characteristic | Example AMP | Sequence |
|---|---|---|---|
| | | prophenin | METQRASLCLGRWSLWLLLLA LVVPSASAQALSYREAVLRAVD RLNEQSSEANLYRLLELDQPPK ADEDPGTPKPVSFTVKETVCP RPTRRPPELCDFKENGRVKQC VGTVTLDQIKDPLDITCNEGVR RFPWWWPFLRRPRLRRQAFP PPNVPGPRFPPPNVPGPRFPP PNFPGPRFPPPNFPGPRFPPP NFPGPPFPPPIFPGPWFPPPPP FRPPPFGPPRFPGRR (SEQ ID NO: 88) |
| | | indolicidin | MQTQRASLSLGRWSLWLLLLG LVVPSASAQALSYREAVLRAVD QLNELSSEANLYRLLELDPPPK DNEDLGTRKPVSFTVKETVCP RTIQQPAEQCDFKEKGRVKQC VGTVTLDPSNDQFDLNCNELQ SVILPWKWPWWPWRRG (SEQ ID NO: 89) |
| Anionic and cationic peptides that contain cysteine and form disulfide bonds | contain 1-3 disulfide bond | protegrin | METQRASLCLGRWSLWLLLLA LVVPSASAQALSYREAVLRAVD RLNEQSSEANLYRLLELDQPPK ADEDPGTPKPVSFTVKETVCP RPTRQPPELCDFKENGRVKQC VGTVTLDQIKDPLDITCNEVQG VRGGRLCYCRRRFCVCVGRG (SEQ ID NO: 90) |
| | | tachyplesins | KWCFRVCYRGICYRRCR (SEQ ID NO: 91) |
| | | defensin | MKCATIVCTIAVVLAATLLNGSV QAAPQEEAALSGGANLNTLLD ELPEETHHAALENYRAKRATC DLASGFGVGSSLCAAHCIARR YRGGYCNSKAVCVCRN (SEQ ID NO: 92) |
| | | drosomycin | MMQIKYLFALFAVLMLVVLGAN EADADCLSGRYKGPCAVWDN ETCRRVCKEEGRSSGHCSPSL KCWCEGC (SEQ ID NO: 93) |

The AMP may be active against any number of target microorganisms. In some instances, the AMP may have antibacterial and/or antifungal activities. In some instances, the AMP may have a narrow-spectrum bioactivity or a broad-spectrum bioactivity. For example, some AMPs target and kill only a few species of bacteria or fungi, while others are active against both gram-negative and gram-positive bacteria as well as fungi.

Further, the AMP may function through a number of known mechanisms of action. For example, the cytoplasmic membrane is a frequent target of AMPs, but AMPs may also interfere with DNA and protein synthesis, protein folding, and cell wall synthesis. In some instances, AMPs with net cationic charge and amphipathic nature disrupt bacterial membranes leading to cell lysis. In some instances, AMPs may enter cells and interact with intracellular target to interfere with DNA, RNA, protein, or cell wall synthesis. In addition to killing microorganisms, AMPs have demonstrated a number of immunomodulatory functions that are involved in the clearance of infection, including the ability to alter host gene expression, act as chemokines and/or induce chemokine production, inhibit lipopolysaccharide induced pro-inflammatory cytokine production, promote wound healing, and modulating the responses of dendritic cells and cells of the adaptive immune response.

In some instances, the AMP is a functionally active variant of the AMPs described herein. In some instances, the variant of the AMP has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of an AMP described herein or a naturally derived AMP.

In some instances, the AMP may be bioengineered to modulate its bioactivity, e.g., increase or decrease or regulate, or to specify a target microorganism. In some instances, the AMP is produced by the translational machinery (e.g. a ribosome, etc.) of a cell. In some instances, the AMP is chemically synthesized. In some instances, the AMP is derived from a polypeptide precursor. The polypeptide precursor can undergo cleavage (for example, processing by a protease) to yield the polypeptide of the AMP itself. As such, in some instances, the AMP is produced from a precursor polypeptide. In some instances, the AMP includes a polypeptide that has undergone post-translational modifications, for example, cleavage, or the addition of one or more functional groups.

The AMPs described herein may be formulated in a composition for any of the uses described herein. The compositions disclosed herein may include any number or type (e.g., classes) of AMPs, such as at least about any one of 1 AMP, 2, 3, 4, 5, 10, 15, 20, or more AMPs. For example, the compositions may include a cocktail of AMPs (e.g., a cocktail of scorpion peptides, e.g., UyCT3, D3, D10, and Uy17). A suitable concentration of each AMP in the composition depends on factors such as efficacy, stability of the AMP, number of distinct AMP in the composition, the formulation, and methods of application of the composition. In some instances, each AMP in a liquid composition is from about 0.1 ng/mL to about 100 mg/mL. In some instances, each AMP in a solid composition is from about 0.1 ng/g to about 100 mg/g. In some instances, wherein the composition includes at least two types of AMPs, the concentration of each type of AMP may be the same or different.

A modulating agent including an AMP as described herein can be contacted with the target host in an amount and for a time sufficient to: (a) reach a target level (e.g., a predetermined or threshold level) of AMP concentration inside a target host; (b) reach a target level (e.g., a predetermined or threshold level) of AMP concentration inside a target host gut; (c) reach a target level (e.g., a predetermined or threshold level) of AMP concentration inside a target host bacteriocyte; (d) modulate the level, or an activity, of one or more microorganism (e.g., endosymbiont) in the target host; or/and (e) modulate fitness of the target host.

(d) Nodule C-Rich Peptides

The modulating agent described herein may include a nodule C-rich peptide (NCR peptide). NCR peptides are produced in certain leguminous plants and play an important role in the mutualistic, nitrogen-fixing symbiosis of the plants with bacteria from the Rhizobiaceae family (*rhizobia*), resulting in the formation of root nodules where plant cells contain thousands of intracellular endosymbionts. NCR peptides possess anti-microbial properties that direct an irreversible, terminal differentiation process of bacteria, e.g., to permeabilize the bacterial membrane, disrupt cell division, or inhibit protein synthesis. For example, in *Medicago truncatula* nodule cells infected with *Sinorhizobium meliloti*, hundreds of NCR peptides are produced which direct irreversible differentiation of the bacteria into large polyploid nitrogen-fixing bacteroids.). Non-limiting examples of NCR peptides are listed in Table 7.

TABLE 7

Examples of NCR Peptides

| NAME | Peptide sequence | Producer |
| --- | --- | --- |
| >gi\|152218086\|gb\|ABS31477.1\| NCR 340 | MTKIVVFIYVVILLLTIFHVSAKKKRYI ECETHEDCSQVFMPPFVMRCVIHE CKIFNGEHLRY (SEQ ID NO: 94) | *Medicago truncatula* |
| >gi\|152218084\|gb\|ABS31476.1\| NCR 339 | MAKIMKFVYNMIPFLSIFIITLQVNVV VCEIDADCPQICMPPYEVRCVNHRC GWVNTDDSLFLTQEFTRSKQYIIS (SEQ ID NO: 95) | *Medicago truncatula* |
| >gi\|152218082\|gb\|ABS31475.1\| NCR 338 | MYKVVESIFIRYMHRKPNMTKFFKF VYTMFILISLFLVVTNANAHNCTDISD CSSNHCSYEGVSLCMNGQCICIYE (SEQ ID NO: 96) | *Medicago truncatula* |
| >gi\|152218080\|gb\|ABS31474.1\| NCR 337 | MVETLRLFYIMILFVSLCLVVVDGES KLEQTCSEDFECYIKNPHVPFGHLR CFEGFCQQLNGPA (SEQ ID NO: 97) | *Medicago truncatula* |
| >gi\|152218078\|gb\|ABS31473.1\| NCR 336 | MAKIVNFVYSMIVFLFLFLVATKAAR GYLCVTDSHCPPHMCPPGMEPRCV RRMCKCLPIGWRKYFVP (SEQ ID NO: 98) | *Medicago truncatula* |
| >gi\|152218076\|gb\|ABS31472.1\| NCR 335 | MQIGKNMVETPKLDYVIIFFFLYFFF RQMIILRLNTTFRPLNFKMLRFWGQ NRNIMKHRGQKVHFSLILSDCKTNK DCPKLRRANVRCRKSYCVPI (SEQ ID NO: 99) | *Medicago truncatula* |
| >gi\|152218074\|gb\|ABS31471.1\| NCR 334 | MLRLYLVSYFLLKRTLLVSYFSYFST YIIECKTDNDCPISQLKIYAWKCVKN GCHLFDVIPMMYE (SEQ ID NO: 100) | *Medicago truncatula* |
| >gi\|152218072\|gb\|ABS31470.1\| NCR 333 | MAEILKFVYIVILFVSLLLIVVASEREC VTDDDCEKLYPTNEYRMMCDSGYC MNLLNGKIIYLLCLKKKKFLIIISVLL (SEQ ID NO: 101) | *Medicago truncatula* |
| >gi\|152218070\|gb\|ABS31469.1\| NCR 332 | MAEIIKFVYIMILCVSLLLIEVAGEECV TDADCDKLYPDIRKPLMCSIGECYSL YKGKFSLSIISKTSFSLMVYNVVTLVI CLRLAYISLLLKFL (SEQ ID NO: 102) | *Medicago truncatula* |

TABLE 7-continued

Examples of NCR Peptides

| NAME | Peptide sequence | Producer |
|---|---|---|
| >gi\|152218068\|gb\|ABS31468.1\| NCR 331 | MAEILKDFYAMNLFIFLIILPAKIRGET LSLTHPKCHHIMLPSLFITEVFQRVT DDGCPKPVNHLRVVKCIEHICEYGY NYRPDFASQIPESTKMPRKRE (SEQ ID NO: 103) | *Medicago truncatula* |
| >gi\|152218066\|gb\|ABS31467.1\| NCR 330 | MVEILKNFYAMNLFIFLIILAVKIRGAH FPCVTDDDCPKPVNKLRVIKCIDHIC QYARNLPDFASEISESTKMPCKGE (SEQ ID NO: 104) | *Medicago truncatula* |
| >gi\|152218064\|gb\|ABS31466.1\| NCR 329 | MFHAQAENMAKVSNFVCIMILFLALF FITMNDAARFECREDSHCVTRIKCV LPRKPECRNYACGCYDSNKYR (SEQ ID NO: 105) | *Medicago truncatula* |
| >gi\|152218062\|gb\|ABS31465.1\| NCR 328 | MQMRQNMATILNFVFVIILFISLLLVV TKGYREPFSSFTEGPTCKEDIDCPSI SCVNPQVPKCIMFECHCKYIPTTLK (SEQ ID NO: 106) | *Medicago truncatula* |
| >gi\|152218060\|gb\|ABS31464.1\| NCR 327 | MATILMYVYITILFISILTVLTEGLYEPL YNFRRDPDCRRNIDCPSYLCVAPKV PRCIMFECHCKDIPSDH (SEQ ID NO: 107) | *Medicago truncatula* |
| >gi\|152218058\|gb\|ABS31463.1\| NCR 326 | MTTSLKFVYVAILFLSLLLVVMGGIR RFECRQDSDCPSYFCEKLTVPKCF WSKCYCK (SEQ ID NO: 108) | *Medicago truncatula* |
| >gi\|152218056\|gb\|ABS31462.1\| NCR 325 | MTTSLKFVYVAILFLSLLLVVMGGIR KKECRQDSDCPSYFCEKLTIAKCIHS TCLCK (SEQ ID NO: 109) | *Medicago truncatula* |
| >gi\|152218054\|gb\|ABS31461.1\| NCR 324 | MQIGKNMVETPKLVYFIILFLSIFLCIT VSNSSFSQIFNSACKTDKDCPKFGR VNVRCRKGNCVPI (SEQ ID NO: 110) | *Medicago truncatula* |
| >gi\|152218046\|gb\|ABS31457.1\| NCR 320 | MTAILKKFINAVFLFIVLFLATTNVED FVGGSNDECVYPDVFQCINNICKCV SHHRT (SEQ ID NO: 111) | *Medicago truncatula* |
| >gi\|152218044\|gb\|ABS31456.1\| NCR 319 | MQKRKNMAQIIFYVYALIILFSPFLAA RLVFVNPEKPCVTDADCDRYRHES AIYSDMFCKDGYCFIDYHHDPYP (SEQ ID NO: 112) | *Medicago truncatula* |
| >gi\|152218042\|gb\|ABS31455.1\| NCR 318 | MQMRKNMAQILFYVYALLILFTPFLV ARIMVVNPNNPCVTDADCQRYRHK LATRMICNQGFCLMDFTHDPYAPSL P (SEQ ID NO: 113) | *Medicago truncatula* |
| >gi\|152218040\|gb\|ABS31454.1\| NCR 317 | MNHISKFVYALIIFLSIYLVVLDGLPIS CKDHFECRRKINILRCIYRQEKPMCI NSICTCVKLL (SEQ ID NO: 114) | *Medicago truncatula* |
| >gi\|152218038\|gb\|ABS31453.1\| NCR 316 | MQREKNMAKIFEFVYAMIIPILLFLVE KNVVAYLKFECKTDDDCQKSLLKTY VWKCVKNECYFFAKK (SEQ ID NO: 115) | *Medicago truncatula* |
| >gi\|152218036\|gb\|ABS31452.1\| NCR 315 | MAGIIKFVHVLIIFLSLFHVVKNDDGS FCFKDSDCPDEMCPSPLKEMCYFL QCKCGVDTIA (SEQ ID NO: 116) | *Medicago truncatula* |
| >gi\|152218034\|gb\|ABS31451.1\| NCR 314 | MANTHKLVSMILFIFLFLASNNVEGY VNCETDADCPPSTRVKRFKCVKGE CRWTRMSYA (SEQ ID NO: 117) | *Medicago truncatula* |

TABLE 7-continued

Examples of NCR Peptides

| NAME | Peptide sequence | Producer |
|---|---|---|
| >gi\|152218032\|gb\|ABS31450.1\| NCR 313 | MQRRKKKAQVVMFVHDLIICIYLFIVI TTRKTDIRCRFYYDCPRLEYHFCECI EDFCAYIRLN (SEQ ID NO: 118) | Medicago truncatula |
| >gi\|152218030\|gb\|ABS31449.1\| NCR 312 | MAKVYMFVYALIIFVSPFLLATFRTRL PCEKDDDCPEAFLPPVMKCVNRFC QYEILE (SEQ ID NO: 119) | Medicago truncatula |
| >gi\|152218028\|gb\|ABS31448.1\| NCR 310 | MIKQFSVCYIQMRRNMTTILKFPYIM VICLLLLHVAAYEDFEKEIFDCKKDG DCDHMCVTPGIPKCTGYVCFCFENL (SEQ ID NO: 120) | Medicago truncatula |
| >gi\|152218026\|gb\|ABS31447.1\| NCR 309 | MQRSRNMTTIFKFAYIMIICVFLLNIA AQEIENGIHPCKKNEDCNHMCVMP GLPWCHENNLCFCYENAYGNTR (SEQ ID NO: 121) | Medicago truncatula |
| >gi\|152218024\|gb\|ABS31446.1\| NCR 304 | MTIIIKFVNVLIIFLSLFHVAKNDDNKL LLSFIEEGFLCFKDSDCPYNMCPSP LKEMCYFIKCVCGVYGPIRERRLYQ SHNPMIQ (SEQ ID NO: 122) | Medicago truncatula |
| >gi\|152218022\|gb\|ABS31445.1\| NCR 303 | MRKNMTKILMIGYALMIFIFLSIAVSIT GNLARASRKKPVDVIPCIYDHDCPR KLYFLERCVGRVCKYL (SEQ ID NO: 123) | Medicago truncatula |
| >gi\|152218020\|gb\|ABS31444.1\| NCR 301 | MAHKLVYAITLFIFLFLIANNIEDDIFCI TDNDCPPNTLVQRYRCINGKCNLSF VSYG (SEQ ID NO: 124) | Medicago truncatula |
| >gi\|152218018\|gb\|ABS31443.1\| NCR 300 | MDETLKFVYILILFVSLCLVVADGVK NINRECTQTSDCYKKYPFIPWGKVR CVKGRCRLDM (SEQ ID NO: 125) | Medicago truncatula |
| >gi\|152218016\|gb\|ABS31442.1\| NCR 290 | MAKIIKFVYVLAIFFSLFLVAKNVNG WTCVEDSDCPANICQPPMQRMCFY GECACVRSKFCT (SEQ ID NO: 126) | Medicago truncatula |
| >gi\|152218014\|gb\|ABS31441.1\| NCR 289 | MVKIIKFVYFMTLFLSMLLVTTKEDG SVECIANIDCPQIFMLPFVMRCINFR CQIVNSEDT (SEQ ID NO: 127) | Medicago truncatula |
| >gi\|152218012\|gb\|ABS31440.1\| NCR 286 | MDEILKFVYTLIIFFSLFFAANNVDANI MNCQSTFDCPRDMCSHIRDVICIFK KCKCAGGRYMPQVP (SEQ ID NO: 128) | Medicago truncatula |
| >gi\|152218008\|gb\|ABS31438.1\| NCR 278 | MQRRKNMANNHMLIYAMIICLFPYL VVTFKTAITCDCNEDCLNFFTPLDNL KCIDNVCEVFM (SEQ ID NO: 129) | Medicago truncatula |
| >gi\|152218006\|gb\|ABS31437.1\| NCR 266 | MVNILKFIYVIIFFILMFFVLIDVDGHV LVECIENRDCEKGMCKFPFIVRCLM DQCKCVRIHNLI (SEQ ID NO: 130) | Medicago truncatula |
| >gi\|152218004\|gb\|ABS31436.1\| NCR 265 | MIIQFSIYYMQRRKLNMVEILKFSHA LIIFLFLSALVTNANIFFCSTDEDCTW NLCRQPWVQKCRLHMCSCEKN (SEQ ID NO: 131) | Medicago truncatula |
| >gi\|152218002\|gb\|ABS31435.1\| NCR 263 | MDEVFKFVYVMIIFPFLILDVATNAEK IRRCFNDAHCPPDMCTLGVIPKCSR FTICIC (SEQ ID NO: 132) | Medicago truncatula |

TABLE 7-continued

Examples of NCR Peptides

| NAME | Peptide sequence | Producer |
|---|---|---|
| >gi\|152218000\|gb\|ABS31434.<br>1\| NCR 244 | MHRKPNMTKFFKFVYTMFILISLFLV<br>VTNANANNCTDTSDCSSNHCSYEG<br>VSLCMNGQCICIYE<br>(SEQ ID NO: 133) | *Medicago truncatula* |
| >gi\|152217998\|gb\|ABS31433.<br>1\| NCR 239 | MQMKKMATILKFVYLIILLIYPLLVVTE<br>ESHYMKFSICKDDTDCPTLFCVLPN<br>VPKCIGSKCHCKLMVN<br>(SEQ ID NO: 134) | *Medicago truncatula* |
| >gi\|152217996\|gb\|ABS31432.<br>1\| NCR 237 | MVETLRLFYIMILFVSLYLVVVDGVS<br>KLAQSCSEDFECYIKNPHAPFGQLR<br>CFEGYCQRLDKPT<br>(SEQ ID NO: 135) | *Medicago truncatula* |
| >gi\|152217994\|gb\|ABS31431.<br>1\| NCR 228 | MTTFLKVAYIMIICVFVLHLAAQVDS<br>QKRLHGCKEDRDCDNICSVHAVTK<br>CIGNMCRCLANVK<br>(SEQ ID NO: 136) | *Medicago truncatula* |
| >gi\|152217992\|gb\|ABS31430.<br>1\| NCR 224 | MRINRTPAIFKFVYTIIIYLFLLRVVAK<br>DLPFNICEKDEDCLEFCAHDKVAKC<br>MLNICFCF<br>(SEQ ID NO: 137) | *Medicago truncatula* |
| >gi\|152217990\|gb\|ABS31429.<br>1\| NCR 221 | MAEILKILYVFIIFLSLILAVISQHPFTP<br>CETNADCKCRNHKRPDCLWHKCYC<br>Y<br>(SEQ ID NO: 138) | *Medicago truncatula* |
| >gi\|152217988\|gb\|ABS31428.<br>1\| NCR 217 | MRKSMATILKFVYVIMLFIYSLFVIES<br>FGHRFLIYNNCKNDTECPNDCGPHE<br>QAKCILYACYCVE<br>(SEQ ID NO: 139) | *Medicago truncatula* |
| >gi\|152217986\|gb\|ABS31427.<br>1\| NCR 209 | MNTILKFIFVVFLFLSIFLSAGNSKSY<br>GPCTTLQDCETHNWFEVCSCIDFEC<br>KCWSLL<br>(SEQ ID NO: 140) | *Medicago truncatula* |
| >gi\|152217984\|gb\|ABS31426.<br>1\| NCR 206 | MAEIIKFVYIMILCVSLLLIAEASGKEC<br>VTDADCENLYPGNKKPMFCNNTGY<br>CMSLYKEPSRYM<br>(SEQ ID NO: 141) | *Medicago truncatula* |
| >gi\|152217982\|gb\|ABS31425.<br>1\| NCR 201 | MAKIIKFVYIMILCVSLLLIVEAGGKEC<br>VTDVDCEKIYPGNKKPLICSTGYCYS<br>LYEEPPRYHK<br>(SEQ ID NO: 142) | *Medicago truncatula* |
| >gi\|152217980\|gb\|ABS31424.<br>1\| NCR 200 | MAKVTKFGYIIIHFLSLFFLAMNVAG<br>GRECHANSHCVGKITCVLPQKPEC<br>WNYACVCYDSNKYR<br>(SEQ ID NO: 143) | *Medicago truncatula* |
| >gi\|152217978\|gb\|ABS31423.<br>1\| NCR 192 | MAKIFNYVYALIMFLSLFLMGTSGMK<br>NGCKHTGHCPRKMCGAKTTKCRN<br>NKCQCV<br>(SEQ ID NO: 144) | *Medicago truncatula* |
| >gi\|152217976\|gb\|ABS31422.<br>1\| NCR 189 | MTEILKFVCVMIIFISSFIVSKSLNGG<br>GKDKCFRDSDCPKHMCPSSLVAKCI<br>NRLCRCRRPELQVQLNP<br>(SEQ ID NO: 145) | *Medicago truncatula* |
| >gi\|152217974\|gb\|ABS31421.<br>1\| NCR 187 | MAHIIMFVYALIYALIIFSSLFVRDGIP<br>CLSDDECPEMSHYSFKCNNKICEYD<br>LGEMSDDDYYLEMSRE<br>(SEQ ID NO: 146) | *Medicago truncatula* |
| >gi\|152217972\|gb\|ABS31420.<br>1\| NCR 181 | MYREKNMAKTLKFVYVIVLFLSLFLA<br>AKNIDGRVSYNSFIALPVCQTAADC<br>PEGTRGRTYKCINNKCRYPKLLKPI<br>Q<br>(SEQ ID NO: 147) | *Medicago truncatula* |

TABLE 7-continued

Examples of NCR Peptides

| NAME | Peptide sequence | Producer |
|---|---|---|
| >gi\|152217970\|gb\|ABS31419.1\| NCR 176 | MAHIFNYVYALLVFLSLFLMVTNGIHI GCDKDRDCPKQMCHLNQTPKCLKN ICKCV (SEQ ID NO: 148) | *Medicago truncatula* |
| >gi\|152217968\|gb\|ABS31418.1\| NCR 175 | MAEILKCFYTMNLFIFLIILPAKIREHI QCVIDDDCPKSLNKLLIIKCINHVCQY VGNLPDFASQIPKSTKMPYKGE (SEQ ID NO: 149) | *Medicago truncatula* |
| >gi\|152217966\|gb\|ABS31417.1\| NCR 173 | MAYISRIFYVLIIFLSLFFVVINGVKSL LLIKVRSFIPCQRSDDCPRNLCVDQII PTCVWAKCKCKNYND (SEQ ID NO: 150) | *Medicago truncatula* |
| >gi\|152217964\|gb\|ABS31416.1\| NCR 172 | MANVTKFVYIAIYFLSLFFIAKNDATA TFCHDDSHCVTKIKCVLPRTPQCRN EACGCYHSNKFR (SEQ ID NO: 151) | *Medicago truncatula* |
| >gi\|152217962\|gb\|ABS31415.1\| NCR 171 | MGEIMKFVYVMIIYLFMFNVATGSEF IPTKKLTSCDSSKDCRSFLCYSPKFP VCKRGICECI (SEQ ID NO: 152) | *Medicago truncatula* |
| >gi\|152217960\|gb\|ABS31414.1\| NCR 169 | MGEMFKFIYTFILFVHLFLVVIFEDIG HIKYCGIVDDCYKSKKPLFKIWKCVE NVCVLWYK (SEQ ID NO: 153) | *Medicago truncatula* |
| >gi\|152217958\|gb\|ABS31413.1\| NCR 165 | MARTLKFVYSMILFLSLFLVANGLKIF CIDVADCPKDLYPLLYKCIYNKCIVFT RIPFPFDWI (SEQ ID NO: 154) | *Medicago truncatula* |
| >gi\|152217956\|gb\|ABS31412.1\| NCR 159 | MANITKFVYIAILFLSLFFIGMNDAAIL ECREDSHCVTKIKCVLPRKPECRNN ACTCYKGGFSFHH (SEQ ID NO: 155) | *Medicago truncatula* |
| >gi\|152217954\|gb\|ABS31411.1\| NCR 147 | MQRVKKMSETLKFVYVLILFISIFHVV IVCDSIYFPVSRPCITDKDCPNMKHY KAKCRKGFCISSRVR (SEQ ID NO: 156) | *Medicago truncatula* |
| >gi\|152217952\|gb\|ABS31410.1\| NCR 146 | MQIRKIMSGVLKFVYAIILFLFLFLVA REVGGLETIECETDGDCPRSMIKM WNKNYRHKCIDGKCEWIKKLP (SEQ ID NO: 157) | *Medicago truncatula* |
| >gi\|152217950\|gb\|ABS31409.1\| NCR 145 | MFVYDLILFISLILVVTGINAEADTSC HSFDDCPWVAHHYRECIEGLCAYRI LY (SEQ ID NO: 158) | *Medicago truncatula* |
| >gi\|152217948\|gb\|ABS31408.1\| NCR 144 | MQRRKKSMAKMLKFFFAIILLLSLFL VATEVGGAYIECEVDDDCPKPMKN SHPDTYYKCVKHRCQWAWK (SEQ ID NO: 159) | *Medicago truncatula* |
| >gi\|152217946\|gb\|ABS31407.1\| NCR 140 | MFVYTLIIFLFPSHVITNKIAIYCVSDD DCLKTFTPLDLKCVDNVCEFNLRCK GKCGERDEKFVFLKALKKMDQKLVL EEQGNAREVKIPKKLLFDRIQVPTPA TKDQVEEDDYDDDDEEEEEEEDDV DMWFHLPDVVCH (SEQ ID NO: 160) | *Medicago truncatula* |
| >gi\|152217944\|gb\|ABS31406.1\| NCR 138 | MAKFSMFVYALINFLSLFLVETAITNI RCVSDDDCPKVIKPLVMKCIGNYCY FFMIYEGP (SEQ ID NO: 161) | *Medicago truncatula* |

TABLE 7-continued

Examples of NCR Peptides

| NAME | Peptide sequence | Producer |
|---|---|---|
| >gi\|152217942\|gb\|ABS31405.1\| NCR 136 | MAHKFVYAIILFIFLFLVAKNVKGYVV CRTVDDCPPDTRDLRYRCLNGKCK SYRLSYG (SEQ ID NO: 162) | *Medicago truncatula* |
| >gi\|152217940\|gb\|ABS31404.1\| NCR 129 | MQRKKNMGQILIFVFALINFLSPILVE MTTTTIPCTFIDDCPKMPLVVKCIDN FCNYFEIK (SEQ ID NO: 163) | *Medicago truncatula* |
| >gi\|152217938\|gb\|ABS31403.1\| NCR 128 | MAQTLMLVYALIIFTSLFLVVISRQTD IPCKSDDACPRVSSHHIECVKGFCT YVVKLD (SEQ ID NO: 164) | *Medicago truncatula* |
| >gi\|152217936\|gb\|ABS31402.1\| NCR 127 | MLRRKNTVQILMFVSALLIYIFLFLVIT SSANIPCNSDSDCPWKIYYTYRCND GFCVYKSIDPSTIPQYMTDLIFPR (SEQ ID NO: 165) | *Medicago truncatula* |
| >gi\|152217934\|gb\|ABS31401.1\| NCR 122 | MAVILKFVYIMIIFLFLLYVVNGTRCN RDEDCPFICTGPQIPKCVSHICFCLS SGKEAY (SEQ ID NO: 166) | *Medicago truncatula* |
| >gi\|152217932\|gb\|ABS31400.1\| NCR 121 | MDAILKFIYAMFLFLFLFVTTRNVEAL FECNRDFVCGNDDECVYPYAVQCI HRYCKCLKSRN (SEQ ID NO: 167) | *Medicago truncatula* |
| >gi\|152217930\|gb\|ABS31399.1\| NCR 119 | MQIGRKKMGETPKLVYVIILFLSIFLC TNSSFSQMINFRGCKRDKDCPQFR GVNIRCRSGFCTPIDS (SEQ ID NO: 168) | *Medicago truncatula* |
| >gi\|152217928\|gb\|ABS31398.1\| NCR 118 | MQMRKNMAQILFYVYALLILFSPFLV ARIMVVNPNNPCVTDADCQRYRHK LATRMVCNIGFCLMDFTHDPYAPSL P (SEQ ID NO: 169) | *Medicago truncatula* |
| >gi\|152217926\|gb\|ABS31397.1\| NCR 111 | MYVYYIQMGKNMAQRFMFIYALIIFL SQFFVVINTSDIPNNSNRNSPKEDVF CNSNDDCPTILYYVSKCVYNFCEYW (SEQ ID NO: 170) | *Medicago truncatula* |
| >gi\|152217924\|gb\|ABS31396.1\| NCR 103 | MAKIVNFVYSMIIFVSLFLVATKGGS KPFLTRPYPCNTGSDCPQNMCPPG YKPGCEDGYCNHCYKRW (SEQ ID NO: 171) | *Medicago truncatula* |
| >gi\|152217922\|gb\|ABS31395.1\| NCR 101 | MVRTLKFVYVIILILSLFLVAKGGGKK IYCENAASCPRLMYPLVYKCLDNKC VKFMMKSRFV (SEQ ID NO: 172) | *Medicago truncatula* |
| >gi\|152217920\|gb\|ABS31394.1\| NCR 96 | MARTLKFVYAVILFLSLFLVAKGDDV KIKCVVAANCPDLMYPLVYKCLNGIC VQFTLTFPFV (SEQ ID NO: 173) | *Medicago truncatula* |
| >gi\|152217918\|gb\|ABS31393.1\| NCR 94 | MSNTLMFVITFIVLVTLFLGPKNVYA FQPCVTTADCMKTLKTDENIWYECI NDFCIPFPIPKGRK (SEQ ID NO: 174) | *Medicago truncatula* |
| >gi\|152217916\|gb\|ABS31392.1\| NCR 93 | MKRVVNMAKIVKYVYVIIIFLSLFLVA TKIEGYYYKCFKDSDCVKLLCRIPLR PKCMYRHICKCKVVLTQNNYVLT (SEQ ID NO: 175) | *Medicago truncatula* |
| >gi\|152217914\|gb\|ABS31391.1\| NCR 90 | MKRGKNMSKILKFIYATLVLYLFLVV TKASDDECKIDGDCPISWQKFHTYK CINQKCKWVLRFHEY (SEQ ID NO: 176) | *Medicago truncatula* |

TABLE 7-continued

Examples of NCR Peptides

| NAME | Peptide sequence | Producer |
|---|---|---|
| >gi\|152217912\|gb\|ABS31390.<br>1\| NCR 88 | MAKTLNFMFALILFISLFLVSKNVAIDI<br>FVCQTDADCPKSELSMYTWKCIDN<br>ECNLFKVMQQMV<br>(SEQ ID NO: 177) | *Medicago truncatula* |
| >gi\|152217910\|gb\|ABS31389.<br>1\| NCR 86 | MANTHKLVSMILFIFLFLVANNVEGY<br>VNCETDADCPPSTRVKRFKCVKGE<br>CRWTRMSYA<br>(SEQ ID NO: 178) | *Medicago truncatula* |
| >gi\|152217908\|gb\|ABS31388.<br>1\| NCR 77 | MAHFLMFVYALITCLSLFLVEMGHLS<br>IHCVSVDDCPKVEKPITMKCINNYCK<br>YFVDHKL<br>(SEQ ID NO: 179) | *Medicago truncatula* |
| >gi\|152217906\|gb\|ABS31387.<br>1\| NCR 76 | MNQIPMFGYTLIIFFSLFPVITNGDRI<br>PCVTNGDCPVMRLPLYMRCITYSCE<br>LFFDGPNLCAVERI<br>(SEQ ID NO: 180) | *Medicago truncatula* |
| >gi\|152217904\|gb\|ABS31386.<br>1\| NCR 74 | MRKDMARISLFVYALIIFFSLFFVLTN<br>GELEIRCVSDADCPLFPLPHNRCID<br>DVCHLFTS<br>(SEQ ID NO: 181) | *Medicago truncatula* |
| >gi\|152217902\|gb\|ABS31385.<br>1\| NCR 68 | MAQILMFVYFLIIFLSLFLVESIKIFTE<br>HRCRTDADCPARELPEYLKCQGGM<br>CRLLIKKD<br>(SEQ ID NO: 182) | *Medicago truncatula* |
| >gi\|152217900\|gb\|ABS31384.<br>1\| NCR 65 | MARVISLFYALIIFLFLFLVATNGDLS<br>PCLRSGDCSKDECPSHLVPKCIGLT<br>CYCI<br>(SEQ ID NO: 183) | *Medicago truncatula* |
| >gi\|152217898\|gb\|ABS31383.<br>1\| NCR 62 | MQRRKNMAQILLFAYVFIISISLFLVV<br>TNGVKIPCVKDTDCPTLPCPLYSKC<br>VDGFCKMLSI<br>(SEQ ID NO: 184) | *Medicago truncatula* |
| >gi\|152217896\|gb\|ABS31382.<br>1\| NCR 57 | MNHISKFVYALIIFLSVYLVVLDGRPV<br>SCKDHYDCRRKVKIVGCIFPQEKPM<br>CINSMCTCIREIVP<br>(SEQ ID NO: 185) | *Medicago truncatula* |
| >gi\|152217894\|gb\|ABS31381.<br>1\| NCR 56 | MKSQNHAKFISFYKNDLFKIFQNND<br>SHFKVFFALIIFLYTYLHVTNGVFVSC<br>NSHIHCRVNNHKIGCNIPEQYLLCVN<br>LFCLWLDY<br>(SEQ ID NO: 186) | *Medicago truncatula* |
| >gi\|152217892\|gb\|ABS31380.<br>1\| NCR 54 | MTYISKVVYALIIFLSIYVGVNDCMLV<br>TCEDHFDCRQNVQQVGCSFREIPQ<br>CINSICKCMKG<br>(SEQ ID NO: 187) | *Medicago truncatula* |
| >gi\|152217890\|gb\|ABS31379.<br>11 NCR 53 | MTHISKFVFALIIFLSIYVGVNDCKRIP<br>CKDNNDCNNNWQLLACRFEREVPR<br>CINSICKCMPM<br>(SEQ ID NO: 188) | *Medicago truncatula* |
| >gi\|152217888\|gb\|ABS31378.<br>1\| NCR 43 | MVQTPKLVYVIVLLLSIFLGMTICNSS<br>FSHFFEGACKSDKDCPKLHRSNVR<br>CRKGQCVQI<br>(SEQ ID NO: 189) | *Medicago truncatula* |
| >gi\|152217886\|gb\|ABS31377.<br>1\| NCR 28 | MTKILMLFYAMIVFHSIFLVASYTDEC<br>STDADCEYILCLFPIIKRCIHNHCKCV<br>PMGSIEPMSTIPNGVHKFHIINN<br>(SEQ ID NO: 190) | *Medicago truncatula* |
| >gi\|152217884\|gb\|ABS31376.<br>1\| NCR 26 | MAKTLNFVCAMILFISLFLVSKNVAL<br>YIIECKTDADCPISKLNMYNWRCIKS<br>SCHLYKVIQFMV<br>(SEQ ID NO: 191) | *Medicago truncatula* |

TABLE 7-continued

Examples of NCR Peptides

| NAME | Peptide sequence | Producer |
| --- | --- | --- |
| >gi\|152217882\|gb\|ABS31375.1\| NCR 24 | MQKEKNMAKTFEFVYAMIIFILLFLVE NNFAAYIIECQTDDDCPKSQLEMFA WKCVKNGCHLFGMYEDDDDP (SEQ ID NO: 192) | Medicago truncatula |
| >gi\|152217880\|gb\|ABS31374.1\| NCR 21 | MAATRKFIYVLSHFLFLFLVTKITDAR VCKSDKDCKDIIIYRYILKCRNGECV KIKI (SEQ ID NO: 193) | Medicago truncatula |
| >gi\|152217878\|gb\|ABS31373.1\| NCR 20 | MQRLDNMAKNVKFIYVIILLLFIFLVII VCDSAFVPNSGPCTTDKDCKQVKG YIARCRKGYCMQSVKRTWSSYSR (SEQ ID NO: 194) | Medicago truncatula |
| >gi\|152217876\|gb\|ABS31372.1\| NCR 19 | MKFIYIMILFLSLFLVQFLTCKGLTVP CENPTTCPEDFCTPPMITRCINFICL CDGPEYAEPEYDGPEPEYDHKGDF LSVKPKIINENMMMRERHMMKEIEV (SEQ ID NO: 195) | Medicago truncatula |
| >gi\|152217874\|gb\|ABS31371.1\| NCR 12 | MAQFLMFIYVLIIFLYLFYVEAAMFEL TKSTIRCVTDADCPNVVKPLKPKCV DGFCEYT (SEQ ID NO: 196) | Medicago truncatula |
| >gi\|152217872\|gb\|ABS31370.1\| NCR 10 | MKMRIHMAQIIMFFYALIIFLSPFLVD RRSFPSSFVSPKSYTSEIPCKATRD CPYELYYETKCVDSLCTY (SEQ ID NO: 197) | Medicago truncatula |

Any NCR peptide known in the art is suitable for use in the methods or compositions described herein. NCR peptide-producing plants include but are not limited to *Pisum sativum* (pea), *Astragalus sinicus* (IRLC legumes), *Phaseolus vulgaris* (bean), *Vigna unguiculata* (cowpea), *Medicago truncatula* (barrelclover), and *Lotus japonicus*. For example, over 600 potential NCR peptides are predicted from the *M. truncatula* genome sequence and almost 150 different NCR peptides have been detected in cells isolated from root nodules by mass spectrometry.

The NCR peptides described herein may be mature or immature NCR peptides. Immature NCR peptides have a C-terminal signal peptide that is required for translocation into the endoplasmic reticulum and cleaved after translocation. The N-terminus of a NCR peptide includes a signal peptide, which may be cleavable, for targeting to a secretory pathway. NCR peptides are generally small peptides with disulfide bridges that stabilize their structure. Mature NCR peptides have a length in the range of about 20 to about 60 amino acids, about 25 to about 55 amino acids, about 30 to about 50 amino acids, about 35 to about 45 amino acids, or any range therebetween. NCR peptides may include a conserved sequence of cysteine residues with the rest of the peptide sequence highly variable. NCR peptides generally have about four or eight cysteines.

NCR peptides may be anionic, neutral, or cationic. In some instances, synthetic cationic NCR peptides having a pI greater than about eight possess antimicrobial activities. For example, NCR247 (pI=10.15) (RNGCIVDPRCP-YQQCR-RPLYCRRR; SEQ ID NO: 198) and NCR335 (pI=11.22) (MAQFLLFVYSLIIFLSLFFGEAAFERTETRMLTIPC-TSDDNCPKVISPCHTKCFDGFCGWYIEGSYEGP; SEQ ID NO: 199) are both effective against gram-negative and gram-positive bacteria as well as fungi. In some instances, neutral and/or anionic NCR peptides, such as NCR001, do not possess antimicrobial activities at a pI greater than about 8.

In some instances, the NCR peptide is effective to kill bacteria. In some instances, the NCR peptide is effective to kill *S. meliloti*, *Xenorhabdus* spp, *Photorhabdus* spp, *Candidatus* spp, *Buchnera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, or *Escherichia* spp.

In some instances, the NCR peptide is a functionally active variant of a NCR peptide described herein. In some instances, the variant of the NCR peptide has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a NCR peptide described herein or naturally derived NCR peptide.

In some instances, the NCR peptide may be bioengineered to modulate its bioactivity, e.g., increase or decrease or regulate, or to specify a target microorganism. In some instances, the NCR peptide is produced by the translational machinery (e.g. a ribosome, etc.) of a cell. In some instances, the NCR peptide is chemically synthesized. In some instances, the NCR peptide is derived from a polypeptide precursor. The polypeptide precursor can undergo cleavage (for example, processing by a protease) to yield the NCR peptide itself. As such, in some instances, the NCR peptide is produced from a precursor polypeptide. In some instances, the NCR peptide includes a polypeptide that has undergone post-translational modifications, for example, cleavage, or the addition of one or more functional groups.

The NCR peptide described herein may be formulated in a composition for any of the uses described herein. The compositions disclosed herein may include any number or type of NCR peptides, such as at least about any one of 1 NCR peptide, 2, 3, 4, 5, 10, 15, 20, 30, 40, 50, 100, or more NCR peptides. A suitable concentration of each NCR peptide in the composition depends on factors such as efficacy, stability of the NCR peptide, number of distinct NCR peptide, the formulation, and methods of application of the composition. In some instances, each NCR peptide in a liquid composition is from about 0.1 ng/mL to about 100 mg/mL. In some instances, each NCR peptide in a solid composition is from about 0.1 ng/g to about 100 mg/g. In some instances, wherein the composition includes at least two types of NCR peptides, the concentration of each type of NCR peptide may be the same or different.

A modulating agent including a NCR peptide as described herein can be contacted with the target host in an amount and for a time sufficient to: (a) reach a target level (e.g., a predetermined or threshold level) of NCR peptide concentration inside a target host; (b) reach a target level (e.g., a predetermined or threshold level) of NCR peptide concentration inside a target host gut; (c) reach a target level (e.g., a predetermined or threshold level) of NCR peptide concentration inside a target host bacteriocyte; (d) modulate the level, or an activity, of one or more microorganism (e.g., endosymbiont) in the target host; or/and (e) modulate fitness of the target host.

(e) Bacteriocyte Regulatory Peptides

The modulating agent described herein may include a bacteriocyte regulatory peptide (BRP). BRPs are peptides expressed in the bacteriocytes of insects. These genes are expressed first at a developmental time point coincident with the incorporation of symbionts and their bacteriocyte-specific expression is maintained throughout the insect's life. In some instances, the BRP has a hydrophobic amino terminal domain, which is predicted to be a signal peptide. In addition, some BRPs have a cysteine-rich domain. In some instances, the bacteriocyte regulatory peptide is a bacteriocyte-specific cysteine rich (BCR) protein. Bacteriocyte regulatory peptides have a length between about 40 and 150 amino acids. In some instances, the bacteriocyte regulatory peptide has a length in the range of about 45 to about 145, about 50 to about 140, about 55 to about 135, about 60 to about 130, about 65 to about 125, about 70 to about 120, about 75 to about 115, about 80 to about 110, about 85 to about 105, or any range therebetween. Non-limiting examples of BRPs and their activities are listed in Table 8.

TABLE 8

Examples of Bacteriocyte Regulatory Peptides

| Name | Peptide Sequence |
| --- | --- |
| Bacteriocyte-specific cysteine rich proteins BCR family, peptide BCR1 | MKLLHGFLIIMLTMHLSIQYAYGGPFLTKYLCDRVCHKLC GDEFVCSCIQYKSLKGLWFPHCPTGKASVVLHNFLTSP (SEQ ID NO: 200) |
| Bacteriocyte-specific cysteine rich proteins BCR family, peptide BCR2 | MKLLYGFLIIMLTIHLSVQYFESPPFETKYNCDTHCNKLCGK IDHCSCIQYHSMEGLWFPHCRTGSAAQMLHDFLSNP (SEQ ID NO: 201) |
| Bacteriocyte-specific cysteine rich proteins BCR family, peptide BCR3 | MSVRKNVLPTMFVVLLIMSPVTPTSVFISAVCYSGCGSLA LVCFVSNGITNGLDYFKSSAPLSTSETSCGEAFDTCTDH CLANFKF (SEQ ID NO: 202) |
| Bacteriocyte-specific cysteine rich proteins BCR family, peptide BCR4 | MRLLYGFLIIMLTIYLSVQDFDPTEFKGPFPTIEICSKYCAV VCNYTSRPCYCVEAAKERDQWFPYCYD (SEQ ID NO: 203) |
| Bacteriocyte-specific cysteine rich proteins BCR family, peptide BCR5 | MRLLYGFLIIMLTIHLSVQDIDPNTLRGPYPTKEICSKYCEY NVVCGASLPCICVQDARQLDHWFACCYDGGPEMLM (SEQ ID NO: 204) |
| Secreted proteins SP family, peptide SP1 | MKLFVVVVLVAVGIMFVFASDTAAAPTDYEDTNDMISLSS LVGDNSPYVRVSSADSGGSSKTSSKNPILGLLKSVIKLLT KIFGTYSDAAPAMPPIPPALRKNRGMLA (SEQ ID NO: 205) |
| Secreted proteins SP family, peptide SP2 | MVACKVILAVAVVFVAAVQGRPGGEPEWAAPIFAELKSV SDNITNLVGLDNAGEYATAAKNNLNAFAESLKTEAAVFSK SFEGKASASDVFKESTKNFQAVVDTYIKNLPKDLTLKDFT EKSEQALKYMVEHGTEITKKAQGNTETEKEIKEFFKKQIE NLIGQGKALQAKIAEAKKA (SEQ ID NO: 206) |
| Secreted proteins SP family, peptide SP3 | MKTSSSKVFASCVAIVCLASVANALPVQKSVAATTENPIV EKHGCRAHKNLVRQNVVDLKTYDSMLITNEVVQKQSNE VQSSEQSNEGQNSEQSNEGQNSEQSNEVQSSEHSNEG QNSKQSNEGQNSEQSNEVQSSEHSNEGQNSEQSNEVQ SSEHSNEGQNSKQSNEGQNSKQSNEVQSSEHWNEGQ NSKQSNEDQNSEQSNEGQNSKQSNEGQNSKQSNEDQ NSEQSNEGQNSKQSNEVQSSEQSNEGQNSKQSNEGQS SEQSNEGQNSKQSNEVQSPEEHYDLPDPESSYESEETK GSHESGDDSEHR (SEQ ID NO: 207) |

TABLE 8-continued

Examples of Bacteriocyte Regulatory Peptides

| Name | Peptide Sequence |
|---|---|
| Secreted proteins SP family, peptide SP4 | MKTIILGLCLFGALFWSTQSMPVGEVAPAVPAVPSEAVP QKQVEAKPETNAASPVSDAKPESDSKPVDAEVKPTVSEV KAESEQKPSGEPKPESDAKPVVASESKPESDPKPAAVVE SKPENDAVAPETNNDAKPENAAAPVSENKPATDAKAETE LIAQAKPESKPASDLKAEPEAAKPNSEVPVALPLNPTETK ATQQSVETNQVEQAAPAAAQADPAAAPAADPAPAPAAA PVAAEEAKLSESAPSTENKAAEEPSKPAEQQSAKPVEDA VPAASEISETKVSPAVPAVPEVPASPSAPAVADPVSAPEA EKNAEPAKAANSAEPAVQSEAKPAEDIQKSGAVVSAENP KPVEEQKPAEVAKPAEQSKSEAPAEAPKPTEQSAAEEPK KPESANDEKKEQHSVNKRDATKEKKPTDSIMKKQKQKK AN (SEQ ID NO: 208) |
| Secreted proteins SP family, peptide SP5a | MNGKIVLCFAVVFIGQAMSAATGTTPEVEDIKKVAEQMS QTFMSVANHLVGITPNSADAQKSIEKIRTIMNKGFTDMET EANKMKDIVRKNADPKLVEKYDELEKELKKHLSTAKDMF EDKVVKPIGEKVELKKITENVIKTTKDMEATMNKAIDGFKK Q (SEQ ID NO: 209) |
| Secreted proteins SP family, peptide SP6 | MHLFLALGLFIVCGMVDATFYNPRSQTFNQLMERRQRSI PIPYSYGYHYNPIEPSINVLDSLSEGLDSRINTFKPIYQNV KMSTQDVNSVPRTQYQPKNSLYDSEYISAKDIPSLFPEE DSYDYKYLGSPLNKYLTRPSTQESGIAINLVAIKETSVFDY GFPTYKSPYSSDSVWNFGSKIPNTVFEDPQSVESDPNTF KVSSPTIKIVKLLPETPEQESIITTTKNYELNYKTTQETPTE AELYPITSEEFQTEDEWHPMVPKENTTKDESSFITTEEPL TEDKSNSITIEKTQTEDESNSIEFNSIRTEEKSNSITTEENQ KEDDESMSTTSQETTTAFNLNDTFDTNRYSSSHESLMLR IRELMKNIADQQNKSQFRTVDNIPAKSQSNLSSDESTNQ QFEPQLVNGADTYK (SEQ ID NO: 210) |
| Colepotericin A, ColA peptide | MTRTMLFLACVAALYVCISATAGKPEEFAKLSDEAPSND QAMYESIQRYRRFVDGNRYNGGQQQQQQPKQWEVRP DLSRDQRGNTKAQVEINKKGDNHDINAGWGKNINGPDS HKDTWHVGGSVRW (SEQ ID NO: 211) |
| RlpA type I | MKETTVVWAKLFLILIILAKPLGLKAVNECKRLGNNSCRSH GECCSGFCFIEPGWALGVCKRLGTPKKSDDSNNGKNIEK NNGVHERIDDVFERGVCSYYKGPSITANGDVFDENEMTA AHRTLPFNTMVKVEGMGTSVVVKINDRKTAADGKVMLLS RAAAESLNIDENTGPVQCQLKFVLDGSGCTPDYGDTCVL HHECCSQNCFREMFSDKGFCLPK (SEQ ID NO: 212) |

In some instances, the BRP alters the growth and/or activity of one or more bacteria resident in the bacteriocyte of the host. In some instances, the BRP may be bioengineered to modulate its bioactivity (e.g., increase, decrease, or regulate) or to specify a target microorganism. In some instances, the BRP is produced by the translational machinery (e.g. a ribosome, etc.) of a cell. In some instances, the BRP is chemically synthesized. In some instances, the BRP is derived from a polypeptide precursor. The polypeptide precursor can undergo cleavage (for example, processing by a protease) to yield the polypeptide of the BRP itself. As such, in some instances, the BRP is produced from a precursor polypeptide. In some instances, the BRP includes a polypeptide that has undergone post-translational modifications, for example, cleavage, or the addition of one or more functional groups.

Functionally active variants of the BRPs as described herein are also useful in the compositions and methods described herein. In some instances, the variant of the BRP has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a BRP described herein or naturally derived BRP.

The BRP described herein may be formulated in a composition for any of the uses described herein. The compositions disclosed herein may include any number or type (e.g., classes) of BRPs, such as at least about any one of 1 BRP, 2, 3, 4, 5, 10, 15, 20, or more BRPs. A suitable concentration of each BRP in the composition depends on factors such as efficacy, stability of the BRP, number of distinct BRP, the formulation, and methods of application of the composition. In some instances, each BRP in a liquid composition is from about 0.1 ng/mL to about 100 mg/mL. In some instances, each BRP in a solid composition is from about 0.1 ng/g to about 100 mg/g. In some instances, wherein the composition includes at least two types of BRPs, the concentration of each type of BRP may be the same or different.

A modulating agent including a BRP as described herein can be contacted with the target host in an amount and for a time sufficient to: (a) reach a target level (e.g., a predetermined or threshold level) of BRP concentration inside a target host; (b) reach a target level (e.g., a predetermined or threshold level) of BRP concentration inside a target host gut; (c) reach a target level (e.g., a predetermined or threshold level) of BRP concentration inside a target host bacteriocyte; (d) modulate the level, or an activity, of one or more microorganism (e.g., endosymbiont) in the target host; or/and (e) modulate fitness of the target host.

iii. Small Molecules

Numerous small molecules (e.g., an antibiotic or a metabolite) may be used in the compositions and methods described herein. In some instances, an effective concentration of any small molecule described herein may alter the level, activity, or metabolism of one or more microorganisms (as described herein) resident in a host, the alteration resulting in an increase in the host's fitness.

A modulating agent comprising a small molecule as described herein can be contacted with the target host in an amount and for a time sufficient to: (a) reach a target level (e.g., a predetermined or threshold level) of a small molecule concentration inside a target host; (b) reach a target level (e.g., a predetermined or threshold level) of small molecule concentration inside a target host gut; (c) reach a target level (e.g., a predetermined or threshold level) of a small molecule concentration inside a target host bacteriocyte; (d) modulate the level, or an activity, of one or more microorganism (e.g., endosymbiont) in the target host; or/and (e) modulate fitness of the target host.

(a) Antibiotics

The modulating agent described herein may include an antibiotic. Any antibiotic known in the art may be used. Antibiotics are commonly classified based on their mechanism of action, chemical structure, or spectrum of activity.

The antibiotic described herein may target any bacterial function or growth processes and may be either bacteriostatic (e.g., slow or prevent bacterial growth) or bactericidal (e.g., kill bacteria). In some instances, the antibiotic is a bactericidal antibiotic. In some instances, the bactericidal antibiotic is one that targets the bacterial cell wall (e.g., penicillins and cephalosporins); one that targets the cell membrane (e.g., polymyxins); or one that inhibits essential bacterial enzymes (e.g., rifamycins, lipiarmycins, quinolones, and sulfonamides). In some instances, the bactericidal antibiotic is an aminoglycoside. In some instances, the antibiotic is a bacteriostatic antibiotic. In some instances the bacteriostatic antibiotic targets protein synthesis (e.g., macrolides, lincosamides and tetracyclines). Additional classes of antibiotics that may be used herein include cyclic lipopeptides (such as daptomycin), glycylcyclines (such as tigecycline), oxazolidinones (such as linezolid), or lipiarmycins (such as fidaxomicin). Examples of antibiotics include oxytetracycline, doxycycline, rifampicin, ciprofloxacin, ampicillin, and polymyxin B. Other non-limiting examples of antibiotics are found in Table 9.

TABLE 9

Examples of Antibiotics

| Antibiotics | Action |
| --- | --- |
| Penicillins, cephalosporins, vancomycin | Cell wall synthesis |
| Polymixin, gramicidin | Membrane active agent, disrupt cell membrane |
| Tetracyclines, macrolides, chloramphenicol, clindamycin, spectinomycin | Inhibit protein synthesis |
| Sulfonamides | Inhibit folate-dependent pathways |

TABLE 9-continued

Examples of Antibiotics

| Antibiotics | Action |
| --- | --- |
| Ciprofloxacin | Inhibit DNA-gyrase |
| Isoniazid, rifampicin, pyrazinamide, ethambutol, (myambutol)l, streptomycin | Antimycobacterial agents |

The antibiotic described herein may have any level of target specificity (e.g., narrow- or broad-spectrum). In some instances, the antibiotic is a narrow-spectrum antibiotic, and thus targets specific types of bacteria, such as gram-negative or gram-positive bacteria. Alternatively, the antibiotic may be a broad-spectrum antibiotic that targets a wide range of bacteria.

The antibiotics described herein may be formulated in a composition for any of the uses described herein. The compositions disclosed herein may include any number or type (e.g., classes) of antibiotics, such as at least about any one of 1 antibiotic, 2, 3, 4, 5, 10, 15, 20, or more antibiotics (e.g., a combination of rifampicin and doxycycline, or a combination of ampicillin and rifampicin). A suitable concentration of each antibiotic in the composition depends on factors such as efficacy, stability of the antibiotic, number of distinct antibiotics, the formulation, and methods of application of the composition. In some instances, wherein the composition includes at least two types of antibiotics, the concentration of each type of antibiotic may be the same or different.

A modulating agent including an antibiotic as described herein can be contacted with the target host in an amount and for a time sufficient to: (a) reach a target level (e.g., a predetermined or threshold level) of antibiotic concentration inside a target host; (b) reach a target level (e.g., a predetermined or threshold level) of antibiotic concentration inside a target host gut; (c) reach a target level (e.g., a predetermined or threshold level) of antibiotic concentration inside a target host bacteriocyte; (d) modulate the level, or an activity, of one or more microorganism (e.g., endosymbiont) in the target host; or/and (e) modulate fitness of the target host.

(b) Secondary Metabolites

In some instances, the modulating agent of the compositions and methods described herein includes a secondary metabolite. Secondary metabolites are derived from organic molecules produced by an organism. Secondary metabolites may act (i) as competitive agents used against bacteria, fungi, amoebae, plants, insects, and large animals; (ii) as metal transporting agents; (iii) as agents of symbiosis between microbes and plants, insects, and higher animals; (iv) as sexual hormones; and (v) as differentiation effectors. Non-limiting examples of secondary metabolites are found in Table 10.

TABLE 10

Examples of Secondary Metabolites

| Phenyl-propanoids | Alkaloids | Terpenoids | Quinones | Steroids | Polyketides |
|---|---|---|---|---|---|
| Anthocyanins | Acridines | Carotenes | Anthra-quinones | Cardiac | Erythromycin |
| Coumarins | Betalaines | Monoterpenes | Bezo-quinones | Gycosides | Lovastatin and other statins |
| Flavonoids | Quino-Iozidines | Sesquiterpenes | Naphtho-quinones | Pregnen-olone | Discoder-molide |
| Hydroxy-cinnamoyl Derivatives | Furono-quinones | Diterpenes | | Derivatives | Aflatoxin B1 |
| | Harring-tonines | Triterpenes | | | Avermectins |
| Isoflavonoids | Isoquino-lines | | | | Nystatin |
| Lignans | Indoles | | | | Rifamycin |
| Phenolenones | Purines | | | | |
| Proantho-cyanidins | Pyridines | | | | |
| Stilbenes | Tropane Alkaloids | | | | |
| Tanins | | | | | |

The secondary metabolite used herein may include a metabolite from any known group of secondary metabolites. For example, secondary metabolites can be categorized into the following groups: alkaloids, terpenoids, flavonoids, glycosides, natural phenols, e.g., gossypol acetic acid), enals (e.g., trans-cinnamaldehyde), phenazines, biphenols and dibenzofurans, polyketides, fatty acid synthase peptides, nonribosomal peptides, ribosomally synthesized and post-translationally modified peptides, polyphenols, polysaccharides (e.g., chitosan), and biopolymers. For an in-depth review of secondary metabolites see, for example, Vining, Annu. Rev. Microbiol. 44:395-427, 1990. Secondary metabolites useful for compositions and methods described herein include those that alter a natural function of an endosymbiont (e.g., primary or secondary endosymbiont), bacteriocyte, or extracellular symbiont. In some instances, one or more secondary metabolites described herein is isolated from a high throughput screening (HTS) for antimicrobial compounds. For example, a HTS screen identified 49 antibacterial extracts that have specificity against gram positive and gram negative bacteria from over 39,000 crude extracts from organisms growing in diverse ecosystems of one specific region. In some instances, the secondary metabolite is transported inside a bacteriocyte.

In some instances, the small molecule is an inhibitor of vitamin synthesis. In some instances, the vitamin synthesis inhibitor is a vitamin precursor analog. In certain instances, the vitamin precursor analog is pantothenol.

In some instances, the small molecule is an amino acid analog. In certain instances, the amino acid analog is L-canvanine, D-arginine, D-valine, D-methionine, D-phenylalanine, D-histidine, D-tryptophan, D-threonine, D-leucine, L-NG-nitroarginine, or a combination thereof.

In some instances the small molecule is a natural antimicrobial compound, such as propionic acid, levulinic acid, trans-cinnamaldehdye, nisin, or low molecular weight chitosan.

The secondary metabolite described herein may be formulated in a composition for any of the uses described herein. The compositions disclosed herein may include any number or type (e.g., classes) of secondary metabolites, such as at least about any one of 1 secondary metabolite, 2, 3, 4, 5, 10, 15, 20, or more secondary metabolites. A suitable concentration of each secondary metabolite in the composition depends on factors such as efficacy, stability of the secondary metabolite, number of distinct secondary metabolites, the formulation, and methods of application of the composition. In some instances, wherein the composition includes at least two types of secondary metabolites, the concentration of each type of secondary metabolite may be the same or different.

A modulating agent including a secondary metabolite as described herein can be contacted with the target host in an amount and for a time sufficient to: (a) reach a target level (e.g., a predetermined or threshold level) of secondary metabolite concentration inside a target host; (b) reach a target level (e.g., a predetermined or threshold level) of secondary metabolite concentration inside a target host gut; (c) reach a target level (e.g., a predetermined or threshold level) of secondary metabolite concentration inside a target host bacteriocyte; (d) modulate the level, or an activity, of one or more microorganism (e.g., endosymbiont) in the target host; or/and (e) modulate fitness of the target host.

iv. Bacteria as Modulating Agents

In some instances, the modulating agent described herein includes one or more bacteria. Numerous bacteria are useful in the compositions and methods described herein. In some instances, the agent is a bacterial species endogenously found in the host. In some instances, the bacterial modulating agent is an endosymbiotic bacterial species. Non-limiting examples of bacteria that may be used as modulating agents include all bacterial species described herein in Section II of the detailed description and those listed in Table 1. For example, the modulating agent may be a bacterial species from any bacterial phyla present in insect guts and/or haemocoel, including Gammaproteobacteria, Alphaproteobacteria, Betaproteobacteria, Bacteroidetes, Firmicutes (e.g., Lactobacillus and Bacillus spp.), Clostridia, Actinomycetes, Spirochetes, Verrucomicrobia, and Actinobacteria.

In some instances, the modulating agent is a bacterium that promotes microbial diversity or otherwise alters the microbiota of the host in a favorable manner. In one instance, bacteria may be provided to promote microbiome development in insects.

The bacterial modulating agents discussed herein can be used to alter the level, activity, or metabolism of target microorganisms as indicated in the sections for increasing the fitness of insects, such as, crickets, grasshoppers, or locusts.

In some instances, such bacterial modulating agents are bacteria which are capable of producing nutrients, including amino acids (e.g., methionine). The nutrient-producing bacteria may be naturally occurring bacteria, e.g., naturally occurring bacteria exogenous to the insect host. Such bacteria may be isolated from a population of bacteria, such as that found in an environmental sample. Bacteria can be isolated that produce one or more amino acids in a manner that increases production of amino acids in the host relative to a host who has not been administered the amino-acid producing bacteria. Amino acids that can be produced by the bacteria in the host include methionine, alanine, arginine, asparagine, aspartic acid, cysteine, glutamine, glutamic acid, glutamate, glycine, histidine, isoleucine, leucine, lysine, methionine, phenylalanine, proline, serine, threonine, tryptophan, tyrosine, or valine. In certain instances, the amino acid-producing bacteria is a methionine-producing bacteria.

In some instances, the nutrient-producing bacteria (e.g., amino acid-producing bacteria, e.g., methionine-producing bacteria) are at a concentration of at least 100,000 cells/ml (e.g., at least about 100,000 cells/ml, at least about 150,000 cells/ml, at least about 200,000 cells/ml, at least about 250,000 cells/ml, at least about 300,000 cells/ml, at least about 350,000 cells/ml, at least about 400,000 cells/ml, at least about 450,000 cells/ml, or at least about 500,000 cells/ml).

Examples 1 to 4 and 8 describe how methionine-producing microorganisms can be identified which can then be used as modulating agents in insect hosts, such as crickets or in the model organism *Drosophila*, to increase the fitness of the hosts (e.g., increase amino acid content (e.g., methionine content). For example, in certain instances, nutrient content is increased in the host prior to use of the host in manufacturing of food or feed.

In some instances, such bacterial modulating agents are bacteria which are capable of degrading pesticides as laid out in Table 12 including insecticides. Such insecticides include neonicotinoids such as imidacloprid, or organophosphorus insecticides, such as fenitrothion. In some instances, the pesticide-metabolizing bacteria are at a concentration of at least 100,000 cells/ml (e.g., at least about 100,000 cells/ml, at least about 150,000 cells/ml, at least about 200,000 cells/ml, at least about 250,000 cells/ml, at least about 300,000 cells/ml, at least about 350,000 cells/ml, at least about 400,000 cells/ml, at least about 450,000 cells/ml, or at least about 500,000 cells/ml).

Examples 5 and 6 describe how imidacloprid and fenitrothion degrading microorganisms can be identified which can then be used a modulating agents in insect hosts, such as crickets, giving the treated insect hosts a competitive advantage. Administering such pesticide-degrading microorganisms, for example imidacloprid- or fenitrothion-degrading microorganisms to insect hosts such as honeybees is understood to be encompassed by the alteration of a level, activity, or metabolism of one or more microorganisms resident in the host.

v. Modifications to Modulating Agents (a) Fusions

Any of the modulating agents described herein may be fused or linked to an additional moiety. In some instances, the modulating agent includes a fusion of one or more additional moieties (e.g., 1 additional moiety, 2, 3, 4, 5, 6, 7, 8, 9, 10, or more additional moieties). In some instances, the additional moiety is any one of the modulating agents described herein (e.g., a peptide, polypeptide, small molecule, or antibiotic). Alternatively, the additional moiety may not act as modulating agent itself but may instead serve a secondary function. For example, the additional moiety may to help the modulating agent access, bind, or become activated at a target site in the host (e.g., at a host gut or a host bacteriocyte) or at a target microorganism resident in the host (e.g., a cricket, a grasshopper, or a locust).

In some instances, the additional moiety may help the modulating agent penetrate a target host cell or target microorganism resident in the host. For example, the additional moiety may include a cell penetrating peptide. Cell penetrating peptides (CPPs) may be natural sequences derived from proteins; chimeric peptides that are formed by the fusion of two natural sequences; or synthetic CPPs, which are synthetically designed sequences based on structure-activity studies. In some instances, CPPs have the capacity to ubiquitously cross cellular membranes (e.g., prokaryotic and eukaryotic cellular membranes) with limited toxicity. Further, CPPs may have the capacity to cross cellular membranes via energy-dependent and/or independent mechanisms, without the necessity of a chiral recognition by specific receptors. CPPs can be bound to any of the modulating agents described herein. For example, a CPP can be bound to an antimicrobial peptide (AMP), e.g., a scorpion peptide, e.g., UY192 fused to a cell penetrating peptide (e.g., YGRKKRRQRRRFLSTIWNGIKGLLFAM; SEQ ID NO: 226). Non-limiting examples of CPPs are listed in Table 11.

TABLE 11

Examples of Cell Penetrating Peptides (CPPs)

| Peptide | Origin | Sequence |
|---|---|---|
| Protein-derived | | |
| Penetratin | Antennapedia | RQIKIWFQNRRMKWKK (SEQ ID NO: 213) |
| Tat peptide | Tat | GRKKRRQRRRPPQ (SEQ ID NO: 214) |
| pVEC | Cadherin | LLIILRRRIRKQAHAHSK (SEQ ID NO: 215) |
| Chimeric | | |
| Transportan | Galanine/Mastoparan | GWTLNSAGYLLGKINLKALAALAKKIL (SEQ ID NO: 216) |

TABLE 11-continued

Examples of Cell Penetrating Peptides (CPPs)

| Peptide | Origin | Sequence |
|---|---|---|
| MPG | HIV-gp41/SV40 T-antigen | GALFLGFLGAAGSTMGAWSQPKKKRKV (SEQ ID NO: 217) |
| Pep-1 | HIV-reverse transcriptase/SV40 T-antigen | KETWWETVVWTEWSQPKKKRKV (SEQ ID NO: 218) |
| Synthetic | | |
| Polyarginines | Based on Tat peptide | $(R)_n$; 6 < n < 12 |
| MAP | de novo | KLALKLALKALKAALKLA (SEQ ID NO: 219) |
| $R_6W_3$ | Based on penetratin | RRWWRRWRR (SEQ ID NO: 220) |

In other instances, the additional moiety helps the modulating agent bind a target microorganism (e.g., a fungi or bacterium) resident in the host. The additional moiety may include one or more targeting domains. In some instances, the targeting domain may target the modulating agent to one or more microorganisms (e.g., bacterium or fungus) resident in the gut of the host. In some instances, the targeting domain may target the modulating agent to a specific region of the host (e.g., host gut or bacteriocyte) to access microorganisms that are generally present in said region of the host. For example, the targeting domain may target the modulating agent to the foregut, midgut, or hindgut of the host. In other instances, the targeting domain may target the modulating agent to a bacteriocyte in the host and/or one or more specific bacteria resident in a host bacteriocyte.

(b) Pre- or Pro-Domains

In some instances, the modulating agent may include a pre- or pro-amino acid sequence. For example, the modulating agent may be an inactive protein or peptide that can be activated by cleavage or post-translational modification of a pre- or pro-sequence. In some instances, the modulating agent is engineered with an inactivating pre- or pro-sequence. For example, the pre- or pro-sequence may obscure an activation site on the modulating agent, e.g., a receptor binding site, or may induce a conformational change in the modulating agent. Thus, upon cleavage of the pre- or pro-sequence, the modulating agent is activated.

Alternatively, the modulating agent may include a pre- or pro-small molecule, e.g., an antibiotic. The modulating agent may be an inactive small molecule described herein that can be activated in a target environment inside the host. For example, the small molecule may be activated upon reaching a certain pH in the host gut. For example, the targeting domain may be *Galanthus nivalis* lectin or agglutinin (GNA) bound to a modulating agent described herein, e.g., an AMP, e.g., a scorpion peptide, e.g., Uy192.

(c) Linkers

In instances where the modulating agent is connected to an additional moiety, the modulating agent may further include a linker. For example, the linker may be a chemical bond, e.g., one or more covalent bonds or non-covalent bonds. In some instances, the linker may be a peptide linker (e.g., 2, 3, 4, 5, 6, 8, 10, 12, 14, 16, 20, 25, 30, 35, 40, or more amino acids longer). The linker maybe include any flexible, rigid, or cleavable linkers described herein.

A flexible peptide linker may include any of those commonly used in the art, including linkers having sequences having primarily Gly and Ser residues ("GS" linker). Flexible linkers may be useful for joining domains that require a certain degree of movement or interaction and may include small, non-polar (e.g. Gly) or polar (e.g. Ser or Thr) amino acids.

Alternatively, a peptide linker may be a rigid linker. Rigid linkers are useful to keep a fixed distance between moieties and to maintain their independent functions. Rigid linkers may also be useful when a spatial separation of the domains is critical to preserve the stability or bioactivity of one or more components in the fusion. Rigid linkers may, for example, have an alpha helix-structure or Pro-rich sequence, $(XP)_n$, with X designating any amino acid, preferably Ala, Lys, or Glu.

In yet other instances, a peptide linker may be a cleavable linker. In some instances, linkers may be cleaved under specific conditions, such as the presence of reducing reagents or proteases. In vivo cleavable linkers may utilize the reversible nature of a disulfide bond. One example includes a thrombin-sensitive sequence (e.g., PRS) between two Cys residues. In vitro thrombin treatment of CPRSC results in the cleavage of the thrombin-sensitive sequence, while the reversible disulfide linkage remains intact. Such linkers are known and described, e.g., in Chen et al., *Adv. Drug Deliv. Rev.* 65(10):1357-1369, 2013. Cleavage of linkers in fusions may also be carried out by proteases that are expressed in vivo under conditions in specific cells or tissues of the host or microorganisms resident in the host. In some instances, cleavage of the linker may release a free functional, modulating agent upon reaching a target site or cell.

Fusions described herein may alternatively be linked by a linking molecule, including a hydrophobic linker, such as a negatively charged sulfonate group; lipids, such as a poly (—CH2—) hydrocarbon chains, such as polyethylene glycol (PEG) group, unsaturated variants thereof, hydroxylated variants thereof, amidated or otherwise N-containing variants thereof, non-carbon linkers; carbohydrate linkers; phosphodiester linkers, or other molecule capable of covalently linking two or more molecules, e.g., two modulating agents. Non-covalent linkers may be used, such as hydrophobic lipid globules to which the modulating agent is linked, for example, through a hydrophobic region of the modulating agent or a hydrophobic extension of the modulating agent, such as a series of residues rich in leucine, isoleucine, valine, or perhaps also alanine, phenylalanine, or even tyrosine, methionine, glycine, or other hydrophobic residue. The modulating agent may be linked using charge-based chemistry, such that a positively charged moiety of the modulating agent is linked to a negative charge of another modulating agent or an additional moiety.

IV. Formulations and Compositions

The compositions described herein may be formulated either in pure form (e.g., the composition contains only the modulating agent) or together with one or more additional agents (such as excipient, delivery vehicle, carrier, diluent, stabilizer, etc.) to facilitate application or delivery of the compositions. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil.

In some instances, the composition includes a delivery vehicle or carrier. In some instances, the delivery vehicle includes an excipient. Exemplary excipients include, but are not limited to, solid or liquid carrier materials, solvents, stabilizers, slow-release excipients, colorings, and surface-active substances (surfactants). In some instances, the delivery vehicle is a stabilizing vehicle. In some instances, the stabilizing vehicle includes a stabilizing excipient. Exemplary stabilizing excipients include, but are not limited to, epoxidized vegetable oils, antifoaming agents, e.g. silicone oil, preservatives, viscosity regulators, binding agents and tackifiers. In some instances, the stabilizing vehicle is a buffer suitable for the modulating agent. In some instances, the composition is microencapsulated in a polymer bead delivery vehicle. In some instances, the stabilizing vehicle protects the modulating agent against UV and/or acidic conditions. In some instances, the delivery vehicle contains a pH buffer. In some instances, the composition is formulated to have a pH in the range of about 4.5 to about 9.0, including for example pH ranges of about any one of 5.0 to about 8.0, about 6.5 to about 7.5, or about 6.5 to about 7.0.

Depending on the intended objectives and prevailing circumstances, the composition may be formulated into emulsifiable concentrates, suspension concentrates, directly sprayable or dilutable solutions, coatable pastes, diluted emulsions, spray powders, soluble powders, dispersible powders, wettable powders, dusts, granules, encapsulations in polymeric substances, microcapsules, foams, aerosols, carbon dioxide gas preparations, tablets, resin preparations, paper preparations, nonwoven fabric preparations, or knitted or woven fabric preparations. In some instances, the composition is a liquid. In some instances, the composition is a solid. In some instances, the composition is an aerosol, such as in a pressurized aerosol can. In some instances, the composition is present in the waste (such as feces) of the pest. In some instances, the composition is present in or on a live pest.

In some instances, the delivery vehicle is the food or water of the host. In other instances, the delivery vehicle is a food source for the host. In some instances, the delivery vehicle is a food bait for the host. In some instances, the composition is a comestible agent consumed by the host. In some instances, the composition is delivered by the host to a second host, and consumed by the second host. In some instances, the composition is consumed by the host or a second host, and the composition is released to the surrounding of the host or the second host via the waste (such as feces) of the host or the second host. In some instances, the modulating agent is included in food bait intended to be consumed by a host or carried back to its colony.

In some instances, the modulating agent may make up about 0.1% to about 100% of the composition, such as any one of about 0.01% to about 100%, about 1% to about 99.9%, about 0.1% to about 10%, about 1% to about 25%, about 10% to about 50%, about 50% to about 99%, or about 0.1% to about 90% of active ingredients (such as phage, lysin or bacteriocin). In some instances, the composition includes at least any of 0.1%, 0.5%, 1%, 5%, 10%, 20%, 30%, 40%, 50%, 60%, 70%, 80%, 90%, 95%, or more active ingredients (such as phage, lysin or bacteriocin). In some instances, the concentrated agents are preferred as commercial products, the final user normally uses diluted agents, which have a substantially lower concentration of active ingredient.

Any of the formulations described herein may be used in the form of a bait, a coil, an electric mat, a smoking preparation, a fumigant, or a sheet.

i. Liquid Formulations

The compositions provided herein may be in a liquid formulation. Liquid formulations are generally mixed with water, but in some instances may be used with crop oil, diesel fuel, kerosene or other light oil as a carrier. The amount of active ingredient often ranges from about 0.5 to about 80 percent by weight.

An emulsifiable concentrate formulation may contain a liquid active ingredient, one or more petroleum-based solvents, and an agent that allows the formulation to be mixed with water to form an emulsion. Such concentrates may be used in agricultural, ornamental and turf, forestry, structural, food processing, livestock, and public health pest formulations. These may be adaptable to application equipment from small portable sprayers to hydraulic sprayers, low-volume ground sprayers, mist blowers, and low-volume aircraft sprayers. Some active ingredients are readily dissolve in a liquid carrier. When mixed with a carrier, they form a solution that does not settle out or separate, e.g., a homogenous solution. Formulations of these types may include an active ingredient, a carrier, and one or more other ingredients. Solutions may be used in any type of sprayer, indoors and outdoors.

In some instances, the composition may be formulated as an invert emulsion. An invert emulsion is a water-soluble active ingredient dispersed in an oil carrier. Invert emulsions require an emulsifier that allows the active ingredient to be mixed with a large volume of petroleum-based carrier, usually fuel oil. Invert emulsions aid in reducing drift. With other formulations, some spray drift results when water droplets begin to evaporate before reaching target surfaces; as a result the droplets become very small and lightweight. Because oil evaporates more slowly than water, invert emulsion droplets shrink less and more active ingredient reaches the target. Oil further helps to reduce runoff and improve rain resistance. It further serves as a sticker-spreader by improving surface coverage and absorption. Because droplets are relatively large and heavy, it is difficult to get thorough coverage on the undersides of foliage. Invert emulsions are most commonly used along rights-of-way where drift to susceptible non-target areas can be a problem.

A flowable or liquid formulation combines many of the characteristics of emulsifiable concentrates and wettable powders. Manufacturers use these formulations when the active ingredient is a solid that does not dissolve in either water or oil. The active ingredient, impregnated on a substance such as clay, is ground to a very fine powder. The powder is then suspended in a small amount of liquid. The resulting liquid product is quite thick. Flowables and liquids share many of the features of emulsifiable concentrates, and they have similar disadvantages. They require moderate agitation to keep them in suspension and leave visible residues, similar to those of wettable powders.

Flowables/liquids are easy to handle and apply. Because they are liquids, they are subject to spilling and splashing. They contain solid particles, so they contribute to abrasive wear of nozzles and pumps. Flowable and liquid suspensions settle out in their containers. Because flowable and liquid formulations tend to settle, packaging in containers of five gallons or less makes remixing easier.

Aerosol formulations contain one or more active ingredients and a solvent. Most aerosols contain a low percentage of active ingredients. There are two types of aerosol formulations—the ready-to-use type commonly available in pressurized sealed containers and those products used in electrical or gasoline-powered aerosol generators that release the formulation as a smoke or fog.

Ready to use aerosol formulations are usually small, self-contained units that release the formulation when the nozzle valve is triggered. The formulation is driven through a fine opening by an inert gas under pressure, creating fine droplets. These products are used in greenhouses, in small areas inside buildings, or in localized outdoor areas. Commercial models, which hold five to 5 pounds of active ingredient, are usually refillable.

Smoke or fog aerosol formulations are not under pressure. They are used in machines that break the liquid formulation into a fine mist or fog (aerosol) using a rapidly whirling disk or heated surface.

ii. Dry or Solid Formulations

Dry formulations can be divided into two types: ready-to-use and concentrates that must be mixed with water to be applied as a spray. Most dust formulations are ready to use and contain a low percentage of active ingredients (less than about 10 percent by weight), plus a very fine, dry inert carrier made from talc, chalk, clay, nut hulls, or volcanic ash. The size of individual dust particles varies. A few dust formulations are concentrates and contain a high percentage of active ingredients. Mix these with dry inert carriers before applying. Dusts are always used dry and can easily drift to non-target sites.

iii. Granule or Pellet Formulations

In some instances, the composition is formulated as granules. Granular formulations are similar to dust formulations, except granular particles are larger and heavier. The coarse particles may be made from materials such as clay, corncobs, or walnut shells. The active ingredient either coats the outside of the granules or is absorbed into them. The amount of active ingredient may be relatively low, usually ranging from about 0.5 to about 15 percent by weight. Granular formulations are most often used to apply to the soil, insects living in the soil, or absorption into plants through the roots. Granular formulations are sometimes applied by airplane or helicopter to minimize drift or to penetrate dense vegetation. Once applied, granules may release the active ingredient slowly. Some granules require soil moisture to release the active ingredient. Granular formulations also are used to control larval mosquitoes and other aquatic pests. Granules are used in agricultural, structural, ornamental, turf, aquatic, right-of-way, and public health (biting insect) pest-control operations.

In some instances, the composition is formulated as pellets. Most pellet formulations are very similar to granular formulations; the terms are used interchangeably. In a pellet formulation, however, all the particles are the same weight and shape. The uniformity of the particles allows use with precision application equipment.

iv. Powders

In some instances, the composition is formulated as a powder. In some instances, the composition is formulated as a wettable powder. Wettable powders are dry, finely ground formulations that look like dusts. They usually must be mixed with water for application as a spray. A few products, however, may be applied either as a dust or as a wettable powder—the choice is left to the applicator. Wettable powders have about 1 to about 95 percent active ingredient by weight; in some cases more than about 50 percent. The particles do not dissolve in water. They settle out quickly unless constantly agitated to keep them suspended. They can be used for most pest problems and in most types of spray equipment where agitation is possible. Wettable powders have excellent residual activity. Because of their physical properties, most of the formulation remains on the surface of treated porous materials such as concrete, plaster, and untreated wood. In such cases, only the water penetrates the material.

In some instances, the composition is formulated as a soluble powder. Soluble powder formulations look like wettable powders. However, when mixed with water, soluble powders dissolve readily and form a true solution. After they are mixed thoroughly, no additional agitation is necessary. The amount of active ingredient in soluble powders ranges from about 15 to about 95 percent by weight; in some cases more than about 50 percent. Soluble powders have all the advantages of wettable powders and none of the disadvantages, except the inhalation hazard during mixing.

In some instances, the composition is formulated as a water-dispersible granule. Water-dispersible granules, also known as dry flowables, are like wettable powders, except instead of being dust-like, they are formulated as small, easily measured granules. Water-dispersible granules must be mixed with water to be applied. Once in water, the granules break apart into fine particles similar to wettable powders. The formulation requires constant agitation to keep it suspended in water. The percentage of active ingredient is high, often as much as 90 percent by weight. Water-dispersible granules share many of the same advantages and disadvantages of wettable powders, except they are more easily measured and mixed. Because of low dust, they cause less inhalation hazard to the applicator during handling v. Bait In some instances, the composition includes a bait. The bait can be in any suitable form, such as a solid, paste, pellet or powdered form. The bait can also be carried away by the host back to a population of said host (e.g., a colony or hive). The bait can then act as a food source for other members of the colony, thus providing an effective modulating agent for a large number of hosts and potentially an entire host colony.

The baits can be provided in a suitable "housing" or "trap." Such housings and traps are commercially available and existing traps can be adapted to include the compositions described herein. The housing or trap can be box-shaped for example, and can be provided in pre-formed condition or can be formed of foldable cardboard for example. Suitable materials for a housing or trap include plastics and cardboard, particularly corrugated cardboard. The inside surfaces of the traps can be lined with a sticky substance in order to restrict movement of the host once inside the trap. The housing or trap can contain a suitable trough inside which can hold the bait in place. A trap is distinguished from a housing because the host cannot readily leave a trap following entry, whereas a housing acts as a "feeding station" which provides the host with a preferred environment in which they can feed and feel safe from predators.

vi. Attractants

In some instances, the composition includes an attractant (e.g., a chemoattractant). The attractant may attract an adult host or immature host (e.g., larva) to the vicinity of the composition. Attractants include pheromones, a chemical that is secreted by an animal, especially an insect, which influences the behavior or development of others of the same species. Other attractants include sugar and protein hydrolysate syrups, yeasts, and rotting meat. Attractants also can be combined with an active ingredient and sprayed onto foliage or other items in the treatment area.

Various attractants are known which influence host behavior as a host's search for food, oviposition or mating sites, or mates. Attractants useful in the methods and compositions described herein include, for example, eugenol, phenethyl propionate, ethyl dimethylisobutyl-cyclopropane carboxylate, propyl benszodioxancarboxylate, cis-7,8-epoxy-2-methyloctadecane, trans-8,trans-0-dodecadienol, cis-9-tetradecenal (with cis-11-hexadecenal), trans-11-tetradecenal, cis-11-hexadecenal, (Z)-11,12-hexadecadienal, cis-7-dodecenyl acetate, cis-8-dodecenyul acetate, cis-9-dodecenyl acetate, cis-9-tetradecenyl acetate, cis-11-tetradecenyl acetate, trans-11-tetradecenyl acetate (with cis-11), cis-9,trans-11-tetradecadienyl acetate (with cis-9,trans-12), cis-9,trans-12-tetradecadienyl acetate, cis-7,cis-11-hexadecadienyl acetate (with cis-7,trans-11), cis-3,cis-13-octadecadienyl acetate, trans-3,cis-13-octadecadienyl acetate, anethole and isoamyl salicylate.

Means other than chemoattractants may also be used to attract insects, including lights in various wavelengths or colors.

vii. Nanocapsules/Microencapsulation/Liposomes

In some instances, the composition is provided in a microencapsulated formulation. Microencapsulated formulations are mixed with water and sprayed in the same manner as other sprayable formulations. After spraying, the plastic coating breaks down and slowly releases the active ingredient.

viii. Carriers

Any of the compositions described herein may be formulated to include the modulating agent described herein and an inert carrier. Such carrier can be a solid carrier, a liquid carrier, gel carrier, and/or a gaseous carrier. In certain instances, the carrier can be a seed coating. The seed coating is any non-naturally occurring formulation that adheres, in whole or part, to the surface of the seed. The formulation may further include an adjuvant or surfactant. The formulation can also include one or more modulating agents to enlarge the action spectrum.

A solid carrier used for formulation includes finely-divided powder or granules of clay (e.g. kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), a substance which can be sublimated and is in the solid form at room temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments.

A liquid carrier may include, for example, aromatic or aliphatic hydrocarbons (e.g., xylene, toluene, alkylnaphthalene, phenylxylylethane, kerosine, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), amides (e.g., N,N-dimethylformamide, N,N-dimethylacetamide, cyclic imides (e.g. N-methylpyrrolidone) alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), or water.

A gaseous carrier may include, for example, butane gas, flon gas, liquefied petroleum gas (LPG), dimethyl ether, and carbon dioxide gas.

ix. Adjuvants

In some instances, the composition provided herein may include an adjuvant. Adjuvants are chemicals that do not possess activity. Adjuvants are either pre-mixed in the formulation or added to the spray tank to improve mixing or application or to enhance performance. They are used extensively in products designed for foliar applications. Adjuvants can be used to customize the formulation to specific needs and compensate for local conditions. Adjuvants may be designed to perform specific functions, including wetting, spreading, sticking, reducing evaporation, reducing volatilization, buffering, emulsifying, dispersing, reducing spray drift, and reducing foaming. No single adjuvant can perform all these functions, but compatible adjuvants often can be combined to perform multiple functions simultaneously.

Among nonlimiting examples of adjuvants included in the formulation are binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

x. Surfactants

In some instances, the composition provided herein includes a surfactant. Surfactants, also called wetting agents and spreaders, physically alter the surface tension of a spray droplet. For a formulation to perform its function properly, a spray droplet must be able to wet the foliage and spread out evenly over a leaf. Surfactants enlarge the area of formulation coverage, thereby increasing the pest's exposure to the chemical. Surfactants are particularly important when applying a formulation to waxy or hairy leaves. Without proper wetting and spreading, spray droplets often run off or fail to cover leaf surfaces adequately. Too much surfactant, however, can cause excessive runoff and reduce efficacy.

Surfactants are classified by the way they ionize or split apart into electrically charged atoms or molecules called ions. A surfactant with a negative charge is anionic. One with a positive charge is cationic, and one with no electrical charge is nonionic. Formulation activity in the presence of a nonionic surfactant can be quite different from activity in the presence of a cationic or anionic surfactant. Selecting the wrong surfactant can reduce the efficacy of a pesticide product and injure the target plant. Anionic surfactants are most effective when used with contact pesticides (pesticides that control the pest by direct contact rather than being absorbed systemically). Cationic surfactants should never be used as stand-alone surfactants because they usually are phytotoxic.

Nonionic surfactants, often used with systemic pesticides, help pesticide sprays penetrate plant cuticles. Nonionic surfactants are compatible with most pesticides, and most EPA-registered pesticides that require a surfactant recommend a nonionic type. Adjuvants include, but are not limited to, stickers, extenders, plant penetrants, compatibility agents, buffers or pH modifiers, drift control additives, defoaming agents, and thickeners.

Among nonlimiting examples of surfactants included in the compositions described herein are alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

xi. Combinations

In formulations and in the use forms prepared from these formulations, the modulating agent may be in a mixture with other active compounds, such as pesticidal agents (e.g., insecticides, sterilants, acaricides, nematicides, molluscicides, or fungicides; see, e.g., pesticides listed in Table 12), attractants, growth-regulating substances, or herbicides. As used herein, the term "pesticidal agent" refers to any substance or mixture of substances intended for preventing, destroying, repelling, or mitigating any pest. A pesticide can be a chemical substance or biological agent used against pests including insects, pathogens, weeds, and microbes that compete with humans for food, destroy property, spread disease, or are a nuisance. The term "pesticidal agent" may further encompass other bioactive molecules such as antibiotics, antivirals pesticides, antifungals, antihelminthics, nutrients, pollen, sucrose, and/or agents that stun or slow insect movement.

In instances where the modulating agent is applied to plants, a mixture with other known compounds, such as herbicides, fertilizers, growth regulators, safeners, semiochemicals, or else with agents for improving plant properties is also possible.

V. Delivery

A host described herein can be exposed to any of the compositions described herein in any suitable manner that permits delivering or administering the composition to the insect. The modulating agent may be delivered either alone or in combination with other active or inactive substances and may be applied by, for example, spraying, microinjection, through plants, pouring, dipping, in the form of concentrated liquids, gels, solutions, suspensions, sprays, powders, pellets, briquettes, bricks and the like, formulated to deliver an effective concentration of the modulating agent. Amounts and locations for application of the compositions described herein are generally determined by the habits of the host, the lifecycle stage at which the microorganisms of the host can be targeted by the modulating agent, the site where the application is to be made, and the physical and functional characteristics of the modulating agent. The modulating agents described herein may be administered to the insect by oral ingestion, but may also be administered by means which permit penetration through the cuticle or penetration of the insect respiratory system.

In some instances, the insect can be simply "soaked" or "sprayed" with a solution including the modulating agent. Alternatively, the modulating agent can be linked to a food component (e.g., comestible) of the insect for ease of delivery and/or in order to increase uptake of the modulating agent by the insect. Methods for oral introduction include, for example, directly mixing a modulating agent with the insects food, spraying the modulating agent in the insect's habitat or field, as well as engineered approaches in which a species that is used as food is engineered to express a modulating agent, then fed to the insect to be affected. In some instances, for example, the modulating agent composition can be incorporated into, or overlaid on the top of, the insect's diet. For example, the modulating agent composition can be sprayed onto a field of crops which an insect inhabits.

In some instances, the composition is sprayed directly onto a plant e.g., crops, by e.g., backpack spraying, aerial spraying, crop spraying/dusting etc. In instances where the modulating agent is delivered to a plant, the plant receiving the modulating agent may be at any stage of plant growth. For example, formulated modulating agents can be applied as a seed-coating or root treatment in early stages of plant growth or as a total plant treatment at later stages of the crop cycle. In some instances, the modulating agent may be applied as a topical agent to a plant, such that the host insect ingests or otherwise comes in contact with the plant upon interacting with the plant.

Further, the modulating agent may be applied (e.g., in the soil in which a plant grows, or in the water that is used to water the plant) as a systemic agent that is absorbed and distributed through the tissues (e.g., stems or leafs) of a plant or animal host, such that an insect feeding thereon will obtain an effective dose of the modulating agent. In some instances, plants or food organisms may be genetically transformed to express the modulating agent such that a host feeding upon the plant or food organism will ingest the modulating agent.

Delayed or continuous release can also be accomplished by coating the modulating agent or a composition containing the modulating agent(s) with a dissolvable or bioerodable coating layer, such as gelatin, which coating dissolves or erodes in the environment of use, to then make the modulating agent available, or by dispersing the agent in a dissolvable or erodable matrix. Such continuous release and/or dispensing means devices may be advantageously employed to consistently maintain an effective concentration of one or more of the modulating agents described herein in a specific host habitat.

The modulating agent can also be incorporated into the medium in which the insect grows, lives, reproduces, feeds, or infests. For example, a modulating agent can be incorporated into a food container, feeding station, protective wrapping, or a hive. For some applications the modulating agent may be bound to a solid support for application in powder form or in a "trap" or "feeding station." As an example, for applications where the composition is to be used in a trap or as bait for a particular host insect, the compositions may also be bound to a solid support or encapsulated in a time-release material. For example, the compositions described herein can be administered by delivering the composition to at least one habitat where the insect grows, lives, reproduces, or feeds.

VI. Screening

Included herein are screening assays for identifying a modulating agent, wherein the modulating agent is effective to alter the microbiota of a host and thereby increase host fitness (e.g., insect fitness). For example, the screening assay may be used to identify one or more modulating agents that target specific microorganisms and/or specific hosts. Further, the screening assays may be used to identify one or more microorganisms with enhanced functionalities. For example, the screening assay may be effective to isolate one or more microorganisms with an enhanced ability to metabolize (e.g., degrade) a pesticide (e.g., insecticide, e.g., neonicotinoid) or plant allelochemical (e.g., caffeine, soyacystatin N, monoterpenes, diterpene acids, or phenolic compounds). Delivery and colonization of an isolated microorganism in the host may increase the host's resistance to the pesticide or plant allelochemical, thereby increasing host fitness. The methods may also be useful for the isolation of microorganisms with an enhanced ability to colonize any of the hosts described herein.

For example, to screen for microorganisms that increase a host's resistance to a pesticide, a starting culture may be used that includes microorganisms (e.g., bacteria) and high concentrations of a pesticide (e.g., a pesticide listed in Table 12 or a pesticide known in the art, e.g., a neonicotinoid). In some instances, the pesticide may be provided in the form of an environmental sample enriched with the pesticide (e.g., a soil sample). Alternatively, the pesticide (e.g., a pesticide listed in Table 12) may be provided in pure form or in combination with other carriers. Further, the one or more microorganism isolates may be inoculated directly into the media (e.g., from a laboratory strain) or may be an environmental sample including one or more microorganism species. The growth media may be either liquid or solid. In some instances, the pesticide of interest is the sole carbon or nitrogen source for the microorganisms in the media. The culture may be sub-cultured (e.g., inoculated into fresh media with high levels of the pesticide) any number of times to enrich for and/or isolate microbial strains (e.g., bacterial strains) capable of metabolizing the pesticide. The original culture or the subcultures may be assessed using any methods known in the art to test for alterations (e.g., decrease) in the levels of the pesticide in the sample (e.g., using HPLC). Isolates that reduce the concentration of the pesticide (e.g., a pesticide listed in Table 12 or a pesticide known in the art, e.g., neonicotinoid) may be isolated for use as a modulating agent in any of the methods or compositions described herein.

The methods may be used to further select for microorganisms described herein, including those isolated from a screening assay, with an enhanced ability to colonize and survive in a host (e.g., insect). For example, a host may be inoculated with a bacterial isolate (e.g., one with the ability to degrade a pesticide). The host may then be tested at regular intervals for the presence of the bacterial isolate (e.g., via culturing or 16s RNA from guts isolated from the host). Bacterial isolates that survive in the host (e.g., the midgut of an insect) may be isolated for use as a modulating agent in any of the methods or compositions described herein.

TABLE 12

| Pesticides |
| --- |
| Aclonifen |
| Acetamiprid |
| Alanycarb |
| Amidosulfuron |
| Aminocyclopyrachlor |
| Amisulbrom |
| Anthraquinone |
| Asulam, sodium salt |
| Benfuracarb |
| Bensulide |
| beta-HCH; beta-BCH |
| Bioresmethrin |
| Blasticidin-S |
| Borax; disodium tetraborate |
| Boric acid |
| Bromoxynil heptanoate |
| Bromoxynil octanoate |
| Carbosulfan |
| Chlorantraniliprole |
| Chlordimeform |
| Chlorfluazuron |
| Chlorphropham |
| Climbazole |
| Clopyralid |
| Copper (II) hydroxide |
| Cyflufenamid |
| Cyhalothrin |
| Cyhalothrin, gamma |
| Decahydrate |
| Diafenthiuron |
| Dimefuron |
| Dimoxystrobin |
| Dinotefuran |
| Diquat dichloride |
| Dithianon |
| E-Phosphamidon |
| EPTC |
| Ethaboxam |
| Ethirimol |
| Fenchlorazole-ethyl |
| Fenothiocarb |
| Fenitrothion |
| Fenpropidin |
| Fluazolate |
| Flufenoxuron |
| Flumetralin |
| Fluxapyroxad |
| Fuberidazole |
| Glufosinate-ammonium |
| Glyphosate |
| Group: Borax, borate salts (see |
| Group: Paraffin oils, Mineral |
| Halfenprox |
| Imiprothrin |
| Imidacloprid |
| Ipconazole |
| Isopyrazam |
| Isopyrazam |

TABLE 12-continued

Pesticides

Lenacil
Magnesium phosphide
Metaflumizone
Metazachlor
Metazachlor
Metobromuron
Metoxuron
Metsulfuron-methyl
Milbemectin
Naled
Napropamide
Nicosulfuron
Nitenpyram
Nitrobenzene
o-phenylphenol
Oils
Oxadiargyl
Oxycarboxin
Paraffin oil
Penconazole
Pendimethalin
Penflufen
Penflufen
Pentachlorbenzene
Penthiopyrad
Penthiopyrad
Pirimiphos-methyl
Prallethrin
Profenofos
Proquinazid
Prothiofos
Pyraclofos
Pyrazachlor
Pyrazophos
Pyridaben
Pyridalyl
Pyridiphenthion
Pyrifenox
Quinmerac
Rotenone
Sedaxane
Sedaxane
Silafluofen
Sintofen
Spinetoram
Sulfoxaflor
Temephos
Thiocloprid
Thiamethoxam
Tolfenpyrad
Tralomethrin
Tributyltin compounds
Tridiphane
Triflumizole
Validamycin
Zinc phosphide

EXAMPLES

The following is an example of the methods of the invention. It is understood that various other embodiments may be practiced, given the general description provided above.

Example 1: Generation of a Library of Natural Microbes

This Example demonstrates the isolation of bacteria from soil that naturally produce the amino acid, methionine.

The medium used for isolation of microorganisms is Starch-Casein-Nitrate agar (Starch, 10.0 g; Casein, 0.003 g; $KNO_3$, 0.02 g; NaCl, 0.02 g; $MgSO_4$, 0.5 mg; $CaCO_3$, 0.2 mg; $FeSO_4$, 0.1 mg; Agar, 12.0 g; $H_2O$, 1 L; pH 7.0) (Kuster and Williams, 1964). Each environmental soil sample (1.0 g) is suspended in 9 ml of sterile water, and 1 ml of the suspension is serially diluted ten-fold in sterile distilled water. One milliliter of the $10^{-5}$ dilution is inoculated onto the agar medium and incubated for 7 days at 30° C. At the end of this period, the plates are observed for growth. White discrete and leathery colonies are picked and grown on new Starch-Casein-Nitrate agar plates to create a library of isolates. After 7 days of growth at 30° C., the plates are kept at 4° C.

Example 2: Screen for Isolates that Produce Methionine

This Example demonstrates the screening assay of isolates from Example 1 that naturally produce the amino acid, methionine.

Screening for Methionine Production:

A modified basal medium ($K_2HPO_4$, 0.3 g; $KH_2PO_4$, 0.7 g; $Na_2CO_3$, 1.0 g; $CaCl_2$), 5.0 mg; $MgSO_4$, 0.3 g; $FeSO_4$, 1.0 mg; $H_2O$, 1 L) containing sucrose (20.0 g) and $NH_4Cl$ (10.0 g) is used for fermentation (Chay, B. P., Galvez, F. C. F., and Padolina, W. G. P. U. L. B. P. (1992). Methionine production by batch fermentation from various carbohydrates. ASEAN Food Journal (Malaysia)). The pH of the medium is 7.2.

Culture conditions: Two loops of the 7 day isolate culture of Example 1 are inoculated into a 250 ml Erlenmeyer flask containing 30 ml of the fermentation medium. Methionine production is assayed after incubation of the flask for 5 days on a rotary shaker (160 rpm) at 30° C. Duplicate flasks are prepared and non-inoculated flasks served as control in all experiments.

The presence of methionine in the culture broths of the isolates is examined by paper chromatography following a modified method of Khanna and Nag (Khanna et al., "Production of amino acids in vitro tissue culture," Indian Journal of Experimental Biology (1973)). The broth culture is centrifuged at 5000×g for 20 min and 2 μL of the supernatant is applied 1.5 cm above one edge of Whatman No. 1 filter paper, with dimensions of 18 cm×22 cm. 1 μL of volume of a standard methionine solution (0.1 mg/mL) is applied alongside with the supernatant, and the chromatogram is developed in a solvent mixture of n-butanol, acetic acid and water (4:1:1) for 18 h. The chromatogram is air-dried at room temperature, sprayed with 0.15% ninhydrin solution in butanol and dried again before heating at 60° C. for 5 min in an oven. The value of the ninhydrin-positive spot (bluish-violet) of the supernatant that corresponds with the value of the standard methionine solution indicates presence of methionine in the broth culture. The concentration of methionine produced in the broth culture of the isolate is estimated as follows. The ninhydrin-positive spot of the supernatant of the isolate on the chromatogram is eluted in 10% ethanol and the spectrophotometric reading of the eluate at 520 nm recorded. The methionine concentration in the supernatant is determined from a standard curve. A plot of the values of optical densities against varying concentrations (0.1 to 0.9 mg/ml) of a methionine solution serve as the standard methionine curve.

Isolates that produce methionine are kept on fresh agar plates and a stock solution is created by suspending two loopfuls of microorganism in an aliquot of 50% glycerol solution.

Example 3: Administration of Methionine Producing Isolates to Increase of Crickets' Amino Acid Content This example demonstrates the ability to treat crickets with methionine producing bacteria to improve their nutritional content.

The world's appetite for meat is growing, and the production of animal feed is an increasing strain on land and water. Insects could provide much of the protein animals need at a much lower environmental cost; many insect species can feed on manure, like Grant's maggots, or other types of organic waste, such as leftover food, offal, and grains discarded by breweries. Insects produce body mass at an astonishing rate, in part because as cold-blooded animals they don't expend energy on regulating their body temperature. Crickets, e.g., *Acheta domesticus*, need only 1.7 kilograms of feed to gain a kilogram of body weight; a typical U.S. chicken consumes 2.5 kilograms, pigs 5 kilograms, and cattle 10 kilograms. Another advantage: most insects can be eaten whole. Only about half of a chicken or a pig is edible; for a cow the fraction is even less. As a result, raising a kilogram of insect protein produces less $CO_2$ than rearing pigs or cattle, and takes up only one-tenth the land.

Insect meal could replace between 25% and 100% of soymeal or fishmeal in the animals' diets with no adverse effects, but most insect meals are deficient in the amino acids methionine and lysine. Synthetic production of methionine requires hazardous chemicals and its use is banned in organic farming. By introducing methionine-producing bacteria into the crickets' microbiome, crickets are expected to naturally increase their nutritional content.

Therapeutic design: Isolated bacteria identified as methionine producing from the Example 2, are formulated with a solution of $10^7$ cells/mL mixed with the feeding substrate, e.g., poultry starter feed and rice bran (Poultry Feed-PF), for crickets.

Experimental Design:

The experimental units in which the crickets are bred are modified gaylord shipping boxes, which have the footprint of standard international shipping pallets (1.2 m (L)×1.0 m (W)×0.61 m (H)). The interior of each enclosure is lined with a 4 mm clear plastic liner and covered with 122 cm×137 cm of nylon mosquito netting to serve as a physical barrier to entrance or exit. To prevent cannibalism and stress-related mortality, 96 egg cartons, 30 cm×30 cm in size, are placed on-edge around the periphery of each box. This provides approximately 172800 $cm^2$ of crawl-able surface area. Access to water is provided by 2 quart-sized poultry water dispensers with cotton and gravel inserted in the dispensing basin to prevent the drowning of newly hatched nymphs. Sides of the water dispensers are sanded to provide purchase for the crickets to crawl vertically. Misting tips with check valves to prevent dripping are affixed at the top interior of each enclosure. To maintain acceptable humidity and provide a dispersed, alternative water source for the large population of crickets, these tips provided pulses of water aimed at the center of the enclosure at automated intervals. Temperature (T) and relative humidity (RH) within the greenhouse are maintained at 29.0±2.1 standard deviation (SD) ° C. and 67.2±14.7 SD %, respectively, over the course of the experiment. Light is provided 24 hr/day.

An egg substrate from Timberline Fisheries (http://timberlinefresh.com) consisting of approximately 50,000 *Acheta domesticus* eggs with a hatch rate of 70% is placed into each of the enclosures. The egg substrate is maintained between 80-90% humidity until they hatch. Once hatching is observed, the substrate is misted twice daily until the nymphs fully emerge. Population growth is monitored every 3 to 4 days by counting and weighing a random sample of 70 individuals from each experimental unit.

From 14 days after hatching until they are either harvested or experienced complete mortality, *Acheta domesticus* populations are administered the following: 2 feed treatments ad libitum: 1) a 5:1 ratio of non-medicated poultry starter feed and rice bran (Poultry Feed-PF), as control; 2) a 5:1 ratio of non-medicated poultry starter feed and rice bran (Poultry Feed-PF) sprayed with 100 mL of a solution of $10^9$ cells/ml of the isolated bacteria described in Example 2 diluted in growth medium described herein.

Once a week for five weeks of culture, the insects are harvested. The insects are stored for half an hour in the freezer at −50° C. Next, the frozen insects are submerged in liquid nitrogen and subsequently grinded using a blender for 15 minutes (Braun Multiquick 5, 600 W, Kronberg, Germany). Amino acid composition of freeze-dried insect powder is analyzed using ion exchange chromatography, following the International standard ISO 13903:2005 following the technique of Yi, L. et al. (2013).

Crickets fed with the methionine producing microbes identified in Example 2 are expected to contain more methionine content than crickets fed the control feed.

Example 4: Administration of Methionine Producing Strains of Bacteria to *Drosophila Melanogaster* Raised on Methionine Deficient Food to Increase their Body Mass, Development Rate, and Survival This example demonstrates the ability to treat *Drosophila melanogaster* raised on methionine poor diet with methionine producing bacteria to increase the body mass, development rate, and survival. This experimental design is also applicable to increase the nutritional content of other insects such as crickets which can be used to produce animal feed rich in methionine.

Experimental Design:

Bacterial strains isolated in Example 2 that produce methionine, as well as the strains that do not produce methionine are grown in nutrient broth at 30° C.

Chemically defined (CD) fly food is prepared as described in Nature, Vol. 11, No. 1, 100-105, 2014. CD food is prepared that lacks methionine, and is referred to as CD-M. The fly food formulations are used for all experiments described in this Example.

Development Rate and Body Mass Assays

On day one, $10^9$ of the methionine producing bacteria as described in Example 1, or bacteria that do not produce methionine (control), are resuspended in 100 µl of phosphate-buffered saline and added to CD-M fly food. These two cohorts are left to dry for 24 hrs at 25° C.

On day two, fertilized embryos collected from flies are treated with 2% hypochlorite solution for 5 min and then washed with sterile water to remove any extracellular microbes from the embryos. 10 µl of the embryo suspension in water (1:3 embryo:water suspension) is added to both the bacterial-seeded and control samples. The fly food cohorts with the embryos is maintained at 25° C. with 12 h light and 12 dark cycle for the rest of the experiment.

The time to puparium formation and the number of pupa formed is measured in each cohort. The time to adult emergence and the rate of emergence is measured in each sample. From the time the first adult emerges from the pupa, the number of emerging adult flies is counted every 12 hours and rate of emergence is computed.

For the body mass assay, ten larvae are collected from both cohorts and their weights, areas, and the total protein content are measured.

Embryos in the CD-M fly food seeded with methionine producing bacteria identified in Example 2 are expected to develop faster and have higher protein content than the embryos on CD-M fly food with non-methionine producing bacteria.

Survival Assay 12 days before day one, sterile embryos are generated as described previously and raised on sterile CD fly food. Sterile adults start to emerge from their pupae 11 days from the time the embryos are collected when raised at 25° C. with 12 h light and 12 h dark cycle.

On day one, $10^9$ of the methionine producing bacteria, or bacteria that do not produce methionine (control), are resuspended in 100 μl phosphate-buffered saline and added to CD-M fly food. These two cohorts are left to dry for 24 hrs at 25° C.

10 newly emerged sterile adult males and females are introduced to CD-M fly food with methionine producing bacteria or control on day two of the experiment. The fly food with the flies is maintained at 25° C. with 12 h light and 12 dark cycle for the rest of the experiment. The number of surviving male and female flies are counted every day until all the flies are dead. Survival analysis are performed to assess the fitness benefit of the methionine producing bacteria on fly survival.

Flies raised on CD-M fly food seeded with methionine producing microbes identified in Example 2 are expected to survive longer than the control.

Example 5: Isolation of Microorganisms that Degrade Fenitrothion, an Organophosphorus Insecticide This Example demonstrates the acquisition of a library of microorganisms able to degrade fenitrothion, an organophosphorus insecticide.

Experimental Design

Soil samples are obtained from various regions where fenitrothion was previously utilized for insect control. Fenitrothion degrading bacteria will be isolated from the soil samples as described in (Microbes Environ. Vol. 21, No. 1, 58-64, 2006). Briefly, 1 g of the soil sample is mixed thoroughly with 9 ml of sterile distilled water. The soil particles are then centrifuged at 1000 rcf for 5 min, and 100 μl of the supernatant is then plated onto fenitrothion with mineral salts medium (0.4 g/l of yeast extract, 0.4 g/l fenitrothion, 15 g/l bacteriological agar). The plates are cloudy when prepared as the fenitrothion is an emulsion.

Colonies that develop clear zones around them and are likely to be degrading or metabolizing fenitrothion, and these colonies are isolated and regrown on LB agar, nutrient agar, yeast glucose agar, TSA agar, BHI agar, or MRS agar. Once unique bacterial colonies are identified, their genomes are extracted using a genomic DNA extraction kit, (Qiagen, DNeasy Blood and Tissue Kit) as per the manufacturer's protocol.

The 16S rRNA gene is amplified using universal bacterial primers 27F (5'-AGAGTTTGATCMTGGCTCAG-3'; SEQ ID NO: 227) and 1492R (5'-TACCTTGTTACGACTT-3'; SEQ ID NO: 228), and using PCR conditions of 94° C. for 2 min, 30 cycles of 94° C. for 1 min, 56° C. for 1 min, and 72° C. for 2 min, and a final extension of 72° C. for 5 min. Gel electrophoresis is used to confirm that the amplicons are of the correct size (~1500 bp), and the products are excised from the gel and purified using a gel extraction kit (Qiagen, QIAquick) as per the manufacturer's protocol. The correct size amplicons are Sanger sequenced and BLAST is used to match the sequence against various repositories of 16s rRNA gene sequences to identify the bacteria.

To determine whether the isolated bacteria is degrading fenitrothion, ~$10^7$ bacterial cells are incubated in 1 ml of 20 mM sodium-potassium phosphate buffer (pH 7) with 1 mM fenitrothion, as described in PNAS, Vol. 109, No. 22, 8618-8622, 2012. After 30 min of incubation at 30° C., the reaction is stopped by adding an equal volume of methanol. Then fenitrothion and its metabolite, 3-methyl-4-nitrophenol, are analyzed by HPLC. The retention times and peak areas of the HPLC profiles are compared to known standards.

Unique bacterial isolates that have fenitrothion degrading capabilities are then stored as frozen glycerol at −80° C.

Example 6: Increasing *Drosophila melanogaster*'s Resistance to Fenitrothion Through the Administration of Fenitrothion-Degrading Bacteria This Example demonstrates the ability to produce an insect model, *Drosophila melanogaster*, that is resistant to one or more negative effects of insecticides in their diet, more specifically fenitrothion, to produce a more robust insect. The following approach is a surrogate for other insects, such as crickets or other insects disclosed herein, e.g., insect sources useful to produce animal feed rich in protein. Many insecticides including fenitrothion have been shown to be toxic to crickets.

Experimental Design:

Therapeutic design: The bacterial isolates selected in Example 5 are formulated at $10^9$ organisms in 100 μl of fly food medium with and without fenitrothion.

The media used to rear flies is cornmeal, molasses and yeast medium (11 g/l yeast, 54 g/l yellow cornmeal, 5 g/l agar, 66 ml/l molasses, and 4.8 ml/l propionic acid). For experimental procedures, fenitrothion at 0, 10, and 100p.p.m. or phosphate-buffered saline as negative controls are infused into sterile fly food medium.

Development Rate Assay

On day one, $10^9$ fenitrothion-degrading bacteria described in Example 5 are suspended in 100 μl phosphate-buffered saline or equal volumes of saline (negative controls) are added to sterile fly food medium with or without fenitrothion. All are left to dry for a day at 25° C. as described in *Appl. Environ. Microbiol*. Vol. 82, No. 20, 6204-6213, 2016.

On day two, fertilized embryos collected from flies are treated with 2% hypochlorite solution for 5 min and then washed with sterile water to remove any extracellular microbes from the embryos. 10 μl of the embryo suspension in water (1:3 embryo:water suspension) is added to the bacteria-seeded or negative control fly food with or without the fenitrothion. The fly food cohorts with the embryos are maintained at 25° C. with 12 h light and 12 dark cycle for the rest of the experiment.

The time to puparium formation and the number of pupa formed is measured in each cohort. The time to adult emergence and the rate of emergence is measured in each sample. From the time the first adult emerges from the pupa, the number of emerging adult flies are counted every 12 hours and rate of emergence is computed.

Embryos in the fenitrothion infused fly food seeded with Fenitrothion-degrading bacteria are expected to develop faster than the embryos on fenitrothion infused food without the fenitrothion-degrading bacteria.

Survival Assay

About 12 days before day one, sterile embryos are generated as described previously and raised on sterile fly food. Adults start to emerge from their pupae 11 days from embryo collection when raised in sterile fly food without fenitrothion at 25° C. with 12 h light and 12 h dark cycle. On day one, $10^9$ of the fenitrothion-degrading bacteria in phosphate-buffered saline are added to sterile fly food medium as described in a previous Example.

On day two, 10 newly emerged sterile adult males and females are introduced to bacteria-seeded or negative control fly food with or without fenitrothion. The fly food with the flies is maintained at 25° C. with 12 h light and 12 dark cycle for the rest of the experiment. The number of surviving male and female flies are counted every day until all the flies are dead. Survival analysis is performed to assess the fitness benefit of fenitrothion-degrading bacteria on the fly survival.

Flies raised on fenitrothion infused fly food seeded with fenitrothion-degrading bacteria are expected to survive longer than flies raised on fenitrothion infused food without the fenitrothion-degrading bacteria.

Example 7: Elimination of Entomopathogenic Bacteria from *Drosophila melanogaster* Using Naturally Occurring Phages This Example demonstrates the ability to eliminate insect bacterial pathogens (such as *Serratia marcescens, Erwinia carotovora*, and *Pseudomonas entomophila*) from *Drosophila melanogaster* using naturally occurring phages. This procedure can be useful as a surrogate assay for eliminating bacteria in other insect species, such as in bees.

Experimental Design:

Therapeutic design: Phage library collections are used having the following phage families: Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, Tectiviridae.

Multiple environmental samples (soil, pond sediments, and sewage water) are collected in sterile 1 L flasks over a period of 2 weeks and are immediately processed after collection and stored thereafter at 4° C. Solid samples are homogenized in sterile double-strength difco luria broth (LB) or tryptic soy broth (TSB) supplemented with 2 mM $CaCl_2$) to a final volume of 100 mL. The pH and phosphate levels are measured using phosphate test strips. For purification, all samples are centrifuged at 3000-6000 g for 10-15 min at 4° C., and filtered through 0.2-µm low protein filters to remove all remaining bacterial cells. The supernatant that contains the phage library is then stored at 4° C. in the presence of chloroform in a glass bottle.

20-30 ml of the phage library is diluted to a volume of 30-40 ml with LB-broth. The target bacterial strain (e.g., *Serratia marcescens, Erwinia carotovora*, and *Pseudomonas entomophila*) is added (50-200 µl overnight culture grown in LB-broth) to enrich phages that target this specific bacterial strain in the culture. This culture is incubated overnight at 37° C., shaken at 230 rpm. Bacteria from this enrichment culture are removed by centrifugation (3000-6000 g 15-20 min, 4° C.) and filtered (0.2 or 0.45 µm filter). 2.5 ml of the bacteria free culture is added to 2.5 ml of LB-broth and 50-100 µl of the target bacteria are added back to the culture to further enrich the phages. The enrichment culture is grown overnight as above. A sample from this enrichment culture is centrifuged at 13,000 g for 15 min at room temperature and 10 µl of the supernatant is plated on an LB-agar petri dish along with 100-300 µl of the target bacteria and 3 ml of melted 0.7% soft-agar. The plates are incubated overnight at 37° C.

Each of the plaques observed on the bacterial lawn are picked and transferred into 500 µl of LB-broth. A sample from this plaque-stock is further plated on the target bacteria. Plaque-purification is performed three times for all discovered phages in order to isolate a single homogenous phage from the heterogeneous phage mix.

Lysates from plates with high-titer phages ($>1\times10^{10}$ PFU/ml) are prepared by harvesting overlay plates of a host bacterium strain exhibiting confluent lysis. After being flooded with 5 ml of buffer, the soft agar overlay is macerated, clarified by centrifugation, and filter sterilized. The resulting lysates are stored at 4° C. High-titer phage lysates are further purified by isopycnic CsCl centrifugation, as described in Summer et al., *J. Bacteriol.* 192:179-190, 2010.

DNA is isolated from CsCl-purified phage suspensions as described in Summer, *Methods Mol. Biol.* 502:27-46, 2009. An individual isolated phage is sequenced as part of two pools of phage genomes by using a 454 pyrosequencing method. Briefly, phage genomic DNA is mixed in equimolar amounts to a final concentration of about 100 ng/L. The pooled DNA is sheared, ligated with a multiplex identifier (MID) tag specific for each of the pools, and sequenced by pyrosequencing using a full-plate reaction on a sequencer (Roche) according to the manufacturer's protocols. The pooled phage DNA is present in two sequencing reactions. The output corresponding to each of the pools is assembled individually by using software (454 Life Sciences), by adjusting the settings to include only reads with a single MID per assembly. The identity of individual contigs is determined by PCR using primers generated against contig sequences and individual phage genomic DNA preparations as the template. Sequence software (Gene Codes Corporation) is used for sequence assembly and editing.

Phage chromosomal end structures are determined experimentally. Cohesive (cos) ends for phages are determined by sequencing off the ends of the phage genome and sequencing the PCR products derived by amplification through the ligated junction of circularized genomic DNA, as described in Summer, *Methods Mol. Biol.* 502:27-46, 2009. Protein-coding regions are initially predicted using gene prediction software (Lukashin et al. *Nucleic Acids Res.* 26:1107-1115, 1998), refined through manual analysis in Artemis (Rutherford et al., *Bioinformatics* 16:944-945, 2000), and analyzed through the use of BLAST (E value cutoff of 0.005) (Camacho et al., *BMC Bioinformatics* 10:421, 2009). Proteins of particular interest are additionally analyzed by sequence searching software (Hunter et al., *Nucleic Acids Res.* 40:D306-D312, 2012).

Electron microscopy of CsCl-purified phage ($>1\times10^{11}$ PFU/ml) that lysed the *Drosophila*'s pathogenic bacterial species is performed by diluting phage stock with the tryptic soy broth buffer. Phages are applied onto thin 400-mesh carbon-coated grids, stained with 2% (wt/vol) uranyl acetate, and air dried. Specimens are observed on a transmission electron microscope operating at an acceleration voltage of 100 kV. Five virions of each phage are measured to calculate mean values and standard deviations for dimensions of capsid and tail, where appropriate.

Incorporating Phages into a Meal

The media used to rear flies is cornmeal, molasses and yeast medium (11 g/l yeast, 54 g/l yellow cornmeal, 5 g/l agar, 66 ml/l molasses, and 4.8 ml/l propionic acid). Phage solutions are infused into the fly food to obtain final concentrations of phages between 0 and $10^8$ pfu/ml.

*S. Marcescens, Erwinia carotovora*, and *Pseudomonas entomphila* bacteria are grown at 30° C. in nutrient broth or LB broth.

Sterile fly embryos are generated by treating fertilized embryos collected from flies with 2% hypochlorite solution for 5 min and then washed with sterile water to remove any extracellular microbes. Fly larvae with the target bacteria are generated by seeding $10^9$ CFUs of bacteria in sterile fly food and adding sterile fly embryos to this food. After 2 days, ten S. marcescens infected first instar fly larvae are added to the fly food with a range (0-$10^8$ pfu/ml) of the phage concentrations. The larvae are left to grow in the food with the phages for 3 days until they become third instars. The larvae are then collected and individually homogenized in nutrient broth or LB broth, and plated on nutrient agar or LB agar plates, and incubated at 30° C. The number of CFUs of S. marcescens obtained from larvae in fly food with varying phage concentrations are recorded. This shows the number of live bacteria that were present in the flies.

The number of live bacteria are expected to be reduced in the larvae grown on fly food with the phages against the bacteria.

Example 8: Administration of Amino Acid Producing Strain of Bacteria to Drosophila melanogaster Through Diet to Increase their Development Rate This Example demonstrates the ability to treat the insect Drosophila melanogaster with amino acid producing bacteria to improve their nutritional content. This experimental design can be extended to reduce the growth time and produce more biomass of other insects, such as crickets, which can be used to produce animal feed rich in protein.

The world's appetite for meat is growing, and the production of animal feed is an increasing strain on land and water. Insects could provide much of the protein humans and animals need at a much lower environmental cost; many insect species can feed on manure, like Grant's maggots, or other types of organic waste, such as leftover food, offal, and grains discarded by breweries. Insects produce body mass at an astonishing rate, in part because as cold-blooded animals they don't expend energy on regulating their body temperature. Crickets, e.g., Acheta domesticus, need only 1.7 kilograms of feed to gain a kilogram of body weight; a typical U.S. chicken consumes 2.5 kilograms, pigs 5 kilograms, and cattle 10 kilograms. Another advantage: most insects can be eaten whole. Only about half of a chicken or a pig is edible; for a cow the fraction is even less. As a result, raising a kilogram of insect protein produces less $CO_2$ than rearing pigs or cattle, and takes up only one-tenth the land.

Insect meal could replace between 25% and 100% of soymeal or fishmeal in animals' diets with no adverse effects. However, most insect meals are deficient in the amino acids methionine and lysine. Synthetic production of methionine requires hazardous chemicals and its use is banned in organic farming. In this Example, the introduction of methionine-producing bacteria into an insect's microbiome naturally increased their nutritional content.

Therapeutic Design:

Isolated bacteria Corynebacterium glutamicum that are glutamate or methionine producing, are formulated with a solution of 109 colony forming units (CFUs) mixed to the feeding substrate for Drosophila flies.

Experimental Design:

Corynebacterium glutamicum strains that produce glutamate or methionine were grown in nutrient broth at 30° C.

The media used to rear flies is cornmeal, molasses and yeast medium (11 g/l yeast, 54 g/l yellow cornmeal, 5 g/l agar, 66 ml/l molasses, and 4.8 ml/l propionic acid). All the components of the diet except propionic acid are heated together to 80° C. in deionized water with constant mixing for 30 minutes and let to cool to 60° C. Propionic acid is then mixed in and 50 ml of the diet is aliquoted into individual bottles and allowed to cool down and solidify. The flies are raised at 26° C., 16:8 hour light:dark cycle, at around 60% humidity.

For the experimental setup to measure the larval growth rate, defined diet was used (Piper et al., 2014, *Nature Methods*). Defined diet eliminates the effects of batch to batch variation in the ingredients used for the cornmeal based diet. In addition, the defined diet allows for the exclusion of individual components to test their effects on fly development.

Development Rate Assay

On day one, 100 ul of a Corynebacterium glutamicum suspension in nutrient broth consisting of $10^9$ colony forming units (CFUs) were added to five replicates of fly food. As controls, nutrient broth without the bacteria was added to five more bottles of fly food. Fertilized embryos collected from fruit flies were treated with 2% hypochlorite solution for five minutes and then washed with sterile water to remove any extracellular microbes from the embryos. 10 ul of the embryo suspension in water (one:three embryo:water suspension) was added to all the bacteria seeded and control fly food bottles. The fly food with the embryos was maintained at 26° C., 16:8 hour light:dark cycle, at around 60% humidity for the rest of the experiment. The time to adult emergence and the rate of emergence was measured in every replicate. From the time the first adult emerges from the pupa, the number of adult flies emerging was counted every 12 hours and rate of emergence was be computed.

Larval Mass Assay

To test whether the presence of bacteria producing amino acids can increase the body mass of developing larvae when raised on defined diet, we produced larvae that are axenic, and mono-associated with a single strain of bacterium. For these assays, three different bacteria were used, Corynebacterium glutamicum—a strain that produces glutamate, Corynebacterium glutamicum—a strain that produces methionine, and E. coli.

First, axenic embryos were generated. Fertilized embryos were collected from fruit flies over a 6 hour period on grape juice agar plates with yeast. To eliminate any bacterial contamination, the embryos were treated with 2% hypochlorite solution for five minutes and then washed thrice with sterile water. One volume of embryos was then suspended in 3 volumes of water.

The defined diet was aliquoted into vials and nine replicates were used for every condition being tested. The conditions were:

1. No bacteria added to the food
2. Food containing C. glutamicum, strain that produces glutamate (C.glu-Glu)
3. Food containing C. glutamicum, a strain that produces methionine (C.glu-Met)
4. Food containing E. coli To each vial of the food that were in conditions 2, 3, and 4, 100 ul of overnight stationary phase cultures was added.

To each of the nine replicates in every condition, 10 ul of the sterile embryo+water suspension was added. The vials were then incubated at 26° C., 60% humidity, 16:8 light:dark cycle.

After 13 days, 10-15 randomly chosen larvae from each replicate were sampled, and their areas were measured, as a proxy to their biomass and weight. The larvae were scooped out from the food with a sterile spatula, rinsed in water to clean the food from their bodies, and an image of every larvae sampled was acquired individually for every replicate in each condition. An Image J script was used to identify, outline and measure the area of the larva in every image.

Amino Acid Producing Bacteria Treatment Increases Insect Development Rate.

Figure 2A:
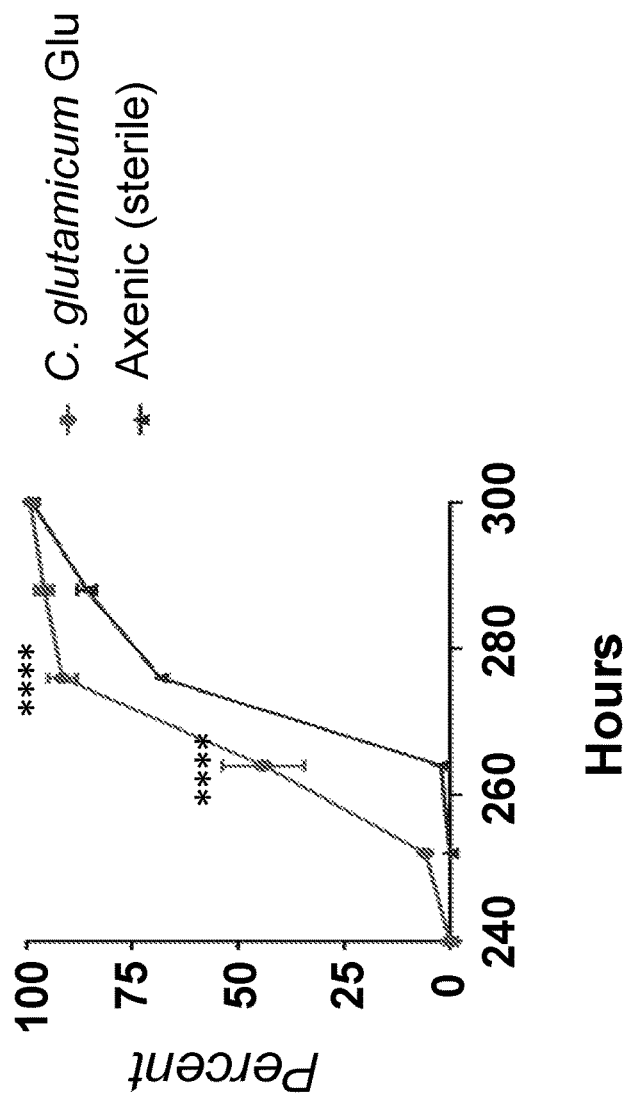
FIG. 2A is a graph showing the effects of male gender on the developmental rate differences in Drosophila melanogaster. The adults emerging from FIG. 11 were sexed and their rate of emergence was plotted.
Figure 2B:
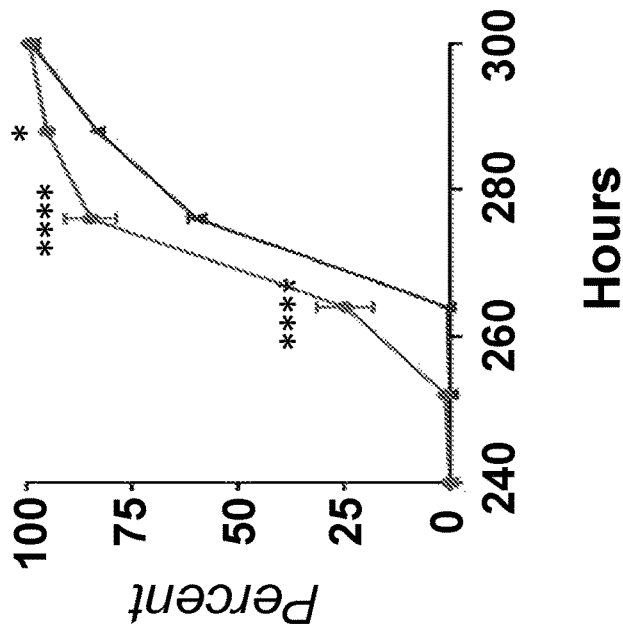
FIG. 2B is a graph showing the effects of female gender on the developmental rate differences in Drosophila melanogaster. The adults emerging from FIG. 1 were sexed and their rate of emergence was plotted. The enhancement in the rate of development in the females due to the presence of bacteria in the diet is significantly more than in their male counterparts. The benefits of the presence of bacteria in the fly diet are higher in the females compared to the males.

Embryos that developed on diet that was seeded with the amino acid producing strain of bacterium reached adulthood significantly faster than those that were raised on the sterile diet (FIG. 1). Further, this effect was slightly stronger in female flies than in male files (FIGS. 2A and 2B).

Amino Acid Producing Bacteria Treatment Increases Larval Body Mass.

Figure 3:
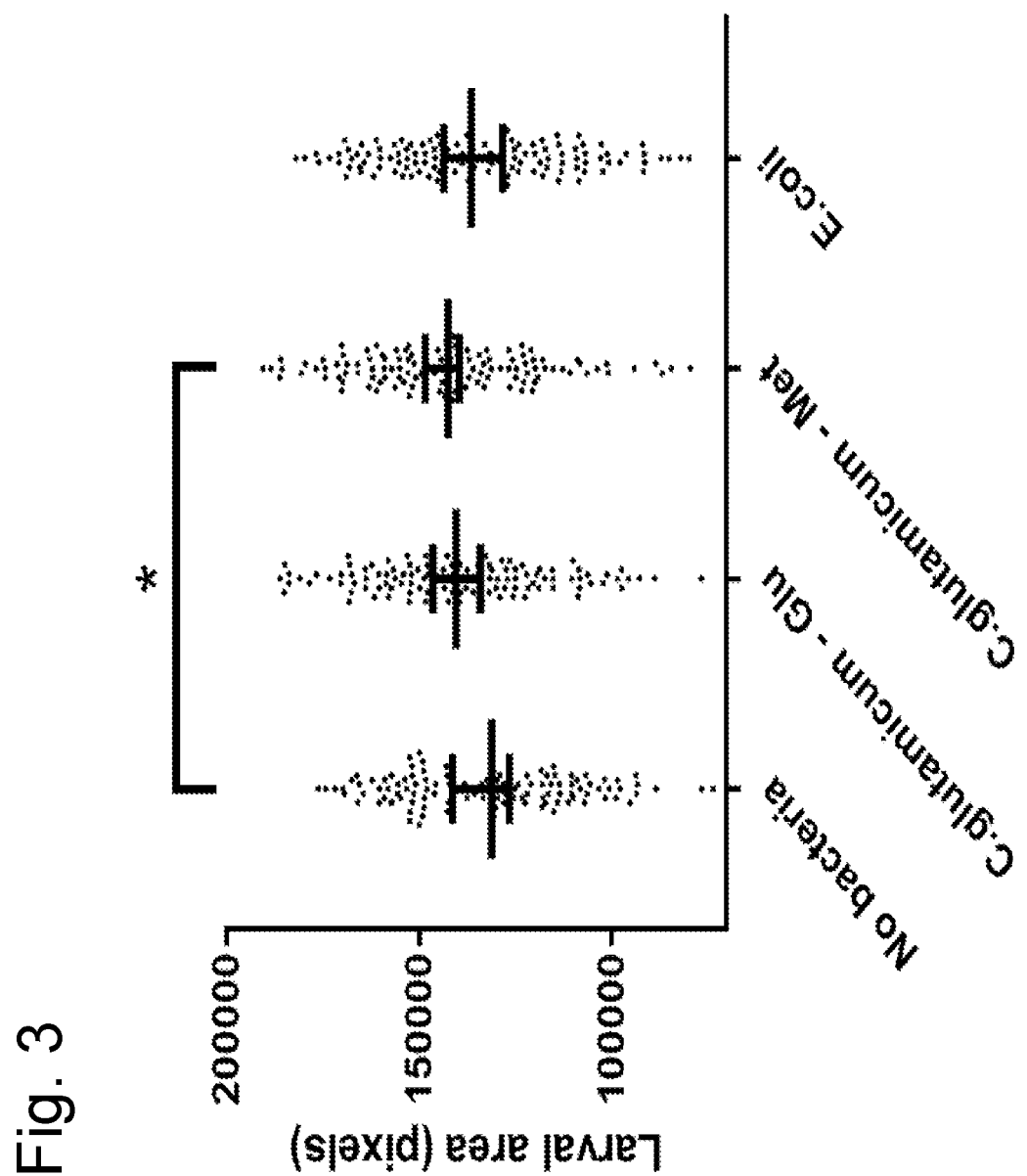
FIG. 3 is a graph showing C. glutamicum strains promoted larval biomass. Larvae raised on diet supplemented with C. glutamicum strains either producing glutamate or methionine are bigger than those raised on sterile diet or diet supplemented with Escherichia coli. The areas of the larvae are measured as the number of pixels in the images of the larvae. The medians and the 95% confidence intervals are shown as lines on the graph.

Larvae from the diet supplemented with C. glu-Met had the largest body size on average, followed by those in diet with C.glu-Glu, E. coli, and no bacteria (FIG. 3). This shows that augmenting the diet of insects with bacteria that produce amino acids produced insect biomass faster than un-supplemented diet.

Together this data demonstrates that augmenting the diet of insects with bacteria that were capable of producing amino acids produced insect biomass faster than un-supplemented diet. Extending this to other insects such as crickets, supplementing their diet with bacteria that are capable of producing methionine can increase their biomass and protein content.

Example 9: Insects Treated with a Solution of Purified Phage

This Example demonstrates the isolation and purification of phages from environmental samples that targeted specific insect bacteria. This Example also demonstrates the efficacy of isolated phages against the target bacteria in vitro by plaque assays, by measuring their oxygen consumption rate, and the extracellular acidification rate. Finally, this Example demonstrates the efficacy of the phages in vivo, by measuring the ability of the phage to the target bacteria from flies by treating them with a phage isolated against the bacteria. This Example demonstrates that a pathogenic bacterium that decreased the fitness of an insect can be cleared using a phage to target the bacteria. Specifically, Serratia marcescens which is a pathogenic bacterium in flies can be cleared with the use of a phage that was isolated from garden compost.

There are several beneficial and commercially useful insects that are affected by naturally occurring bacterial pathogens.

Experimental Design

Isolation of Specific Bacteriophages from Natural Samples:

Bacteriophages against target bacteria were isolated from environmental source material. Briefly, a saturated culture of Serratia marcescens was diluted into fresh double-strength tryptic soy broth (TSB) and grown for ~120 minutes to early log-phase at 24-26° C., or into double-strength Luria-Bertani (LB) broth and grown for ~90 min at 37° C. Garden compost was prepared by homogenization in PBS and sterilized by 0.2 µm filtration. Raw sewage was sterilized by 0.2 µm filtration. One volume of filtered source material was added to log-phase bacterial cultures and incubation was continued for 24 h. Enriched source material was prepared by pelleting cultures and filtering supernatant fluid through 0.45 µm membranes.

Phages were isolated by plating samples onto double-agar bacterial lawns. Stationary bacterial cultures were combined with molten 0.6% agar LB or TSB and poured onto 1.5% agar LB or TSB plates. After solidification, 2.5 µL of phage sample dilutions were spotted onto the double-agar plates and allowed to absorb. Plates were then wrapped and incubated overnight at 25° C. (TSA) or 37° C. (LB), then assessed for the formation of visible plaques. Newly isolated plaques were purified by serial passaging of individual plaques on the target strain by picking plaques into SM Buffer (50 mM Tris-HCl [pH 7.4], 10 mM MgSO4, 100 mM NaCl) and incubating for 15 min at 55° C., then repeating the double-agar spotting method from above using the plaque suspension.

Bacteriophages were successfully isolated from both sewage and compost, as detailed above. Plaque formation was clearly evident after spotting samples onto lawns of the S. marcescens bacteria used for the enrichments.

Passaging, Quantification, and Propagation of Bacteriophages:

Propagation and generation of phage lysates for use in subsequent experiments was performed using bacteriophages isolated and purified as above. Briefly, saturated bacterial cultures were diluted 100-fold into fresh medium and grown for 60-120 minutes to achieve an early-logarithmic growth state for effective phage infection. Phage suspensions or lysates were added to early log phase cultures and incubation was continued until broth clearing, indicative of phage propagation and bacterial lysis, was observed, or until up to 24 h post-infection. Lysates were harvested by pelleting cells at 7,197×g for 20 min, then filtering the supernatant fluid through 0.45 or 0.2 µm membranes. Filtered lysates were stored at 4° C.

Enumeration of infective phage particles was performed using the double-agar spotting method. Briefly, a 1:10 dilution series of samples was performed in PBS and dilutions were spotted onto solidified double-agar plates prepared with the host bacteria as above. Plaque-forming units (PFU) were counted after overnight incubation to determine the approximate titer of samples.

In Vitro Analysis of Isolated Phages Measuring Bacterial Respiration:

A Seahorse XFe96 Analyzer (Agilent) was used to measure the effects of phages on bacteria by monitoring oxygen consumption rate (OCR) and extracellular acidification rate (ECAR) during infection. XFe96 plates were coated the day prior to experiments by 15 µL of a 1 mg/mL poly-L-lysine stock per well and dried overnight at 28° C. and XFe96 probes were equilibrated by placing into wells containing 200 µL of XF Calibrant and incubating in the dark at room temperature. The following day, poly-L-lysine coated plates were washed twice with ddH2O. Saturated overnight cultures of E. coli BL21 (LB, 37° C.) or S. marcescens (TSB, 25° C.) were subcultured at 1:100 into the same media and grown with aeration for ~2.5 h at 30° C. Cultures were then diluted to O.D.600 nm~0.02 using the same media. Treatments were prepared by diluting stocks into SM Buffer at 10× final concentration and loading 20 µL of the 10× solutions into the appropriate injection ports of the probe plate. While the probes were equilibrating in the XFe96 Flux Analyzer, bacterial plates were prepared by adding 90 µL of bacterial suspensions or media controls and spun at 3,000 rpm for 10 min. Following centrifugation, an additional 90 µL of the appropriate media were added gently to the wells so as not to disturb bacterial adherence, bringing the total volume to 180 µL per well.

The XFe96 Flux Analyzer was run at ~30° C., following a Mix, Wait, Read cycling of 1:00, 0:30, 3:00. Four cycles were completed to permit equilibration/normalization of bacteria, then the 20 µL treatments were injected and cycling continued as above, for a total time of approximately 6 h. Data were analyzed using the Seahorse XFe96 Wave software package.

Figure 4:
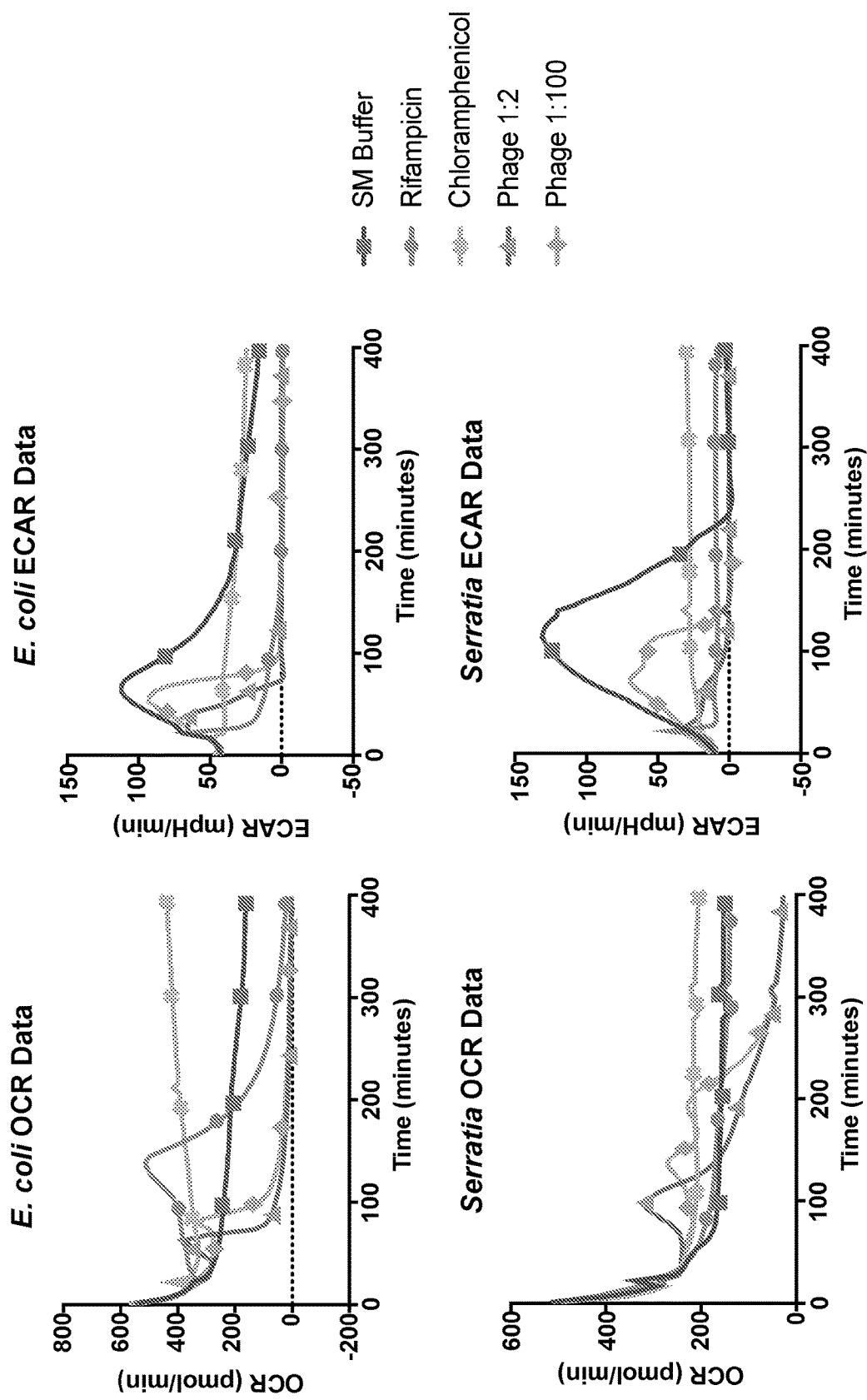
FIG. 4 is a panel of graphs showing the results of a Seahorse flux assay for bacterial respiration. Bacteria were grown to logarithmic phase and loaded into Seahorse XFe96 plates for temporal measurements of oxygen consumption rate (OCR) and extracellular acidification rate (ECAR) as described in methods. Treatments were injected into the wells after approximately 20 minutes and bacteria were monitored to detect changes in growth. Rifampicin=100 µg/mL; Chloramphenicol=25 µg/mL; Phages (T7 for E. coli and ΦSmVL-C1 for Serratia marcescens) were lysates diluted either 1:2 or 1:100 in SM Buffer. The markers on each line are solely provided as indicators of the condition to which each line corresponds, and are not indicative of data points

The effects of isolated bacteriophages were assayed by measuring oxygen consumption rate (OCR) and extracellular acidification rate (ECAR) of bacteria with a Seahorse XFe96 Analyzer. When $E.$ $coli$ was infected with phage T7 and $S.$ $marcescens$ infected with the newly isolated φSmVL-C1, dramatic decreases in OCR were observed following brief bursts in this rate (FIG. 4). For both phages with both host organisms, the Seahorse assay permitted the detection of successful phage infection without the need for plaque assays. Thus, this method is applicable for detecting phage infection of a host organism not amenable to traditional phage detection methods.

SYBR Gold Transduction Assay for Infection Identification:

Bacteriophage preparations were prepared for staining by pretreating with nucleases to remove extraviral nucleic acids that could interfere with fluorescent signal interpretation. Briefly, MgCl2 was added to 10 mL of phage lysate at 10 mM final concentration, and RNase A (Qiagen) and DNase I (Sigma) were both added to final concentrations of 10 μg/mL. Samples were incubated for 1 h at room temperature. After nuclease treatment, 5 mL of lysates were combined with 1 μL of SYBR Gold (Thermo, 10,000×) and incubated at room temperature for ~1.5 h. Excess dye was subsequently removed from samples using Amicon ultrafiltration columns. Briefly, Amicon columns (15 mL, 10 k MWCO) were washed by adding 10 mL of SM Buffer and spinning at 5,000×g, 4° C. for 5 min. Labeled phage samples were then spun through the columns at 5,000×g, 4° C. until the volume had decreased by approximately 10-fold (15-30 min). To wash samples, 5 mL SM Buffer was added to each reservoir and the spin repeated, followed by two additional washes. After the third wash, the retained samples were pipetted out from the Amicon reservoirs and brought up to approximately 1 mL using SM Buffer. To remove larger contaminants, washed and labeled phage samples were spun at 10,000×g for 2 min, and the supernatants were subsequently filtered through 0.2 μm membranes into black microtubes and stored at 4° C.

Saturated bacterial cultures ($E.$ $coli$ MG1655 grown in LB at 37° C., $S.$ $marcescens$ and $S.$ $symbiotica$ grown in TSB at 26° C.) were prepared by spinning down 1 mL aliquots and washing once with 1 mL PBS before a final resuspension using 1 mL PBS. Positive control labeled bacteria were stained by combining 500 μL of washed bacteria with 1 μL of SYBR Gold and incubating for 1 h in the dark at room temperature. Bacteria were pelleted by spinning at 8,000×g for 5 min and washed twice with an equal volume of PBS, followed by resuspension in a final volume of 500 μL PBS. A volume of 25 μL of stained bacteria was combined with 25 μL of SM Buffer in a black microtube, to which 50 μL of 10% formalin (5% final volume, ~2% formaldehyde) was added and mixed by flicking. Samples were fixed at room temperature for ~3 h and then washed using Amicon ultrafiltration columns. Briefly, 500 μL of picopure water was added to Amicon columns (0.5 mL, 100 k MWCO) and spun at 14,000×g for 5 min to wash membranes. Fixed samples were diluted by adding 400 μL of PBS and then transferred to pre-washed spin columns and spun at 14,000×g for 10 min. Columns were transferred to fresh collection tubes, and 500 μL of PBS was added to dilute out fixative remaining in the retentate. Subsequently, two additional PBS dilutions were performed, for a total of three washes. The final retentates were diluted to roughly 100 μL, then columns were inverted into fresh collection tubes and spun at 1,000×g for 2 min to collect samples. Washed samples were transferred to black microtubes and stored at 4° C.

For transduction experiments and controls, 25 μL of bacteria (or PBS) and 25 μL of SYBR Gold labeled phage (or SM Buffer) were combined in black microtubes and incubated static for 15-20 min at room temperature to permit phage adsorption and injection into recipient bacteria. Immediately after incubation, 50 μL of 10% formalin was added to samples and fixation was performed at room temperature for ~4 h. Samples were washed with PBS using Amicon columns, as above.

Injection of bacteriophage nucleic acid was required for a phage to successfully infect a host bacterial cell. Coliphage P1kc labeled with SYBR Gold and co-incubated with $S.$ $marcescens$ revealed the presence of fluorescent bacteria by microscopy, validating the use of this assay in a phage isolation pipeline. As with the Seahorse assay, this approach provided an alternative to traditional phage methods to permit expansion to organisms not amenable to plaque assay. Additionally, the SYBR Gold transduction assay did not require bacterial growth, so is applicable to analysis of phages targeting difficult or even non-culturable organisms, including endosymbionts such as $Buchnera$.

Testing In Vivo Efficacy of the Phages Against $S.$ $marcescens$ in $Drosophila$ $melanogaster$ Flies $S.$ $marcescens$ cultures were grown in Tryptic Soy Broth (TSB) at 30° C. with constant shaking at 200 rpm.

The media used to rear fly stocks was cornmeal, molasses and yeast medium (11 g/l yeast, 54 g/l yellow cornmeal, 5 g/l agar, 66 ml/l molasses, and 4.8 ml/l propionic acid). All the components of the diet except propionic acid were heated together to 80° C. in deionized water with constant mixing for 30 minutes and let to cool to 60° C. Propionic acid was then mixed in and 50 ml of the diet was aliquoted into individual bottles and allowed to cool down and solidify. The flies were raised at 26° C., 16:8 hour light:dark cycle, at around 60% humidity.

To infect the flies with $S.$ $marcescens$, a fine needle (About 10 um wide tip) was dipped in a dense overnight stationary phase culture and the thorax of the flies was punctured. For this experiment, four replicates of 10 males and 10 females each were infected with $S.$ $marcescens$ using the needle puncturing method as the positive control for fly mortality. For the treatment group, four replicates of 10 males and 10 females each were pricked with $S.$ $marcescens$ and a phage solution containing about 108 phage particles/ml. Finally, two replicates of 10 males and 10 females each that were not pricked or treated in anyway were used as a negative control for mortality.

Figure 5:
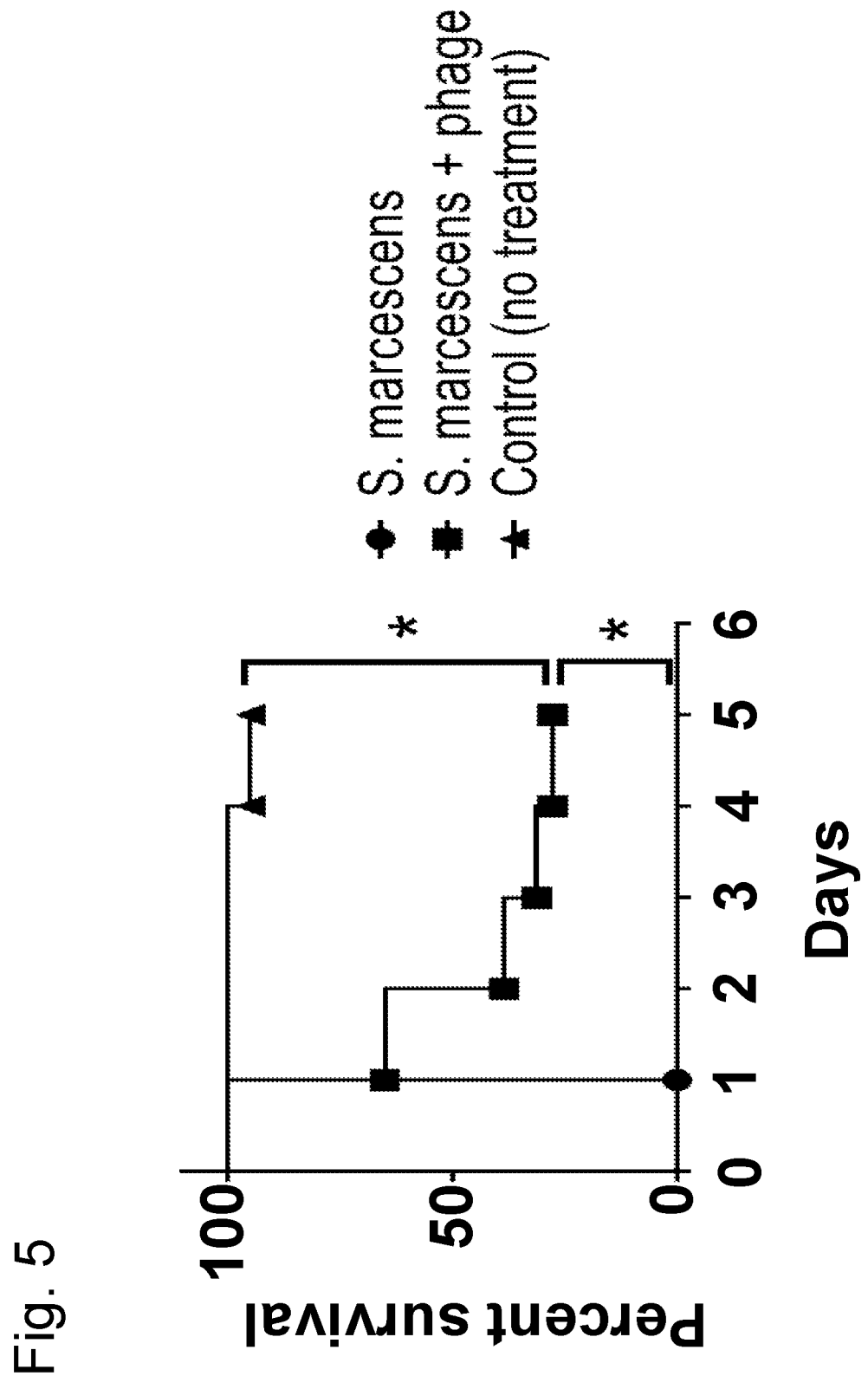
FIG. 5 is a graph showing phage against S. marcescens reduced fly mortality. Flies that were pricked with S. marcescens were all dead within a day, whereas a sizeable portion of the flies that were pricked with both S. marcescens and the phage survived for five days after the treatment. Almost all of the control flies which were not treated in anyway survived till the end of the experiment. Log-rank test was used to compare the curves for statistical significance, asterisk denotes p<0.0001.

Flies in all conditions were placed in food bottles and incubated at 26° C., 16:8 light:dark cycle, at 60% humidity. The number of alive and dead flies were counted every day for four days after the pricking. All The flies pricked with $S.$ $marcescens$ alone were all dead within 24 hours of the treatment. In comparison, more than 60% of the flies in the phage treatment group, and all the flies in the untreated control group were alive at that time point (FIG. 5). Further, most of the flies in the phage treatment group and the negative control group went on to survive for four more days when the experiment was terminated.

To ascertain the reason of death of the flies, dead flies from both the $S.$ $marcescens$ and $S.$ $marcescens$+phage pricked flies were homogenized and plated out. Four dead flies from each of the four replicates of both the $S.$ $marcescens$ and the $S.$ $marcescens$+phage treatment were homogenized in 100 ul of TSB. A 1:100 dilution was also produced by diluting the homogenate in TSB. 10 ul of the concentrated homogenate as well as the 1:100 dilution was plated out onto TSA plates, and incubated overnight at 30° C. Upon inspection of the plates for bacteria growth, all the plates from the dead *S. marcescens* pricked flies had a lawn of bacteria growing on them, whereas the plates from the dead *S. marcescens*+phage pricked flies had no bacteria on them. This shows that in the absence of the phage, *S. marcescens* likely induced septic shock in the flies leading to their fatality. However, in the presence of the phage, the mortality may have been due to injury caused by the pricking with the needle.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method for increasing a nutritional profile of an insect, the method comprising:

delivering to the insect an insect comestible composition comprising a feeding substrate and an effective amount of a solution comprising at least $10^7$ cells/mL of an exogenous strain of a methionine-producing bacteria to the insect, wherein the exogenous strain of methionine-producing bacteria populate the insect's microbiome and wherein the insect comestible composition is coated on a plant, a root, a stem, a shoot, a leaf, pollen, or a seed.

2. The method of claim 1, wherein the insect is a cricket, a grasshopper, or a locust.

3. The method of claim 1, wherein the insect is developmentally an embryo, larva, pupa, or adult.

4. The method of claim 1, wherein the delivery comprises delivering the composition to at least one habitat where the insect grows, lives, reproduces, or feeds.

5. The method of claim 1, wherein the insect comestible composition is coated on a plant.

6. The method of claim 1, wherein the insect comestible composition is coated on a root.

7. The method of claim 1, wherein the insect comestible composition is coated on a stem.

8. The method of claim 1, wherein the insect comestible composition is coated on a shoot.

9. The method of claim 1, wherein the insect comestible composition is coated on a leaf.

10. The method of claim 1, wherein the insect comestible composition is coated on pollen.

11. The method of claim 1, wherein the insect comestible composition is coated on a seed.

* * * * *